US008394939B2

(12) United States Patent
de Sauvage et al.

(10) Patent No.: US 8,394,939 B2
(45) Date of Patent: *Mar. 12, 2013

(54) NUCLEIC ACID ENCODING FUSED

(75) Inventors: Frederic de Sauvage, Foster City, CA (US); Arnon Rosenthal, Burlingame, CA (US); Maximilien Murone, Millbrae, CA (US)

(73) Assignee: Genentech, Inc., South San Francisco, CA (US)

( * ) Notice: Subject to any disclaimer, the term of this patent is extended or adjusted under 35 U.S.C. 154(b) by 952 days.

This patent is subject to a terminal disclaimer.

(21) Appl. No.: 11/536,932

(22) Filed: Sep. 29, 2006

(65) Prior Publication Data
US 2007/0042415 A1    Feb. 22, 2007

Related U.S. Application Data

(60) Continuation of application No. 10/174,653, filed on Jun. 17, 2002, now Pat. No. 7,259,245, which is a division of application No. 09/392,277, filed on Sep. 3, 1999, now Pat. No. 6,451,977, which is a continuation-in-part of application No. 09/258,000, filed on Feb. 25, 1999, now Pat. No. 6,531,579.

(60) Provisional application No. 60/076,072, filed on Feb. 26, 1998.

(51) Int. Cl.
*C07H 21/04* (2006.01)
*C12N 15/12* (2006.01)
*C07K 14/47* (2006.01)

(52) U.S. Cl. ...... 536/23.2; 435/69.1; 530/350; 536/23.5

(58) Field of Classification Search .................. None
See application file for complete search history.

(56) References Cited

U.S. PATENT DOCUMENTS

| 5,602,171 A | 2/1997 | Tang et al. |
| 5,710,173 A | 1/1998 | Tang et al. |
| 5,807,706 A | 9/1998 | Carter et al. |
| 6,022,708 A | 2/2000 | de Sauvage et al. |

FOREIGN PATENT DOCUMENTS

| WO | WO 94/01548 | 1/1994 |
| WO | WO 96/35124 | 11/1996 |
| WO | WO 96/40276 | 12/1996 |

OTHER PUBLICATIONS

Wells (1990) Biochemistry 29(37): 8509-8517.*
Ngo et al (1994) "The Protein Folding Problem and Tertiary Structure Prediction, Chapter 14: Computational Complexity Protein Structure Prediction, and the Levinthal Paradox" pp. 433-440 and 492-495 only.*
Murone et al (2000. Nature Cell Biology. vol. 2. pp. 310-312 plus 1 unnumbered page of Supplementary Information.*
Accession No. AA005195 (Blast Results, p. A-1).
Accession No. AA005279 (Blast Results, p. A-1).
Accession No. AA227595 (Blast Results, p. A-1).
Accession No. AA227895 (Blast Results, p. A-1).
Accession No. AA367411 (Blast Results, p. A-1).
Accession No. AA524236 (Blast Results, p. A-1).
Accession No. AA551070 (Blast Results, p. A-1).
Accession No. AA557146 (Blast Results, p. A-1).
Accession No. AA578578 (Blast Results, p. A-1).
Accession No. AA690149 (Blast Results, p. A-1).
Accession No. AA699496 (Blast Results, p. A-1).
Accession No. AA953702 (Blast Results, p. A-1).
Accession No. AA977132 (Blast Results, p. A-1).
Accession No. AA992176 (Blast Results, p. A-1).
Accession No. AI043075 (Blast Results, p. A-1).
Accession No. AI124737 (Blast Results, p. A-1).
Accession No. AI131405 (Blast Results, p. A-1).
Accession No. AI242910 (Blast Results, p. A-1).
Accession No. AI351935 (Blast Results, p. A-1).
Accession No. AI363751 (Blast Results, p. A-1).
Accession No. AI381813 (Blast Results, p. A-1).
Accession No. AI479301 (Blast Results, p. A-1).
Accession No. AI499649 (Blast Results, p. A-1).
Accession No. AI561067 (Blast Results, p. A-1).
Accession No. AQ340913 (Blast Results, p. B-1).
Accession No. DMFUSED_1 (Blast Results, p. C-1).
Accession No. DROFUSEDST_1 (Blast Results, p. C-1).
Accession No. F01568 (Blast Results, p. A-1).
Accession No. F30327 (Blast Results, p. A-1).
Accession No. F36543 (Blast Results, p. A-1).
Accession No. FUSE_DROME (Blast Results, p. C-1).
Accession No. G27519 (Blast Results, p. B-1).
Accession No. GEN13411 (Blast Results, p. C-1).
Accession No. JC4234 (Blast Results, p. C-1).
Accession No. P_T25004 (Blast Results, p. A-1).
Accession No. W88953 (Blast Results, p. A-1).
Accession No. Z42044 (Blast Results, p. A-1).
Akimaru et al., "Drosophila CBP is a Co-Activator of Cubitus Interruptus in Hedgehog Signalling." *Nature*. 386:735-738 (Apr. 17, 1997).
Alcedo et al., "The Drosophila Smoothened Gene Encodes a Seven-Pass Membrane Protein, A Putative Receptor for the Hedgehog Signal." *Cell*. 86:221-232 (1996).
Alexandre et al., "Transcriptional Activation of Hedgehog Target Genes in Drosophila is Mediated Directly by the Cubitus Interruptus Protein, A Member of the GLI Family of Zinc Finger DNA-Binding Proteins." *Genes & Development*. 10(16):2003-2013 (Aug. 15, 1996).
Apelqvist et al., "Sonic Hedgehog Directs Specialised Mesoderm Differentiation in the Intestine and Pancreas." *Current Biology*. 7(10):801-804 (Oct. 1, 1997).

(Continued)

*Primary Examiner* — Zachary Howard
(74) *Attorney, Agent, or Firm* — Brian L. Buckwalter

(57) ABSTRACT

The present invention relates to nucleotide sequences, including expressed sequence tags (ESTs), oligonucleotide probes, polypeptides, vectors and host cells expressing, immunoadhesins, agonists and antagonists (including antibodies) to human & vertebrate fused.

16 Claims, 55 Drawing Sheets

OTHER PUBLICATIONS

Aza-Blanc et al., "Proteolysis that is inhibited by Hedgehog targets Cubitus interruptus protein to the nucleus and converts it to a repressor" *Cell* 89:1043-1053 (1997).
Bellusci et al., "Involvement of Sonic Hedgehog (Shh) in Mouse Embryonic Lung Growth and Morphogenesis." *Development*. 124(1):53-63 (Jan. 1997).
Bitgood et al., "Hedgehog and Bmp genes are coexpressed at many diverse sites of cell-cell interaction in the mouse embryo" *Developmental Biology* 172(1):126-138 (Nov. 1995).
Bitgood et al., "Sertoli Cell Signaling by Desert Hedgehog Regulates the Male Germline." *Current Biology*. 6(3):298-304 (1996).
Blanchet-Tournier et al., "The Segment-Polarity Gene Fused is Highly Conserved in Drosophila" *Gene* 161:157-162 (1995).
BLAST Results A-1-A-3 (GenBank), "Accession U92715 (Jun. 19, 1998)" (GenBank).
Blast Results B-1-B-14 (GenBank).
Blast Results C-1-C-41 (Dayhoff).
Busson et al., "Genetic Analysis of Viable and Lethal Fused Mutants of Drosophila Melanogaster." *Roux's Archives of Developmental Biology* 197:221-230 (1988).
Chen and Struhl., "Dual Roles for Patched in Sequestering and Transducing Hedgehog." *Cell*. 87(3):553-563 (Nov. 1, 1996).
Chen et al., "Protein kinase A directly regulates the activity and proteolysis of cubitus interruptus". *Proc. Natl. Acad. Sci. USA* 95:2349-2354 (1998).
Chiang et al., "Cyclopia and Defective Axial Patterning in Mice Lacking Sonic Hedgehog Gene Function." *Nature*. 383(6599):407-413 (Oct. 3, 1996).
Chidambaram et al., "Mutations in the Human Homologue of the Drosophila Patched Gene in Caucasian and African-American Nevoid Basal Cell Carcinoma Syndrome Patients." *Cancer Research*. 56(20):4599-4601 (Oct. 15, 1996).
Dominguez et al., "Sending and Receiving the Hedgehog Signal: Control by the Drosophila Gli Protein Cubitus Interruptus." *Science*. 272(5268):1621-1625 (Jun. 14, 1996).
Echelard et al., "Sonic Hedgehog, a Member of a Family of Putative Signaling Molecules, is Implicated in the Regulation of CNS Polarity." *Cell*. 75:1417-1430 (1993).
Ekker et al., "Patterning activities of vertebrate hedgehog proteins in the developing eye and brain" *Current Biology* 5(8):944-955 (Aug. 1, 1995).
Ericson et al., "Sonic Hedgehog Induces the Differentiation of Ventral Forebrain Neurons: A Common Signal for Ventral Patterning Within the Neural Tube." *Cell*. 81(5):747-756 (Jun. 2, 1995).
Fan and Tessier-Lavigne., "Patterning of Mammalian Somites by Surface Ectoderm and Notochord: Evidence for Sclerotome Induction by a Hedgehog Homolog." *Cell*. 79(7):1175-1186 (Dec. 30, 1994).
Gailani et al., "The Role of the Human Homologue of Drosophila Patched in Sporadic Basal Cell Carcinomas." *Nature Genetics*. 14:78-81 (Sep. 1996).
Goodrich and Scott, "Hedgehog and partched in neural development and disease" *Neuron* 21:1243-1257 (1998).
Hahn et al., "Mutations of the Human Homolog of Drosophila Patched in the Nevoid Basal Cell Carcinoma Syndrome" *Cell* 85:841-851 (1996).
Hammerschmidt et al., "Protein Kinase A is a Common Negative Regulator of Hedgehog Signaling in the Vertebrate Embryo." *Genes & Development*. 10(6):647-658 (Mar. 15, 1996).
Hammerschmidt et al., "The World According to Hedgehog" *Trends in Genetics* 13(1):14-21 (1997).
Hanks et al., "Protein kinase catalytic domain sequence database: identification of conserved features of primary structure and classification of family members" *Methods in Enzymology* 200:38-62 (1991).
Hooper and Scott., "The Drosophila Patched Gene Encodes a Putative Membrane Protein Required for Segmental Patterning." *Cell*. 59:751-765 (1989).
Hynes et al., "Control of Cell Pattern in the Neural Tube by the Zinc Finger Transcription Factor and Oncogene Gli-1." *Neuron*. 19(1):15-26 (Jul. 1997).

Hynes et al., "Induction of Midbrain Dopaminergic Neurons by Sonic Hedgehog" *Neuron* 15:35-44 (1995).
"The Immune System in Health and Disease" *Immunobiology*, Janeway and Travers, Third edition (1997).
Ingham, "Signalling by Hedgehog Family Proteins in Drosophila and Vertebrate Development." *Curr. Opin. Genet. Dev*. 5:492-498 (1995).
Ingham, "Transducing Hedgehog: The Story So Far." *EMBO Journal* 17:3505-3511 (1998).
Jiang and Struhl, "Regulation of the Hedgehog and Wingless Signalling Pathways by the F-box/WD40-repeat Protein Slimb." *Nature* 391:493-496 (Jan. 29, 1998).
Johnson et al., "Ectopic Expression of Sonic Hedgehog Alters Dorsal-Ventral Patterning of somites." *Cell*. 79:1165-1173 (1994).
Johnson et al., "Human Homolog of Patched, a Candidate Gene for the Basal Cell Nevus Syndrome" *Science* 272:1668-1671 (1996).
Krauss et al., "A Functionally Conserved Homolog of the Drosophila Segment Polarity Gene hh is Expressed in Tissues with Polarizing Activity in Zebrafish Embryos." *Cell*. 75:1431-1444 (1993).
Krishnan et al., "Mediation of Sonic Hedgehog-Induced Expression of COUP-TFII by a Protein Phosphatase." *Science*. 278(5345):1947-1950 (Dec. 12, 1997).
Laufer et al., "Sonic Hedgehog and Fgf-4 Act Through a Signaling Cascade and Feedback Loop to Integrate Growth and Patterning of the Developing Limb Bud." *Cell*. 79(6):993-1003 (Dec. 16, 1994).
Lee et al., "Gli1 is a Target of Sonic Hedgehog that Induces Ventral Neural Tube Development." *Development*. 124(13):2537-2552 (Jul. 1997).
Li et al., "A single morphogenetic field gives rise to two retina primordia under the influence of the prechordal plate" *Development* 124(3):603-615 (Feb. 1997).
Li et al., "Function of Protein Kinase A in Hedgehog signal transduction and drosophila imaginal disc development" *Cell* 80:553-562 (1995).
Macdonald et al., "Midline signalling is required for Pax gene regulation and patterning of the eyes" *Development* 121(10):3267-3278 (Oct. 1995).
Marigo et al., "Biochemical Evidence that Patched is the Hedgehog Receptor." *Nature*. 384(6605):176-179 (Nov. 14, 1996).
Marti et al., "Requirement of 19K Form of Sonic Hedgehog for Induction of Distinct Ventral Cell Types in CNS Explants." *Nature*. 375(6529):322-325 (May 25, 1995).
Methot and Basler, "Hedgehog Controls Limb Development by Regulating the activities of distinct transcriptional activator and repressor forms of cubitus interruptus" *Cell* 96:819-831 (1999).
Monnier et al., "Suppressor of Fused Links Fused and Cubitus Interruptus on the Hedgehog Signalling Pathway." *Curr. Biol*. 8:583-586 (1998).
Myers (Human sequence tagged site SHGC-32400. GenBank accession No. G27519) (1996).
Nakano et al., "A protein with several possible membrane-spanning domains encoded by the Drosophila segment polarity gene patched" *Nature* 341:508-513 (1989).
Nusslein-Volhard et al., "Mutations Affecting the Pattern of the Larval Cuticle in Drosophila Melanogaster" *Roux's Archives of Developmental Biology* 193(5):267-282 (1984).
Orenic et al., "Cloning and Characterization of the Segment Polarity Gene Cubitus Interruptus Dominant of Drosophila." *Genes & Development*. 4(6):1053-1067 (Jun. 1990).
Oro et al., "Basal Cell Carcinomas in Mice Overexpressing Sonic Hedgehog." *Science*. 276(5313):817-821. (May 2, 1997).
Pan and Rubin, "cAMP-dependent protein kinase and Hedgehog act antagonistically in regulating decapentaplegic transcription in drosophila imaginal discs" *Cell* 80:543-552 (1995).
Perrimon, N., "Hedgehog and Beyond." *Cell*. 80:517-520 (Feb. 1995).
Pham et al., "The Suppressor of Fused Gene Encodes a Novel PEST Protein Involved in Drosophila Segment Polarity Establishment." *Genetics*. 140(2):587-598 (Jun. 1995).
Preat et al., "A Putative Serine/Threonine Protein Kinase Encoded by the Segment-Polarity Fused Gene of Drosophila." *Nature*. 347(6288):87-89 (Sep. 6, 1990).

Preat et al., "Segmental Polarity in Drosophila Melanogaster: Genetic Dissection of Fused in a Suppressor of Fused Background Reveals Interaction with Costal-2." *Genetics*. 135(4):1047-1062 (Dec. 1993).

Preat., "Characterization of Suppressor of Fused, A Complete Suppressor of the Fused Segment Polarity Gene of Drosophila Melanogaster." *Genetics*. 132(3):725-736 (Nov. 1992).

Ramsdell and Yost *Trends in Genetics* 14:459-465 (1998).

Riddle et al., "Sonic Hedgehog Mediates the Polarizing Activity of the ZPA." *Cell*. 75:1401-1416 (1993).

Robbins et al., "Hedgehog Elicits Signal Transduction by Means of a Large Complex Containing the Kinesin-Related Protein Costal2." *Cell*. 90(2):225-234 (Jul. 25, 1997).

Roberts et al., "Sonic Hedgehog is an Endodermal Signal Inducing Bmp-4 and Hox Genes During Induction and Regionalization of the Chick Hindgut." *Development*. 121:3163-3174 (1995).

Roelink et al., "Floor Plate and Motor Neuron Induction by Different Concentrations of the Amino-Terminal Cleavage Product of Sonic Hedgehog Autoproteolysis." *Cell*. 81(3):445-455 (May 5, 1995).

Ruiz i Altaba, A., "Combinatorial Gli gene function in floor plate and neuronal inductions by sonic hedgehog" *Development* 125:2203-2212 (1998).

Sasaki et al., "A binding site for Gli proteins is essential for HNF-3β floor plate enhancer activity in transgenics and can respond to Shh in vitro" *Development* 124:1313-1322 (1997).

Sisson et al., "Costal2, A Novel Kinesin-Related Protein in the Hedgehog Signaling Pathway." *Cell*. 90(2):235-245 (Jul. 25, 1997).

Stone et al., "The Tumour-Suppressor Gene Patched Encodes a Candidate Receptor for Sonic Hedgehog." *Nature*. 384(14):129-134 (Nov. 1996).

Therond et al., "Functional Domains of Fused, A Serine-Threonine Kinase Required for Signaling in Drosophila." *Genetics*. 142(4):1181-1198 (Apr. 1996).

Therond et al., "Phosphorylation of the Fused Protein Kinase in Response to Signaling from Hedgehog." *Proc. Natl. Acad. Sci. USA* 93(9):4224-4228 (Apr. 30, 1996).

Unden at al., "Mutations in the Human Homlogue of Drosophila Patched (PTCH) in Basal Cell Carcinomas and the Gorlin Syndrome: Different In Vivo Mechanisms of PTCH Inactivation." *Cancer Research*. 56(20):4562-4565 (Oct. 15, 1996).

Ungar et al., "Inhibition of protein kinase A phenocopies ectopic expression of hedgehog in the CNS of wild-type and cyclops mutant embryos" *Developmental Biology* 178(1):186-191 (Aug. 25, 1996).

van den Heuvel and Ingham, "Smoothened Encodes a Receptor-Like Serpentine Protein Required for Hedgehog Signalling" *Nature* 382:547-551 (1996).

Vortkamp et al., "Regulation of rate of cartilage differentiation by Indian hedgehog and PTH-related protein" *Science* 273:613-622 (1996).

Westendorf et al., "Cloning of cDNAs for M-phase phosphoproteins recognized by the MPM2 monoclonal antibody and determination of the phosphorylated epitope" *Proc. Natl. Acad. Science* 91(2):714-718 (Jan. 18, 1994).

Wicking et al., "Most Germ-Line Mutations in the Nevoid Basal Cell Carcinoma Syndrome Lead to a Premature Termination of the PATCHED Protein, and No Genotype-Phenotype Correlations are Evident." *Am. J. Hum. Genet*. 60(1):21-26 (Jan. 1997).

Xie et al., "Activating Smoothened Mutations in Sporadic Basal-Cell Carcinoma." *Nature*. 391(6662)1;90-92 (Jan. 1, 1998).

Zamecnik et al., "Inhibition of Replication and Expression of Human T-Cell Lymphotropic Virus Type III in Cultured Cells by Exogenous Synthetic Oligonucleotides Complementary to Viral RNA" *Proc. Natl. Acad. Sci*. 83:4143-4146 (Jun. 1986).

* cited by examiner

> length: 4880 bp (circular)

```
  1 CCCGGGGATC CTCTAGAGAT CCCTCGACCT CGACCCACGC GTCCGCCCAC GGCGTCCCAG ATGTTGTGGA ACTGTCCCTG
    GGGCCCCTAG GAGATCTCTA GGGAGCTGGA GCTGGGTGCG CAGGCGGGTG CCGCAGGGTC TGCGCAGGGTC TACAACACCT TGACAGGGAC

101 GATCTATAGC TCTTCACCGT CTCTACTTTC TTCCCTTCTAA GAGATCCTGA AACCTCTGTC ATGGAAAAGT ACCACGTGTT GGAGAAGGCT
    CTAGATATCG AGAAGTGGCA GAGATGAAAG AAGGAAGATT CTCTAGGACT TTGGAGACAG TACCTTTTCA TGGTGCACAA CCTCTTCCGA
  1                                                                 M  E  K  Y  H  V  L  E  M  I  G  E  G  S

201 CTTTTGGGAG GGTGTACAAG AATACAGTGC TCAGGTCGTG GCCCTGAAGT TCATCCCAAA ATTGGGCGC TCAGAGAAGG AGCTGAGGAA
    GAAAACCCTC CCACATGTTC TTATGTCACG AGTCCAGCAC CGGGACTTCA AGTAGGGTTT TAACCCGCG AGTCTCTTCC TCGACTCCTT
 15    F  G  R  V  Y  K     G  R  R  K  Y  S  A    Q  V  V    A  L  K  F    I  P  K    L  G  R    S  E  K  E    L  R  N

301 TTTGCAACGA GAGATTGAAA TAATGCGGGG TCTGCGGCAT CCCAACATTG TGACAGCTTT GAAACTGATA AAGAGGTGGT GGTGGTGACA
    AAACGTTGCT CTCTAACTTT ATTACGCCCC AGACGCCGTA GGGTTGTAAC ACTGTCGAAA CTTGACTAT TTCTCCACCA CCACCACTGT
 48  L  Q  R  E  I  E  I    M  R  G    L  R  H    P  N  I  V    H  M  L    D  S  F    E  T  D  K    E  V  V    V  V  T

401 GACTATGCTG AGGGAGAGCT CTTTCAGATC CTAGAAGATG ACGGAAAACT TCCTGAAGAC CAGGTTCAGG CCATTGCTGC TCAGCCCTGT
    CTGATACGAC TCCCTCTCGA GAAAGTCTAG GATCTTCTAC TGCCTTTTGA AGGACTTCTG GTCCAAGTCC GGTAACGACG AGTCGGGACA
 81  D  Y  A  E    G  E  L    F  Q  I    L  E  D  D    G  K  L    P  E  D    Q  V  Q  A    I  A  A    Q  L  V    S  A  L  Y

501 ACTATCTGCA TTCCCACCGC GAGATATGAA GCCTCAGAAC ATCCTCTATAT CACTCTATAT GTCTCCAGAG CTGGTGGAGG TTGGATTGCT
    TGATAGACGT AAGGGTGGCG CTCTATACTT CGGAGTCTTG TAGGAGGATA GTGAGATATA CAGAGGTCTC GACCACCTCC AACCTAACG
115    Y  L  H    S  H  R    I  L  H  R    D  M  K    P  Q  N    I  L  L  A    K  G  G    I  K    L  C  D  F    G  F  A

601 CCCGGGCTAT AGCACCAATA CAATGGTGCT GACATCCATC AAAGGCACAC CACTCTTGTC GTCTCCAGAG CTGGTGGAGG AGCGACCACCATA CGACCACACA
    GGGCCCGATAC TCGTGGTTAT GTTACCACGA CTGTAGGTAG TTTCCGTGTG GTGAGATATA CAGAGGTCTC GACCACCTCC TCGCTGGTAT GCTGGTGTGT
148  R  A  M    S  T  N  T    M  V  L    T  S  I    K  G  T  P    L  Y  M    S  P  E    L  V  E  E    R  P  Y    D  H  T

701 GCGGACCCT GGTCTGTTGG CTGCATACTA TATGAACTGG CAGTAGGCAC CCCTCCCTTC TATGCTACAA GCATCTTTCA GCTGGTCAGC CTCATTCTCA
    CGCCTGGGAGA CCAGACAACC GACGTATGAT ATACTTGACC GTCATCCGTG GGAGGGAAG ATACGATGTT CGTAGAAAGT CGACCAGTCG GAGTAAGAGT
181  A  D  L  W    S  V  G    C  I  L    Y  E  L  A    V  G  T    P  P  F    Y  A  T  S    I  F  Q    L  V  S    L  I  L  K
```

FIG._1A

```
 801  AGGACCCTGT GGCTGGCGCC TCAACCATCA GTCCCTGCTT TAAGAACTTC CTGCAGGGAC TGCTCACCAA AGACCCACGG CAGGGACTGT CCTGGCCAGA
      TCCTGGGACA CCGACCGCGG AGTTGGTAGT CAGGGACGAA ATTCTTGAAG GACGTCCCTG ACGAGTGGTT TCTGGGTGCC GTCCCTGACA GGACCGGTCT
 215   D  P  V   A  G  A   L  N  H  Q   S  L  L   *  E  L   L  Q  G   L  L  T  K   D  P  R   Q  R  L  S   W  P  D

901  CCTCTTATAT CACCCCTTTA TGCTGGGTCA TGTCACCATA ATAACTGAAG CAGCAGGCCC AGATTTGGGG TCTAAACCCC TGGGTAAGT ACCCCCAGAA
      GGAGAATATA GTGGGGAAAT ACGACCCAGT ACAGTGGTAT TATTGACTTC GTCGTCCGGG TCTAAACCCC AGATTTGGGG ACCCCATTCA TGGGGGTCTT
 248   L  L  Y   H  P  F   I  A  G  H   V  T  I    I  T  E  P   A  G  P   D  L  G   T  P  F  T   S  R  L   P  P  E

1001  CTTCAGGTCC TAAAGGACGA ACAGGCCCAT CGGTTGGCCC CCAAGGGTAA TCAGTCTCGC ATCCTTGACTC AGGCCTATAA ACGCATGCT GAGGAGGCCA
      GAAGTCCAGG ATTTCCTGCT TGTCCGGGTA GCCAACCGGG GGTTCCCATT AGTCAGAGCG TAGAACTGAG TCCGGATATT TGCCGTACGA CTCCTCCGGT
 281   L  Q  V  L   K  D  E   Q  A  H   R  L  A  P   K  G  N   Q  S  R   I  L  T  Q   A  Y  K   R  M  A   E  E  A  M

1101  TGCAGAAGAA ACATCAGAAC ACAGGACCTG TGTCCTGGAC CCCTTGAGCA GGGAACTCGT TGGTCGTTCC ACCAGCAAGG TGGCTCCTGG CACAGCCCCT CTGCCCAGAC TCGGGGCCAC
      ACGTCTTCTT TGTAGTCTTG TGTCCTGGAC ACAGGACCTG GGGAACTCGT CCCTTGAGCA ACCAGCAAGG AGGACAAG TCTCCTGTTC TGGTCGTTC GACGGGTCTG AGCCCCGGTG
 315   Q  K  K   H  Q  N    T  G  P  A    L  E  Q    E  D  K   T  S  K  V   A  P  G    T  A  P    L  P  R  L   G  A  T

1201  TCCTCAGGAA TCAAGCCTCC TGGGCCGGGAT CTTAGCCTCA GAATTGAAGA GCAGCTGGGC TAAATCAGGG ACTGGAGAGG TGCCCCTCTGC ACCTCGGGAA
      AGGAGTCCTT AGTTCGGAGG ACCGCCCTA GAATCGGAGT CTTAACTTCT CGTCGACCCG ATTTAGTCCC TGACCTCTCC ACGGGAGACG TGGAGCCCCTT
 348   P  Q  E    S  S  L  L    A  G  I    L  A  S    E  L  K  S    S  W  A   K  S  G    T  G  E  V    P  S  A    P  R  E

1301  AACCGGACCA CCCCAGATTG TGAACAGACA TTCCCAGAGG AGAGGCCAGA GGTGCTGGGC CAGGGAGCA CTGATGTAGT GGACCTGGAA AATGAGGAGC
      TTGGCCTGGT GGGGTCTAAC ACTTGCTGAT AAGGGTCTCC TCTCGGTCTT CCACGACCCG GTCGACCATA CTGATGTAGT CCTGGACCTT TTACTCCTCG
 381   N  R  T  T    P  D  C    E  R  A    F  P  E  E    R  P  E    V  L  G    Q  R  S  T    D  V  V    D  L  E   N  E  E  P

1401  CAGACAGTGA CAATGAGTGG CAGAGTCAGC CAGCACCTGC TAGAGACCAC CGAGCCCGTG CCTATTCAAC TGGATAAGTG ACTCCGAGG AGAGTGAAAC GACTGAAGAC
      GTCTGTCACT GTTACTCACC GTCTCAGTCG GTCGTGGACG ATCTCTGGTG GCTCGGGCAC GGATAAGTTG ACCTATTCAG TGAGGCTCC TCTCACCTTG ACTGGAAC GACACATTAG GACTGAAGAC
 415   D  S  D    N  E  W    Q  H  L  L    E  T  T    E  P  V    P  I  Q  L    E  T  T    E  P  V    L  T  L    C  N  P    D  F  C

1501  CCAGCGCATC CAGAGTCAGC TGCATGAAGC ATCCTGAAAG GCATCTTTGA CACATCCTGC GGGTGCTTCC CTGCATTCCG GGTCCTGAGC
      GGTCGCGTAG GTCTCAGTCG ACGTACTTCG TAGGACTTTC CGTAGAAACT GTGTAGGACG CCCACGAAGG GACGTAAGGC CCAGGACTCG
 448   Q  R  I    Q  S  Q  L    H  E  A    I  L  E    G  A  S    H  I  L  P    A  F  R    V  L  S

1601  AGTCTTCTCT CCAGCTGCAG TGATTCTGTT GCCTTGTATT CCTTCTGCCG GGAGGCAGG CTTCCTGGGC TGCTGCTGAG TCTACTCAGG CACAGTCAGG
      TCAGAAGAGA GGTCGACGTC ACTAAGACAA CGGAACATAA GGAAGACGGC CCTCCGTCC GAAGGACCCG ACGACGACTC AGATGAGTCC GTGTCAGTCC
 481   S  L  L  S    C  S    D  S  V    A  L  Y  S    F  C  R    E  A  G    L  P  G  L    L  L  S    L  L  R    H  S  Q  E
```

FIG._1B

```
1701 AGAGCAACAG CCTCCAGCAG CAATCTTGGT ATGGGACCTT CTTACAGGAC CTGATGGCTG TGATTCAGGC CTACTTTGCC TGTACCTTCA ATCTGGAGAG
     TCTCGTTGTC GGAGGTCGTC GTTAGAACCA TACCCTGGAA GAATGTCCTG GACTACCGAC ACTAAGTCCG GATGAAACGG ACATGGAAGT TAGACCTCTC
 515  S  N  S   L  Q  Q   Q  S  W  Y   G  T  F   L  Q  D   L  M  A  V   I  Q  A   Y  F  A   C  T  F  N   L  E  R

1801 GAGCCAGACA AGTGACAGCC TGCAGGTGTT TCAGGAGGCT GCCAACTTT GTTGGGGAAA CTGCTGGCCC AACCAGATGA CTCTGAGCAG
     CTCGGTCTGT TCACTGTCGG ACGTCCACAA AGTCCTCCGA CGGTTGGAAA CAACCCCTTT GACGACCGGG TTGGTCTACT GAGACTCGTC
 548  S  Q  T   S  D  S  L   Q  V  F   Q  E  A   A  N  L  F   L  D  L   L  G  K   L  L  A  Q   P  D  D   S  E  Q

1901 ACTTTGCGA GGGACAGCCT TATGTGCTTT ACTGTCCTGT GCGAAGCCAT GGATGGGAAC AGCCGGCCA TCTCCAAAGC CTTTTACTCC AGCTTGCTGA
     TGAAACGCCT CCCTGTCGGA ATACACGAAA TGACAGGACA CGCTTCGGTA CCTACCCTTG TCGGCCGGT AGAGGTTTCG GAAAATGAGG TCGAACGACT
 581  T  L  R  R   D  S  L   M  C  F   T  V  L  C   E  A  M   D  G  N   S  R  A  I   S  K  A   F  Y  S   S  L  L  T

2001 CGACACAGCA GGTTGTCTTG GATGGGCTC TTCATGGCTT GACAGTTCCA CAGCTCCCTG TCCACACTCC CCAAGGAGCC CCGCAAGTGA GCCAGCCACT
     GCTGTGTCGT CCAACAGAAC CTACCCGAG AAGTACCGAA CTGTCAAGGT GTCGAGGGAC AGGTGTGAGG GGTTCCTCGG GGCGTTCACT CGGTCGGTGA
 615  T  Q  Q   V  V  L   D  G  L  L   H  G  L   T  V  P   Q  L  P  V   H  T  P   Q  G  A   P  Q  V  S   Q  P  L

2101 GCGAGAGCAG AGTGAGGATA TACTGGAGC CATTTCCTCT GCCCTGGCAG CCATATGCAC TGCTCCTGTG GGACTGCCCG ACTGCTGGGA TGCCAAGGAG
     CGCTCTCGTC TCACTCCTAT ATGACCTCG GTAAAGGAGA CGGGACCGTC GGTATACGTG ACGAGGACAC CCTGACGGGC TGACGACCCT ACGGTTCCTC
 648  R  E  Q   S  E  D  I   P  G  A   I  S  S   A  L  A  A   I  C  T   A  P  V   G  L  P  D   C  W  D   A  K  E

2201 CAGGTCTGT GGCATTTGGC AAATCAGCTA ACTGAAGACA GCAGCCAGCT CAGGCCATCC GCCTGCAGCA TCCATCCCTG TGCCTGCACC
     GTCCAGACA CCGTAAACCG TTTAGTCGAT TGACTTCTGT CGTCGGTCGA GTCCGGTAGG GCGGACGTCGT AGGTAGGGAC ACGGACGTGG
 681  Q  V  C  W   H  L  A   N  Q  L   T  E  D  S   S  Q  L   R  P  S   L  I  S  G   L  Q  H   P  I  L   C  L  H  L

2301 TTCTCAAGGT TCTATACTCC TGCTGCCTTG TCAGTGAGGG CCTCTGGGGC CTTCTGGGGA AGGAGCCCCT GGCCTTGAA TCCCTGTTTA TGTTGATTCA
     AAGAGTTCCA AGATATGAGG ACGACGGAAC AGTCACTCCC GGAGACCCCG GAAGACCCCT TCCTCGGGGA CCGGAACCTT AGGGACAAAT ACAACTAAGT
 715  L  K  V   L  Y  S   C  C  L  V   S  E  G   L  C  R   L  L  G  Q   E  P  L   A  L  E   S  L  F  M   L  I  Q

2401 GGGCAAGGTA AAAGTAGTAG ATTGGGAAGA GTCTACTGAA GTGACACTCT ACTTCCTCTC CCTTCTTGTC AAAACCTGCC TTGTGGAATG
     CCCGTTCCAT TTTCATCATC TAACCCTTCT CAGATGACTT CACTGTGAGA TGAAGGAGAG GGAAGAACAG TTTTGGACGG AACACCTTAC
 748  G  K  V   K  V  V  D   W  E  E   S  T  E   V  T  L  Y   F  L  S   L  L  V   F  R  L  Q   N  L  P   C  G  M

2501 GAGAAGCTAG GCAGTGACGT CGTCACTGCA TGCTACTCTC TTTACCCATT CGCATGTCGT AGTGCAGCAG CCTGTCTATT GGGACAGCTT GGTCAGCAAG
     CTCTTCGATC CGTCACTGCA GCATGAGAG AAATGGGTAA GCGTACAGCA TCACGTCGTC GGACAGATAA CCCTGTCGAA CCAGTCGTTC
 781  E  K  L  G   S  D  V   A  T  L   F  T  H  S   H  V  V   S  L  V   S  A  A  A   C  L  L   G  Q  L   G  Q  Q   G
```

*FIG. 1C*

```
2601 GGGTGACCTT TGACCTCCAG CCCATGGAAT GGATGGCTGC AGCCACACAT GCCTTGTCTG CCCCTGCAGA GGTTCGGTTG ACTCCACCAG GTAGTTGTGG
     CCCACTGGAA ACTGGAGGTC GGGTACCTTA CCTACCGACG TCGGTGTGTA CGGAACAGAC GGGGACGTCT CCAAGCCAAC TGAGGTGGTC CATCAACACC
 815  V  T  F   D  L  Q   P  M  E   W  M  A   A  T  H   A  L  S   A  P  A   E  V  R   L  T  P   P  G  S   C  G

2701 ATTCTATGAT GGCCTCCTTA TCCTTCTGTT GCAGCTCCTC ACTGAGCAGG GGAAGGCTAG CCTAATCAGG GAGCTTTCGC GATATGTCCA GTTCAGAAAT GTGGACCGTT
     TAAGATACTA CCGGAGGAAT AGGAAGACAA CGTCGAGGAG TGACTCGTCC CCTTCCGATC GGATTAGTCC CTCGAAAGCG CTATACAGGT CAAGTCTTTA CACCTGGCAA
 848  F  Y  D   G  L  L   I  L  L   L  Q  L   L  T  E   Q  G  K   A  S  L   I  R  D   M  S  S   E  M  W   T  V

2801 TTGTGGCACC GCTTCTCCAT GGTCCTGAGG CTGAAGAGTA CCAGGAGCTCC GAGGGCTCC TGTCCTTCCC TATCCAGTCC ACCAAGCCCT GAGCCAGACT
     AACACCGTGG CGAAGAGGTA CCAGGACTCC GACTTCTCAT GGTCCTCGAG CTCCCGAGG ACAGGAAGGG ATAGGTCAGG TGGTTCGGGA CTCGGTCTGA
 881  L  W  H   R  F  S   M  V  L   R  L  P   E  E  A   S  A  Q   E  G  E   L  S  L   S  S  P   P  S  P   E  P  D  W

2901 GGACACTGAT TTCTCCCCAG GGCATGGCAG CCTGGCCATG GGCATGGCAG CCCTGCTGAG GCCACCTTTA CCCAGGAGCC CTGAGCTGCC TGTCCCAGCA
     CCTGTGACTA AAGAGGGGTC CCGTACCGTC GGACCGGTAC CGGACCGGTAC GGGACGACTC CGGTGGAAAT GGGTCCTCGG GACTCGACGG ACAGGGTCGT
 915  T  L  I   S  P  Q   G  M  A   A  L  L   S  L  A   M  A  T   F  T  Q   E  P  Q   L  C  L   S  Q  H

3001 TGGAAGTATC CTCATGTCCA TCCTGAAGCA TCTGCTTTGC CCCAGCTTCC TGAATCAACT GCTGCTGGTT CTTATAGTTG CCTCATGGGT CTGAGTTTCT CCCTGTCGTG
     ACCTTCATAG GAGTACAGGT AGGACTTCGT AGACGAAACG GGGTCGAAGG ACTTAGTTGA CGACGACCAA GAATATCAAC GGAGTACCCA GACTCAAAGA GGGACAGCAC
 948  G  S  I   L  M  S   I  L  K   H  L  L   C  P  S   F  L  N   Q  L  R   Q  A  P   H  G  S   E  F  L   P  V  V

3101 GTGCTCTCTG TCTGCCAGCT CCCTTGCTTC CCCTTTGCGC TGGACATGGA TGCTGACCTC AGAACCGGCT GGAGTCCCTG AGTCTTCAAC TCAGAAGTTG
     CACGAGAGAC AGACGGTCGA GGGAACGAAG GGGAAACGCG ACCTGTACCT ACGACTGGAG TCTTGGCCGA CCTCAGGGAC CTCAGAAGTT AGTCTTCAAC
 981  V  L  S   V  C  Q   L  L  C   F  P  F   A  L  D   M  D  A   D  L  L   I  V  V   L  A  D   L  R  D   S  E  V  A

3201 CAGCCCATCT GCTGCAGGTC CGACGCAGGT TAGAAGGCAA CTACGTTCAC GATGCAAGTG GAGCTGCCCA TCAGCCTTCT CACACGCCTG GCCCTCATGG ATCCCACCTC
     GTCGGGTAGA CGACGTCCAG GCTGCGTCCA ATCTTCCGTT GATGCAAGTCAC CTACGTTCAC CTCGACGGGT AGTCGGAAGA GTGTGCGGAC CGGGAGTACC TAGGGTGGAG
1015  A  H  L   Q  V  C   C  Y  H   L  P  L   M  Q  V   E  L  P   I  S  L   L  T  R   L  A  L   M  D  P   T  S

3301 TCTCAACCAG TTTGTGAACA CAGTGTCTGC CTCCCCTAGA CTCCAACCAG GAGGGGATCT CGTTTCTCTC AGTTGCCCTC CTGAGTGACC AGCCACTGTT GACCTCCGAC
     AGAGTTGGTC AAACACTTGT GTCACAGACG GAGGGGATCT GAGGTTGGTC CTCCCCTAGA GCAAAGAGAG TCAACGGGAG GACTCACTGG TCGGTGACAA CTGGAGGCTG
1048  L  N  Q   F  V  N   T  V  S   A  S  P   R  T  I   V  S  F   L  S  V   A  L  L   S  D  Q   P  L  L   T  S  D

3401 CTTCTCTCTC TGCTGGCCCA GTCCTGTCTC TACTGCCAGG GTCGGTGGTCC CAAGCCCACTT GTCCTTTATC CAAGAGCTTC TGGCTGGCTC TGATGAATCC TATCGGCCCC
     GAAGAGAGAG ACGACCGGGT CAGGACAGAG ATGACGGTCC CAGGACAGAG GTTCGGGTGAA CAGGAAATAG GTTCTCGAAG ACCGACCGAG ACTACTTAGG ATAGCCGGGG
1081  L  L  S   L  L  A   H  T  A   R  V  L   S  P  S   H  L  S   F  I  Q   E  L  L   A  G  S   D  E  S   Y  R  P  L
```

*FIG._1D*

```
3501 TGCGCAGCCT CCTGGGCCAC CCAGAGAATT CTGTGCGGGC CCAACACAGC ATGGCCCTGC GTGGGGCACT
     ACGCGTCGGA GGACCCGGTG GGTCTCTTAA GACACGCCCG GGTTGTGTCG TACCGGGACG CACCCCGTGA
1115   R  S  L  L  G  H  P  E  N  S  V  R  A  H  T  Y  R  L  L  G  H  L  L  Q  H  S  M  A  L  R  G  A  L

3601 GCAGAGCCAG TCTGGACTGC TCAGCCTTCT GCTGCTTGGG CTTGGAGACA AGGATCCTGT AGTGCCAGCT TGTGCGGTGC AGTGCCAGCT TTGCTGTGGG CAATGCAGCC
     CGTCTCGGTC AGACCTGACG AGTCGGAAGA CGACGAACCG GAACCTCTGT TCCTAGGACA TCACGGTCGA ACACGCCACG TCACGGTCGA AACGACACCC GTTACGTCGG
1148   Q  S  Q  S  G  L  L  S  L  L  L  L  G  L  G  D  K  D  P  V  V  R  C  S  A  S  F  A  V  G  N  A  A

3701 TACCAGGCTG GTCCCTCTGG ACCTGCCCTG GCAGCTGCAG TGCCCAGTAT GACCCAGCTG CTCGGAGATC TATCCGGCGC AATGTTGCAT
     ATGGTCCGAC CAGGGAGACC TGGACGGGAC CGTCGACGTC ACGGGTCATA CTGGGTCGAC GAGCCTCTAG ATAGGCCGCG TTACAACGTA
1181   Y  Q  A  G  P  L  G  P  A  L  A  A  V  P  S  M  T  Q  L  L  G  D  P  Q  A  G  I  R  R  N  V  A  S

3801 CAGCTCTGGG CAACTTGGGA CCTGAAGGTT TGGGAGAGGA GCTGTTACAG TGCGAAGTAC CCCAGCGGCT CCTAGAAATG GCATGTGGAG ACCCCCAGCC
     GTCGAGACCC GTTGAACCCT GGACTTCCAA ACCCTCTCCT CGACAATGTC ACGCTTCATG GGGTCGCCGA GGATCTTTAC CGTACACCTC TGGGGGTCGG
1215   A  L  G  N  L  G  P  E  G  L  G  E  E  L  L  Q  C  E  V  P  Q  R  L  L  E  M  A  C  G  D  P  Q  P

3901 AAATGTGAAG GAGGCTGCCC TCATTGCCCT CCGGAGCCTG GTGTCCCTGG TCAGGTACTG GTGCCAGTGA GAAACTATCC
     TTTACACTTC CTCCGACGGG AGTAACGGGA GGCCTCGGAC CACAGGGACC AGTCCATGAC CACGGTCACT CTTTGATAGG
1248   N  V  K  E  A  A  L  I  A  L  R  S  L  Q  V  S  L  G  A  S  E  K  L  S

4001 TTGCTCTCTC TGGGAATCA GTCACTGCCA CACAGCAGTC CTAGGCCTGC CTCTGCCAAA CACTGCAGGA AACTCATTCA CCTCCTGAGG CCAGCCCATA
     AACGAGAGAG ACCCCTTAGT CAGTGACGGT GTGTCGTCAG GATCCGGACG GAGACGGTTT GTGACGTCCT TTGAGTAAGT GGAGGACTCC GGTCGGGTAT
1281   L  L  S  L  G  N  Q  S  L  P  H  S  S  P  R  P  A  S  A  K  H  C  R  K  L  I  H  L  L  R  P  A  H  S
```

FIG._1E

```
4101 GCATGTGATT CCAGATTCCT GCGGTCCAGC CTCCAACTTT GGTGCCAGCT CTTTCTTATN TAATACACAA GGCCAAYTC AACTGAGAGC TAAAGAGACT
     CGTACACTAA GGTCTAAGGA CGCCAGGTCG GAGGTTGAAA CCACGGTCGA GAAAGAATAN ATTATGTGTT CCGGTTRAG TTGACTCTCG ATTTCTCTGA
1315 M  O

4201 AGAAAAGAGA TAAGCTGCCA ACTCAACTGA GAACAGGAAA CTNGAAGAGA TTTATATATA AAGCTTCTTC CTTCTCCCAG ATGCAGGATG TTTTCAACCA
     TCTTTTCTCT ATTCGACGGT TGAGTTGACT CTTGTCCTTT GANCTTCTCT AAATATATAT TTCGAAGAAG GAAGAGGGTC TACGTCCTAC AAAAGTTGGT

4301 GTAAATTTTA TTGCTGTTGG TGCCAGAGAA CCTCAACCTG GAGTCCCTTT CTTCTCTACA GAAGAGATGT TCCAGGGGCC NTTTTCTCCA ATAATGTGCC TTTAACTCTA GGGACCTGCC
     CATTTAAAAT AACGACAACC ACGGTCTCTT GGAGTTGGAC CTCAGGGAAA GAAGAGATGT AGGTCCCCGG NAAAAGAGGT TATTACACGG CCCTGGACGG

4401 TCACGGACCT TAGGGAAAAA CCTCAACCTG TGGGGATCAA TGCCATCAGT CCCTGTTATT GAGGGATTAT CCCTAGCCA ACATTCCTAT
     AGTGCCTGGA ATCCCTTTTT GGACAGAGTC ACCCCTAGTT ACGGTAGTCA GGGACAATAA CTCCCTAATA GGGAATCGGT TGTAAGGATA

4501 GGACAGTGAT GAAGACAGAG CCTGTCTCAG CTCTAGGCTG TGGGGATCAA TGCCATCAGT CCCTGTTATT GAGGGATTAT CCCTAGCCA ACATTCCTAT
     CCTGTCACTA CTTCGTCTC GGACAGAGTC GAGATCCGAC ACCCCTAGTT ACGGTAGTCA GGGACAATAA CTCCCTAATA GGGAATCGGT TGTAAGGATA

4601 CTGTGGGTGG CCGTGGAGAG TGTATCTTTT TTTGGGGTGT GTGTGTATAT GTGTGTGTGT ATGTGTGTGT GTTCTGTTTG TAAACTCTTT
     GACACCCACC CGCACCTCTC ACATAGAAAA AAACCCCACA CACACATATA CACACACACA TACACACACA CAAGACAAAC ATTTGAGAAA

4701 TAATAAAAGT TGTGCCTCAC CATNCTTGAA GCTCCCAGGA AGGGTTGA GAGGCTCAAC CCCTCTTTCA GCTTCTATGT GGTGTTGGAG GTGCTGGTAT
     ATTATTTTCA ACACGGAGTG GTATGAACTT CGAGGGTCCT GTTCCCAACT CTCCGAGTTG GGGAGAAAGT CGAAGATACA CCACAACCTC CACGACCATA

4801 CGTGTTCACA CAAAAAAAAA AAAAAAAAAA AAAAAAAAA AAAAAAAAA AAAAAAAAA
     GCACAAGTGT GTTTTTTTTT TTTTTTTTT TTTTTTTTT TTTTTTTT TTTTTTTT
```

FIG._1F

```
CCCGGGCTATGAGCACCAATACAATGGTGCTGACATCCATCAAAGGCACACCACTCTATA
TGTCTCCAGAGCTGGTGGAGGAGCGACCATACGACCACACAGCGGACCTCTGGTCTGTTG
GCTGCATACTATATGAACTGGCAGTAGGCACCCCCTCCCTTCTAATGCTACAAGCATCTTT
CAGCTGGTCAGCC
```

FIG._2

```
hfused    1  MEKYHVLEMIGEGSFGRVYKGRRKYSAQVVALKFIPKLGRSEKELRNLQR
dfused    1  MDRYAVSSLVGQGSFGCVYKAQRDDDKVVAIKVISKRGRSNRELKNLRR hfused   51  EIEIMRGLRHPNIVHMLDSFETDKEVVVTDYAEGELFQILEDDGKLPED
dfused   51  ECDIQARLKHPHVIEMVESFESKFDLFVVTEFALMDLHRYLSFNGAMPEE hfused  101  QVQAIAAQLVSALYYLHSHRILHRDMKPQNILLAKGGIKLCDFGFARAM
dfused  101  HAQRVVCHLVSALYYLHSNRILHRDLKPQNVLLDKNMHAKLCDFGLARNM hfused  151  STNTMVLTSIKGTPLYMSPELVEERPYDHTADLWSVGCILYELAVGTPPF
dfused  151  TMGTHVLTSIKGTPLYMAPELLAEQPYDHQADMWSLGCIAYESMAGQPPF hfused  201  YATSIFQLVSLILKDPVRWPSTISPCFKNFLQGLLTKDPRQRLSWPDLLY
dfused  201  CATSILHLVKLIKHEDVKWPSTLSSECRSFLQGLLEKDPSMRISWTQLLC
```

FIG._3A

```
hfused  251  HPF IAGHVT I - - TE PAGPDLGTPFTSR L PPELQVLK DE QAHRLAPKGNQSR
dfused  251  HPF VEGKL - Y I AEVQAAQTSPF INPQ L AKDTK - - KS QQLRHVGADLGDV - hfused  301  ILTQAYKRMAE E AMQKKHQNTGPA LEQED KTSKVAPGTAPLPR L GAT PQE
dfused  297  LAALKLSDVAN E NLSTSRDSIN - A IAPS D IEQLETDVEDNVHR L - IV P - - hfused  351  SSLLAG I LASE LKSSWAKSGTGEVPSAPRENRTTPD C - ERAFFPEERPEV L
dfused  343  - - - - FAD I SYRE LPCG - - - TAAAARRAGAMPLINSQT C FVSGNSNMILNH L hfused  400  GQRSTDVVDLENEEPDSDNEWQHL LETTEPPVPIQ L KAPLTLLCNPDF C QR
dfused  387  NDNFAIEAPASSATKSMKSKLKLAL NIKQSRSKD L EKRKLSQNLDNF S LR hfused  450  IQSQLHEAGGQILKGI LEGAS HILPAFRVLSSL L SSCSD S VALYSFCREA
dfused  437  LGQSIDIEVQRKTTEM L TQQS QAQQLQDRKTQQ L KQSMH S TNDEKLSSDN
```

*FIG._3B*

```
hfused  500  GLPGLLLSLLR·HSQESNSLQQQSWYGTFLQDLMAVIQAYFACTFNLE·R
dfused  487  SPPCLLPGWDSCDESQSPPIENDEWLAFLHRSIQELLDGEFDSLKQHNLV hfused  548  SQTSDSLQVFQEAANLFLDLLGKLLAQPDDSEQTLORDSLMCFTVLCEAM
dfused  537  SIIVAPLRNSKAIPKV·LQSVAQLLSLP····FVLAEQHLVAEEAI··KGV hfused  598  DGNSRAISKAFYSSLLTTQQVVLDGLLHGLTVPQLPVHTPQGAPQVSQPL
dfused  580  YIDVKLVPNLMYACKLLSQRHLTD·····SAASLPAGTGVSLSRTVRSC hfused  648  REQSEDIPGAISSALAAICTAPVGLPDCWDAKEQVCWHLAN·QLTEDSSQ
dfused  625  SDLSAEEMSTACSLYELVCHLVHQQQQFL···TQFCDAVAILAVNDMFIN hfused  697  LRPSLISGLQHPILCLHLLKVLYSCCLVSE··GLCRLLGQEPLALE·SLF
dfused  672  FLTHDFKDSRPVRLASCML·ALF·CCVLRELPENAELVEKIVFDSRLQLA
```

*FIG._3C*

```
hfused  744  ML I Q GKVKVVDWEESTEVTLYF L SLL VFR L QNLPCG-MEK L GS DVATLFT
dfused  720  VL L Q SRHHLL-RQRACQM---LLL ARFS L RGVQ C IWSGEL KS ALQAWPM ↓
hfused  793  HSHVV S LVSA AA CLL GQL GQ QGVTF D LQP MEWMAAATHALSAPAEVRLTP
dfused  766  QQTCQ S LRLE AA QTL DEL SQFSF - V AQ ATA hfused  843  PGSCGFYDGLLILLLQLLTEQGKASLIRDMSSSEMWTVLWHRFSMVLRLP hfused  893  EEASAQEGELSLSSPPSPEPDWTLISPQGMAALLSLAMATFTQEPQLCLS hfused  943  CLSQHGSILMSILKHLLCPSFLNQLRQAPHGSEFLPVVVLSVCQLLCFPF hfused  993  ALDMDADLLIVVLADLRDSEVAAHLLQVCCYHLPLMQVELPISLLTRLAL
```

*FIG._3D*

```
hfused  1043  MDPTSLNQFVNTVSASPRTIVSFLSVALLSDQPLLTSDLLSLLAHTARVL hfused  1093  SPSHLSFIQELLAGSDESYRPLRSLLGHPENSVRAHTYRLLGHLLQHSMA hfused  1143  LRGALQSQSGLLSLLLLGLGDKDPVVRCSASFAVGNAAYQAGPLGPALAA hfused  1193  AVPSMTQLLGDPQAGIRRNVASALGNLGPEGLGEELLQCEVPQRLLEMAC hfused  1243  GDPQPNVKEAALIALRSLQQEPGIHQVLVSLGASEKLSLLSLGNQSLPHS hfused  1293  SPRPASAKHCRKLIHLLRPAHSM
```

FIG._3E

> length: 5125 bp (circular)

```
  1 CCCACGGGTC CGCCCACGCG TCCGGGGCGT CCCAGATGTT GTGGAACTGT CCCTGATCT ATAGCTCTTC ACCGTCTCTA CTTTCTTCCT TCTAAGAGAT
    GGGTGCCCAG GCGGGTGCGC AGGCCCCGCA GGGTCTACAA CACCTTGACA GGGACCTAGA TATCGAGAAG TGGCAGAGAT GAAAGAAGGA AGATTCTCTA

101 CCTGAAACCT CTGTCCATGGA AAAGTACCAC GTGTTGGAGA TGATTGGAGA AGGCTCTTTT TCCGAGAAAA CCCTCCACA TGTTCCCAGC TTCTTTATG TCACGAGTCC
    GGACTTTGGA GACAGTACCT TTTCATGGTG CACAACCTCT ACTAACCTCT TCCGAGAAAA CCCTCCACA TGTTCCCAGC TTCTTTATG TCACGAGTCC
  1              M  E  K  Y  H  V  L  E  M  I  G  E  G  S  F  G  R  V  Y  K  G  R  R  K  Y  S  A  Q  V
                 ^Start of 1st ORF!

201 TCGTGGCCCT GAAGTTCATC CCAAAATTGG GGCGCTCAGA GAAGGAGCTG AGGAATTTGC AACGAGAGAT TGAAATAAATG CGGGGTCTGC GGCATCCCAA
    AGCACCGGGA CTTCAAGTAG GGTTTTAACC CCGCGAGTCT CTTCCTCGAC TTGCTCTCTA ACTTTATTAC GCCCCAGACG CCGTAGGGTT
 30  V  A  L  K  F  I  P  K  L  G  R  S  E  K  E  L  R  N  L  Q  R  E  I  E  I  M  R  G  L  R  H  P  N

301 CATTGTGCAT ATGCTTGACA GCTTTGAAAC TGATAAAGAG GTGGTGGTGG TGACAGACTA TGCTGAGGGA GAGCTCTTTC AGATCCTAGA AGATGACGGA
    GTAACACGTA TACGAACTGT CGAAACTTTG ACTATTCT ACTATTTCTC CACCACCACC ACTGTCTGAT ACGACTCCCT CTCGAGAAAG TCTAGGATCT TCTACTGCCT
 63  I  V  H  M  L  D  S  F  E  T  D  K  E  V  V  V  V  T  D  Y  A  E  G  E  L  F  Q  I  L  E  D  D  G

401 AAACTTCCTG AAGACCAGGT TCAGGCCATT TGGTGTCAGC CCTGTACTAT CTGCATTCCC ACCGCATCCT ACACCGAGAT ATGAAGCCTC
    TTTGAAGGAC TTCTGGTCCA AGTCCGGTAA CAGCGGGTCA GGACATGATA GACGTAAGGG TGGCGTAGGA TGTGGCTCTA TACTTCGGAG
 96  K  L  P  E  D  Q  V  Q  A  I  A  A  Q  L  V  S  A  L  Y  Y  L  H  S  H  R  I  L  H  R  D  M  K  P  Q

501 AGAACATCCT CCTCGCCAAG GGTGGTGGCA TCAAGCTCTG AGTTCGAGAC ACTGAAACCT GATGCTGACAT GTGCTGACAT CCATCAAAGG
    TCTTGTAGGA GGAGCGGTTC CCACCACCGT AGTTCGAGAC TCAAGCTCTG ACTGAAACCT GATACTCGTG GTTATGTTAC CACGACTGTA GGTAGTTTCC
130  N  I  L  L  A  K  G  G  G  I  K  L  C  D  F  G  F  A  R  A  M  S  T  N  T  M  V  L  T  S  I  K  G

601 CACACCACTC TATATGTCTC CAGAGCTGGT GGAGGAGCGA CCATACGACC ACACAGCGGA CCTCTGGTCT GTTGGCTGCA TACTATATGA ACTGGCAGTA
    GTGTGGTGAG ATATACAGAG GTCTCGACCA CCTCCTCGCT GGTATGCTGG TGTGTCGCCT GGAGACCAGA CAACGACGT ATGATATACT TGACCGTCAT
163  T  P  L  Y  M  S  P  E  L  V  E  E  R  P  Y  D  H  T  A  D  L  W  S  V  G  C  I  L  Y  E  L  A  V
```

FIG._4A

```
701  GGCACCCCTC CCTTCTATGC TACAAGCATC TTTCAGCTGG TCAGCCTCAT CCTGTGCGCT GGCCCTCAAC CATCAGTCCC TGCTTTAAGA
     CCGTGGGGAG GGAAGATACG ATGTTCGTAG AAAGTCGACC AGTCGGAGTA AGAGTTCCTG GGACACGCGA CCGGGAGTTG GTAGTCAGGG ACGAAATTCT
196   G  T  P  P  F  Y  A   T  S  I  F   Q  L  V   S  L  I  L   K  D  P   V  R  W   P  S  T   I  S  P   C  F  K  N

801  ACTTCCTGCA GGGACTGCTC ACCAAAGACC CCAGGCAGCG ACTGTCCTGG CCAGACCTCT TATATCACCC CTTTATTGCT GGTCATGTCA CCATAATAAC
     TGAAGGACGT CCCTGACGAG TGGTTTCTGG GGTCCGTCGC TGACAGGACC GGTCTGGAGA ATATAGTGGG GAAATAACGA CCAGTACAGT GGTATTATTG
230   F  L  Q   G  L  L   T  K  D  P   R  Q  R   L  S  W   P  D  L  L   Y  H  P   F  I  A   G  H  V  T   I  I  I  T

901  TGAGCCAGCA GGCCCAGATT TGGGGACCCC CGGGGTCTAA ACCCCTGGGG TAAGTGGTCG GTCTTGAAGT CCAGGATTTC GCCGATGGAG CCCATCGGTT GGCCCCCAAG
     ACTCGGTCGT CCGGGTCTAA ACCCCTGGGG GTCGCCACGGC TGCCCAGGTCG CGGAACCAGG CTGCTTGTCC GGGTAGCCAA CCGGGGGTTC
263   E  P  A   G  P  D  L   G  T  P   F  F  T  S   R  L  P  P   E  L  Q   V  L  K   D  E  Q   A  H  R  L   A  P  K

1001 GGTAATCAGT CTCGGATCTT GACTCAGGCC TATAAACGCA CCCCTCTGCC AGGAATCAAG CCTCCTGGCC GGGATCTTAG CCTCAGAATT
     CCATTAGTCA GAGCCTAGAA CTGAGTCCGG ATATTTGCGT ACCGACTCCT GGGGAGACGG TCCTTAGTTC CCCTAGAATC GGAGTCTTAA
296   G  N  Q  S   R  I  L   T  Q  A   Y  K  R  M   A  E  E   A  M  Q   K  K  H  Q   E  S  S   L  L  A   G  I  L  A   S  E  L

1101 ACAAGACCAG CAAGGTGGCT CCTGGCACAG CAGGGACTGG TCTGCACCTC GGGAAAACCG GACCACCCCA GATTGTGAAC GAGCATTCCC AGAGGAGAGG
     TGTTCTGGTC GTTCCACCGA GGACCGTGTC GTCCCTGACC AGACGTGGAG CCCTTTTGGC CTGGTGGGGT CTAACACTTG CTCGTAAGGG TCTCCTCTCC
330   K  T  S   K  V  A   P  G  T   A  P  L  P   R  L  G   A  T  P  Q   E  S  S   L  L  A   G  I  L  A   S  E  L

1201 GAAGAGCAGC TGGGCTAAAT CAGGGACTGG GAGCACTGAT GTAGTGGACC GGAAAAATGA GGAGCCAGAC AGTGGCAGCA CCTGCTAGAG ACCACTGAGC
     CTTCTCGTCG ACCCGATTTA GTCCCTGACC CTCGTGACTA CATCACCTGG CCTTTTTACT CCTCGGTCTG TCACTGTTAC TCAGGCTGGA GGACGATCTC TGGTGACTCG
363   K  S  S   W  A  K  S   G  T  G   E  V  P   S  V  V  D   G  T  G   D  C  E  R   T  T  P   D  C  E  R   T  T  P   A  F  P   E  E  R

1301 CCAGAGGTGC TGGGCCAGCG ACCCGGTCGC CTCGTGACTA CATCACCTGG CCTTTTTACT CCTCGGTCTG TCACTGTTAC TCAGGCTGGA GGACGATCTC TGGTGACTCG
     GGTCTCCACG TGGGCCAGCG CTCGTGACTA CATCACCTGG CCTTTTTACT CCTCGGTCTG TCACTGTTAC TCAGGCTGGA GGACGATCTC TGGTGACTCG
396   P  E  V  L   G  Q  R   S  T  D   V  V  D  L   E  N  E   E  P  D   S  D  N  E   W  Q  H   L  L  E   T  T  E  P

1401 CTGTGCCTAT TCAACTGAAG AGTTGACTTC CGAGGAGAGT GGAACGACAC CTTGCGTGTG TAATCCTGAC ATTAGGACTG AAGACGGTCG CGTAGGTCTC AGTGCGACTA CTTCGACCTC CCGTCTAGGA
     GACACGGATA AGTTGACTTC CGAGGAGAGT GGAACGACAC CTTGCGTGTG TAATCCTGAC ATTAGGACTG AAGACGGTCG CGTAGGTCTC AGTGCGACTA CTTCGACCTC CCGTCTAGGA
430   V  P  I   Q  L  K   A  P  L  T   L  L  C   N  P  D   F  C  Q  R   I  Q  S   Q  L  H   E  A  G  G   Q  I  L

1501 GAAAGGCATC TTGGAGGGTG CTTCCCACAT CCTGCCTGCA TTCCGGGTCC TCTCTCCAGC TGAGCAGTCT TGCAGTGATT CTGTTGCCTT GTATTCCTTC
     CTTTCCGTAG AACCTCCCAC GAAGGGTGTA GGACGGACGT AAGGCCCAGG AGAGAGGTCG ACTCGTCAGA ACGTCACTAA GACAACGGAA CATAAGGAAG
463   K  G  I   L  E  G  A   S  H  I   L  P  A   F  R  V  L   S  S  L  L  S   S  C  S  D  S   V  A  L   Y  S  F
```

FIG._4B

```
1601 TGCCGGGAGG CAGGGCTTCC TGGGCTGCTG CTGAGTCTAC TCAGGCACAG AACAGCCTCC AGCAGCAATC TTGGTATGGG ACCTTCTTAC
     ACGGCCCTCC GTCCGAAGG  ACCCGACGAC GACTCAGATG AGTCCGTGTC TTGTCGGAGG TCGTCGTTAG AACCATACCC TGGAAGAATG
 496  C  R  E  A  G  L  P   L  L  S  L   L  R  H  S   Q  E  S  N   S  L  Q  Q   Q  S  W  Y   G  T  F  L  Q

1701 AGGACCTGAT GGCTGTGATT CAGGCCTACT TTGCCTGTAC CTTCAATCTG GAGAGGAGCC AGACAAGTGA CAGCCTGCAG GTGTTTCAGG AGCTGCCAA
     TCCTGGACTA CCGACACTAA GTCCGGATGA AACGGACATG GAAGTTAGAC CTCTCCCTCG TCTGTTCACT GTCGGACGTC CACAAAGTCC TCGACGGTT
 530  D  L  M  A  V  I   Q  A  Y  F   A  C  T  F   N  L  E  R   S  Q  T  S   D  S  L  Q   V  F  Q  E   A  A  N

1801 CCTTTTTCTG GACCTGTTGG GGAAACTGCT GGCCCAACCA GATGACTCTG AGCAGACTTT GCAGAGGGAC AGCCTTATGT GCTTTACTGT CCTGTGCCAA
     GGAAAAAGAC CTGGACAACC CCTTTGACGA CCGGGTTGGT CTACTGAGAC CGTCTGAAA  CGTCTCCCTG TCGGAATACA CGAAATGACA GGACACGCTT
 563  L  F  L  D  L  L  G   K  L  L   A  Q  P   D  D  S  E   Q  T  L   Q  R  D   S  L  M  C   F  T  V   L  C  E

1901 GCCATGGATG GGAACAGCCG GGCCATCTCC AAAGCCTTTT ACTCCAGCTT GCTGACGACA CAGCAGGTTG TCTTGGATGG GCTCCTTCAT GGCTGACAG
     CGGTACCTAC CCTTGTCGGC CCGGTAGAGG TTTCGGAAAA TGAGGTCGAA CGACTGCTGT GTCGTCCAAC AGAACCTACC CGAGGAAGTA CCGAACTGTC
 596  A  M  D  G   N  S  R   A  I  S   K  A  F  Y   S  S  L   L  T  T   Q  Q  V  V   L  D  G   L  L  H   G  L  T  V

2001 TTCCACAGCT CCCTGTCCAC ACTCCCCAAG GTAACCAGAG AGGTTCTCTT GACTTACTTG TTGCATAGGT CAGGCTCCGC TCTTTCTATT
     AAGGTGTCGA GGGACAGGTG TGAGGGGTTC CATTGGTCTC TCCAAGAGAA CTGAATGAAC AACGTATCCA GTCCGAGGCG AGAAAGATAA
 630  P  Q  L   P  V  H   T  P  Q  G   N  Q  S   G  E  G   R  F  S  Q
                                                ^Start of intron sequence 2101 GCCATCACCT AGATCGCACC TGGCATTTAG TAGGTGCTCA ATAAATAACT GTGAACTGAG AGAATGAATG GGGATCTGAG GGAAACAAAC AGACCTCATC
     CGGTAGTGGA TCTAGCGTGG ACCGTAAATC ATCCACGAGT TATTTATTGA CACTTGACTC TCTTACTTAC CCCTAGACTC CCTTGTTTG  TCTGGAGTAG 2201 CTGCATTCTT CCCACTCCCT TAGGTTCCCT ACTCCTGCTG CCATGTCGGT GCTATTGTCT CGATAACAGA TCCCGTTCTC AGGGCAAGAG CCTCAGGCCT TTGGAGTTAC
     GACGTAAGAA GGGTGAGGGA ATCCAAGGGA TGAGGACGAC GGTACAGCCA CGATAACAGA AGCTATTGTCT AGGGCAAGAG TCCCGTTCTC GGAGTCCGGA AACCTCAATG
                                                                                                      2nd ORF starts from here!^

2301 TCTTTTGCTTT TCTTCCACAGG AGCCCCGCCAA GTGAGCCAGC GCAGAGTGAG CACTGCGAGA GAGCCATTTC CTCTGCCCTG GCAGCCATAT
     AGAAACGAAA AGAGGTGTCC TCGGGGCGTT CACTCGGTCG CGTCTCACTC GTGACGCTCT CTCGGTAAAG GAGACGGGAC CGTCGGTATA
   3  S  L  F   S  T  G   A  P  Q   V  S  Q  P   L  R  E   Q  S  E   D  I  P  G   A  I  S   S  A  L   A  A  I  C

2401 GCACTGCTCC TGTGGGACTG CCCGACTGCT GGGATGCAGTC TGTTGGCATT GGCAAAATCA GCTAACTGAA ACCGTTTAGT CGATTGACTT CTGTCGCGG TCGAGTCCGG
     CGTGACGAGG ACACCCTGAC GGCTGAGGA  CCCTACGTCAG ACAACCGTAA ACCGTTTAGT CGATTGACTT CTGTCGCGG
  37  T  A  P  V  G  L   P  D  C  W   D  A  K   E  Q  V   C  W  H  L   A  N  Q   L  T  E   D  S  S  Q   L  R  P
```

FIG._4C

| | | | | | |
|---|---|---|---|---|---|
2501 ATCCCTCCATC TCTGGCCTGC AGCATCCCAT CCTGTGCCTG AGTTCTATA CTCCTGCTGC CTTGTCAGTG AGGGCCTGTG CCGTCTTCTG
     TAGGGAGTAG AGACCGGACG TCGTAGGGTA GGACACGGAC GTCCAAGATAT GAGGACGACG GAACAGTCAC TCCCGGACAC GGCAGAAGAC
  70  S   L   I   S   G   L   Q   H   P   I   L   C   L   H   L   L   K   V   L   Y   S   C   C   L   V   S   E   G   L   C   R   L   L

2601 GGGCAGGAGC CCCTGGCCTT GAATCCCTG TTTATGTTGA TTCAGGGCAA GGTAAAAGTA AAGAGTCTAC TGAAGTGACA CTCTACTTCC
     CCCGTCCTCG GGGACCGGAA CCTTAGGGAC AAATACAACT AAGTCCCGTT CCATTTTCAT TTCTCAGATG ACTTCACTGT GAGATGAAGG
 103  G   Q   E   P   L   A   L   E   S   L   F   M   L   I   Q   G   K   V   K   V   D   W   E   E   S   T   E   V   T   L   Y   F   L

2701 TCTCCCTTCT TGTCTTTCGG CTCCAAAACC TGCCTTGTGG AATGGAGAAG CTAGGCAGTG ACGTTGCTAC TCTCTTTACC CATTCGGATG TCGTCTCTCT
     AGAGGGAAGA ACAGAAAGCC GAGGTTTTGG ACGGAACACC TTACCCTCTTC GATCCGTCAC TGCAACGATG AGAGAAATGG GTAAGCGTAC AGCAGAGAGA
 137  S   L   L   V   F   R   L   Q   N   L   P   C   G   M   E   K   L   G   S   D   V   A   T   L   F   T   H   S   H   V   V   S   L

2801 TGTGAGTGCA GCAGCCTGTC TATTGGGACA GCTTGGTCAG CAAGGGGTGA CCTTTGACCT CCAGCCCATG GAATGGATGG CTGCAGCCAC ACATGCCTTG
     ACACTCACGT CGTCGGACAG ATAACCCTGT CGAACCAGTC GTTCCCCACT GGAAACTGGA GGTCGGGTAC CTTACCTACC GACGTCGGTG TGTACGGAAC
 170  V   S   A   A   A   C   L   L   G   Q   L   G   D   Q   F   D   L   Q   P   M   E   W   M   A   A   A   T   H   A   L

2901 TCTGCCCCTG CAGAGGTTCG GTTGACTCCA CCAGGTAGTT CAACTGAGGT GGTCCATCAA CACCTAAGAT ACTACCGGAG CTTATCCCTTC TGTTGCAGCT CCTCACTGAG CAGGGGAAGG
     AGACGGGGAC GTCTCCAAGC CAACTGAGGT GTTGACTCCA GTTGACTCCA GTGGATTCTA TGATGGCCTC CTTATCCCTTC GAATAGGGAA ACAACGTCGA GGAGTGACTC GTCCCCTTCC
 203  S   A   P   A   E   V   R   L   T   P   P   G   S   C   G   F   Y   D   G   L   L   I   L   L   Q   L   T   E   Q   G   K   A

3001 CTAGCCTAAT CAGGGATATG TCCAGTTCAG AAATGTGGAC CGTTTTGTGG CACCGCTTCT CCATGGTCCT GGTACCAGGA CTCCGAGGGG CTCCTCCGTA GACGTGTCCT
     GATCGGATTA GTCCCTATAC AGTCAAGTC TTTACACCTG GCAAAACACC GTGGCGAAGA GGTACCAGGA CCATGGTCCT CCATGGTCCT CTCCTCCGTA GACGTGTCCT
 237  S   L   I   R   D   M   S   S   S   E   M   W   T   V   L   W   H   R   F   S   M   V   L   R   L   P   E   E   A   S   A   Q   E

3101 AGGGGAGCTT TCGCTATCCA GTCCACCAAG CCCTGAGCCA GACTGGACAC TGATTTCTCC ACTAAAGAGG CCAGGGCATG GCAGCCCTGC TGAGCCTGGC CATGGCCACC
     TCCCCTCGAA AGCGATAGGT CAGGTGGTTC GGGACTCGGT CTGACCTGTG ACTAAAGAGG TGATCTTCTCC GGTCCCGTAC CGTCGGGACG ACTCGGACCG GTACCGGTGG
 270  G   E   L   S   L   S   S   P   P   S   P   E   P   D   W   T   L   I   S   P   Q   G   M   A   A   L   L   S   L   A   M   T

3201 TTTACCAGG AGCCCCAGTT ATGCCTGAGC TGCCTGTCCC AGCATGGAAG TCCATCCTGA TATCCTCATG AGCATCCTTC ATAGGAGTAC AGTAGGACT TCGTAGACGA TTGCCTGAATC TTCCTGAATC AAGGACTTAG
     AAATGGGTCC TCGGGGTCAA TACGGACTCG ACGGACAGGG TCGTACCTTC AGGTAGGACT ATAGGAGTAC TCGTAGACGA TCGTAGACGA AACGGGGTCG AAGGACTTAG
 303  F   T   Q   E   P   Q   L   C   L   S   C   L   S   Q   H   G   S   I   L   M   S   I   L   K   H   L   L   C   P   S   F   L   N   Q

3301 AACTCGCGCCA GGGCCTCAT GGTCTCTGAGT TTCTCCCCTGT CGTGGTGCTC TCTGTCTGCC AGTCCCCTTTG CTTCCCCTTT GCGCTGGACA TGGATGCTGA
     TTGACGCGGT CCGCGAGTA CCAGACTCA AAGAGGACA GCACCACGAG AGACAGACGG TCAGGGGAAAC GAAGGGAAAC CGCGACCTGT ACCTACGACT
 337  L   R   Q   A   P   H   G   S   E   F   L   P   V   V   L   S   V   C   Q   L   L   C   F   P   F   A   L   D   M   D   A   D

*FIG._4D*

```
3401 CCTCCTTATA GTTGTCTTGG CCGACCTCAG GGACTCAGAA GTTGCAGCCC ATCTGCTGCA GGTCTGCTGC TACCATCTTC CGTTGATGCA AGTGGAGCTG
     GGAGAATAT CAACAGAACC GGCTGGAGTC CCTGAGTCTT CAACGTCGGG TAGACGACGT CCAGACGACG ATGGTAGAAG GCAACTACGT TCACCTCGAC
 370  L  L  I   V  V  L  A   D  L  R   D  S  E   V  A  A  H   L  L  Q   V  C  C    Y  H  L  P   L  M  Q   V  E  L

3501 CCCATCAGCC TTCTCACACG CCTGGCCCTC ATGGATCCCA CCTCTCTCAA CCAGTTTGTG AACACAGTGT CTGCCTCCCC TAGAACCATC GTCTCGTTTC
     GGGTAGTCGG AAGAGTGTGC GGACCGGGAG TACCTAGGGT GGAGAGAGTT GGTCAAACAC TTGTGTCACA GACGGAGGGG ATCTTGGTAG CAGAGCAAAG
 403  P  I  S   L  T  R   L  A  L   M  D  P  T   S  L  N   Q  F  V   N  T  V  S   A  S  P    R  T  I    V  S  F  L

3601 TCTCAGTTGC CCTCCTGAGT GACCAGCCAC TGTTGACCTC CGACCTTCTC TCTCTGCTGG CCCATACTGC CAGGGTCCTG TCTCCCAGCC ACTTGTCCTT
     AGAGTCAACG GGAGGACTCA CTGGTCGGTG ACAACTGGAG GCTGGAAGAG AGAGACGACC GGGTATGACG GTCCCAGGAC AGAGGGTCGG TGAACAGGAA
 437  S  V  A   L  L  S   D  Q  P   L  L  T  S   D  L  L   S  L  L  A   H  T  A   R  V  L    S  P  S  H   L  S  F

3701 TATCCAAGAG CTTCTGGCTG ATCCTATCGG GCTCTGATGA AATTCTGTGC GGGCACACAC CCACCCAGAG CCCCTGCGCA TTATAGGCTC GGCACACAC
     ATAGGTTCTC GAAGACCGAC TAGGATAGCC CGAGACTACT TTAAGACACG CCCGTGTGTG GGTGGGTCTC CGGGGACGCGT AATATCCGAG CCGTGTGTG
 470  I  Q  E   L  L  A  G   S  D  E   S  Y  R   P  L  R  S   L  L  G   H  P  E   N  S  V  R   A  H  T   Y  R  L

3801 CTGGGACACT TGCTCCACAA CAGCATGGCC CTGCGTGGGG CACTGCAGAG CTGCTCAGCC TTCTGCTGCT TGGGCTTGGA GACAAGGATC
     GACCCTGTGA ACGAGGTTGT GTCGTACCGG GACGCACCCC GTGACGTCTC GACGAGTCGG AAGACGACGA ACCCGAACCT CTGTTCCTAG
 503  L  G  H  L   L  Q  H   S  M  A   L  R  G  A   L  Q  S   C  S  A   F  T  L  L   G  L  G   D  K  D  P

3901 CTGTTGTGCG GTGCAGTGCC AGCTTTGCTC TGGCAATGC CTGGTCCTC CCTGGACCTGC GCAGTGCCCA GTATGACCA
     GACAACACG CACGTCACGG TCGAAACGAC ACCGTTACG GACCAGGAG GGACCGTCGA CGTCACGGGT CATACTGGT
 537  V  V  R   C  S  A   S  F  A  V   G  N  A   A  Y  Q    L  Q  S  L    G  P  A   A  V  P  S   M  T  Q

4001 GCTGCTTGGA GATCCTCAGG CTGGTATCCG GCGCAATGTT GCATCAGCTC TGGGCAACTT GGGACCTGAA GGTTGGGAG AGGAGCTGTT ACAGTGCGAA
     CGACGAACCT CTAGGAGTCC GACCATAGGC CGCGTTACAA CGTAGTCGAG ACCCGTTGAA CCCTGGACTT CCAAACCCTC TCCTCGACAA TGTCACGCTT
 570  L  L  G   D  P  Q   A   G  I  R   R  N  V   A  S  A  L   G  N  L   G  P  E   G  L  G  E   L  L    Q  C  E

4101 GTACCCCAGC GGCTCCTAGA AATGGCCATG GAGACCCCCC AGCCAAATGT GAAGGAGGCT CCCCTCATTG GCCTCCGGAG CCTGCAACAG GAGCCTGGCA
     CATGGGGTCG CCGAGGATCT TTACCGGTAC CTCTGGGGGG TCGGTTTACA CTTCCTCCGA GGGGAGTAAC CGGAGGCCTC GGACGTTGTC CTCGGACCGT
 603  V  P  Q  R   L  L  E   M  A  C   G  D  P  Q   P  N  V   K  E  A   P  L  I  G   L  R  S   L  Q  Q   E  P  G  I
```

FIG._4E

```
4201 TCCATCAGGT ACTGGTGTCC CTGGGTGCCA GTGAGAAACT ATCCTGCTC TCTCTGGGGA ATCAGTCACT GCCACACAGC AGTCCTAGGC CTGCCTCTGC
     AGGTAGTCCA TGACCACAGG GACCCACGGT CACTCTTTGA TAGGAACGAG AGAGACCCCT TAGTCAGTGA CGGTGTGTCG TCAGGATCCG GACGGAGACG
 637  H  Q  V    L  V  S     L  G  A  S    E  K  L     S  L  L     S  L  G  N    Q  S  L     P  H  S     S  P  R  P    A  S  A

4301 CAAACACTGC AGGAAACTCA TTCACCTCCT GAGGCCAGCC CATAGCATGT GATTCCAGAT TCCTGCGGTC CAGCCTCCAA CTTTGGTTGC CAGCTCTTTC
     GTTTGTGACG TCCTTTGAGT AAGTGGAGGA CTCCGGTCGG GTATCGTACA CTAAGGTCTA AGGACGCCAG GTCGGAGGTT GAAACCAACG GTCGAGAAAG
 670  K  H  C    R  K  L  I    H  L  L    R  P  A    H  S  M  Q

4401 TTATTCTACT ACACAAGCCG CCAACTCAAC TGAGAGCTAA AGAGACTAGA AAAGAGATAA GCTGCCAACT CAAGAAACTA CAAGAAACTT GAAGAGATTT
     AATAAGATGA TGTGTTCGGC GGTTGAGTTG ACTCTCGATT TCTCTGATCT TTTCTCTATT CGACGGTTGA GTTGACTCTT GTTCTTTGAT CTTCTCTAAA

4501 ATATATAAAG CTTCTTCCTT CTCCCAGATG CAGGATGTTT TCAACCAGTA AATTTTATTG TCAACCAGTA AGTTGGTCAT CAGAGAAGAG TCCTTTCTTC TCTACATCCA
     TATATATTTC GAAGAAGGAA GAGGGTCTAC GTCCTACAAA AGTTGGTCAT TTAAAATAAC GTTGGTCAT GTCTCCTCTC GACAACCACG AGGAAGAAG AGATGTAGGT

4601 GGGGCCTTTT CTCCAATAAT GTGCCTTTAA CTCTAGGGAC CTGCCTCACG GACCTTAGGG AAAAACCTCA ACCTGAAAGA TCTCTTCCTT TCTGGAGCTC
     CCCCGGAAAA GAGGTTATTA CACGGAAATT GAGATCCCTG GACGGAGTGC CTGGAATCCC TTTTTGGAGT TGGACTTTCT AGAGAAGGAA AGACCTCGAG

4701 CTTTAATCTT CCCAGCAGGT TTTTGCCTTA GACGTGAAGA CCCCAGGACA GTGATGAAGA CAGAGCCTGT CTCAGCTCTA GGCTGTGGGG ATCAATGCCA
     GAAATTAGAA GGGTCGTCCA AAAACGGAAT CTGCACTTCT GGGGTCCTGT CACTACTTCT GTCTCGGACA GAGTCGAGAT CCGACACCCC TAGTTACGGT

4801 TCAGTCCCCTG ATTATCCCTT AGCCAACATT CCTATCTGTG GGTGGGCGTG GAGAGTGTAT CTTTTTTTGG CTTTTTTGTG TATATGTGTG
     AGTCAGGGAC TAATAACTCC TCGGTTGTAA GGATAGACAC CCACCCGCAC CTCTCACATA GAAAAAAACC CCACACACAC ATATACACAC

4901 TGTGTATGTG TGTGTGTGTT TAATAGTTCT GTTTGTAAAC TCTTTTAATA AAGTTGTGC CTCACCATAC TTGAAGCTCC CAGGACAAGG GTTGAGAGGC
     ACACATACAC ACACACACAA ATTATCAAGA CAAACATTTG AGAAAATTAT TTTCAACACG GAGTGGTATG AACTTCGAGG GTCCTGTTCC CAACTCTCCG

5001 TCAACCCCTC TTTCAGCTTC TATGTGGTGT TGGAGGTGCT GGTATCGTGT TCACACAAAA AAAAAAAAAA AAAAAAAAAA AAAAAAAAAA AAAAAAAAAA
     AGTTGGGGAG AAAGTCGAAG ATACACCACA ACCTCCACGA AGTGTGTTTT TTTTTTTTTT TTTTTTTTTT TTTTTTTTTT TTTTTTTTTT

5101 AAAAAAAAAA AAAAAAAAAA AAAAA
     TTTTTTTTTT TTTTTTTTTT TTTTT
```

FIG._4F

> length: 5252 bp (circular)

```
  1 GGAGCTTGGA GCTCCTAGGC TGGGGGCGTC CCAGATGTTG TGGAACTGTC CCTGGATCTA TAGCTCTTCA CCGTCTCTAC TTTCTTCCTT CTAAGAGATC
    CCTCGAACCT CGAGGATCCG ACCCCCGCAG GGTCTACAAC ACCTTGACAG GGACCTAGAT ATCGAGAAGT GGCAGAGATG AAAGAAGGAA GATTCTCTAG

101 CTGAAACCTC TGTCATGGAA AAGTACCACG TGTTGGAGAT GATTGGAGAA GGCTCTTTTG GGAGGGTGTA CAAGGGTGTA AGAAAATACA GTGCTCAGGT
    GACTTTGGAG ACAGTACCTT TTCATGGTGC ACAACCTCTA CTAACCTCTT CCGAGAAAAC CCTCCCACAT GTTCCCACAT TCTTTTATGT CACGAGTCCA
  1                      M  E  K  Y  H  V  L  E  M  I  G  E  G  S  F  G  R  V  Y  K  G  R  R  K  Y  S  A  Q  V
                        ^Translation ATG starts here 201 CGTGGCCCTG AAGTTCATCC CAAAATTGGG GCGCTCAGAG AAGGAGCTGA CGAGAGATT GAAATAAATGC ACGAGAGATT GAAATAATGC GCATCCCAAC
    GCACCGGGAC TTCAAGTAGG GTTTTAACCC CGCGAGTCTC TTCCTCGACT CCTTAAACGT TGCTCTCTAA CTTTATTACG CGTAGGGTTG
 30  V  A  L  K  F  I  P  K  L  G  R  S  E  K  E  L  R  N  L  Q  R  E  I  E  I  M  R  G  L  R  H  P  N 301 ATTGTGCATA TGCTTGACAG CTTTGAAACT GATAAAGAGG TGGTGGTGGT GACAGACTAT GCTGAGGGAG AGCTCTTTCA GATCCTAGAA GATGACGGAA
    TAACACGTAT ACGAACTGTC GAAACTTTGA CTATTTCTCC ACCACCACCA CTGTCTGATA CGACTCCCTC TCGAGAAAGT CTAGGATCTT CTACTGCCTT
 63  I  V  H  M  L  D  S  F  E  T  D  K  E  V  V  V  V  T  D  Y  A  E  G  E  L  F  Q  I  L  E  D  D  G  K 401 AACTTCCTGA AGACCAGGTT CAGGCCATTG CTGCCCAGTT GGTGTCAGCC CCGCATCCTA CCGCATCCTA CCACCGAGATA CACCGAGATA TGAAGCCTCA
    TTGAAGGACT TCTGGTCCAA GTCCGGTAAC GACGGGTCAA CCACAGTCGG GACATGATAG GGCGTAGGAT GTGGCTCTAT ACTTCGGAGT
 97  L  P  E  D  Q  V  Q  A  I  A  A  Q  L  V  S  A  L  Y  Y  L  H  S  H  R  I  L  H  R  D  M  K  P  Q 501 GAACATCCTC CTCGCCAAGG GTGGTGGCAT CAAGCTCTGT GACTTTGGAT TTGCCCGGGC TATGAGCACC AATACAATGG TGCTGACATC CATCAAAGGC
    CTTGTAGGAG GAGCGGTTCC CACCACCGTA GTTCGAGACA CTGAAACCTA AACGGGCCCG ATACTCGTGG TTATGTTACC ACGACTGTAG GTAGTTTCCG
130  N  I  L  L  A  K  G  G  I  K  L  C  D  F  G  F  A  R  A  M  S  T  N  T  M  V  L  T  S  I  K  G 601 ACACCACTCT ATATGTCTCC AGAGCTGGTG TCTCGACCAC GAGGAGCGAC CATACGACCA CTCCTCGCTG GTGTCGCCTG GAGACCAGAC CATACGACCA GTATGCTGGT GAGACCAGAC AACCGACGTA TGATATACTT GACCGTCATC
    TGTGGTGAGA TATACAGAGA TCTCGACCAC TCGTCCACTG GAGGAGCGAC CATACGACCA CTCCTCGCTG GTGTCGCCTG GAGACCAGAC AACCGACGTA TGATATACTT GACCGTCATC
163  T  P  L  Y  M  S  P  E  L  V  E  E  R  P  Y  D  H  T  A  D  L  W  S  V  G  C  I  L  Y  E  L  A  V  G
```

FIG._5A

```
701  GCACCCCTCC CTTCTATGCT ACAAGCATCT TTCAGCTGGT CAGCCTCATT CTCAAGGACC CTGTGGCGCTG GCCCTCAACC ATCAGTCCCT GCTTTAAGAA
     CGTGGGGAGG GAAGATACGA TGTTCGTAGA AAGTCGACCA GTCGGAGTAA GAGTTCCTGG GACACCGCAA CGGGAGTTGG TAGTCAGGGA CGAAATTCTT
197   T  P  P  P   F  Y  A   T  S  I  F   Q  L  V   S  L  I   L  K  D  P   V  R  W   P  S  T   I  S  P  C   F  K  N

801  CTTCCTGCAG GGACTGCTCA CCAAAGACCC ACGGCAGCGA CTGTCCTGGC CAGACCTCTT ATATCACCCC TTTATTGCTG GTCATGTCAC CATAATAACT
     GAAGGACGTC CCTGACGAGT GGTTTCTGGG TGCCGTCGCT GACAGGACCG GTCTGGAGAA TATAGTGGGG AAATAACGAC CAGTACAGTG GTATTATTGA
230   F  L  Q   G  L  L  T   K  D  P   R  Q  R   L  S  W  P   D  L  L   Y  H  P   F  I  A  G   H  V  T   I  I  T

901  GAGCCAGCAG GCCCAGATTT GGGGACCCCA TTCACCAGCC GCCTACCCCC AGAACTTCAG GTCCTAAAGG ACGAACAGGC CCATCGGTTG GCCCCCAAGG
     CTCGGTCGTC CGGGTCTAAA CCCCTGGGGT AAGTGGTCGG CGGATGGGGG TCTTGAAGTC CAGGATTTCC TGCTTGTCCG GGTAGCCAAC CGGGGGTTCC
263   E  P  A  G   P  D  L   G  T  P   F  T  S  R   L  P  P   E  L  Q   V  L  K  D   E  Q  A   H  R  L   A  P  K  G

1001 GTAATCAGTC TCGCATCTTG ACTCAGGCCT ATAAACGCAT GGCTGAGGAG GCCATGCAGA AGAAACATCA CCTGCCCTTG AGCAAGAGGA
     CATTAGTCAG AGCGTAGAAC TGAGTCCGGA TATTTGCGTA CCGACTCCTC CGGTACGTCT TCTTTGTAGT GGACGGGAAC TCGTTCTCCT
297   N  Q  S   R  I  L   T  Q  A  Y   K  R  M   A  E  E   A  M  Q  K   K  H  Q   P  A  L  E   Q  E  D

1101 CAAGACCAGC AAGGTGGCTC CCCTCTGCCC AGACTCGGGG TCTGAGCCCC CCTTAGTTCG GGAATCAAGC CTCCTGGCCG GGATCTTAGC CTCAGAATTG
     GTTCTGGTCG TTCCACCGAG GGGAGACGGG TCTGAGCCCC GACTCGGGGG GGAATCAAGC GACTCAAGCG CCTAGTTCG GAGGACCGGC CCTAGAATCG GAGTCTTAAC
330   K  T  S   K  V  A  P   L  P  L  P   R  L  G  A   T  P  Q   E  S  S   L  L  A  G   I  L  A   S  E  L

1201 AAGAGCAGCT GGGCTAAATC AGGGACTGGA GAGGTGCCCT CTGCACCTCG GGAAAAACCG ATTGTGAACG AGCATTCCCA GAGGAGAGGC
     TTCTCGTCGA CCCGATTTAG TCCCTGACCT CTCCACGGGA GACGTGGAGC CCTTTTGGCC TAACACTTGC TCGTAAGGGT CTCCTCTCCG
363   K  S  S  W   A  K  S   G  T  G   E  V  P  S   A  P  R   E  N  R   T  T  P  D   C  E  R   A  F  P   E  E  R  P

1301 CAGAGGGTGCT GGGCCAGCGG AGCACTGATG TAGTGGACCT GTGACAATGA GAGCCAGACA CATCCAGAGT CTGCCAGCCT GCAGATCCTG
     GTCTCCACGA CCCGGTCGCC TCGTGACTAC ATCACCTGGA CACTGTTACT CTCGGTCTGT CTAGGTCTCA GACGGTCGGA CGTCTAGGAC
397   E  V  L   G  Q  R   S  T  D  V   V  D  L   E  N  E   E  P  D  S   D  N  E   W  Q  H   L  L  E  T   T  E  P

1401 TGTGCCTATT CAACTGAAGG CTCCTCTCAC CTTGCTGTGT AATCCTGACT TTAGGACTGA AGACGGTCGC CATCCAGCCG AAGCTGGAGG GCAGATCCTG
     ACACGGATAA GTTGACTTCC GAGGAGAGTG GAACGACACA TTAGGACTGA ATCCTGACT TCTGCCAGCG GTAGGTCTCA TTCGACCTCC CGTCTAGGAC
430   V  P  I   Q  L  K  A   P  L  T   L  L  C   N  P  D  F   C  Q  R   I  Q  S   Q  L  H  E   A  G  G   Q  I  L

1501 AAAGGCATCT TGGAGGGTGC TTCCCACATC CTGCCTGCAT TCCGGGTCCT GAGCAGTCTT CTCTCCAGCT GCAGTGATTC TGTTGCCTTG TATTCCTTCT
     TTTCCGTAGA ACCTCCCACG AAGGGTGTAG GACGGACGTA AGGCCCAGGA CTCGTCAGAA GAGAGGTCGA CGTCACTAAG ACAACGGAAC ATAAGGAAGA
463   K  G  I  L   E  G  A   S  H  I   L  P  A  F   R  V  L   S  S  L   L  S  S  C   S  D  S   V  A  L   Y  S  F  C
```

*FIG. 5B*

```
1601  GCCGGGAGGC AGGGCTTCCT GGGCTGCTGC TGAGTCTACT CAGGCACAGT CAGGAGAGCA ACAGCCTCCA GCAGCAATCT TGGTATGGGA CCTTCTTACA
      CGGCCCTCCG TCCCGAAGGA CCCGACGACG ACTCAGATGA GTCCGTGTCA GTCCTCTCGT TGTCGGAGGT CGTCGTTAGA ACCATACCCT GGAAGAATGT
497     R  E  A   G  L  P    G  L  L  L   S  L  L    R  H  S    Q  E  S  N    S  L  Q    Q  Q  S    W  Y  G  T    F  L  Q

1701  GGACCTGATG GCTGTGATTC AGGCCTACTT TGCCTGTACC TTCAATCTGG AGAGGAGCCA GACAAGTGAC AGCCTGCAGG TGTTTCAGGA GGCTGCCAAC
      CCTGGACTAC CGACACTAAG TCCGGATGAA ACGGACATGG AAGTTAGACC TCTCCTCGGT CTGTTCACTG TCGGACGTCC ACAAAGTCCT CCGACGGTTG
530     D  L  M   A  V  I  Q   A  Y  F    A  C  T    F  N  L  E    R  S  Q    T  S  D    S  L  Q  V    F  Q  E    A  A  N

1801  CTTTTTCTGG ACCTGTTGGG GAAACTGCTG GCCCAACCAG ATGACTCTGA GCAGACTCTG CGGAGGGACA GCCTTATGTG CTTTACTGTC CTGTGCGAAG
      GAAAAAGACC TGGACAACCC CTTTGACGAC CGGGTTGGTC TACTGAGACT CGTCTGAGAC GCCTCCCTGT CGGAATACAC GAAATGACAG GACACGCTTC
563     L  F  L   D  L  L  G   K  L  L    A  Q  P  D   D  S  E    Q  T  L    R  R  D  S    L  M  C    F  T  V    L  C  E  A

1901  CCATGGATGG GAACAGCCGG CTCCAGCTTG CTGACGACAC GAGGTCGAAC AGCAGGTTGT CTGTGCTGTG TCGTCCAACA GAACCTACCC CTCCTTCATG GCTTGACAGT
      GGTACCTACC CTTGTCGGCC GAGGTCGAAC GACTGCTGTG CTCCAGCTTG TCGTCCAACA GACACGACAC AGCAGGTTGT GAGGAAGTAC CGAACTGTCA
597     M  D  G   N  S  R   A  I  S  K    A  F  Y    S  S  L    L  T  T  Q    Q  V  V    L  D  G    L  L  H  G    L  T  V

2001  TCCACAGCTC CCTGTCCACA TTCCCTACTC CTGCTGCCAT GTCGGTGAGT ACTGGTGCTA TTGTCTAGGG CAAGAGCCTC AGGCCTTTGG
      AGTGTCGAG GGACAGGTGT GAGGGTTCC GACGACGGTA CAGCCACTCA TGACCACGAT AACAGATCCC GTTCTCGGAG TCCGAAACC
630     P  Q  L   P  V  H  T   P  Q  G    S  L  L    L  P  C   R  Q

2101  AGTTACTCTT TGCTTTTCTC CACAGGAGCC GCCAGCAGTGA GCGAGAGCAG AGTGAGGATA TACCTGGAGC CATTTCCTCT GCCCTGGCAG
      TCAATGAGAA ACGAAAAGAG GTGTCCTCGG CGGTCGTCACT CGCTCTCGTC TCACTCCTAT ATGGACCTCG GTAAAGGAGA CGGGACCGTC
  1     S  Y  S   L  L  F  S   T  G  A    P  Q  V  S   Q  P  L  R   E  Q    S  E  D  I   P  G  A    I  S  S    A  L  A  A
      ^2nd ORF starts from here 2201  CCATATGCAC TGCTCCTGTG GGACTGCCCG TGCCAAGGAG CAGGTCTGTT GGCATTTGGC AAATCAGCTA ACTGAAGACA GCAGCCAGCT
      GGTATACGTG ACGAGGACAC CCTGACGGGC ACGGTTCCTC GTCCAGACAA CCGTAAACCG TTTAGTCGAT TGACTTCTGT CGTCGGTCGA
 35     I  C  T   A  P  V    G  L  P  D    C  W  D    A  K  E    Q  V  C  W    H  L  A    N  Q  L    T  E  D  S    S  Q  L 2301  CAGGCCATCC CTCATCTCTG GCCTGCAGCA TCCCATCCTG TGCCTGCACC TTCTCAAGGT TCTATACTCC TGCTGCCTTG CCTGTCCCGT
      GTCCGGTAGG GAGTAGAGAC CGGACGTCGT AGGGTAGGAC ACGGACGTGG AAGAGTTCCA AGATATGAGG ACGACGGAAC GGACAGGGCA
 68     R  P  S   L  I  S  G   L  Q  H    P  I  L    C  L  H  L   L  K  V    L  Y  S    C  C  L  V    S  E  G    L  C  R 2401  CTTCTGGGGC AGGAGCCCCT GGCCTTGGAA CCGGAACCTT AGGGACAATT GGCCAAGGTA AAAGTAGTAG ATTGGGAAGA GTCTACTGAA GTGACACTCT
      GAAGACCCCG TCCTCGGGGA CCGGAACCTT GGCCTTGGAA TCCCTGTTAA CCGGTTCCAT TTTCATCATC TAACCCTTCT CAGATGACTT CACTGTGAGA
101     L  L  G   Q  E  P  L   A  L  E    S  L  F  M   L  I  Q    G  K  V    K  V  V  D    W  E  E    S  T  E    V  T  L  Y
```

FIG. 5C

```
2501  ACTTCCTCTC CCTTCTTGTC TTTCGGCTCC AAAACCTGCC TTGTGGAATG GAGAAGCTAG GCAGTGACGT TGCTACTCTC TTTACCCATT CGCATGTCGT
      TGAAGGAGAG GGAAGAACAG AAAGCCGAGG TTTTGGACGG AACACCTTAC CTCTTCGATC CGTCACTGCA ACGATGAGAG AAATGGGTAA GCGTACAGCA
135    F   L   S   L   L   V   F   R   L   Q   N   L   P   C   G   M   E   K   L   G   S   D   V   A   T   L   F   T   H   S   H   V   V

2601  CTCTCTTGTG AGTGCAGCAG CCTGTCTATT GGGACAGCTT GGTCAGCAAG GGGTGACCTT TGACCTCCAG CCCATGGAAT GGATGGCTGC AGCCACACAT
      GAGAGAACAC TCACGTCGTC GGACAGATAA CCCTGTCGAA CCAGTCGTTC CCCACTGGAA ACTGGAGGTC GGGTACCTTA CCTACCGACG TCGGTGTGTA
168    S   L   V   S   A   A   A   C   L   L   G   Q   L   G   Q   Q   G   V   T   F   D   L   Q   P   M   E   W   M   A   A   A   T   H

2701  GCCTTGTCTG CCCCTGCAGA GCTCCTCCACT GAGGTACAGA TGGATCTTGG GATGGATGGG AAGTAAAGAG AGAGGAACTG GGCATTTTGG GGAGCCTCTG
      CGGAACAGAC GGGGACGTCT CGAGGAGTGA CTCCATGTCT ACCTAGAACC CTACCTACCC TTCATTTCTC TCTCCTTGAC CCGTAAAACC CCTCGGAGAC
201    A   L   S   A   P   A   E   L   L   T   E   V   Q   M   D   L   G   M   D   G   K   Q

2801  GACCAGAGGA ATGAAGAAGC AACCCACAGC CTTCCCTCTC AAGTACTGTG GCCTGTGATA GCCCTCAGTA CTGACCCTTT
      CTGGTCTCCT TACTTCTTCG TTGGGTGTCG GAAGGGAGAG TTCGATGACA CGGACACTAT AAGGGGCGGA CGGGAGTCAT GACTGGGAAA

2901  GAAGGAAACC ATTCGCTGCG TCCCCTGGGA GATAAAATGA ATTCCCTGGG TTTCAGCAGA CATACACATG AGTTGTGAGG TCAGAGGGTT
      CTTCCTTTGG TAAGCGACGC AGGGGACCCT CTATTTTACT TAAGGGACCC AAAGTCGTCT GTATGTGTAC TCAACACTCC AGTCTCCCAA

3001  AAGGTTTGAT AAGAAAATGA AATAAGACGA CAGGGAAATA CTAGGTGGGA AAGCGGAAGG TCTTTTCACTT GGGACTTCCT TTACTTGTAA GTCAGGGACA
      TTCCAAACTA TTCTTTTACT TTATTCTGCT GTCCCTTTAT GATCCACCCT TTCGCCTTCC AGAAAGTGAA AATAGAGATC CCTGAAGGA AATGAACATT CAGTCCCTGT

3101  GGAATGAATA AAAGCATTTG GATTCCTGAC CGTTTTGTGG TTTCTGTCTTT CCCCCCGCCC TCTTTTCACTT CAGGGAAGG CTAGCCTAAT CAGGGATATG
      CCTTACTTAT TTTCGTAAAC CTAAGGACTG GCAAAACACC AGAAACAGAA GGGGGGCGGG AGAAAGTGAA GTCCCCTTCC GATCGGATTA GTCCCTATAC

3201  TCCAGTTCAG AAATGTGGAC CGTTTTGTGG CACCGCTTCT CCATGGTCCT GAGGCTCCCC GAGGAGGCAT CTGCACAGGA AGGGGAGCTT TCGCTATCCA
      AGGTCAAGTC TTTACACCTG GCAAAACACC GTGGCGAAGA GGTACCAGGA CTCCGAGGG CTCCTCCGTA GACGTGTCCT TCCCCTCGAA AGCGATAGGT

3301  GTCCACCAAG CCCTGAGCCA GACTGGACAC TGATTTCTCC CCAGGGCATG GCAGCCCTGC TGAGCCTGGC CATGGCCACC TTTACCCAGG AGCCCCAGTT
      CAGGTGGTTC GGGACTCGGT CTGACCTGTG ACTAAAGAGG GGTCCCGTAC CGTCGGGACG ACTCGGACCG GTACCGGTGG AAATGGGTCC TCGGGGTCAA

3401  ATGCCTGAGC TGCCTGTCCC AGCATGGAAG TCCATCCTGA TATCCTCATG TTGCCCCAGC AGCATCTGCT TTCCTGAATC AACTGCGCCA GGCGCCTCAT
      TACGGACTCG ACGGACAGGG TCGTACCTTC AGGTAGGACT ATAGGAGTAC AGGGTCG TCGTAGACGA AAGGACTTAG TTGACGCGGT CCGCGGAGTA

3501  GGGTCTGAGT TTCTCCCTGT CGTGGTGCTC AGCTCCTTTG CTTCCCTTTG GGCTGGACA TGGATGCTGA CCTCCTTATA GGTGTCTTGG
      CCCAGACTCA AAGAGGGACA GCACCACGAG TCGAGGAAAC GAAGGGAAAC CGCGCTGAGACT GGAGGAATAT CCACAGAACC
```

FIG._5D

```
3601  CCGACCTCAG GGACTCAGAA GTTGCAGCCC ATCTGCTGCA GGTCTGCTGC TACCATCTTC CGTTGATGCA AGTGGAGCTG CCCATCAGCC TTCTCACACG
      GGCTGGAGTC CCTGAGTCTT CAACGTCGGG TAGACGACGT CCAGACGACG ATGGTAGAAG GCAACTACGT TCACCTCGAC GGGTAGTCGG AAGAGTGTGC

3701  CCTGGCCCTC ATGGATCCCA CCTCTCTCAA CCAGTTTGTG AACACAGTGT CTGCCTCCCC TAGAACCATC GTCTCGTTTC TCTCAGTTGC CCTCCTGAGT
      GGACCGGGAG TACCTAGGGT GGAGAGAGTT GGTCAAACAC TTGTGTCACA GACGGAGGGG ATCTTGGTAG CAGAGACAAA G AGAGTCAACG GGAGGACTCA

3801  GACCAGCCAC TGTTGACCTC CGACCTTCTC TCTCTGCTGG CAGGGTCCTG TCTCCCAGCC ACTTGTCCTT TATCCAAGAG CTTCTGGCTG
      CTGGTCGGTG ACAACTGGAG GCTGGAAGAG AGAGACGACC GTCCCAGGAC AGAGGGTCGG TGAACAGGAA ATAGGTTCTC GAAGACCGAC

3901  GCTCTGATGA ATCCTATCGG CCCCTGCGCA GCCTCCTGGG CCACCCAGAG AATTTCTGTGC GGGCACACAC TTATAGGCTC TGTCTCAACA
      CGAGACTACT TAGGATAGCC GGGGACGCGT CGGAGGACCC GGTGGGTCTC TTAAGACACG CCCGTGTGTG GACCCTGTGA ACGAGGTTGT

4001  CAGCATGGCC CTGCGTGGGG CACTGCAGAG CCAGTCTGGA CTGCTCAGCC TTCTGCTGCT TGGGCTTGGA GACAAGGATC CTGTTGTGCG GTGCAGTGCC
      GTCGTACCGG GACGACCCCC GTGACGTCTC GGTCAGACCT GACGAGTCGG AAGACGACGA ACCCGAACCT CTGTTCCTAG CACGTCACGG

4101  AGCTTTGCTG TGGGCAATGC AGCCTACCAG GCTGGTCCTC TGGGACCTGC CCTGGCAGCT GTATGACCCA GCTGCTTGGA GATCCTCAGG
      TCGAAACGAC ACCCGTTACG TCGGATGGTC CGACCAGGAG ACCCTGGACG GGACCGTCGA CATACTGGGT CGACGAACCT CTAGGAGTCC

4201  CTGGTATCCG GCGCAATGTT GCATCAGCTC TGGGCAACTT GGGGACCTGA GGTTTGGGAG AGGAGCTGTT ACAGTGCGAA GCTCCTAGA
      GACCATAGGC CGCGTTACAA CGTAGTCGAG ACCCGTTGAA CCCTGGACTT CCAAACCCTC TCCTCGACAA TGTCACGCTT CATGGGGTCG CCGAGGATCT

4301  AATGGCATGT GGAGACCCCC AGCCAAATGT GAAGGAGGCT CCCTCCATTG CCCTCCGGAG GCCACACAGC GAGCCTGGCA TCCATCAGGT ACTGGTGTCC
      TTACCGTACA CCTCTGGGGG TCGGTTTACA CTTCCTCCGA GGGAGTAAC CGGAGGCCTC CGGTGTGTCG CTCGGACCGT AGGTAGTCCA TGACCACAGG

4401  CTGGGTGCCA GTGAGAAACT ATCCTTGCTC TCTCTGGGGA ATCAGTCACT GCCACACAGC AGTCCTAGGC CTGCCTCTGC AGGAAACTCA
      GACCCACGGT CACTCTTTGA TAGGAACGAG AGAGACCCCT TAGTCAGTGA CGGTGTGTCG TCAGGATCCG GACGGAGACG TCCTTTGAGT

4501  TTCACCTCCT GAGGCCAGCC CATAGCATGT GATTCCAGAT TCCTGCGGTC CAGCCTCCAA CTTTGGTTGC CAGCTCTTTC TTATTCTACT ACACAAGCCG
      AAGTGGAGGA CTCCGGTCGG GTATCGTACA CTAAGGTCTA AGGACGCCAG GTCGGAGGTT GAAACCAACG GTCGAGAAAG AATAAGATGA TGTGTTCGGC

4601  CCAACTCAAC TGAGAGCTAA AAAGAGATAA GCTGCCAACT CAAGAAACTA CAAGAAACTA GAAGAGATT ATATATAAAG CTTCTTCCTT
      GGTTGAGTTG ACTCTCGATT TTTCTCTATT CGACGGTTGA GTTGACTCTT GTTGACTCTT CTTCTCTAAA TATATATTTC GAAGAAGAA
```

*FIG._5E*

```
4701  CTCCCAGATG CAGGATGTTT TCAACCAGTA AATTTTATTG CTGTTGGTGC CAGAGAAGAG TCCTTTCTTC TCTACATCCA GGGGCCTTTT CTCCAATAAT
      GAGGGTCTAC GTCCTACAAA AGTTGGTCAT TTAAAATAAC GACAACCACG GTCTCTTCTC AGGAAAGAAG AGATGTAGGT CCCCGGAAAA GAGGTTATTA

4801  GTGCCTTTAA CTCTAGGGAC CTGCCTCACG GACCTTAGGG AAAAACCTCA ACCTGAAAGA TCTCTTCCTT TCTGGAGCTC CTTTAATCTT CCCAGCAGGT
      CACGGAAATT GAGATCCCTG GACGGAGTGC CTGGAATCCC TTTTTGGAGT TGGACTTTCT AGAGAAGGAA AGACCTCGAG GAAATTAGAA GGGTCGTCCA

4901  TTTTGCCTTA GACGTGCTGG CCCCAGGACA GTGATGAAGA CAGAGCCTGT CTCAGCTCTA GGCTGTGGGG ATCAATGCCA TCAGTCCCTG TTATTGAGGG
      AAAACGGAAT CTGCACGACC GGGGTCCTGT CACTACTTCT GTCTCGGACA GAGTCGAGAT CCGACACCCC TAGTTACGGT AGTCAGGGAC AATAACTCCC

5001  ATTATCCCTT AGCCAACATT CCTATCTGTG GGTGGGCGTG GAGAGTGTAT CTTTTTTTGG TATATGTGTG TGTGTATGTG TGTGTGTGTT
      TAATAGGGAA TCGGTTGTAA GGATAGACAC CCACCCGCAC CTCTCACATA GAAAAAAACC CCACACACAC ATATACACAC ACACACACAA

5101  TAATAGTTCT GTTTGTAAAC TCTTTTAATA AAAGTTGTGC CTCACCATAC CAGGACAAGG GTTGAGAGGC TCAACCCCTC TTTCAGCTTC
      ATTATCAAGA CAAACATTTG AGAAAATTAT TTTCAACACG GAGTGGTATG GTCCTGTTCC CAACTCTCCG AGTTGGGGAG AAAGTCGAAG

5201  TATGTGGTGT TGGAGGTGCT GGTATCGTGT TCACACAAAA AAAAAAAAA AA
      ATACACCACA ACCTCCACGA CCATAGCACA AGTGTGTTTT TTTTTTTTT TT
```

FIG._5F

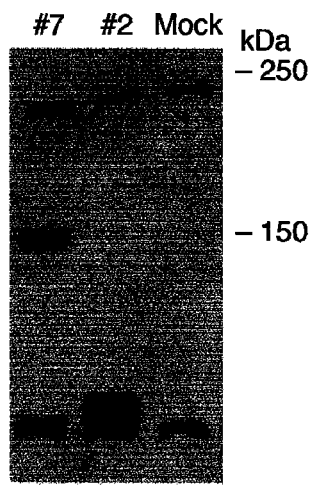
FIG._6
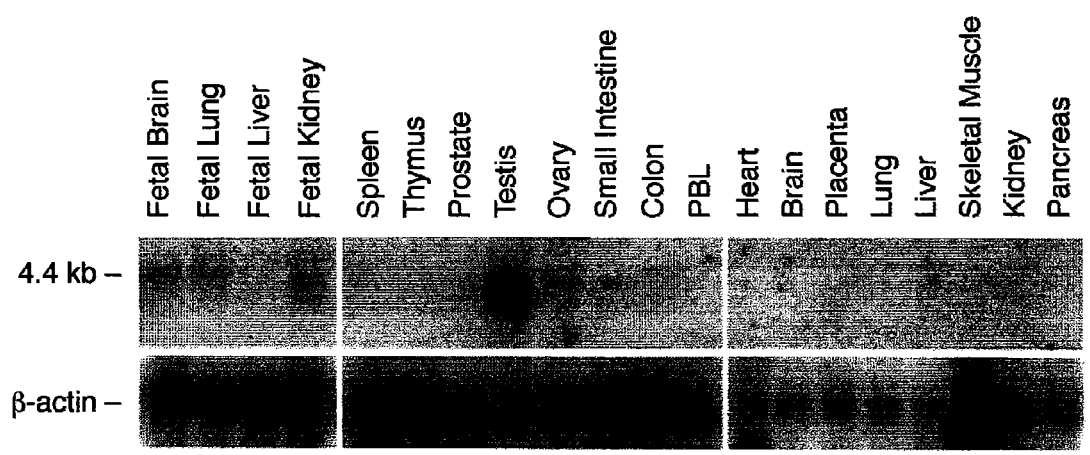
FIG._7

FIG._8A
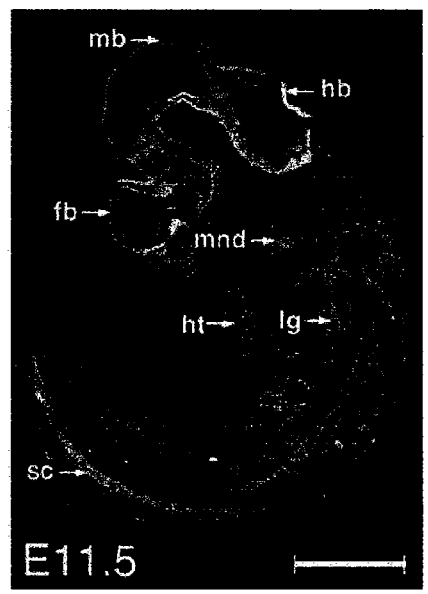
FIG._8B
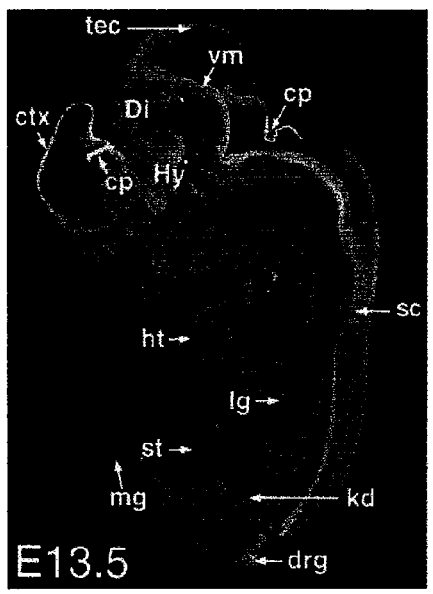
FIG._8C
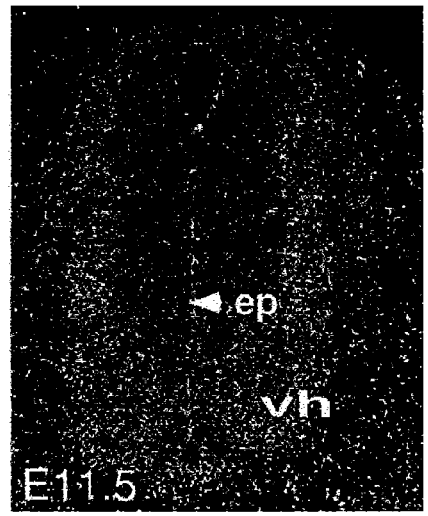
FIG._8D
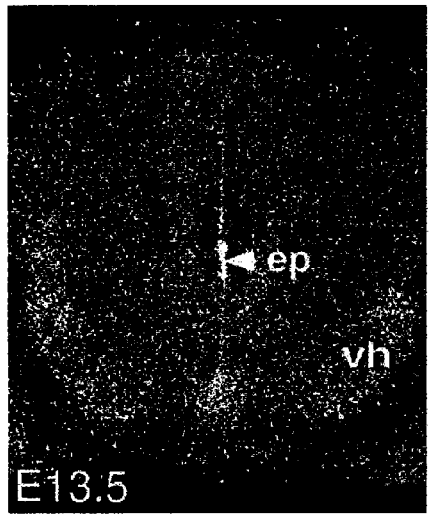
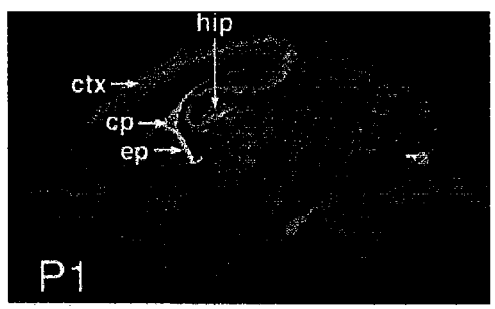
FIG._8E
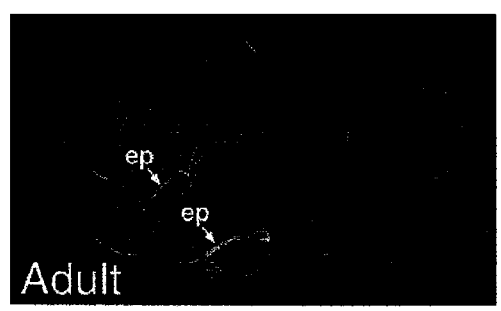
FIG._8F

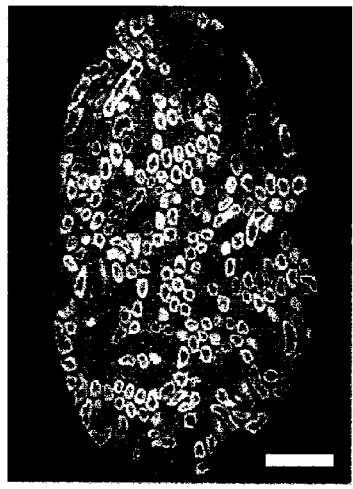 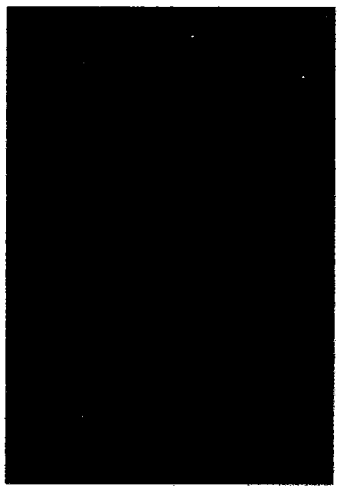 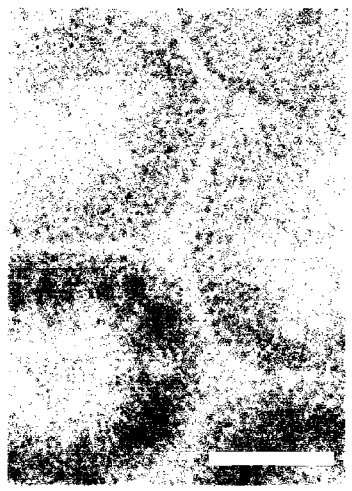
FIG._9A   FIG._9B   FIG._9C

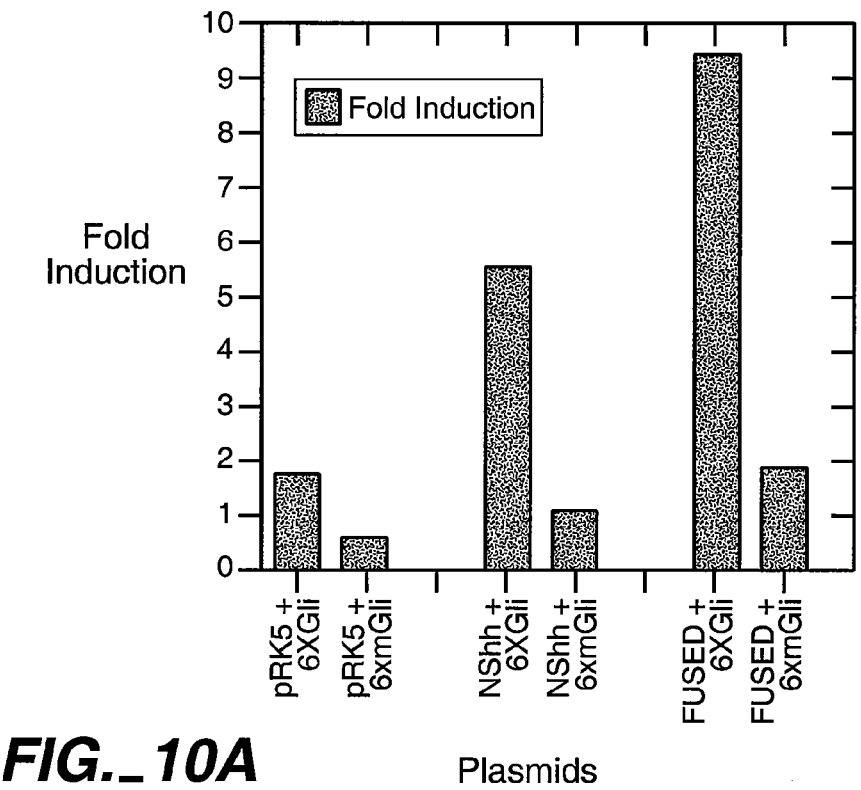
FIG._10A
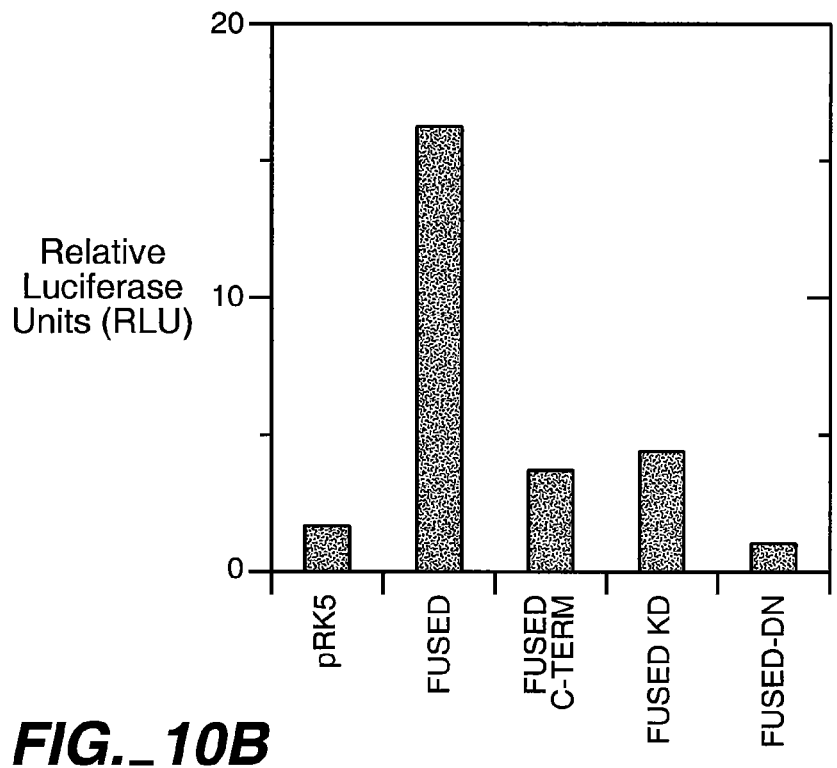
FIG._10B

FIG._11A
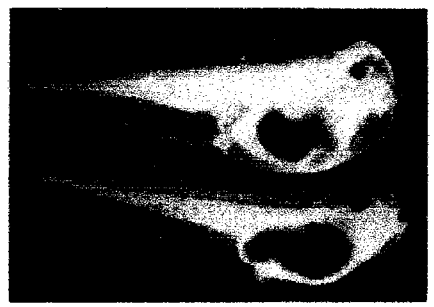
FIG._11B
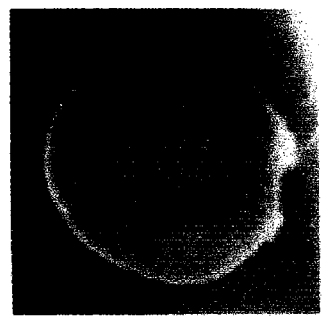
FIG._11C
FIG._11D
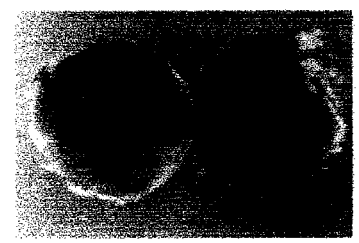
FIG._11E
FIG._12

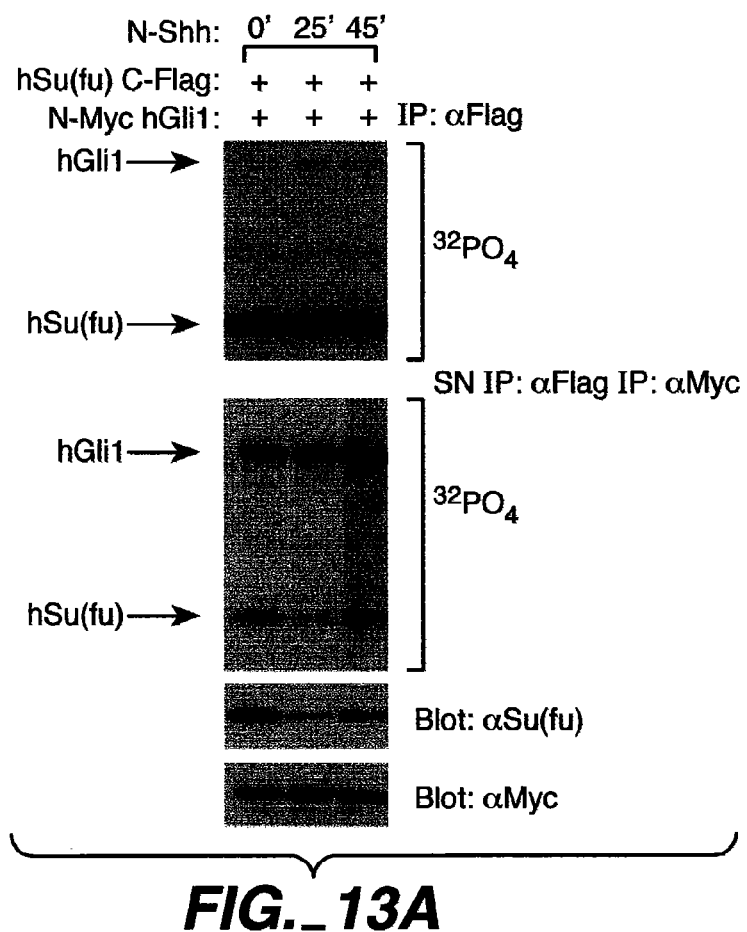
FIG._13A
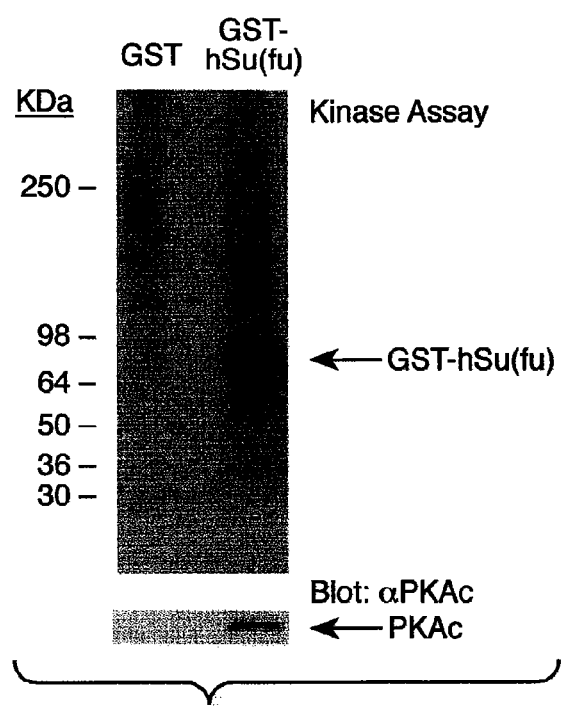
FIG._13B

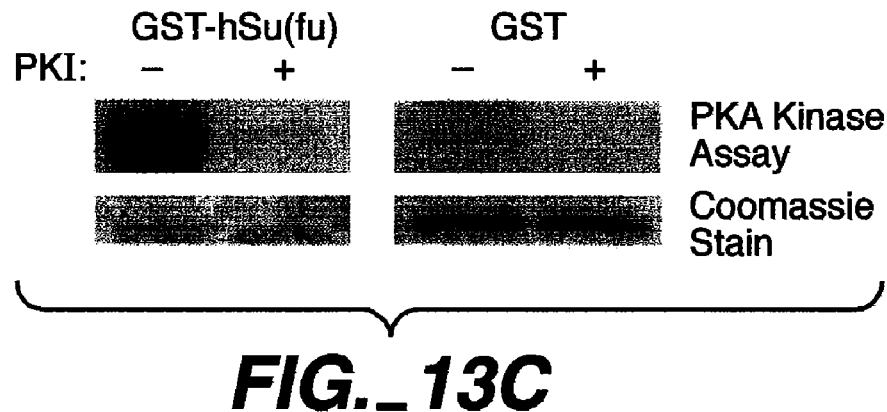
FIG._13C
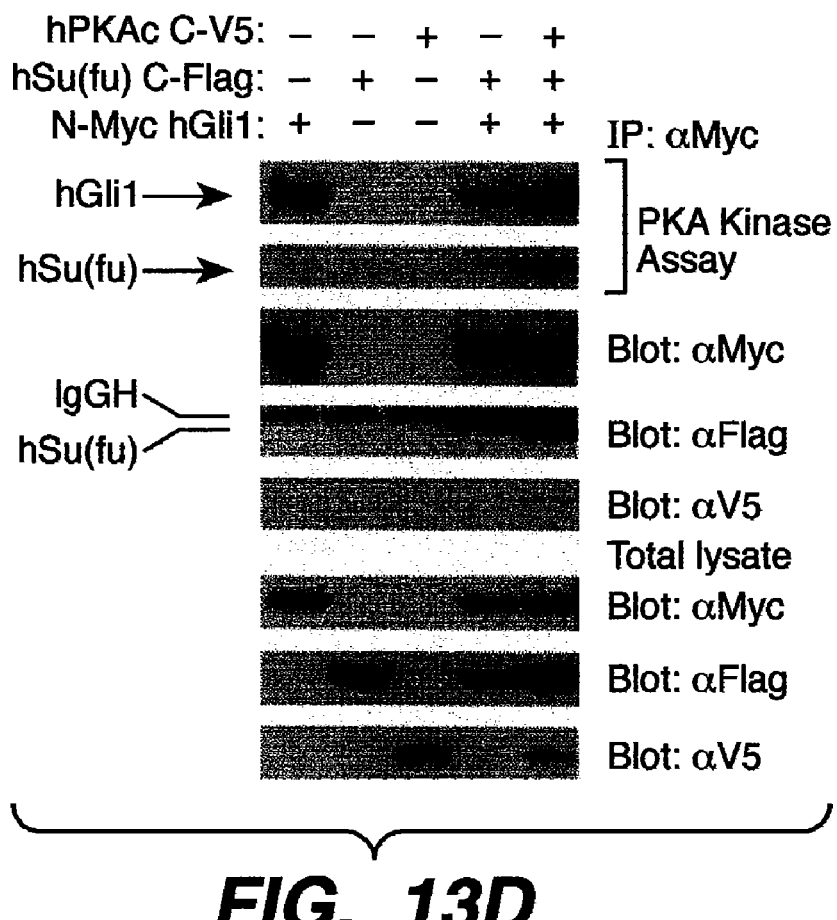
FIG._13D

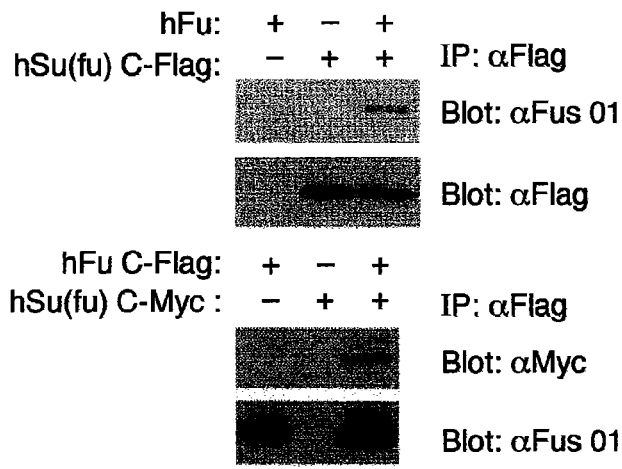
FIG._14A
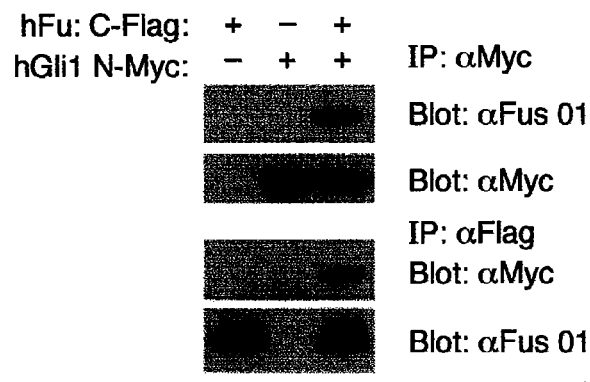
FIG._14B
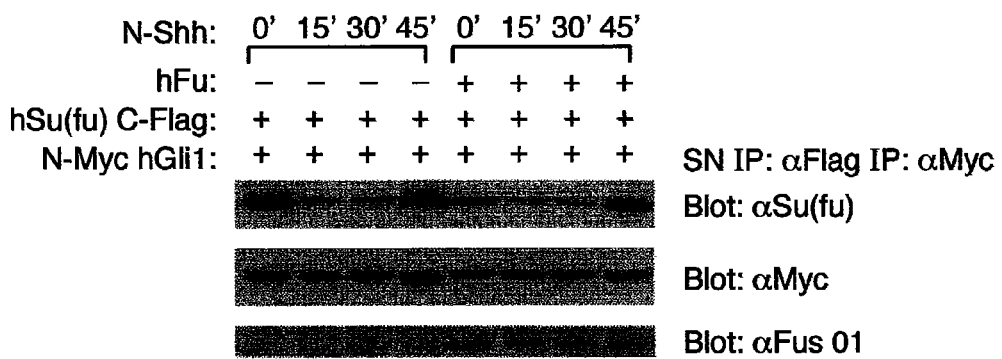
FIG._14C

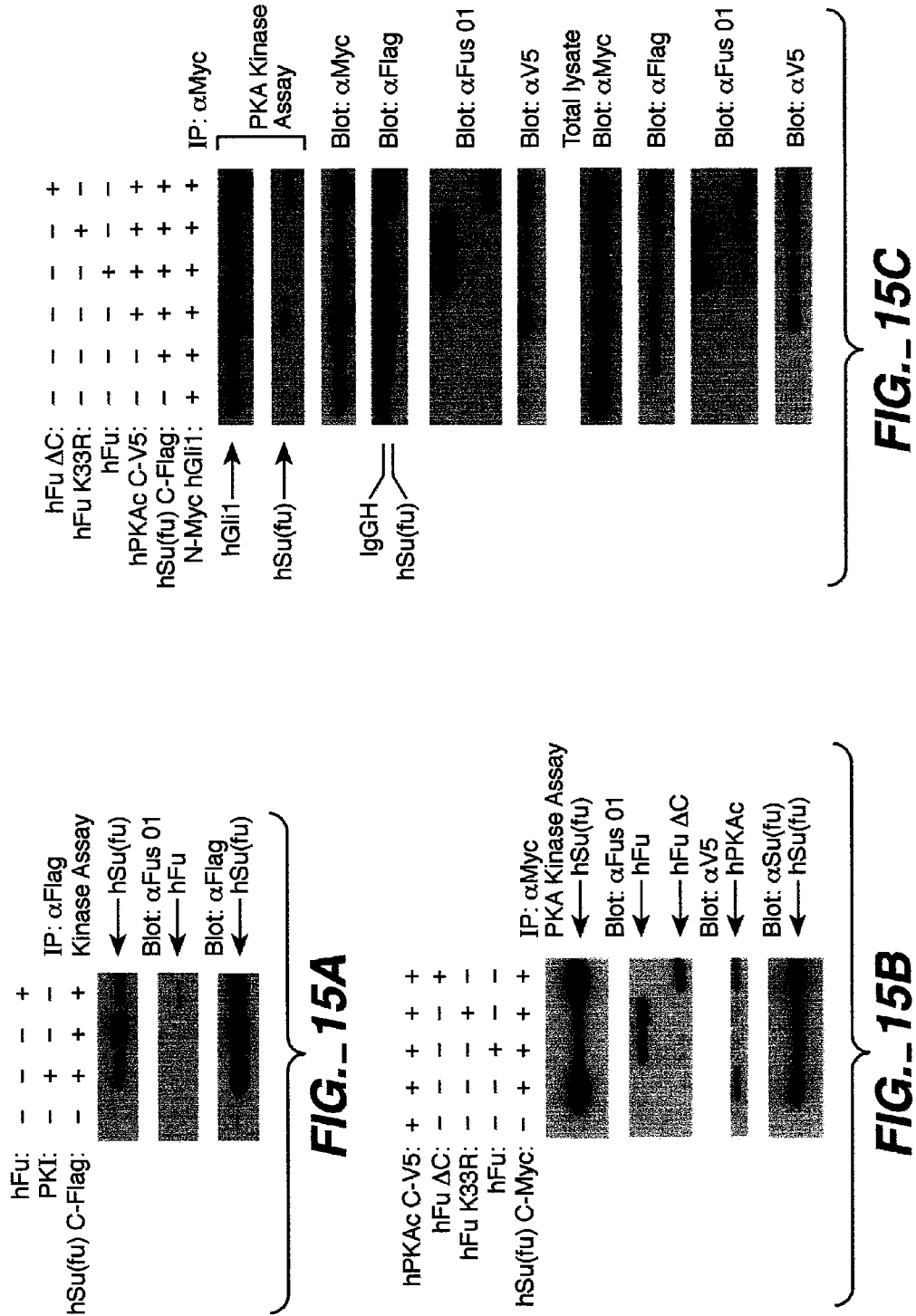

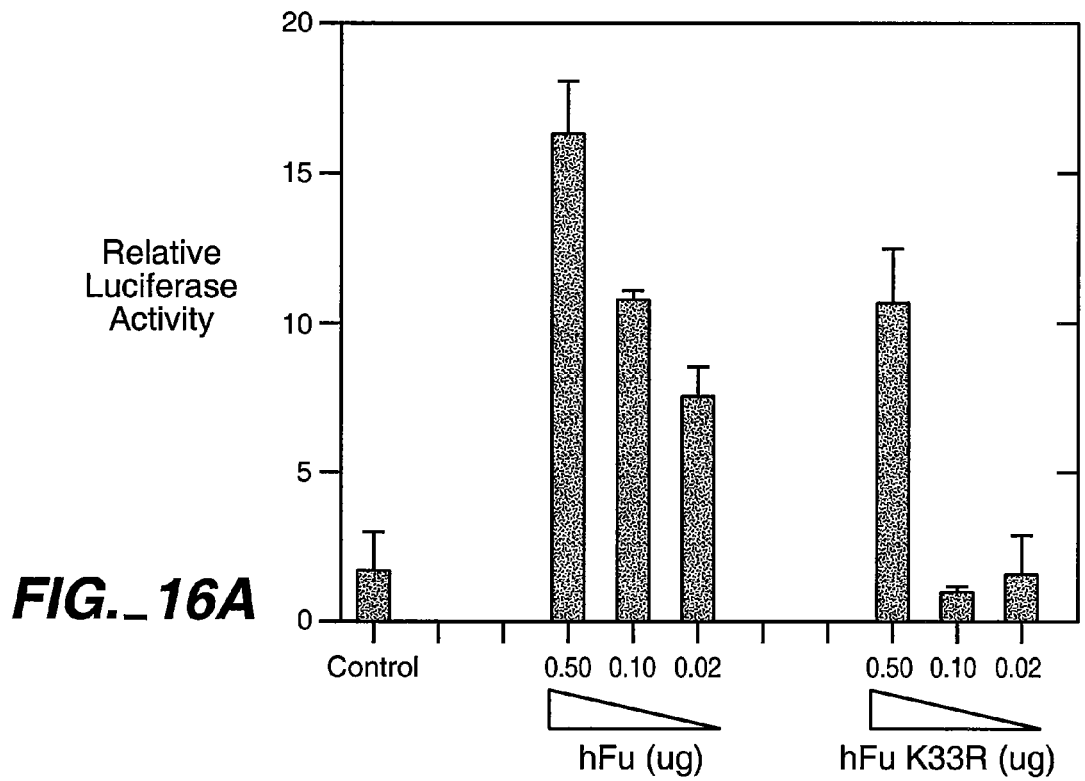
FIG._16A
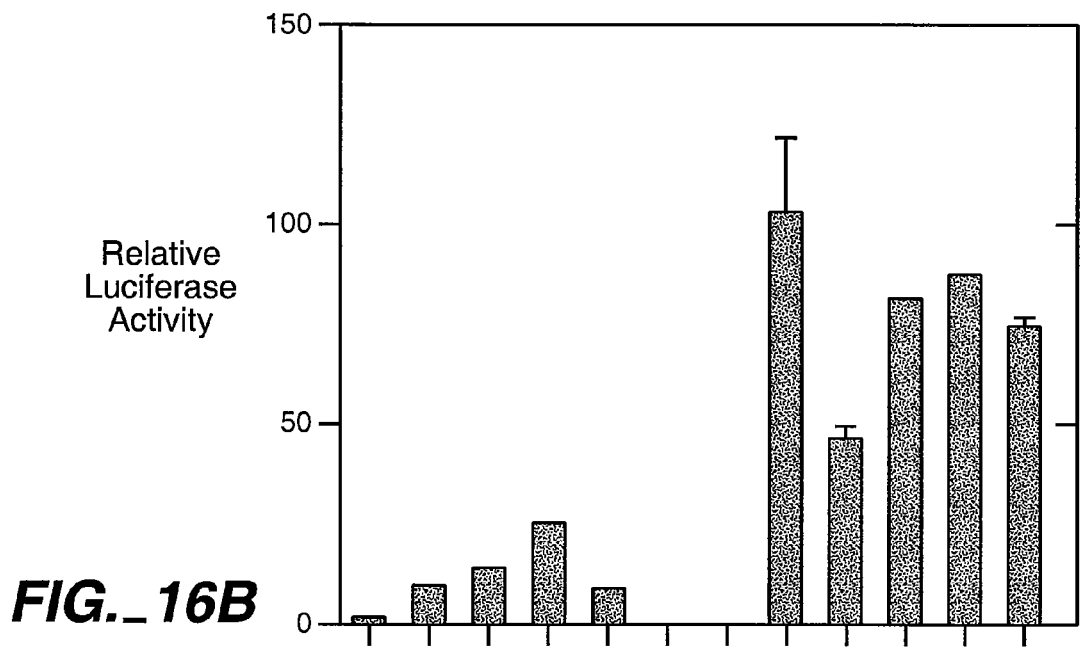
FIG._16B

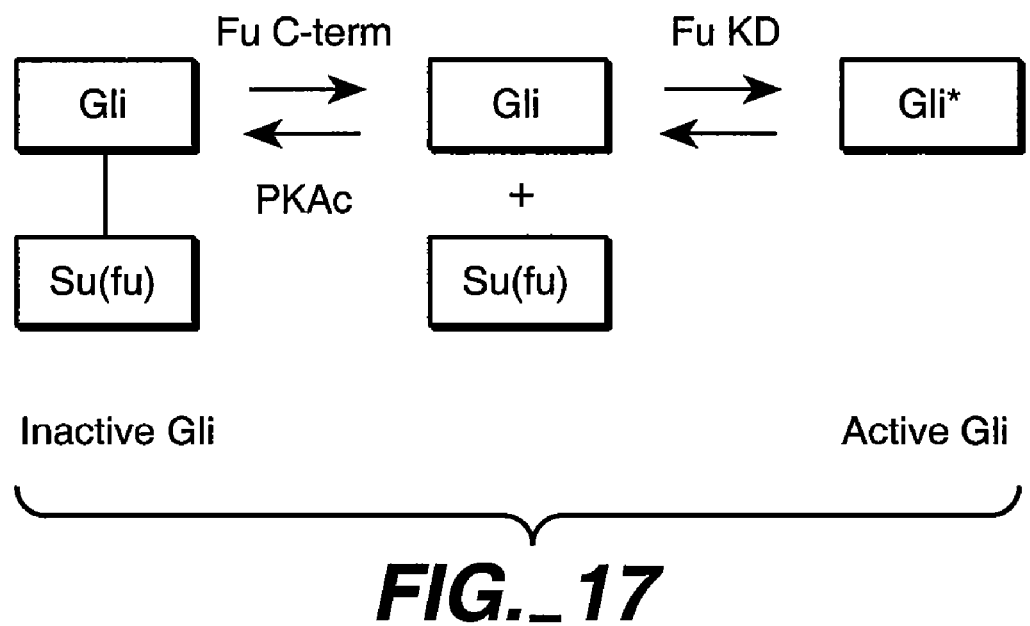
FIG._17

PRO              XXXXXXXXXXXXXXX    (Length = 15 amino acids)
Comparison Protein    XXXXXYYYYYYY       (Length = 12 amino acids)
% amino acid sequence identity =
(the number of identically matching amino acid residues between the two polypeptide
sequences as determined by ALIGN-2) divided by (the total number of amino acid residues
of the PRO polypeptide) =
5 divided by 15 = 33.3%

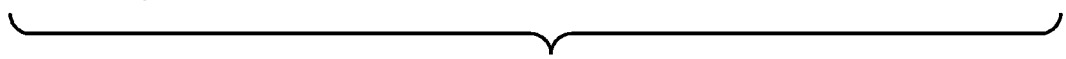

PRO              XXXXXXXXXX         (Length = 10 amino acids)
Comparison Protein    XXXXXYYYYYYZZYZ    (Length = 15 amino acids)
% amino acid sequence identity =
(the number of identically matching amino acid residues between the two polypeptide
sequences as determined by ALIGN-2) divided by (the total number of amino acid residues
of the PRO polypeptide) =
5 divided by 10 = 50%

PRO-DNA          NNNNNNNNNNNNNN     (Length = 14 nucleotides)
Comparison DNA   NNNNNNLLLLLLLLLL   (Length = 16 nucleotides)
% nucleic acid sequence identity =
(the number of identically matching nucleotides between the two nucleic acid sequences
as determined by ALIGN-2) divided by (the total number of nucleotides of the PRO-DNA
nucleic acid sequence) =
6 divided by 14 = 42.9%

PRO-DNA          NNNNNNNNNNNN       (Length = 12 nucleotides)
Comparison DNA   NNNNLLLVV          (Length = 9 nucleotides)
% nucleic acid sequence identity =
(the number of identically matching nucleotides between the two nucleic acid sequences
as determined by ALIGN-2) divided by (the total number of nucleotides of the PRO-DNA
nucleic acid sequence) =
4 divided by 12 = 33.3%

FIG. 19A

```
/*
 * C-C increased from 12 to 15
 * Z is average of EQ
 * B is average of ND
 * match with stop is _M; stop-stop = 0; J (joker) match = 0
 */
define _M  -8    /* value of a match with a stop */ int _day[26][26] = {
/*      A    B    C    D    E    F    G    H    I    J    K    L    M    N    O    P    Q    R    S    T    U    V    W    X    Y    Z   */
/* A */{ 2,  0, -2,  0,  0, -4,  1, -1, -1,  0, -1, -2, -1,  0, _M,  1,  0, -2,  1,  1,  0,  0, -6,  0, -3,  0},
/* B */{ 0,  3, -4,  3,  2, -5,  0,  1, -2,  0, -0, -3, -2, _M, -1,  1,  0,  0,  0, -2, -5,  0, -3,  1},
/* C */{-2, -4, 15, -5, -5, -4, -3, -3, -2,  0, -5, -6, -5, -4, _M, -3, -5, -4,  0, -2,  0, -2, -8,  0,  0, -5},
/* D */{ 0, -3, -5,  4,  3, -6,  1,  1, -2,  0,  0, -4, -3,  2, _M, -1,  2, -1,  0,  0,  0, -2, -7,  0, -4,  2},
/* E */{ 0,  2, -5,  3,  4, -5,  0,  1, -2,  0,  0, -3, -2,  1, _M, -1,  2, -1,  0,  0,  0, -2, -7,  0, -4,  3},
/* F */{-4, -5, -4, -6, -5,  9, -5, -2,  1,  0, -5,  2,  0, -4, _M, -5, -5, -4, -3, -3,  0, -1,  0,  0,  7, -5},
/* G */{ 1,  0, -3,  1,  0, -5,  5, -2, -3,  0, -2, -4, -3,  0, _M, -1, -1, -3,  1,  0, -1, -1, -7,  0, -5,  0},
/* H */{-1,  1, -3,  1,  1, -2, -2,  6, -2,  0,  0, -2, -2,  2, _M,  0,  3,  2, -1, -1,  0, -2, -3,  0,  0,  2},
/* I */{-1, -2, -2, -2, -2,  1, -3, -2,  5,  0, -2, -2, -2, -2, _M, -2, -2, -2, -1,  0,  0,  4, -5,  0, -1, -2},
/* J */{ 0,  0,  0,  0,  0,  0,  0,  0,  0,  0,  0,  0,  0,  0,  0,  0,  0,  0,  0,  0,  0,  0,  0,  0,  0,  0},
/* K */{-1,  0, -5,  0, -0, -5, -2,  0, -2,  0,  5, -3,  0,  1, _M, -1,  1,  3,  0,  0,  0, -2, -3,  0, -4,  0},
/* L */{-2, -3, -6, -4, -3,  2, -4, -2,  2,  0, -3,  6,  4, -3, _M, -3, -2, -3, -3, -1,  0,  2, -2,  0, -1, -2},
/* M */{-1, -2, -5, -3, -2,  0, -3, -2,  2,  0,  0,  4,  6, -2, _M, -2, -1, -0, -2, -1,  0,  2, -4,  0, -2, -1},
/* N */{ 0,  2,  4,  2,  1, -4,  0,  2, -2,  0,  1, -3, -2,  2, _M, -1,  1,  0,  1,  0,  0, -2,  0, -5,  0,  1},
/* O */{_M, _M, _M, _M, _M, _M, _M, _M, _M, _M, _M, _M, _M, _M,  0, _M, _M, _M, _M, _M, _M, _M, _M, _M, _M, _M},
/* P */{ 1, -1, -3, -1, -1, -5, -1, -0, -2, -1,  0, -3, -2, -1, _M,  6,  0,  0,  1,  0, -0, -1, -6,  0, -5,  0},
/* Q */{ 0,  1, -5,  2,  2, -5, -1,  3, -2,  0,  1, -2, -1,  1, _M,  0,  4,  1, -1, -1,  0, -2, -5,  0, -4,  3},
/* R */{-2,  0, -4, -1, -1, -4,  3,  2, -2,  0,  3, -3, -0,  0, _M, -0,  1,  6,  0, -1,  0, -2, -2,  0, -4,  0},
/* S */{ 1,  0,  0,  0,  0, -3,  1, -1, -1,  0,  0, -3, -2,  1, _M,  1, -1,  0,  2,  1, -0, -1,  2,  0, -3,  0},
/* T */{ 1,  0,  0,  0,  0, -3,  0, -1, -0,  0,  0, -1, -1,  0, _M,  0, -1, -1,  1,  3,  0,  0, -5,  0, -3,  0},
/* U */{ 0,  0,  0,  0,  0,  0,  0,  0,  0,  0,  0,  0,  0,  0, _M,  0,  0,  0,  0,  0,  0,  0,  0,  0,  0,  0},
/* V */{ 0, -2,  0, -2, -2, -1, -1, -2,  4,  0, -2, -2,  2, -2, _M, -1, -2, -2, -1,  0,  0,  4, -6,  0, -2, -2},
/* W */{-6, -5, -8, -7, -7,  0, -7, -3, -5,  0, -3, -2, -4, -4, _M, -6, -5, -2, -5, -4,  0, -6, 17,  0,  0, -6},
/* X */{ 0,  0,  0,  0,  0,  0,  0,  0,  0,  0,  0,  0,  0,  0, _M,  0,  0,  0,  0,  0,  0,  0,  0,  0,  0,  0},
/* Y */{-3, -3,  0, -4, -4,  7, -5,  0, -1,  0, -4, -1, -2, -2, _M, -5, -4, -4, -3,  0,  0, -2,  0,  0, 10, -4},
/* Z */{ 0,  1, -5,  2,  3, -5,  0,  2,  0, -2, -2,  0, -1,  1, _M,  0,  3,  0,  0,  0,  0, -2, -6,  0, -4,  4}
};
```

Page 1 of day.h

FIG._19B

```c
/*
*/
#include <stdio.h>
include <ctype.h> define    MAXJMP    16     /* max jumps in a diag */
define    MAXGAP    24     /* don't continue to penalize gaps larger than this */
#define    JMPS      1024   /* max jmps in an path */
define    MX        4      /* save if there's at least MX-1 bases since last jmp */ define    DMAT      3      /* value of matching bases */
define    DMIS      0      /* penalty for mismatched bases */
#define    DINS0     8      /* penalty for a gap */
#define    DINS1     1      /* penalty per base */
#define    PINS0     8      /* penalty for a gap */
define    PINS1     4      /* penalty per residue */ struct jmp {
        short           n[MAXJMP];      /* size of jmp (neg for dely) */
        unsigned short  x[MAXJMP];      /* base no. of jmp in seq x */
};                                      /* limits seq to 2^16 -1 */ struct diag {
        int             score;          /* score at last jmp */
        long            offset;         /* offset of prev block */
        short           ijmp;           /* current jmp index */
        struct jmp      jp;             /* list of jmps */
};

struct path {
        int             spc;            /* number of leading spaces */
        short           n[JMPS];        /* size of jmp (gap) */
        int             x[JMPS];        /* loc of jmp (last elem before gap) */
};

char            *ofile;                 /* output file name */
char            *namex[2];              /* seq names: getseqs() */
char            *prog;                  /* prog name for err msgs */
char            *seqx[2];               /* seqs: getseqs() */
int             dmax;                   /* best diag: nw() */
int             dmax0;                  /* final diag */
int             dna;                    /* set if dna: main() */
int             endgaps;                /* set if penalizing end gaps */
int             gapx, gapy;             /* total gaps in seqs */
int             len0, len1;             /* seq lens */
int             ngapx, ngapy;           /* total size of gaps */
int             smax;                   /* max score: nw() */
int             *xbm;                   /* bitmap for matching */
long            offset;                 /* current offset in jmp file */
struct diag     *dx;                    /* holds diagonals */
struct path     pp[2];                  /* holds path for seqs */ char            *calloc(), *malloc(), *index(), *strcpy();
char            *getseq(), *g_calloc();
```

Page 1 of nw.h

FIG._19C

```
/* Needleman-Wunsch alignment program
 *
 * usage: progs file1 file2
 * where file1 and file2 are two dna or two protein sequences.
 * The sequences can be in upper- or lower-case an may contain ambiguity
 * Any lines beginning with ';', '>' or '<' are ignored
 * Max file length is 65535 (limited by unsigned short x in the jmp struct)
 * A sequence with 1/3 or more of its elements ACGTU is assumed to be DNA
 * Output is in the file "align.out"
 *
 * The program may create a tmp file in /tmp to hold info about traceback.
 * Original version developed under BSD 4.3 on a vax 8650
 */
include "nw.h"
#include "day.h"

static _dbval[26] = {
        1,14,2,13,0,0,4,11,0,0,12,0,3,15,0,0,0,5,6,8,8,7,9,0,10,0
};

static _pbval[26] = {
        1, 2|(1<<('D'-'A'))|(1<<('N'-'A')), 4, 8, 16, 32, 64,
        128, 256, 0xFFFFFFF, 1<<10, 1<<11, 1<<12, 1<<13, 1<<14,
        1<<15, 1<<16, 1<<17, 1<<18, 1<<19, 1<<20, 1<<21, 1<<22,
        1<<23, 1<<24, 1<<25|(1<<('E'-'A'))|(1<<('Q'-'A'))
};

main(ac, av)                                                                    main
        int     ac;
        char    *av[];
{
        prog = av[0];
        if (ac != 3) {
                fprintf(stderr,"usage: %s file1 file2\n", prog);
                fprintf(stderr,"where file1 and file2 are two dna or two protein sequences.\n");
                fprintf(stderr,"The sequences can be in upper- or lower-case\n");
                fprintf(stderr,"Any lines beginning with ';' or '<' are ignored\n");
                fprintf(stderr,"Output is in the file \"align.out\"\n");
                exit(1);
        }
        namex[0] = av[1];
        namex[1] = av[2];
        seqx[0] = getseq(namex[0], &len0);
        seqx[1] = getseq(namex[1], &len1);
        xbm = (dna)? _dbval : _pbval;

endgaps = 0;            /* 1 to penalize endgaps */
        ofile = "align.out";    /* output file */ nw();        /* fill in the matrix, get the possible jmps */
        readjmps();  /* get the actual jmps */
        print();     /* print stats, alignment */ cleanup(0);  /* unlink any tmp files */
}
```

FIG._19D

```
/* do the alignment, return best score: main()
 * dna: values in Fitch and Smith, PNAS, 80, 1382-1386, 1983
 * pro: PAM 250 values
 * When scores are equal, we prefer mismatches to any gap, prefer
 * a new gap to extending an ongoing gap, and prefer a gap in seqx
 * to a gap in seq y.
 */
nw()                                                                        nw
{
        char        *px, *py;         /* seqs and ptrs */
        int         *ndely, *dely;    /* keep track of dely */
        int         ndelx, delx;      /* keep track of delx */
        int         *tmp;             /* for swapping row0, row1 */
        int         mis;              /* score for each type */
        int         ins0, ins1;       /* insertion penalties */
        register    id;               /* diagonal index */
        register    ij;               /* jmp index */
        register    *col0, *col1;     /* score for curr, last row */
        register    xx, yy;           /* index into seqs */ dx = (struct diag *)g_calloc("to get diags", len0+len1+1, sizeof(struct diag));

ndely = (int *)g_calloc("to get ndely", len1+1, sizeof(int));
        dely = (int *)g_calloc("to get dely", len1+1, sizeof(int));
        col0 = (int *)g_calloc("to get col0", len1+1, sizeof(int));
        col1 = (int *)g_calloc("to get col1", len1+1, sizeof(int));
        ins0 = (dna)? DINS0 : PINS0;
        ins1 = (dna)? DINS1 : PINS1;

smax = -10000;
        if (endgaps) {
                for (col0[0] = dely[0] = -ins0, yy = 1; yy <= len1; yy++) {
                        col0[yy] = dely[yy] = col0[yy-1] - ins1;
                        ndely[yy] = yy;
                }
                col0[0] = 0;   /* Waterman Bull Math Biol 84 */
        }
        else
                for (yy = 1; yy <= len1; yy++)
                        dely[yy] = -ins0;

/* fill in match matrix
         */
        for (px = seqx[0], xx = 1; xx <= len0; px++, xx++) {
                /* initialize first entry in col
                 */
                if (endgaps) {
                        if (xx == 1)
                                col1[0] = delx = -(ins0+ins1);
                        else
                                col1[0] = delx = col0[0] - ins1;
                        ndelx = xx;
                }
                else {
                        col1[0] = 0;
                        delx = -ins0;
                        ndelx = 0;
                }
```

Page 2 of nw.c

...nw

```
for (py = seqx[1], yy = 1; yy <= len1; py++, yy++) {
    mis = col0[yy-1];
    if (dna)
            mis += (xbm[*px-'A']&xbm[*py-'A'])? DMAT : DMIS;
    else
            mis += _day[*px-'A'][*py-'A'];

/* update penalty for del in x seq;
     * favor new del over ongong del
     * ignore MAXGAP if weighting endgaps
     */
    if (endgaps || ndely[yy] < MAXGAP) {
            if (col0[yy] - ins0 >= dely[yy]) {
                    dely[yy] = col0[yy] - (ins0+ins1);
                    ndely[yy] = 1;
            } else {
                    dely[yy] -= ins1;
                    ndely[yy]++;
            }
    } else {
            if (col0[yy] - (ins0+ins1) >= dely[yy]) {
                    dely[yy] = col0[yy] - (ins0+ins1);
                    ndely[yy] = 1;
            } else
                    ndely[yy]++;
    }

/* update penalty for del in y seq;
     * favor new del over ongong del
     */
    if (endgaps || ndelx < MAXGAP) {
            if (col1[yy-1] - ins0 >= delx) {
                    delx = col1[yy-1] - (ins0+ins1);
                    ndelx = 1;
            } else {
                    delx -= ins1;
                    ndelx++;
            }
    } else {
            if (col1[yy-1] - (ins0+ins1) >= delx) {
                    delx = col1[yy-1] - (ins0+ins1);
                    ndelx = 1;
            } else
                    ndelx++;
    }

/* pick the maximum score; we're favoring
     * mis over any del and delx over dely
     */
```

Page 3 of nw.c

```
                id = xx - yy + len1 - 1;
                if (mis >= delx && mis >= dely[yy])
                        col1[yy] = mis;
                else if (delx >= dely[yy]) {
                        col1[yy] = delx;
                        ij = dx[id].ijmp;
                        if (dx[id].jp.n[0] && (!dna || (ndelx >= MAXJMP
                          && xx > dx[id].jp.x[ij]+MX) || mis > dx[id].score+DINS0)) {
                                dx[id].ijmp++;
                                if (++ij >= MAXJMP) {
                                        writejmps(id);
                                        ij = dx[id].ijmp = 0;
                                        dx[id].offset = offset;
                                        offset += sizeof(struct jmp) + sizeof(offset);
                                }
                        }
                        dx[id].jp.n[ij] = ndelx;
                        dx[id].jp.x[ij] = xx;
                        dx[id].score = delx;
                }
                else {
                        col1[yy] = dely[yy];
                        ij = dx[id].ijmp;

if (dx[id].jp.n[0] && (!dna || (ndely[yy] >= MAXJMP
          && xx > dx[id].jp.x[ij]+MX) || mis > dx[id].score+DINS0)) {
                        dx[id].ijmp++;
                        if (++ij >= MAXJMP) {
                                writejmps(id);
                                ij = dx[id].ijmp = 0;
                                dx[id].offset = offset;
                                offset += sizeof(struct jmp) + sizeof(offset);
                        }
                }
                dx[id].jp.n[ij] = -ndely[yy];
                dx[id].jp.x[ij] = xx;
                dx[id].score = dely[yy];
        }
        if (xx == len0 && yy < len1) {
                /* last col
                 */
                if (endgaps)
                        col1[yy] -= ins0+ins1*(len1-yy);
                if (col1[yy] > smax) {
                        smax = col1[yy];
                        dmax = id;
```

FIG._19F-1

```
                }
            }
        }
        if (endgaps && xx < len0)
            col1[yy-1] -= ins0+ins1*(len0-xx);
        if (col1[yy-1] > smax) {
            smax = col1[yy-1];
            dmax = id;
        }
        tmp = col0; col0 = col1; col1 = tmp;
    }
    (void) free((char *)ndely);
    (void) free((char *)dely);
    (void) free((char *)col0);
    (void) free((char *)col1);
}
```

Page 4 of nw.c

```
/*
*
* print() -- only routine visible outside this module
*
* static:
* getmat() -- trace back best path, count matches: print()
* pr_align() -- print alignment of described in array p[]: print()
* dumpblock() -- dump a block of lines with numbers, stars: pr_align()
* nums() -- put out a number line: dumpblock()
* putline() -- put out a line (name, [num], seq, [num]): dumpblock()
* stars() - -put a line of stars: dumpblock()
* stripname() -- strip any path and prefix from a seqname
*/ include "nw.h"

define SPC        3
#define P_LINE     256    /* maximum output line */
define P_SPC      3      /* space between name or num and seq */ extern    _day[26][26];
int       olen;              /* set output line length */
FILE      *fx;               /* output file */ print()                                                                print
{
        int     lx, ly, firstgap, lastgap;      /* overlap */ if ((fx = fopen(ofile, "w")) == 0) {
                fprintf(stderr,"%s: can't write %s\n", prog, ofile);
                cleanup(1);
        }
        fprintf(fx, "<first sequence: %s (length = %d)\n", namex[0], len0);
        fprintf(fx, "<second sequence: %s (length = %d)\n", namex[1], len1);
        olen = 60;
        lx = len0;
        ly = len1;
        firstgap = lastgap = 0;
        if (dmax < len1 - 1) {          /* leading gap in x */
                pp[0].spc = firstgap = len1 - dmax - 1;
                ly -= pp[0].spc;
        }
        else if (dmax > len1 - 1) {     /* leading gap in y */
                pp[1].spc = firstgap = dmax - (len1 - 1);
                lx -= pp[1].spc;
        }
        if (dmax0 < len0 - 1) {         /* trailing gap in x */
                lastgap = len0 - dmax0 -1;
                lx -= lastgap;
        }
        else if (dmax0 > len0 - 1) {/* trailing gap in y */
                lastgap = dmax0 - (len0 - 1);
                ly -= lastgap;
        }
        getmat(lx, ly, firstgap, lastgap);
        pr_align();
}
```

Page 1 of nwprint.c

FIG._19H

```
/*
 * trace back the best path, count matches
 */
static
getmat(lx, ly, firstgap, lastgap)                                                         getmat
        int     lx, ly;                         /* "core" (minus endgaps) */
        int     firstgap, lastgap;              /* leading trailing overlap */
{
        int             nm, i0, i1, siz0, siz1;
        char            outx[32];
        double          pct;
        register        n0, n1;
        register char   *p0, *p1;

/* get total matches, score
         */
        i0 = i1 = siz0 = siz1 = 0;
        p0 = seqx[0] + pp[1].spc;
        p1 = seqx[1] + pp[0].spc;
        n0 = pp[1].spc + 1;
        n1 = pp[0].spc + 1;

nm = 0;
        while ( *p0 && *p1 ) {
                if (siz0) {
                        p1++;
                        n1++;
                        siz0--;
                }
                else if (siz1) {
                        p0++;
                        n0++;
                        siz1--;
                }
                else {
                        if (xbm[*p0-'A']&xbm[*p1-'A'])
                                nm++;
                        if (n0++ == pp[0].x[i0])
                                siz0 = pp[0].n[i0++];
                        if (n1++ == pp[1].x[i1])
                                siz1 = pp[1].n[i1++];
                        p0++;
                        p1++;
                }
        }

/* pct homology:
         * if penalizing endgaps, base is the shorter seq
         * else, knock off overhangs and take shorter core
         */
        if (endgaps)
                lx = (len0 < len1)? len0 : len1;
        else
                lx = (lx < ly)? lx : ly;
        pct = 100.*(double)nm/(double)lx;
        fprintf(fx, "\n");
        fprintf(fx, "<%d match%s in an overlap of %d: %.2f percent similarity\n",
                nm, (nm == 1)? "" : "es", lx, pct);
```

Page 2 of nwprint.c

```
        fprintf(fx, "<gaps in first sequence: %d", gapx);                              ...getmat
        if (gapx) {
                (void) sprintf(outx, " (%d %s%s)",
                        ngapx, (dna)? "base":"residue", (ngapx == 1)? "":"s");
                fprintf(fx,"%s", outx);

fprintf(fx, ", gaps in second sequence: %d", gapy);
        if (gapy) {
                (void) sprintf(outx, " (%d %s%s)",
                        ngapy, (dna)? "base":"residue", (ngapy == 1)? "":"s");
                fprintf(fx,"%s", outx);
        }
        if (dna)
                fprintf(fx,
                "\n<score: %d (match = %d, mismatch = %d, gap penalty = %d + %d per
                        base)\n", smax, DMAT, DMIS, DINS0, DINS1);
        else
                fprintf(fx,
                "\n<score: %d (Dayhoff PAM 250 matrix, gap penalty = %d + %d per
                        residue)\n", smax, PINS0, PINS1);
        if (endgaps)
                fprintf(fx,
                "<endgaps penalized. left endgap: %d %s%s, right endgap: %d %s%s\n",
                firstgap, (dna)? "base" : "residue", (firstgap == 1)? "" : "s",
                lastgap, (dna)? "base" : "residue", (lastgap == 1)? "" : "s");
        else
                fprintf(fx, "<endgaps not penalized\n");
} static          nm;                     /* matches in core -- for checking */
        static          lmax;                   /* lengths of stripped file names */
        static          ij[2];                  /* jmp index for a path */
        static          nc[2];                  /* number at start of current line */
        static          ni[2];                  /* current elem number -- for gapping */
        static          siz[2];
        static char     *ps[2];                 /* ptr to current element */
        static char     *po[2];                 /* ptr to next output char slot */
        static char     out[2][P_LINE];         /* output line */
        static char     star[P_LINE];           /* set by stars() */
/*
 * print alignment of described in struct path pp[]
 */
static
pr_align()                                                                              pr_align
```

FIG._19I-1

```
{
    int         nn;      /* char count */
    int         more;
    register    i;

for (i = 0, lmax = 0; i < 2; i++) {
        nn = stripname(namex[i]);
        if (nn > lmax)
            lmax = nn;

nc[i] = 1;
        ni[i] = 1;
        siz[i] = ij[i] = 0;
        ps[i] = seqx[i];
        po[i] = out[i];
    }
```

Page 3 of nwprint.c

*FIG. \_19I-2*

```
                    for (nn = nm = 0, more = 1; more; ) {                        ...pr_align
                            for (i = more = 0; i < 2; i++) {
                                    /*
                                     * do we have more of this sequence?
                                     */
                                    if (!*ps[i])
                                            continue;
                                    more++;
                                    if (pp[i].spc) {        /* leading space */
                                            *po[i]++ = ' ';
                                            pp[i].spc--;
                                    }
                                    else if (siz[i]) {      /* in a gap */
                                            *po[i]++ = '-';
                                            siz[i]--;
                                    }
                                    else {          /* we're putting a seq element
                                                     */
                                            *po[i] = *ps[i];
                                            if (islower(*ps[i]))
                                                    *ps[i] = toupper(*ps[i]);
                                            po[i]++;
                                            ps[i]++;
                                            /*
                                             * are we at next gap for this seq?
                                             */
                                            if (ni[i] == pp[i].x[ij[i]]) {
                                                    /*
                                                     * we need to merge all gaps
                                                     * at this location
                                                     */
                                                    siz[i] = pp[i].n[ij[i]++];
                                                    while (ni[i] == pp[i].x[ij[i]])
                                                            siz[i] += pp[i].n[ij[i]++];
                                            }
                                            ni[i]++;
                                    }
                            }
                            if (++nn == olen || !more && nn) {
                                    dumpblock();
                                    for (i = 0; i < 2; i++)
                                            po[i] = out[i];
                                    nn = 0;
                            }
                    }
            }
            /*
             * dump a block of lines, including numbers, stars: pr_align()
             */
            static
            dumpblock()                                                          dumpblock
            {
                    register    i;

for (i = 0; i < 2; i++)
                            *po[i]-- = '\0';
```

FIG._19J

Page 4 of nwprint.c

...dumpblock

```
                (void) putc('\n', fx);
                for (i = 0; i < 2; i++) {
                        if (*out[i] && (*out[i] != ' ' || *(po[i]) != ' ')) {
                                if (i == 0)
                                        nums(i);
                                if (i == 0 && *out[1])
                                        stars();
                                putline(i);
                                if (i == 0 && *out[1])
                                        fprintf(fx, star);
                                if (i == 1)
                                        nums(i);
                        }
                }
        }
}
/*
 * put out a number line: dumpblock()
 */
static
nums(ix)
        int     ix;     /* index in out[] holding seq line */
{
        char            nline[P_LINE];
        register        i, j;
        register char   *pn, *px, *py;
        for (pn = nline, i = 0; i < lmax+P_SPC; i++, pn++)
                *pn = ' ';
        for (i = nc[ix], py = out[ix]; *py; py++, pn++) {
                if (*py == ' ' || *py == '-')
                        *pn = ' ';
                else {
                        if (i%10 == 0 || (i == 1 && nc[ix] != 1)) {
                                j = (i < 0)? -i : i;
                                for (px = pn; j; j /= 10, px--)
                                        *px = j%10 + '0';
                                if (i < 0)
                                        *px = '-';
                        }
                        else
                                *pn = ' ';
                        i++;
                }
        }
        *pn = '\0';
        nc[ix] = i;
        for (pn = nline; *pn; pn++)
                (void) putc(*pn, fx);
        (void) putc('\n', fx);
}
/*
 * put out a line (name, [num], seq, [num]): dumpblock()
 */
static
putline(ix)
        int     ix;
{
``` nums putline

FIG._19K

...putline

```
        int             i;
        register char   *px;

for (px = namex[ix], i = 0; *px && *px != ':'; px++, i++)
                (void) putc(*px, fx);
        for (; i < lmax+P_SPC; i++)
                (void) putc(' ', fx);

/* these count from 1:
         * ni[] is current element (from 1)
         * nc[] is number at start of current line
         */
        for (px = out[ix]; *px; px++)
                (void) putc(*px&0x7F, fx);
        (void) putc('\n', fx);
}

/*
 * put a line of stars (seqs always in out[0], out[1]): dumpblock()
 */
static
stars()                                                                 stars
{
        int             i;
        register char   *p0, *p1, cx, *px;

if (!*out[0] || (*out[0] == ' ' && *(po[0]) == ' ') ||
            !*out[1] || (*out[1] == ' ' && *(po[1]) == ' '))
                return;
        px = star;
        for (i = lmax+P_SPC; i; i--)
                *px++ = ' ';

for (p0 = out[0], p1 = out[1]; *p0 && *p1; p0++, p1++) {
                if (isalpha(*p0) && isalpha(*p1)) {
                        if (xbm[*p0-'A']&xbm[*p1-'A']) {
                                cx = '*';
                                nm++;
                        }
                        else if (!dna && _day[*p0-'A'][*p1-'A'] > 0)
                                cx = '.';
                        else
                                cx = ' ';
                }
                else
                        cx = ' ';
                *px++ = cx;
        }
        *px++ = '\n';
        *px = '\0';
}
```

Page 6 of nwprint.c

FIG._19L

```
/*
 * strip path or prefix from pn, return len: pr_align()
 */
static
stripname(pn)
        char   *pn;    /* file name (may be path) */
{
        register char       *px,.*py;

py = 0;
        for (px = pn; *px; px++)
                if (*px == '/')
                        py = px + 1;
        if (py)
                (void) strcpy(pn, py);
        return(strlen(pn));

}
``` stripname

Page 7 of nwprint.c

FIG._19M

```
/*
 * cleanup() -- cleanup any tmp file
 * getseq() -- read in seq, set dna, len, maxlen
 * g_calloc() -- calloc() with error checkin
 * readjmps() -- get the good jmps, from tmp file if necessary
 * writejmps() -- write a filled array of jmps to a tmp file: nw()
 */
include "nw.h"
include <sys/file.h> char    *jname = "/tmp/homgXXXXXX";       /* tmp file for jmps */
FILE    *fj;

int     cleanup();                         /* cleanup tmp file */
long    lseek();

/*
 * remove any tmp file if we blow
 */
cleanup(i)                                                          cleanup
        int     i;
{
        if (fj)
                (void) unlink(jname);
        exit(i);
}
/*
 * read, return ptr to seq, set dna, len, maxlen
 * skip lines starting with ';', '<', or '>'
 * seq in upper or lower case
 */
char    *
getseq(file, len)                                                   getseq
        char    *file;  /* file name */
        int     *len;   /* seq len */
{
        char            line[1024], *pseq;
        register char        *px, *py;
        int             natgc, tlen;
        FILE            *fp;

if ((fp = fopen(file,"r")) == 0) {
                fprintf(stderr,"%s: can't read %s\n", prog, file);
                exit(1);
        }
        tlen = natgc = 0;
        while (fgets(line, 1024, fp)) {
                if (*line == ';' || *line == '<' || *line == '>')
                        continue;
                for (px = line; *px != '\n'; px++)
                        if (isupper(*px) || islower(*px))
                                tlen++;
        }
        if ((pseq = malloc((unsigned)(tlen+6))) == 0) {
                fprintf(stderr,"%s: malloc() failed to get %d bytes for %s\n", prog, tlen+6,
                        file);
                exit(1);
        }
        pseq[0] = pseq[1] = pseq[2] = pseq[3] = '\0';
```

FIG._19N

Page 1 of nwsubr.c

```
                            py = pseq + 4;
                            *len = tlen;
                            rewind(fp);

while (fgets(line, 1024, fp)) {
                                    if (*line == ';' || *line == '<' || *line == '>')
                                            continue;
                                    for (px = line; *px != '\n'; px++) {
                                            if (isupper(*px))
                                                    *py++ = *px;
                                            else if (islower(*px))
                                                    *py++ = toupper(*px);
                                            if (index("ATGCU",*(py-1)))
                                                    natgc++;
                                    }
                            }
                            *py++ = '\0';
                            *py = '\0';
                            (void) fclose(fp);
                            dna = natgc > (tlen/3);
                            return(pseq+4);
}
char    *
g_calloc(msg, nx, sz)                                                           g_calloc
            char    *msg;           /* program, calling routine */
            int     nx, sz;         /* number and size of elements */
{
            char        *px, *calloc();

if ((px = calloc((unsigned)nx, (unsigned)sz)) == 0) {
                    if (*msg) {
                            fprintf(stderr, "%s: g_calloc() failed %s (n=%d, sz=%d)\n", prog, msg,
                                nx, sz);
                            exit(1);
                    }
            }
            return(px);
}
/*
 * get final jmps from dx[] or tmp file, set pp[], reset dmax: main()
 */
readjmps()                                                                      readjmps
{
            int         fd = -1;
            int         siz, i0, i1;
            register    i, j, xx;

if (fj) {
                    (void) fclose(fj);
                    if ((fd = open(jname, O_RDONLY, 0)) < 0) {
                            fprintf(stderr, "%s: can't open() %s\n", prog, jname);
                            cleanup(1);
                    }
            }
            for (i = i0 = i1 = 0, dmax0 = dmax, xx = len0; ; i++) {
                    while (1) {
                            for (j = dx[dmax].ijmp; j >= 0 && dx[dmax].jp.x[j] >= xx; j--)
                                    ;
```

FIG._19O   Page 2 of nwsubr.c

```
                                                                           ...readjmps
                if (j < 0 && dx[dmax].offset && fj) {
                        (void) lseek(fd, dx[dmax].offset, 0);
                        (void) read(fd, (char *)&dx[dmax].jp, sizeof(struct jmp));
                        (void) read(fd, (char *)&dx[dmax].offset,
                        sizeof(dx[dmax].offset));
                        dx[dmax].ijmp = MAXJMP-1;
                }
                else
                        break;
        }
        if (i >= JMPS) {
                fprintf(stderr, "%s: too many gaps in alignment\n", prog);
                cleanup(1);
        }
        if (j >= 0) {
                siz = dx[dmax].jp.n[j];
                xx = dx[dmax].jp.x[j];
                dmax += siz;
                if (siz < 0) {          /* gap in second seq */
                        pp[1].n[i1] = -siz;
                        xx += siz;

/* id = xx - yy + len1 - 1
                         */
                        pp[1].x[i1] = xx - dmax + len1 - 1;
                        gapy++;
                        ngapy -= siz;
/* ignore MAXGAP when doing endgaps */
                        siz = (-siz < MAXGAP || endgaps)? -siz : MAXGAP;
                        i1++;
                }
                else if (siz > 0) {     /* gap in first seq */
                        pp[0].n[i0] = siz;
                        pp[0].x[i0] = xx;
                        gapx++;
                        ngapx += siz;
/* ignore MAXGAP when doing endgaps */
                        siz = (siz < MAXGAP || endgaps)? siz : MAXGAP;
                        i0++;
                }
        }
        else
                break;
}
```

FIG._19P-1

```
/* reverse the order of jmps
 */
for (j = 0, i0--; j < i0; j++, i0--) {
        i = pp[0].n[j]; pp[0].n[j] = pp[0].n[i0]; pp[0].n[i0] = i;
        i = pp[0].x[j]; pp[0].x[j] = pp[0].x[i0]; pp[0].x[i0] = i;
}
for (j = 0, i1--; j < i1; j++, i1--) {
        i = pp[1].n[j]; pp[1].n[j] = pp[1].n[i1]; pp[1].n[i1] = i;
        i = pp[1].x[j]; pp[1].x[j] = pp[1].x[i1]; pp[1].x[i1] = i;
}
if (fd >= 0)
        (void) close(fd);
if (fj) {
        (void) unlink(jname);
        fj = 0;
        offset = 0;
}
```

Page 3 of nwsubr.c

FIG._19P-2

```
/*
 * write a filled jmp struct offset of the prev one (if any): nw()
 */
writejmps(ix)                                                          writejmps
        int     ix;
{
        char    *mktemp();

if (!fj) {
                if (mktemp(jname) < 0) {
                        fprintf(stderr, "%s: can't mktemp() %s\n", prog, jname);
                        cleanup(1);
                }
                if ((fj = fopen(jname, "w")) == 0) {
                        fprintf(stderr, "%s: can't write %s\n", prog, jname);
                        exit(1);
                }
        }
        (void) fwrite((char *)&dx[ix].jp, sizeof(struct jmp), 1, fj);
        (void) fwrite((char *)&dx[ix].offset, sizeof(dx[ix].offset), 1, fj);
}
```

Page 4 of nwsubr.c

FIG._19Q

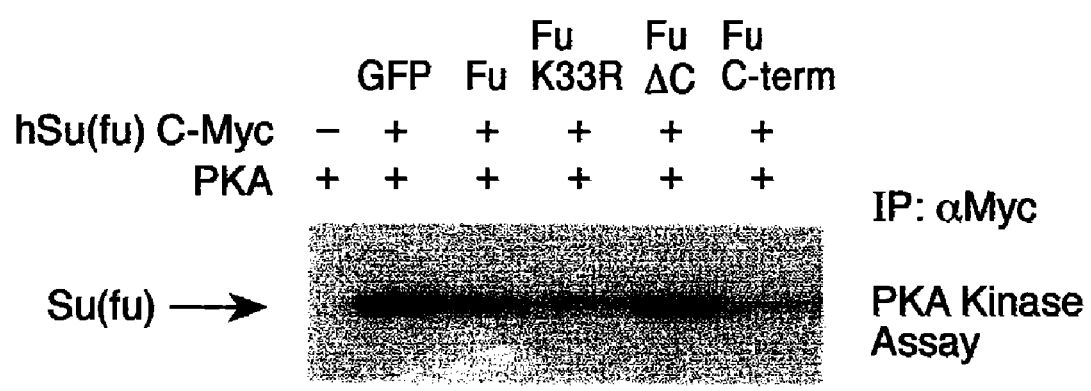
FIG._20

SEQUENCE LISTING

<160> NUMBER OF SEQ ID NOS: 28

<210> SEQ ID NO 1
<211> LENGTH: 4880
<212> TYPE: DNA
<213> ORGANISM: Homo sapiens
<220> FEATURE:
<221> NAME/KEY: unknown N
<222> LOCATION: 4160, 4243, 4361
<223> OTHER INFORMATION: unknown

<400> SEQUENCE: 1

```
cccggggatc ctctagagat ccctcgacct cgacccacgc gtccgcccac              50
gcgtccgccc acgcgtccgg ggcgtcccag atgttgtgga actgtccctg             100
gatctatagc tcttcaccgt ctctactttc ttccttctaa gagatcctga             150
aacctctgtc  atg gaa aag tac cac gtg ttg gag atg att               190
            Met Glu Lys Tyr His Val Leu Glu Met Ile
              1               5                  10 gga gaa ggc tct ttt ggg agg gtg tac aag ggt cga aga                229
Gly Glu Gly Ser Phe Gly Arg Val Tyr Lys Gly Arg Arg
                15                  20 aaa tac agt gct cag gtc gtg gcc ctg aag ttc atc cca                268
Lys Tyr Ser Ala Gln Val Val Ala Leu Lys Phe Ile Pro
 25                  30                  35 aaa ttg ggg cgc tca gag aag gag ctg agg aat ttg caa                307
Lys Leu Gly Arg Ser Glu Lys Glu Leu Arg Asn Leu Gln
                40                  45 cga gag att gaa ata atg cgg ggt ctg cgg cat ccc aac                346
Arg Glu Ile Glu Ile Met Arg Gly Leu Arg His Pro Asn
 50                  55                  60 att gtg cat atg ctt gac agc ttt gaa act gat aaa gag                385
Ile Val His Met Leu Asp Ser Phe Glu Thr Asp Lys Glu
                65                  70                  75 gtg gtg gtg gtg aca gac tat gct gag gga gag ctc ttt                424
Val Val Val Val Thr Asp Tyr Ala Glu Gly Glu Leu Phe
                80                  85 cag atc cta gaa gat gac gga aaa ctt cct gaa gac cag                463
Gln Ile Leu Glu Asp Asp Gly Lys Leu Pro Glu Asp Gln
 90                  95                 100 gtt cag gcc att gct gcc cag ttg gtg tca gcc ctg tac                502
Val Gln Ala Ile Ala Ala Gln Leu Val Ser Ala Leu Tyr
                105                 110 tat ctg cat tcc cac cgc atc cta cac cga gat atg aag                541
Tyr Leu His Ser His Arg Ile Leu His Arg Asp Met Lys
115                 120                 125 cct cag aac atc ctc ctc gcc aag ggt ggt ggc atc aag                580
```

-continued

| | | |
|---|---|---|
| Pro Gln Asn Ile Leu Leu Ala Lys Gly Gly Ile Lys<br>130                135                140 | | |
| ctc tgt gac ttt gga ttt gcc cgg gct atg agc acc aat<br>Leu Cys Asp Phe Gly Phe Ala Arg Ala Met Ser Thr Asn<br>                145                150 | 619 | |
| aca atg gtg ctg aca tcc atc aaa ggc aca cca ctc tat<br>Thr Met Val Leu Thr Ser Ile Lys Gly Thr Pro Leu Tyr<br>    155                160                165 | 658 | |
| atg tct cca gag ctg gtg gag gag cga cca tac gac cac<br>Met Ser Pro Glu Leu Val Glu Glu Arg Pro Tyr Asp His<br>        170              175 | 697 | |
| aca gcg gac ctc tgg tct gtt ggc tgc ata cta tat gaa<br>Thr Ala Asp Leu Trp Ser Val Gly Cys Ile Leu Tyr Glu<br>180                185                190 | 736 | |
| ctg gca gta ggc acc cct ccc ttc tat gct aca agc atc<br>Leu Ala Val Gly Thr Pro Pro Phe Tyr Ala Thr Ser Ile<br>            195                200              205 | 775 | |
| ttt cag ctg gtc agc ctc att ctc aag gac cct gtg cgc<br>Phe Gln Leu Val Ser Leu Ile Leu Lys Asp Pro Val Arg<br>                210                215 | 814 | |
| tgg ccc tca acc atc agt ccc tgc ttt aag aac ttc ctg<br>Trp Pro Ser Thr Ile Ser Pro Cys Phe Lys Asn Phe Leu<br>    220                225                230 | 853 | |
| cag gga ctg ctc acc aaa gac cca cgg cag cga ctg tcc<br>Gln Gly Leu Leu Thr Lys Asp Pro Arg Gln Arg Leu Ser<br>        235              240 | 892 | |
| tgg cca gac ctc tta tat cac ccc ttt att gct ggt cat<br>Trp Pro Asp Leu Leu Tyr His Pro Phe Ile Ala Gly His<br>245                250                255 | 931 | |
| gtc acc ata ata act gag cca gca ggc cca gat ttg ggg<br>Val Thr Ile Ile Thr Glu Pro Ala Gly Pro Asp Leu Gly<br>            260                265              270 | 970 | |
| acc cca ttc acc agc cgc cta ccc cca gaa ctt cag gtc<br>Thr Pro Phe Thr Ser Arg Leu Pro Pro Glu Leu Gln Val<br>                275                280 | 1009 | |
| cta aag gac gaa cag gcc cat cgg ttg gcc ccc aag ggt<br>Leu Lys Asp Glu Gln Ala His Arg Leu Ala Pro Lys Gly<br>    285                290                295 | 1048 | |
| aat cag tct cgc atc ttg act cag gcc tat aaa cgc atg<br>Asn Gln Ser Arg Ile Leu Thr Gln Ala Tyr Lys Arg Met<br>        300              305 | 1087 | |
| gct gag gag gcc atg cag aag aaa cat cag aac aca gga<br>Ala Glu Glu Ala Met Gln Lys Lys His Gln Asn Thr Gly<br>310                315                320 | 1126 | |
| cct gcc ctt gag caa gag gac aag acc agc aag gtg gct<br>Pro Ala Leu Glu Gln Glu Asp Lys Thr Ser Lys Val Ala<br>            325                330              335 | 1165 | |
| cct ggc aca gcc cct ctg ccc aga ctc ggg gcc act cct<br>Pro Gly Thr Ala Pro Leu Pro Arg Leu Gly Ala Thr Pro<br>                340                345 | 1204 | |
| cag gaa tca agc ctc ctg gcc ggg atc tta gcc tca gaa<br>Gln Glu Ser Ser Leu Leu Ala Gly Ile Leu Ala Ser Glu<br>    350                355                360 | 1243 | |
| ttg aag agc agc tgg gct aaa tca ggg act gga gag gtg<br>Leu Lys Ser Ser Trp Ala Lys Ser Gly Thr Gly Glu Val<br>        365              370 | 1282 | |
| ccc tct gca cct cgg gaa aac cgg acc acc cca gat tgt<br>Pro Ser Ala Pro Arg Glu Asn Arg Thr Thr Pro Asp Cys<br>375                380                385 | 1321 | |
| gaa cga gca ttc cca gag gag agg cca gag gtg ctg ggc | 1360 | |

-continued

```
        Glu Arg Ala Phe Pro Glu Glu Arg Pro Glu Val Leu Gly
                390                 395                 400 cag cgg agc act gat gta gtg gac ctg gaa aat gag gag         1399
Gln Arg Ser Thr Asp Val Val Asp Leu Glu Asn Glu Glu
                405                 410 cca gac agt gac aat gag tgg cag cac cta gag acc             1438
Pro Asp Ser Asp Asn Glu Trp Gln His Leu Leu Glu Thr
    415                 420                 425 act gag cct gtg cct att caa ctg aag gct cct ctc acc         1477
Thr Glu Pro Val Pro Ile Gln Leu Lys Ala Pro Leu Thr
                430                 435 ttg ctg tgt aat cct gac ttc tgc cag cgc atc cag agt         1516
Leu Leu Cys Asn Pro Asp Phe Cys Gln Arg Ile Gln Ser
440                 445                 450 cag ctg cat gaa gct gga ggg cag atc ctg aaa ggc atc         1555
Gln Leu His Glu Ala Gly Gly Gln Ile Leu Lys Gly Ile
                455                 460                 465 ttg gag ggt gct tcc cac atc ctg cct gca ttc cgg gtc         1594
Leu Glu Gly Ala Ser His Ile Leu Pro Ala Phe Arg Val
                    470                 475 ctg agc agt ctt ctc tcc agc tgc agt gat tct gtt gcc         1633
Leu Ser Ser Leu Leu Ser Ser Cys Ser Asp Ser Val Ala
480                 485                 490 ttg tat tcc ttc tgc cgg gag gca ggg ctt cct ggg ctg         1672
Leu Tyr Ser Phe Cys Arg Glu Ala Gly Leu Pro Gly Leu
                495                 500 ctg ctg agt cta ctc agg cac agt cag gag agc aac agc         1711
Leu Leu Ser Leu Leu Arg His Ser Gln Glu Ser Asn Ser
505                 510                 515 ctc cag cag caa tct tgg tat ggg acc ttc tta cag gac         1750
Leu Gln Gln Gln Ser Trp Tyr Gly Thr Phe Leu Gln Asp
        520                 525                 530 ctg atg gct gtg att cag gcc tac ttt gcc tgt acc ttc         1789
Leu Met Ala Val Ile Gln Ala Tyr Phe Ala Cys Thr Phe
                535                 540 aat ctg gag agg agc cag aca agt gac agc ctg cag gtg         1828
Asn Leu Glu Arg Ser Gln Thr Ser Asp Ser Leu Gln Val
    545                 550                 555 ttt cag gag gct gcc aac ctt ttt ctg gac ctg ttg ggg         1867
Phe Gln Glu Ala Ala Asn Leu Phe Leu Asp Leu Leu Gly
                560                 565 aaa ctg ctg gcc caa cca gat gac tct gag cag act ttg         1906
Lys Leu Leu Ala Gln Pro Asp Asp Ser Glu Gln Thr Leu
570                 575                 580 cgg agg gac agc ctt atg tgc ttt act gtc ctg tgc gaa         1945
Arg Arg Asp Ser Leu Met Cys Phe Thr Val Leu Cys Glu
        585                 590                 595 gcc atg gat ggg aac agc cgg gcc atc tcc aaa gcc ttt         1984
Ala Met Asp Gly Asn Ser Arg Ala Ile Ser Lys Ala Phe
                600                 605 tac tcc agc ttg ctg acg aca cag cag gtt gtc ttg gat         2023
Tyr Ser Ser Leu Leu Thr Thr Gln Gln Val Val Leu Asp
    610                 615                 620 ggg ctc ctt cat ggc ttg aca gtt cca cag ctc cct gtc         2062
Gly Leu Leu His Gly Leu Thr Val Pro Gln Leu Pro Val
                625                 630 cac act ccc caa gga gcc ccg caa gtg agc cag cca ctg         2101
His Thr Pro Gln Gly Ala Pro Gln Val Ser Gln Pro Leu
635                 640                 645 cga gag cag agt gag gat ata cct gga gcc att tcc tct         2140
```

```
                    Arg Glu Gln Ser Glu Asp Ile Pro Gly Ala Ile Ser Ser
                            650                 655                 660 gcc ctg gca gcc ata tgc act gct cct gtg gga ctg ccc                         2179
Ala Leu Ala Ala Ile Cys Thr Ala Pro Val Gly Leu Pro
                665                 670 gac tgc tgg gat gcc aag gag cag gtc tgt tgg cat ttg                         2218
Asp Cys Trp Asp Ala Lys Glu Gln Val Cys Trp His Leu
        675                 680                 685 gca aat cag cta act gaa gac agc agc cag ctc agg cca                         2257
Ala Asn Gln Leu Thr Glu Asp Ser Ser Gln Leu Arg Pro
                690                 695 tcc ctc atc tct ggc ctg cag cat ccc atc ctg tgc ctg                         2296
Ser Leu Ile Ser Gly Leu Gln His Pro Ile Leu Cys Leu
700                 705                 710 cac ctt ctc aag gtt cta tac tcc tgc tgc ctt gtc agt                         2335
His Leu Leu Lys Val Leu Tyr Ser Cys Cys Leu Val Ser
            715                 720                 725 gag ggc ctg tgc cgt ctt ctg ggg cag gag ccc ctg gcc                         2374
Glu Gly Leu Cys Arg Leu Leu Gly Gln Glu Pro Leu Ala
                    730                 735 ttg gaa tcc ctg ttt atg ttg att cag ggc aag gta aaa                         2413
Leu Glu Ser Leu Phe Met Leu Ile Gln Gly Lys Val Lys
        740                 745                 750 gta gta gat tgg gaa gag tct act gaa gtg aca ctc tac                         2452
Val Val Asp Trp Glu Glu Ser Thr Glu Val Thr Leu Tyr
                755                 760 ttc ctc tcc ctt ctt gtc ttt cgg ctc caa aac ctg cct                         2491
Phe Leu Ser Leu Leu Val Phe Arg Leu Gln Asn Leu Pro
765                 770                 775 tgt gga atg gag aag cta ggc agt gac gtt gct act ctc                         2530
Cys Gly Met Glu Lys Leu Gly Ser Asp Val Ala Thr Leu
            780                 785                 790 ttt acc cat tcg cat gtc gtc tct ctt gtg agt gca gca                         2569
Phe Thr His Ser His Val Val Ser Leu Val Ser Ala Ala
                    795                 800 gcc tgt cta ttg gga cag ctt ggt cag caa ggg gtg acc                         2608
Ala Cys Leu Leu Gly Gln Leu Gly Gln Gln Gly Val Thr
        805                 810                 815 ttt gac ctc cag ccc atg gaa tgg atg gct gca gcc aca                         2647
Phe Asp Leu Gln Pro Met Glu Trp Met Ala Ala Ala Thr
                820                 825 cat gcc ttg tct gcc cct gca gag gtt cgg ttg act cca                         2686
His Ala Leu Ser Ala Pro Ala Glu Val Arg Leu Thr Pro
830                 835                 840 cca ggt agt tgt gga ttc tat gat ggc ctc ctt atc ctt                         2725
Pro Gly Ser Cys Gly Phe Tyr Asp Gly Leu Leu Ile Leu
            845                 850                 855 ctg ttg cag ctc ctc act gag cag ggg aag gct agc cta                         2764
Leu Leu Gln Leu Leu Thr Glu Gln Gly Lys Ala Ser Leu
                    860                 865 atc agg gat atg tcc agt tca gaa atg tgg acc gtt ttg                         2803
Ile Arg Asp Met Ser Ser Ser Glu Met Trp Thr Val Leu
        870                 875                 880 tgg cac cgc ttc tcc atg gtc ctg agg ctc ccc gag gag                         2842
Trp His Arg Phe Ser Met Val Leu Arg Leu Pro Glu Glu
                885                 890 gca tct gca cag gaa ggg gag ctt tcg cta tcc agt cca                         2881
Ala Ser Ala Gln Glu Gly Glu Leu Ser Leu Ser Ser Pro
895                 900                 905 cca agc cct gag cca gac tgg aca ctg att tct ccc cag                         2920
```

```
                                                     -continued

Pro Ser Pro Glu Pro Asp Trp Thr Leu Ile Ser Pro Gln
        910             915             920 ggc atg gca gcc ctg ctg agc ctg gcc atg gcc acc ttt              2959
Gly Met Ala Ala Leu Leu Ser Leu Ala Met Ala Thr Phe
                925             930 acc cag gag ccc cag tta tgc ctg agc tgc ctg tcc cag              2998
Thr Gln Glu Pro Gln Leu Cys Leu Ser Cys Leu Ser Gln
        935             940             945 cat gga agt atc ctc atg tcc atc ctg aag cat ctg ctt              3037
His Gly Ser Ile Leu Met Ser Ile Leu Lys His Leu Leu
                950             955 tgc ccc agc ttc ctg aat caa ctg cgc cag gcg cct cat              3076
Cys Pro Ser Phe Leu Asn Gln Leu Arg Gln Ala Pro His
960             965             970 ggg tct gag ttt ctc cct gtc gtg gtg ctc tct gtc tgc              3115
Gly Ser Glu Phe Leu Pro Val Val Val Leu Ser Val Cys
        975             980             985 cag ctc ctt tgc ttc ccc ttt gcg ctg gac atg gat gct              3154
Gln Leu Leu Cys Phe Pro Phe Ala Leu Asp Met Asp Ala
                990             995 gac ctc ctt ata gtt gtc ttg gcc gac ctc agg gac tca              3193
Asp Leu Leu Ile Val Val Leu Ala Asp Leu Arg Asp Ser
        1000            1005            1010 gaa gtt gca gcc cat ctg ctg cag gtc tgc tgc tac cat              3232
Glu Val Ala Ala His Leu Leu Gln Val Cys Cys Tyr His
                1015            1020 ctt ccg ttg atg caa gtg gag ctg ccc atc agc ctt ctc              3271
Leu Pro Leu Met Gln Val Glu Leu Pro Ile Ser Leu Leu
1025            1030            1035 aca cgc ctg gcc ctc atg gat ccc acc tct ctc aac cag              3310
Thr Arg Leu Ala Leu Met Asp Pro Thr Ser Leu Asn Gln
        1040            1045            1050 ttt gtg aac aca gtg tct gcc tcc cct aga acc atc gtc              3349
Phe Val Asn Thr Val Ser Ala Ser Pro Arg Thr Ile Val
                1055            1060 tcg ttt ctc tca gtt gcc ctc ctg agt gac cag cca ctg              3388
Ser Phe Leu Ser Val Ala Leu Leu Ser Asp Gln Pro Leu
        1065            1070            1075 ttg acc tcc gac ctt ctc tct ctg ctg gcc cat act gcc              3427
Leu Thr Ser Asp Leu Leu Ser Leu Leu Ala His Thr Ala
                1080            1085 agg gtc ctg tct ccc agc cac ttg tcc ttt atc caa gag              3466
Arg Val Leu Ser Pro Ser His Leu Ser Phe Ile Gln Glu
1090            1095            1100 ctt ctg gct ggc tct gat gaa tcc tat cgg ccc ctg cgc              3505
Leu Leu Ala Gly Ser Asp Glu Ser Tyr Arg Pro Leu Arg
        1105            1110            1115 agc ctc ctg ggc cac cca gag aat tct gtg cgg gca cac              3544
Ser Leu Leu Gly His Pro Glu Asn Ser Val Arg Ala His
                1120            1125 act tat agg ctc ctg gga cac ttg ctc caa cac agc atg              3583
Thr Tyr Arg Leu Leu Gly His Leu Leu Gln His Ser Met
        1130            1135            1140 gcc ctg cgt ggg gca ctg cag agc cag tct gga ctg ctc              3622
Ala Leu Arg Gly Ala Leu Gln Ser Gln Ser Gly Leu Leu
                1145            1150 agc ctt ctg ctg ctt ggg ctt gga gac aag gat cct gtt              3661
Ser Leu Leu Leu Leu Gly Leu Gly Asp Lys Asp Pro Val
1155            1160            1165 gtg cgg tgc agt gcc agc ttt gct gtg ggc aat gca gcc              3700
```

| | | |
|---|---|---|
| Val Arg Cys Ser Ala Ser Phe Ala Val Gly Asn Ala Ala<br>     1170               1175             1180 | | |
| tac cag gct ggt cct ctg gga cct gcc ctg gca gct gca<br>Tyr Gln Ala Gly Pro Leu Gly Pro Ala Leu Ala Ala Ala<br>               1185             1190 | | 3739 |
| gtg ccc agt atg acc cag ctg ctt gga gat cct cag gct<br>Val Pro Ser Met Thr Gln Leu Leu Gly Asp Pro Gln Ala<br>     1195              1200             1205 | | 3778 |
| ggt atc cgg cgc aat gtt gca tca gct ctg ggc aac ttg<br>Gly Ile Arg Arg Asn Val Ala Ser Ala Leu Gly Asn Leu<br>           1210              1215 | | 3817 |
| gga cct gaa ggt ttg gga gag gag ctg tta cag tgc gaa<br>Gly Pro Glu Gly Leu Gly Glu Glu Leu Leu Gln Cys Glu<br>1220              1225             1230 | | 3856 |
| gta ccc cag cgg ctc cta gaa atg gca tgt gga gac ccc<br>Val Pro Gln Arg Leu Leu Glu Met Ala Cys Gly Asp Pro<br>     1235              1240             1245 | | 3895 |
| cag cca aat gtg aag gag gct gcc ctc att gcc ctc cgg<br>Gln Pro Asn Val Lys Glu Ala Ala Leu Ile Ala Leu Arg<br>           1250              1255 | | 3934 |
| agc ctg caa cag gag cct ggc atc cat cag gta ctg gtg<br>Ser Leu Gln Gln Glu Pro Gly Ile His Gln Val Leu Val<br>     1260              1265             1270 | | 3973 |
| tcc ctg ggt gcc agt gag aaa cta tcc ttg ctc tct ctg<br>Ser Leu Gly Ala Ser Glu Lys Leu Ser Leu Leu Ser Leu<br>           1275              1280 | | 4012 |
| ggg aat cag tca ctg cca cac agc agt cct agg cct gcc<br>Gly Asn Gln Ser Leu Pro His Ser Ser Pro Arg Pro Ala<br>1285              1290             1295 | | 4051 |
| tct gcc aaa cac tgc agg aaa ctc att cac ctc ctg agg<br>Ser Ala Lys His Cys Arg Lys Leu Ile His Leu Leu Arg<br>     1300              1305             1310 | | 4090 |
| cca gcc cat agc atg tgatt ccagattcct gcggtccagc<br>Pro Ala His Ser Met<br>           1315 | | 4130 |
| ctccaacttt ggtgccagct ctttcttatn taatacacaa gcgccaaytc | | 4180 |
| aactgagagc taaagagact agaaaagaga taagctgcca actcaactga | | 4230 |
| gaacaggaaa ctngaagaga tttatatata aagcttcttc cttctcccag | | 4280 |
| atgcaggatg ttttcaacca gtaaatttta ttgctgttgg tgccagagaa | | 4330 |
| gagtcccttt cttctctaca tccagggggcc nttttctcca ataatgtgcc | | 4380 |
| tttaactcta gggacctgcc tcacggacct tagggaaaaa cctcaacctg | | 4430 |
| aaagatctct tcctttctgg agctccttta atcttcccag caggttttttg | | 4480 |
| ccttagacgt gctggcccca ggacagtgat gaagacagag cctgtctcag | | 4530 |
| ctctaggctg tggggatcaa tgccatcagt ccctgttatt gagggattat | | 4580 |
| cccttagcca acattcctat ctgtgggtgg gcgtggagag tgtatctttt | | 4630 |
| tttggggtgt gtgtgtatat gtgtgtgtgt atgtgtgtgt gtgtttaata | | 4680 |
| gttctgtttg taaactcttt taataaaagt tgtgcctcac catacttgaa | | 4730 |
| gctcccagga caagggttga gaggctcaac ccctctttca gcttctatgt | | 4780 |
| ggtgttggag gtgctggtat cgtgttcaca caaaaaaaaa aaaaaaaaa | | 4830 |
| aaaaaaaaaa aaaaaaaaaa aaaaaaaaaa aaaaaaaaaa aaaaaaaaaa | | 4880 |

<210> SEQ ID NO 2
<211> LENGTH: 1315

```
<212> TYPE: PRT
<213> ORGANISM: Homo sapiens

<400> SEQUENCE: 2

Met Glu Lys Tyr His Val Leu Glu Met Ile Gly Glu Gly Ser Phe
 1               5                  10                  15

Gly Arg Val Tyr Lys Gly Arg Arg Lys Tyr Ser Ala Gln Val Val
                20                  25                  30

Ala Leu Lys Phe Ile Pro Lys Leu Gly Arg Ser Glu Lys Glu Leu
                35                  40                  45

Arg Asn Leu Gln Arg Glu Ile Glu Ile Met Arg Gly Leu Arg His
                50                  55                  60

Pro Asn Ile Val His Met Leu Asp Ser Phe Glu Thr Asp Lys Glu
                65                  70                  75

Val Val Val Val Thr Asp Tyr Ala Glu Gly Glu Leu Phe Gln Ile
                80                  85                  90

Leu Glu Asp Asp Gly Lys Leu Pro Glu Asp Gln Val Gln Ala Ile
                95                  100                 105

Ala Ala Gln Leu Val Ser Ala Leu Tyr Tyr Leu His Ser His Arg
                110                 115                 120

Ile Leu His Arg Asp Met Lys Pro Gln Asn Ile Leu Leu Ala Lys
                125                 130                 135

Gly Gly Gly Ile Lys Leu Cys Asp Phe Gly Phe Ala Arg Ala Met
                140                 145                 150

Ser Thr Asn Thr Met Val Leu Thr Ser Ile Lys Gly Thr Pro Leu
                155                 160                 165

Tyr Met Ser Pro Glu Leu Val Glu Glu Arg Pro Tyr Asp His Thr
                170                 175                 180

Ala Asp Leu Trp Ser Val Gly Cys Ile Leu Tyr Glu Leu Ala Val
                185                 190                 195

Gly Thr Pro Pro Phe Tyr Ala Thr Ser Ile Phe Gln Leu Val Ser
                200                 205                 210

Leu Ile Leu Lys Asp Pro Val Arg Trp Pro Ser Thr Ile Ser Pro
                215                 220                 225

Cys Phe Lys Asn Phe Leu Gln Gly Leu Leu Thr Lys Asp Pro Arg
                230                 235                 240

Gln Arg Leu Ser Trp Pro Asp Leu Leu Tyr His Pro Phe Ile Ala
                245                 250                 255

Gly His Val Thr Ile Ile Thr Glu Pro Ala Gly Pro Asp Leu Gly
                260                 265                 270

Thr Pro Phe Thr Ser Arg Leu Pro Pro Glu Leu Gln Val Leu Lys
                275                 280                 285

Asp Glu Gln Ala His Arg Leu Ala Pro Lys Gly Asn Gln Ser Arg
                290                 295                 300

Ile Leu Thr Gln Ala Tyr Lys Arg Met Ala Glu Ala Met Gln
                305                 310                 315

Lys Lys His Gln Asn Thr Gly Pro Ala Leu Glu Gln Glu Asp Lys
                320                 325                 330

Thr Ser Lys Val Ala Pro Gly Thr Ala Pro Leu Pro Arg Leu Gly
                335                 340                 345

Ala Thr Pro Gln Glu Ser Ser Leu Leu Ala Gly Ile Leu Ala Ser
                350                 355                 360

Glu Leu Lys Ser Ser Trp Ala Lys Ser Gly Thr Gly Glu Val Pro
                365                 370                 375
```

-continued

```
Ser Ala Pro Arg Glu Asn Arg Thr Thr Pro Asp Cys Glu Arg Ala
            380                 385                 390
Phe Pro Glu Glu Arg Pro Glu Val Leu Gly Gln Arg Ser Thr Asp
            395                 400                 405
Val Val Asp Leu Glu Asn Glu Glu Pro Asp Ser Asp Asn Glu Trp
            410                 415                 420
Gln His Leu Leu Glu Thr Thr Glu Pro Val Pro Ile Gln Leu Lys
            425                 430                 435
Ala Pro Leu Thr Leu Leu Cys Asn Pro Asp Phe Cys Gln Arg Ile
            440                 445                 450
Gln Ser Gln Leu His Glu Ala Gly Gly Gln Ile Leu Lys Gly Ile
            455                 460                 465
Leu Glu Gly Ala Ser His Ile Leu Pro Ala Phe Arg Val Leu Ser
            470                 475                 480
Ser Leu Leu Ser Ser Cys Ser Asp Ser Val Ala Leu Tyr Ser Phe
            485                 490                 495
Cys Arg Glu Ala Gly Leu Pro Gly Leu Leu Leu Ser Leu Leu Arg
            500                 505                 510
His Ser Gln Glu Ser Asn Ser Leu Gln Gln Gln Ser Trp Tyr Gly
            515                 520                 525
Thr Phe Leu Gln Asp Leu Met Ala Val Ile Gln Ala Tyr Phe Ala
            530                 535                 540
Cys Thr Phe Asn Leu Glu Arg Ser Gln Thr Ser Asp Ser Leu Gln
            545                 550                 555
Val Phe Gln Glu Ala Ala Asn Leu Phe Leu Asp Leu Leu Gly Lys
            560                 565                 570
Leu Leu Ala Gln Pro Asp Asp Ser Glu Gln Thr Leu Arg Arg Asp
            575                 580                 585
Ser Leu Met Cys Phe Thr Val Leu Cys Glu Ala Met Asp Gly Asn
            590                 595                 600
Ser Arg Ala Ile Ser Lys Ala Phe Tyr Ser Ser Leu Leu Thr Thr
            605                 610                 615
Gln Gln Val Val Leu Asp Gly Leu Leu His Gly Leu Thr Val Pro
            620                 625                 630
Gln Leu Pro Val His Thr Pro Gln Gly Ala Pro Gln Val Ser Gln
            635                 640                 645
Pro Leu Arg Glu Gln Ser Glu Asp Ile Pro Gly Ala Ile Ser Ser
            650                 655                 660
Ala Leu Ala Ala Ile Cys Thr Ala Pro Val Gly Leu Pro Asp Cys
            665                 670                 675
Trp Asp Ala Lys Glu Gln Val Cys Trp His Leu Ala Asn Gln Leu
            680                 685                 690
Thr Glu Asp Ser Ser Gln Leu Arg Pro Ser Leu Ile Ser Gly Leu
            695                 700                 705
Gln His Pro Ile Leu Cys Leu His Leu Leu Lys Val Leu Tyr Ser
            710                 715                 720
Cys Cys Leu Val Ser Glu Gly Leu Cys Arg Leu Leu Gly Gln Glu
            725                 730                 735
Pro Leu Ala Leu Glu Ser Leu Phe Met Leu Ile Gln Gly Lys Val
            740                 745                 750
Lys Val Val Asp Trp Glu Glu Ser Thr Glu Val Thr Leu Tyr Phe
            755                 760                 765
Leu Ser Leu Leu Val Phe Arg Leu Gln Asn Leu Pro Cys Gly Met
            770                 775                 780
```

```
Glu Lys Leu Gly Ser Asp Val Ala Thr Leu Phe Thr His Ser His
                785                 790                 795
Val Val Ser Leu Val Ser Ala Ala Cys Leu Leu Gly Gln Leu
                800                 805                 810
Gly Gln Gln Gly Val Thr Phe Asp Leu Gln Pro Met Glu Trp Met
                815                 820                 825
Ala Ala Ala Thr His Ala Leu Ser Ala Pro Ala Glu Val Arg Leu
                830                 835                 840
Thr Pro Pro Gly Ser Cys Gly Phe Tyr Asp Gly Leu Leu Ile Leu
                845                 850                 855
Leu Leu Gln Leu Leu Thr Glu Gln Gly Lys Ala Ser Leu Ile Arg
                860                 865                 870
Asp Met Ser Ser Ser Glu Met Trp Thr Val Leu Trp His Arg Phe
                875                 880                 885
Ser Met Val Leu Arg Leu Pro Glu Glu Ala Ser Ala Gln Glu Gly
                890                 895                 900
Glu Leu Ser Leu Ser Ser Pro Pro Ser Pro Glu Pro Asp Trp Thr
                905                 910                 915
Leu Ile Ser Pro Gln Gly Met Ala Ala Leu Leu Ser Leu Ala Met
                920                 925                 930
Ala Thr Phe Thr Gln Glu Pro Gln Leu Cys Leu Ser Cys Leu Ser
                935                 940                 945
Gln His Gly Ser Ile Leu Met Ser Ile Leu Lys His Leu Leu Cys
                950                 955                 960
Pro Ser Phe Leu Asn Gln Leu Arg Gln Ala Pro His Gly Ser Glu
                965                 970                 975
Phe Leu Pro Val Val Val Leu Ser Val Cys Gln Leu Leu Cys Phe
                980                 985                 990
Pro Phe Ala Leu Asp Met Asp Ala Asp Leu Leu Ile Val Val Leu
                995                 1000                1005
Ala Asp Leu Arg Asp Ser Glu Val Ala Ala His Leu Leu Gln Val
                1010                1015                1020
Cys Cys Tyr His Leu Pro Leu Met Gln Val Glu Leu Pro Ile Ser
                1025                1030                1035
Leu Leu Thr Arg Leu Ala Leu Met Asp Pro Thr Ser Leu Asn Gln
                1040                1045                1050
Phe Val Asn Thr Val Ser Ala Ser Pro Arg Thr Ile Val Ser Phe
                1055                1060                1065
Leu Ser Val Ala Leu Leu Ser Asp Gln Pro Leu Leu Thr Ser Asp
                1070                1075                1080
Leu Leu Ser Leu Leu Ala His Thr Ala Arg Val Leu Ser Pro Ser
                1085                1090                1095
His Leu Ser Phe Ile Gln Glu Leu Leu Ala Gly Ser Asp Glu Ser
                1100                1105                1110
Tyr Arg Pro Leu Arg Ser Leu Leu Gly His Pro Glu Asn Ser Val
                1115                1120                1125
Arg Ala His Thr Tyr Arg Leu Gly His Leu Leu Gln His Ser
                1130                1135                1140
Met Ala Leu Arg Gly Ala Leu Gln Ser Gln Ser Gly Leu Leu Ser
                1145                1150                1155
Leu Leu Leu Leu Gly Leu Gly Asp Lys Asp Pro Val Val Arg Cys
                1160                1165                1170
Ser Ala Ser Phe Ala Val Gly Asn Ala Ala Tyr Gln Ala Gly Pro
```

```
                   1175                1180                1185
Leu Gly Pro Ala Leu Ala Ala Val Pro Ser Met Thr Gln Leu
                1190                1195                1200

Leu Gly Asp Pro Gln Ala Gly Ile Arg Arg Asn Val Ala Ser Ala
                1205                1210                1215

Leu Gly Asn Leu Gly Pro Glu Gly Leu Gly Glu Leu Leu Gln
                1220                1225                1230

Cys Glu Val Pro Gln Arg Leu Leu Glu Met Ala Cys Gly Asp Pro
                1235                1240                1245

Gln Pro Asn Val Lys Glu Ala Ala Leu Ile Ala Leu Arg Ser Leu
                1250                1255                1260

Gln Gln Glu Pro Gly Ile His Gln Val Leu Val Ser Leu Gly Ala
                1265                1270                1275

Ser Glu Lys Leu Ser Leu Leu Ser Leu Gly Asn Gln Ser Leu Pro
                1280                1285                1290

His Ser Ser Pro Arg Pro Ala Ser Ala Lys His Cys Arg Lys Leu
                1295                1300                1305

Ile His Leu Leu Arg Pro Ala His Ser Met
                1310                1315

<210> SEQ ID NO 3
<211> LENGTH: 193
<212> TYPE: DNA
<213> ORGANISM: Homo sapiens

<400> SEQUENCE: 3
cccgggctat gagcaccaat acaatggtgc tgacatccat caaaggcaca        50
ccactctata tgtctccaga gctggtggag gagcgaccat acgaccacac       100
agcggacctc tggtctgttg ctgcatact atatgaactg gcagtaggca        150
cccctccctt ctaatgctac aagcatcttt cagctggtca gcc              193

<210> SEQ ID NO 4
<211> LENGTH: 5125
<212> TYPE: DNA
<213> ORGANISM: Homo sapiens

<400> SEQUENCE: 4
cccacgcgtc cgcccacgcg tccggggcgt cccagatgtt gtggaactgt        50
ccctggatct atagctcttc accgtctcta ctttcttcct tctaagagat       100
cctgaaacct ctgtc    atg gaa aag tac cac gtg ttg gag          139
                 Met Glu Lys Tyr His Val Leu Glu
                  1               5 atg att gga gaa ggc tct ttt ggg agg gtg tac aag ggt           178
Met Ile Gly Glu Gly Ser Phe Gly Arg Val Tyr Lys Gly
 10              15                  20 cga aga aaa tac agt gct cag gtc gtg gcc ctg aag ttc           217
Arg Arg Lys Tyr Ser Ala Gln Val Val Ala Leu Lys Phe
          25                  30 atc cca aaa ttg ggg cgc tca gag aag gag ctg agg aat           256
Ile Pro Lys Leu Gly Arg Ser Glu Lys Glu Leu Arg Asn
 35              40                  45 ttg caa cga gag att gaa ata atg cgg ggt ctg cgg cat           295
Leu Gln Arg Glu Ile Glu Ile Met Arg Gly Leu Arg His
         50                  55                  60 ccc aac att gtg cat atg ctt gac agc ttt gaa act gat           334
Pro Asn Ile Val His Met Leu Asp Ser Phe Glu Thr Asp
                 65                  70
```

| | | |
|---|---|---|
| aaa gag gtg gtg gtg gtg aca gac tat gct gag gga gag<br>Lys Glu Val Val Val Val Thr Asp Tyr Ala Glu Gly Glu<br>75　　　　　　　　80　　　　　　　　85 | | 373 |
| ctc ttt cag atc cta gaa gat gac gga aaa ctt cct gaa<br>Leu Phe Gln Ile Leu Glu Asp Asp Gly Lys Leu Pro Glu<br>　　　　　　90　　　　　　　　95 | | 412 |
| gac cag gtt cag gcc att gct gcc cag ttg gtg tca gcc<br>Asp Gln Val Gln Ala Ile Ala Ala Gln Leu Val Ser Ala<br>100　　　　　　　105　　　　　　　110 | | 451 |
| ctg tac tat ctg cat tcc cac cgc atc cta cac cga gat<br>Leu Tyr Tyr Leu His Ser His Arg Ile Leu His Arg Asp<br>　　　　　　115　　　　　　　120　　　　　　125 | | 490 |
| atg aag cct cag aac atc ctc ctc gcc aag ggt ggt ggc<br>Met Lys Pro Gln Asn Ile Leu Leu Ala Lys Gly Gly Gly<br>　　　　　　　130　　　　　　　135 | | 529 |
| atc aag ctc tgt gac ttt gga ttt gcc cgg gct atg agc<br>Ile Lys Leu Cys Asp Phe Gly Phe Ala Arg Ala Met Ser<br>140　　　　　　　145　　　　　　　150 | | 568 |
| acc aat aca atg gtg ctg aca tcc atc aaa ggc aca cca<br>Thr Asn Thr Met Val Leu Thr Ser Ile Lys Gly Thr Pro<br>　　　　　　155　　　　　　　160 | | 607 |
| ctc tat atg tct cca gag ctg gtg gag gag cga cca tac<br>Leu Tyr Met Ser Pro Glu Leu Val Glu Glu Arg Pro Tyr<br>165　　　　　　　170　　　　　　　175 | | 646 |
| gac cac aca gcg gac ctc tgg tct gtt ggc tgc ata cta<br>Asp His Thr Ala Asp Leu Trp Ser Val Gly Cys Ile Leu<br>　　　　　　180　　　　　　　185　　　　　　190 | | 685 |
| tat gaa ctg gca gta ggc acc cct ccc ttc tat gct aca<br>Tyr Glu Leu Ala Val Gly Thr Pro Pro Phe Tyr Ala Thr<br>　　　　　　　195　　　　　　　200 | | 724 |
| agc atc ttt cag ctg gtc agc ctc att ctc aag gac cct<br>Ser Ile Phe Gln Leu Val Ser Leu Ile Leu Lys Asp Pro<br>205　　　　　　　210　　　　　　　215 | | 763 |
| gtg cgc tgg ccc tca acc atc agt ccc tgc ttt aag aac<br>Val Arg Trp Pro Ser Thr Ile Ser Pro Cys Phe Lys Asn<br>　　　　　　220　　　　　　　225 | | 802 |
| ttc ctg cag gga ctg ctc acc aaa gac cca cgg cag cga<br>Phe Leu Gln Gly Leu Leu Thr Lys Asp Pro Arg Gln Arg<br>230　　　　　　　235　　　　　　　240 | | 841 |
| ctg tcc tgg cca gac ctc tta tat cac ccc ttt att gct<br>Leu Ser Trp Pro Asp Leu Leu Tyr His Pro Phe Ile Ala<br>　　　　　　245　　　　　　　250　　　　　　255 | | 880 |
| ggt cat gtc acc ata ata act gag cca gca ggc cca gat<br>Gly His Val Thr Ile Ile Thr Glu Pro Ala Gly Pro Asp<br>　　　　　　　260　　　　　　　265 | | 919 |
| ttg ggg acc cca ttc acc agc cgc cta ccc cca gaa ctt<br>Leu Gly Thr Pro Phe Thr Ser Arg Leu Pro Pro Glu Leu<br>270　　　　　　　275　　　　　　　280 | | 958 |
| cag gtc cta aag gac gaa cag gcc cat cgg ttg gcc ccc<br>Gln Val Leu Lys Asp Glu Gln Ala His Arg Leu Ala Pro<br>　　　　　　285　　　　　　　290 | | 997 |
| aag ggt aat cag tct cgc atc ttg act cag gcc tat aaa<br>Lys Gly Asn Gln Ser Arg Ile Leu Thr Gln Ala Tyr Lys<br>295　　　　　　　300　　　　　　　305 | | 1036 |
| cgc atg gct gag gag gcc atg cag aag aaa cat cag aac<br>Arg Met Ala Glu Glu Ala Met Gln Lys Lys His Gln Asn<br>　　　　　　310　　　　　　　315　　　　　　320 | | 1075 |
| aca gga cct gcc ctt gag caa gag gac aag acc agc aag<br>Thr Gly Pro Ala Leu Glu Gln Glu Asp Lys Thr Ser Lys<br>　　　　　　　325　　　　　　　330 | | 1114 |

-continued

| | |
|---|---|
| gtg gct cct ggc aca gcc cct ctg ccc aga ctc ggg gcc<br>Val Ala Pro Gly Thr Ala Pro Leu Pro Arg Leu Gly Ala<br>335                       340                       345 | 1153 |
| act cct cag gaa tca agc ctc ctg gcc ggg atc tta gcc<br>Thr Pro Gln Glu Ser Ser Leu Leu Ala Gly Ile Leu Ala<br>               350                       355 | 1192 |
| tca gaa ttg aag agc agc tgg gct aaa tca ggg act gga<br>Ser Glu Leu Lys Ser Ser Trp Ala Lys Ser Gly Thr Gly<br>360                       365                     370 | 1231 |
| gag gtg ccc tct gca cct cgg gaa aac cgg acc acc cca<br>Glu Val Pro Ser Ala Pro Arg Glu Asn Arg Thr Thr Pro<br>             375                     380              385 | 1270 |
| gat tgt gaa cga gca ttc cca gag gag agg cca gag gtg<br>Asp Cys Glu Arg Ala Phe Pro Glu Glu Arg Pro Glu Val<br>                       390                     395 | 1309 |
| ctg ggc cag cgg agc act gat gta gtg gac ctg gaa aat<br>Leu Gly Gln Arg Ser Thr Asp Val Val Asp Leu Glu Asn<br>400                       405                     410 | 1348 |
| gag gag cca gac agt gac aat gag tgg cag cac ctg cta<br>Glu Glu Pro Asp Ser Asp Asn Glu Trp Gln His Leu Leu<br>             415                     420 | 1387 |
| gag acc act gag cct gtg cct att caa ctg aag gct cct<br>Glu Thr Thr Glu Pro Val Pro Ile Gln Leu Lys Ala Pro<br>425                       430                     435 | 1426 |
| ctc acc ttg ctg tgt aat cct gac ttc tgc cag cgc atc<br>Leu Thr Leu Leu Cys Asn Pro Asp Phe Cys Gln Arg Ile<br>             440                     445              450 | 1465 |
| cag agt cag ctg cat gaa gct gga ggg cag atc ctg aaa<br>Gln Ser Gln Leu His Glu Ala Gly Gly Gln Ile Leu Lys<br>                       455                     460 | 1504 |
| ggc atc ttg gag ggt gct tcc cac atc ctg cct gca ttc<br>Gly Ile Leu Glu Gly Ala Ser His Ile Leu Pro Ala Phe<br>465                       470                     475 | 1543 |
| cgg gtc ctg agc agt ctt ctc tcc agc tgc agt gat tct<br>Arg Val Leu Ser Ser Leu Leu Ser Ser Cys Ser Asp Ser<br>             480                     485 | 1582 |
| gtt gcc ttg tat tcc ttc tgc cgg gag gca ggg ctt cct<br>Val Ala Leu Tyr Ser Phe Cys Arg Glu Ala Gly Leu Pro<br>490                       495                     500 | 1621 |
| ggg ctg ctg ctg agt cta ctc agg cac agt cag gag agc<br>Gly Leu Leu Leu Ser Leu Leu Arg His Ser Gln Glu Ser<br>             505                     510              515 | 1660 |
| aac agc ctc cag cag caa tct tgg tat ggg acc ttc tta<br>Asn Ser Leu Gln Gln Gln Ser Trp Tyr Gly Thr Phe Leu<br>                       520                     525 | 1699 |
| cag gac ctg atg gct gtg att cag gcc tac ttt gcc tgt<br>Gln Asp Leu Met Ala Val Ile Gln Ala Tyr Phe Ala Cys<br>530                       535                     540 | 1738 |
| acc ttc aat ctg gag agg agc cag aca agt gac agc ctg<br>Thr Phe Asn Leu Glu Arg Ser Gln Thr Ser Asp Ser Leu<br>             545                     550 | 1777 |
| cag gtg ttt cag gag gct gcc aac ctt ttt ctg gac ctg<br>Gln Val Phe Gln Glu Ala Ala Asn Leu Phe Leu Asp Leu<br>555                       560                     565 | 1816 |
| ttg ggg aaa ctg ctg gcc caa cca gat gac tct gag cag<br>Leu Gly Lys Leu Leu Ala Gln Pro Asp Asp Ser Glu Gln<br>             570                     575              580 | 1855 |
| act ttg cag agg gac agc ctt atg tgc ttt act gtc ctg<br>Thr Leu Gln Arg Asp Ser Leu Met Cys Phe Thr Val Leu<br>                       585                     590 | 1894 |

|  |  |
|---|---|
| tgc gaa gcc atg gat ggg aac agc cgg gcc atc tcc aaa<br>Cys Glu Ala Met Asp Gly Asn Ser Arg Ala Ile Ser Lys<br>595                    600                   605 | 1933 |
| gcc ttt tac tcc agc ttg ctg acg aca cag cag gtt gtc<br>Ala Phe Tyr Ser Ser Leu Leu Thr Thr Gln Gln Val Val<br>            610                    615 | 1972 |
| ttg gat ggg ctc ctt cat ggc ttg aca gtt cca cag ctc<br>Leu Asp Gly Leu Leu His Gly Leu Thr Val Pro Gln Leu<br>620                    625                   630 | 2011 |
| cct gtc cac act ccc caa ggt aac cag agt gga gaa ggg<br>Pro Val His Thr Pro Gln Gly Asn Gln Ser Gly Glu Gly<br>            635                    640                   645 | 2050 |
| agg ttc tct t gacttacttg ttgcataggt caggctccgc<br>Arg Phe Ser<br>648 | 2090 |
| tctttctatt gccatcacct agatcgcacc tggcatttag taggtgctca | 2140 |
| ataataact gtgaactgag agaatgaatg gggatctgag ggaaacaaac | 2190 |
| agacctcatc ctgcattctt cccactccct taggttccct actcctgctg | 2240 |
| ccatgtcggt gagtactggt gctattgtct agggcaagag cctcaggcct | 2290 |
| ttgg    agt tac tct ttg ctt ttc tcc aca gga gcc ccg<br>           Ser Tyr Ser Leu Leu Phe Ser Thr Gly Ala Pro<br>            1                5                      10 | 2327 |
| caa gtg agc cag cca ctg cga gag cag agt gag gat ata<br>Gln Val Ser Gln Pro Leu Arg Glu Gln Ser Glu Asp Ile<br>             15                    20 | 2366 |
| cct gga gcc att tcc tct gcc ctg gca gcc ata tgc act<br>Pro Gly Ala Ile Ser Ser Ala Leu Ala Ala Ile Cys Thr<br>25                    30                  35 | 2405 |
| gct cct gtg gga ctg ccc gac tgc tgg gat gcc aag gag<br>Ala Pro Val Gly Leu Pro Asp Cys Trp Asp Ala Lys Glu<br>            40                    45                   50 | 2444 |
| cag gtc tgt tgg cat ttg gca aat cag cta act gaa gac<br>Gln Val Cys Trp His Leu Ala Asn Gln Leu Thr Glu Asp<br>               55                    60 | 2483 |
| agc agc cag ctc agg cca tcc ctc atc tct ggc ctg cag<br>Ser Ser Gln Leu Arg Pro Ser Leu Ile Ser Gly Leu Gln<br>65                    70                  75 | 2522 |
| cat ccc atc ctg tgc ctg cac ctt ctc aag gtt cta tac<br>His Pro Ile Leu Cys Leu His Leu Leu Lys Val Leu Tyr<br>            80                    85 | 2561 |
| tcc tgc tgc ctt gtc agt gag ggc ctg tgc cgt ctt ctg<br>Ser Cys Cys Leu Val Ser Glu Gly Leu Cys Arg Leu Leu<br>90                    95                  100 | 2600 |
| ggg cag gag ccc ctg gcc ttg gaa tcc ctg ttt atg ttg<br>Gly Gln Glu Pro Leu Ala Leu Glu Ser Leu Phe Met Leu<br>             105                   110               115 | 2639 |
| att cag ggc aag gta aaa gta gta gat tgg gaa gag tct<br>Ile Gln Gly Lys Val Lys Val Val Asp Trp Glu Glu Ser<br>                    120                   125 | 2678 |
| act gaa gtg aca ctc tac ttc ctc tcc ctt ctt gtc ttt<br>Thr Glu Val Thr Leu Tyr Phe Leu Ser Leu Leu Val Phe<br>130                   135                 140 | 2717 |
| cgg ctc caa aac ctg cct tgt gga atg gag aag cta ggc<br>Arg Leu Gln Asn Leu Pro Cys Gly Met Glu Lys Leu Gly<br>             145                   150 | 2756 |
| agt gac gtt gct act ctc ttt acc cat tcg cat gtc gtc<br>Ser Asp Val Ala Thr Leu Phe Thr His Ser His Val Val<br>155                   160                 165 | 2795 |

| | | |
|---|---|---|
| tct ctt gtg agt gca gca gcc tgt cta ttg gga cag ctt<br>Ser Leu Val Ser Ala Ala Ala Cys Leu Leu Gly Gln Leu<br>          170                175               180 | | 2834 |
| ggt cag caa ggg gtg acc ttt gac ctc cag ccc atg gaa<br>Gly Gln Gln Gly Val Thr Phe Asp Leu Gln Pro Met Glu<br>               185                      190 | | 2873 |
| tgg atg gct gca gcc aca cat gcc ttg tct gcc cct gca<br>Trp Met Ala Ala Ala Thr His Ala Leu Ser Ala Pro Ala<br>195                   200                 205 | | 2912 |
| gag gtt cgg ttg act cca cca ggt agt tgt gga ttc tat<br>Glu Val Arg Leu Thr Pro Pro Gly Ser Cys Gly Phe Tyr<br>         210                 215 | | 2951 |
| gat ggc ctc ctt atc ctt ctg ttg cag ctc ctc act gag<br>Asp Gly Leu Leu Ile Leu Leu Gln Leu Leu Thr Glu<br>220                  225               230 | | 2990 |
| cag ggg aag gct agc cta atc agg gat atg tcc agt tca<br>Gln Gly Lys Ala Ser Leu Ile Arg Asp Met Ser Ser Ser<br>         235              240              245 | | 3029 |
| gaa atg tgg acc gtt ttg tgg cac cgc ttc tcc atg gtc<br>Glu Met Trp Thr Val Leu Trp His Arg Phe Ser Met Val<br>               250                 255 | | 3068 |
| ctg agg ctc ccc gag gag gca tct gca cag gaa ggg gag<br>Leu Arg Leu Pro Glu Glu Ala Ser Ala Gln Glu Gly Glu<br>260                   265                 270 | | 3107 |
| ctt tcg cta tcc agt cca cca agc cct gag cca gac tgg<br>Leu Ser Leu Ser Ser Pro Pro Ser Pro Glu Pro Asp Trp<br>         275              280 | | 3146 |
| aca ctg att tct ccc cag ggc atg gca gcc ctg ctg agc<br>Thr Leu Ile Ser Pro Gln Gly Met Ala Ala Leu Leu Ser<br>285                   290                 295 | | 3185 |
| ctg gcc atg gcc acc ttt acc cag gag ccc cag tta tgc<br>Leu Ala Met Ala Thr Phe Thr Gln Glu Pro Gln Leu Cys<br>               300                 305              310 | | 3224 |
| ctg agc tgc ctg tcc cag cat gga agt atc ctc atg tcc<br>Leu Ser Cys Leu Ser Gln His Gly Ser Ile Leu Met Ser<br>               315                 320 | | 3263 |
| atc ctg aag cat ctg ctt tgc ccc agc ttc ctg aat caa<br>Ile Leu Lys His Leu Leu Cys Pro Ser Phe Leu Asn Gln<br>325                   330                 335 | | 3302 |
| ctg cgc cag gcg cct cat ggg tct gag ttt ctc cct gtc<br>Leu Arg Gln Ala Pro His Gly Ser Glu Phe Leu Pro Val<br>         340              345 | | 3341 |
| gtg gtg ctc tct gtc tgc cag ctc ctt tgc ttc ccc ttt<br>Val Val Leu Ser Val Cys Gln Leu Leu Cys Phe Pro Phe<br>350                   355                 360 | | 3380 |
| gcg ctg gac atg gat gct gac ctc ctt ata gtt gtc ttg<br>Ala Leu Asp Met Asp Ala Asp Leu Leu Ile Val Val Leu<br>         365              370               375 | | 3419 |
| gcc gac ctc agg gac tca gaa gtt gca gcc cat ctg ctg<br>Ala Asp Leu Arg Asp Ser Glu Val Ala Ala His Leu Leu<br>               380                 385 | | 3458 |
| cag gtc tgc tgc tac cat ctt ccg ttg atg caa gtg gag<br>Gln Val Cys Cys Tyr His Leu Pro Leu Met Gln Val Glu<br>390                   395                 400 | | 3497 |
| ctg ccc atc agc ctt ctc aca cgc ctg gcc ctc atg gat<br>Leu Pro Ile Ser Leu Leu Thr Arg Leu Ala Leu Met Asp<br>         405              410 | | 3536 |
| ccc acc tct ctc aac cag ttt gtg aac aca gtg tct gcc<br>Pro Thr Ser Leu Asn Gln Phe Val Asn Thr Val Ser Ala<br>415                   420                 425 | | 3575 |

| | |
|---|---|
| tcc cct aga acc atc gtc tcg ttt ctc tca gtt gcc ctc<br>Ser Pro Arg Thr Ile Val Ser Phe Leu Ser Val Ala Leu<br>430 435 440 | 3614 |
| ctg agt gac cag cca ctg ttg acc tcc gac ctt ctc tct<br>Leu Ser Asp Gln Pro Leu Leu Thr Ser Asp Leu Leu Ser<br>445 450 | 3653 |
| ctg ctg gcc cat act gcc agg gtc ctg tct ccc agc cac<br>Leu Leu Ala His Thr Ala Arg Val Leu Ser Pro Ser His<br>455 460 465 | 3692 |
| ttg tcc ttt atc caa gag ctt ctg gct ggc tct gat gaa<br>Leu Ser Phe Ile Gln Glu Leu Leu Ala Gly Ser Asp Glu<br>470 475 | 3731 |
| tcc tat cgg ccc ctg cgc agc ctc ctg ggc cac cca gag<br>Ser Tyr Arg Pro Leu Arg Ser Leu Leu Gly His Pro Glu<br>480 485 490 | 3770 |
| aat tct gtg cgg gca cac act tat agg ctc ctg gga cac<br>Asn Ser Val Arg Ala His Thr Tyr Arg Leu Leu Gly His<br>495 500 505 | 3809 |
| ttg ctc caa cac agc atg gcc ctg cgt ggg gca ctg cag<br>Leu Leu Gln His Ser Met Ala Leu Arg Gly Ala Leu Gln<br>510 515 | 3848 |
| agc cag tct gga ctg ctc agc ctt ctg ctt ggg ctt<br>Ser Gln Ser Gly Leu Leu Ser Leu Leu Leu Gly Leu<br>520 525 530 | 3887 |
| gga gac aag gat cct gtt gtg cgg tgc agt gcc agc ttt<br>Gly Asp Lys Asp Pro Val Val Arg Cys Ser Ala Ser Phe<br>535 540 | 3926 |
| gct gtg ggc aat gca gcc tac cag gct ggt cct ctg gga<br>Ala Val Gly Asn Ala Ala Tyr Gln Ala Gly Pro Leu Gly<br>545 550 555 | 3965 |
| cct gcc ctg gca gct gca gtg ccc agt atg acc cag ctg<br>Pro Ala Leu Ala Ala Ala Val Pro Ser Met Thr Gln Leu<br>560 565 570 | 4004 |
| ctt gga gat cct cag gct ggt atc cgg cgc aat gtt gca<br>Leu Gly Asp Pro Gln Ala Gly Ile Arg Arg Asn Val Ala<br>575 580 | 4043 |
| tca gct ctg ggc aac ttg gga cct gaa ggt ttg gga gag<br>Ser Ala Leu Gly Asn Leu Gly Pro Glu Gly Leu Gly Glu<br>585 590 595 | 4082 |
| gag ctg tta cag tgc gaa gta ccc cag cgg ctc cta gaa<br>Glu Leu Leu Gln Cys Glu Val Pro Gln Arg Leu Leu Glu<br>600 605 | 4121 |
| atg gca tgt gga gac ccc cag cca aat gtg aag gag gct<br>Met Ala Cys Gly Asp Pro Gln Pro Asn Val Lys Glu Ala<br>610 615 620 | 4160 |
| gcc ctc att gcc ctc cgg agc ctg caa cag gag cct ggc<br>Ala Leu Ile Ala Leu Arg Ser Leu Gln Gln Glu Pro Gly<br>625 630 635 | 4199 |
| atc cat cag gta ctg gtg tcc ctg ggt gcc agt gag aaa<br>Ile His Gln Val Leu Val Ser Leu Gly Ala Ser Glu Lys<br>640 645 | 4238 |
| cta tcc ttg ctc tct ctg ggg aat cag tca ctg cca cac<br>Leu Ser Leu Leu Ser Leu Gly Asn Gln Ser Leu Pro His<br>650 655 660 | 4277 |
| agc agt cct agg cct gcc tct gcc aaa cac tgc agg aaa<br>Ser Ser Pro Arg Pro Ala Ser Ala Lys His Cys Arg Lys<br>665 670 | 4316 |
| ctc att cac ctc ctg agg cca gcc cat agc atg t<br>Leu Ile His Leu Leu Arg Pro Ala His Ser Met<br>675 680 685 | 4350 |

| | |
|---|---|
| gattccagat tcctgcggtc cagcctccaa ctttggttgc cagctctttc | 4400 |
| ttattctact acacaagccg ccaactcaac tgagagctaa agagactaga | 4450 |
| aaagagataa gctgccaact caactgagaa caagaaacta gaagagattt | 4500 |
| atatataaag cttcttcctt ctcccagatg caggatgttt tcaaccagta | 4550 |
| aattttattg ctgttggtgc cagagaagag tcctttcttc tctacatcca | 4600 |
| ggggcctttt ctccaataat gtgcctttaa ctctagggac ctgcctcacg | 4650 |
| gaccttaggg aaaaacctca acctgaaaga tctcttcctt tctggagctc | 4700 |
| ctttaatctt cccagcaggt ttttgcctta gacgtgctgg ccccaggaca | 4750 |
| gtgatgaaga cagagcctgt ctcagctcta ggctgtgggg atcaatgcca | 4800 |
| tcagtccctg ttattgaggg attatccctt agccaacatt cctatctgtg | 4850 |
| ggtgggcgtg gagagtgtat cttttttttgg ggtgtgtgtg tatatgtgtg | 4900 |
| tgtgtatgtg tgtgtgtgtt taatagttct gtttgtaaac tcttttaata | 4950 |
| aaagttgtgc ctcaccatac ttgaagctcc caggacaagg gttgagaggc | 5000 |
| tcaacccctc tttcagcttc tatgtggtgt tggaggtgct ggtatcgtgt | 5050 |
| tcacacaaaa aaaaaaaaaa aaaaaaaaaa aaaaaaaaaa aaaaaaaaaa | 5100 |
| aaaaaaaaaa aaaaaaaaaa aaaaa | 5125 |

<210> SEQ ID NO 5
<211> LENGTH: 648
<212> TYPE: PRT
<213> ORGANISM: Homo sapiens

<400> SEQUENCE: 5

```
Met Glu Lys Tyr His Val Leu Glu Met Ile Gly Glu Gly Ser Phe
 1               5                  10                  15

Gly Arg Val Tyr Lys Gly Arg Lys Tyr Ser Ala Gln Val Val
                20                  25                  30

Ala Leu Lys Phe Ile Pro Lys Leu Gly Arg Ser Glu Lys Glu Leu
                35                  40                  45

Arg Asn Leu Gln Arg Glu Ile Glu Ile Met Arg Gly Leu Arg His
                50                  55                  60

Pro Asn Ile Val His Met Leu Asp Ser Phe Glu Thr Asp Lys Glu
                65                  70                  75

Val Val Val Val Thr Asp Tyr Ala Glu Gly Glu Leu Phe Gln Ile
                80                  85                  90

Leu Glu Asp Asp Gly Lys Leu Pro Glu Asp Gln Val Gln Ala Ile
                95                 100                 105

Ala Ala Gln Leu Val Ser Ala Leu Tyr Tyr Leu His Ser His Arg
               110                 115                 120

Ile Leu His Arg Asp Met Lys Pro Gln Asn Ile Leu Leu Ala Lys
               125                 130                 135

Gly Gly Gly Ile Lys Leu Cys Asp Phe Gly Phe Ala Arg Ala Met
               140                 145                 150

Ser Thr Asn Thr Met Val Leu Thr Ser Ile Lys Gly Thr Pro Leu
               155                 160                 165

Tyr Met Ser Pro Glu Leu Val Glu Glu Arg Pro Tyr Asp His Thr
               170                 175                 180

Ala Asp Leu Trp Ser Val Gly Cys Ile Leu Tyr Glu Leu Ala Val
               185                 190                 195
```

-continued

Gly Thr Pro Pro Phe Tyr Ala Thr Ser Ile Phe Gln Leu Val Ser
            200                 205                 210

Leu Ile Leu Lys Asp Pro Val Arg Trp Pro Ser Thr Ile Ser Pro
            215                 220                 225

Cys Phe Lys Asn Phe Leu Gln Gly Leu Leu Thr Lys Asp Pro Arg
            230                 235                 240

Gln Arg Leu Ser Trp Pro Asp Leu Leu Tyr His Pro Phe Ile Ala
            245                 250                 255

Gly His Val Thr Ile Ile Thr Glu Pro Ala Gly Pro Asp Leu Gly
            260                 265                 270

Thr Pro Phe Thr Ser Arg Leu Pro Pro Glu Leu Gln Val Leu Lys
            275                 280                 285

Asp Glu Gln Ala His Arg Leu Ala Pro Lys Gly Asn Gln Ser Arg
            290                 295                 300

Ile Leu Thr Gln Ala Tyr Lys Arg Met Ala Glu Glu Ala Met Gln
            305                 310                 315

Lys Lys His Gln Asn Thr Gly Pro Ala Leu Glu Gln Glu Asp Lys
            320                 325                 330

Thr Ser Lys Val Ala Pro Gly Thr Ala Pro Leu Pro Arg Leu Gly
            335                 340                 345

Ala Thr Pro Gln Glu Ser Ser Leu Leu Ala Gly Ile Leu Ala Ser
            350                 355                 360

Glu Leu Lys Ser Ser Trp Ala Lys Ser Gly Thr Gly Glu Val Pro
            365                 370                 375

Ser Ala Pro Arg Glu Asn Arg Thr Thr Pro Asp Cys Glu Arg Ala
            380                 385                 390

Phe Pro Glu Glu Arg Pro Glu Val Leu Gly Gln Arg Ser Thr Asp
            395                 400                 405

Val Val Asp Leu Glu Asn Glu Glu Pro Asp Ser Asp Asn Glu Trp
            410                 415                 420

Gln His Leu Leu Glu Thr Thr Glu Pro Val Pro Ile Gln Leu Lys
            425                 430                 435

Ala Pro Leu Thr Leu Leu Cys Asn Pro Asp Phe Cys Gln Arg Ile
            440                 445                 450

Gln Ser Gln Leu His Glu Ala Gly Gly Gln Ile Leu Lys Gly Ile
            455                 460                 465

Leu Glu Gly Ala Ser His Ile Leu Pro Ala Phe Arg Val Leu Ser
            470                 475                 480

Ser Leu Leu Ser Ser Cys Ser Asp Ser Val Ala Leu Tyr Ser Phe
            485                 490                 495

Cys Arg Glu Ala Gly Leu Pro Gly Leu Leu Ser Leu Leu Arg
            500                 505                 510

His Ser Gln Glu Ser Asn Ser Leu Gln Gln Gln Ser Trp Tyr Gly
            515                 520                 525

Thr Phe Leu Gln Asp Leu Met Ala Val Ile Gln Ala Tyr Phe Ala
            530                 535                 540

Cys Thr Phe Asn Leu Glu Arg Ser Gln Thr Ser Asp Ser Leu Gln
            545                 550                 555

Val Phe Gln Glu Ala Ala Asn Leu Phe Leu Asp Leu Leu Gly Lys
            560                 565                 570

Leu Leu Ala Gln Pro Asp Asp Ser Glu Gln Thr Leu Gln Arg Asp
            575                 580                 585

Ser Leu Met Cys Phe Thr Val Leu Cys Glu Ala Met Asp Gly Asn
            590                 595                 600

-continued

```
Ser Arg Ala Ile Ser Lys Ala Phe Tyr Ser Ser Leu Leu Thr Thr
            605                 610                 615

Gln Gln Val Val Leu Asp Gly Leu Leu His Gly Leu Thr Val Pro
            620                 625                 630

Gln Leu Pro Val His Thr Pro Gln Gly Asn Gln Ser Gly Glu Gly
            635                 640                 645

Arg Phe Ser
        648

<210> SEQ ID NO 6
<211> LENGTH: 5252
<212> TYPE: DNA
<213> ORGANISM: Homo sapiens

<400> SEQUENCE: 6
ggagcttgga gctcctaggc tgggggcgtc ccagatgttg tggaactgtc              50
cctggatcta tagctcttca ccgtctctac tttcttcctt ctaagagatc             100
ctgaaacctc tgtc atg gaa aag tac cac gtg ttg gag atg               141
             Met Glu Lys Tyr His Val Leu Glu Met
              1               5 att gga gaa ggc tct ttt ggg agg gtg tac aag ggt cga               180
Ile Gly Glu Gly Ser Phe Gly Arg Val Tyr Lys Gly Arg
 10              15                  20 aga aaa tac agt gct cag gtc gtg gcc ctg aag ttc atc               219
Arg Lys Tyr Ser Ala Gln Val Val Ala Leu Lys Phe Ile
     25                  30                  35 cca aaa ttg ggg cgc tca gag aag gag ctg agg aat ttg               258
Pro Lys Leu Gly Arg Ser Glu Lys Glu Leu Arg Asn Leu
             40                  45 caa cga gag att gaa ata atg cgg ggt ctg cgg cat ccc               297
Gln Arg Glu Ile Glu Ile Met Arg Gly Leu Arg His Pro
 50                  55                  60 aac att gtg cat atg ctt gac agc ttt gaa act gat aaa               336
Asn Ile Val His Met Leu Asp Ser Phe Glu Thr Asp Lys
             65                  70 gag gtg gtg gtg gtg aca gac tat gct gag gga gag ctc               375
Glu Val Val Val Val Thr Asp Tyr Ala Glu Gly Glu Leu
 75              80                  85 ttt cag atc cta gaa gat gac gga aaa ctt cct gaa gac               414
Phe Gln Ile Leu Glu Asp Asp Gly Lys Leu Pro Glu Asp
     90                  95                 100 cag gtt cag gcc att gct gcc cag ttg gtg tca gcc ctg               453
Gln Val Gln Ala Ile Ala Ala Gln Leu Val Ser Ala Leu
            105                 110 tac tat ctg cat tcc cac cgc atc cta cac cga gat atg               492
Tyr Tyr Leu His Ser His Arg Ile Leu His Arg Asp Met
115                 120                 125 aag cct cag aac atc ctc ctc gcc aag ggt ggt ggc atc               531
Lys Pro Gln Asn Ile Leu Leu Ala Lys Gly Gly Gly Ile
            130                 135 aag ctc tgt gac ttt gga ttt gcc cgg gct atg agc acc               570
Lys Leu Cys Asp Phe Gly Phe Ala Arg Ala Met Ser Thr
140                 145                 150 aat aca atg gtg ctg aca tcc atc aaa ggc aca cca ctc               609
Asn Thr Met Val Leu Thr Ser Ile Lys Gly Thr Pro Leu
            155                 160                 165 tat atg tct cca gag ctg gtg gag gag cga cca tac gac               648
Tyr Met Ser Pro Glu Leu Val Glu Glu Arg Pro Tyr Asp
                170                 175
```

-continued

| | |
|---|---|
| cac aca gcg gac ctc tgg tct gtt ggc tgc ata cta tat<br>His Thr Ala Asp Leu Trp Ser Val Gly Cys Ile Leu Tyr<br>180                         185                       190 | 687 |
| gaa ctg gca gta ggc acc cct ccc ttc tat gct aca agc<br>Glu Leu Ala Val Gly Thr Pro Pro Phe Tyr Ala Thr Ser<br>            195                     200 | 726 |
| atc ttt cag ctg gtc agc ctc att ctc aag gac cct gtg<br>Ile Phe Gln Leu Val Ser Leu Ile Leu Lys Asp Pro Val<br>205                        210                   215 | 765 |
| cgc tgg ccc tca acc atc agt ccc tgc ttt aag aac ttc<br>Arg Trp Pro Ser Thr Ile Ser Pro Cys Phe Lys Asn Phe<br>         220                   225               230 | 804 |
| ctg cag gga ctg ctc acc aaa gac cca cgg cag cga ctg<br>Leu Gln Gly Leu Leu Thr Lys Asp Pro Arg Gln Arg Leu<br>               235                   240 | 843 |
| tcc tgg cca gac ctc tta tat cac ccc ttt att gct ggt<br>Ser Trp Pro Asp Leu Leu Tyr His Pro Phe Ile Ala Gly<br>245                        250                   255 | 882 |
| cat gtc acc ata ata act gag cca gca ggc cca gat ttg<br>His Val Thr Ile Ile Thr Glu Pro Ala Gly Pro Asp Leu<br>         260                   265 | 921 |
| ggg acc cca ttc acc agc cgc cta ccc cca gaa ctt cag<br>Gly Thr Pro Phe Thr Ser Arg Leu Pro Pro Glu Leu Gln<br>270                        275                   280 | 960 |
| gtc cta aag gac gaa cag gcc cat cgg ttg gcc ccc aag<br>Val Leu Lys Asp Glu Gln Ala His Arg Leu Ala Pro Lys<br>         285                   290               295 | 999 |
| ggt aat cag tct cgc atc ttg act cag gcc tat aaa cgc<br>Gly Asn Gln Ser Arg Ile Leu Thr Gln Ala Tyr Lys Arg<br>               300                   305 | 1038 |
| atg gct gag gag gcc atg cag aag aaa cat cag aac aca<br>Met Ala Glu Glu Ala Met Gln Lys Lys His Gln Asn Thr<br>310                        315                   320 | 1077 |
| gga cct gcc ctt gag caa gag gac aag acc agc aag gtg<br>Gly Pro Ala Leu Glu Gln Glu Asp Lys Thr Ser Lys Val<br>         325                   330 | 1116 |
| gct cct ggc aca gcc cct ctg ccc aga ctc ggg gcc act<br>Ala Pro Gly Thr Ala Pro Leu Pro Arg Leu Gly Ala Thr<br>335                        340                   345 | 1155 |
| cct cag gaa tca agc ctc ctg gcc ggg atc tta gcc tca<br>Pro Gln Glu Ser Ser Leu Leu Ala Gly Ile Leu Ala Ser<br>         350                   355               360 | 1194 |
| gaa ttg aag agc agc tgg gct aaa tca ggg act gga gag<br>Glu Leu Lys Ser Ser Trp Ala Lys Ser Gly Thr Gly Glu<br>               365                   370 | 1233 |
| gtg ccc tct gca cct cgg gaa aac cgg acc acc cca gat<br>Val Pro Ser Ala Pro Arg Glu Asn Arg Thr Thr Pro Asp<br>375                        380                   385 | 1272 |
| tgt gaa cga gca ttc cca gag gag agg cca gag gtg ctg<br>Cys Glu Arg Ala Phe Pro Glu Glu Arg Pro Glu Val Leu<br>         390                   395 | 1311 |
| ggc cag cgg agc act gat gta gtg gac ctg gaa aat gag<br>Gly Gln Arg Ser Thr Asp Val Val Asp Leu Glu Asn Glu<br>400                        405                   410 | 1350 |
| gag cca gac agt gac aat gag tgg cag cac ctg cta gag<br>Glu Pro Asp Ser Asp Asn Glu Trp Gln His Leu Leu Glu<br>               415                   420               425 | 1389 |
| acc act gag cct gtg cct att caa ctg aag gct cct ctc<br>Thr Thr Glu Pro Val Pro Ile Gln Leu Lys Ala Pro Leu<br>         430                   435 | 1428 |

```
acc ttg ctg tgt aat cct gac ttc tgc cag cgc atc cag         1467
Thr Leu Leu Cys Asn Pro Asp Phe Cys Gln Arg Ile Gln
    440             445                 450 agt cag ctg cat gaa gct gga ggg cag atc ctg aaa ggc         1506
Ser Gln Leu His Glu Ala Gly Gly Gln Ile Leu Lys Gly
                455                 460 atc ttg gag ggt gct tcc cac atc ctg cct gca ttc cgg         1545
Ile Leu Glu Gly Ala Ser His Ile Leu Pro Ala Phe Arg
465                 470                 475 gtc ctg agc agt ctt ctc tcc agc tgc agt gat tct gtt         1584
Val Leu Ser Ser Leu Leu Ser Ser Cys Ser Asp Ser Val
            480                 485                 490 gcc ttg tat tcc ttc tgc cgg gag gca ggg ctt cct ggg         1623
Ala Leu Tyr Ser Phe Cys Arg Glu Ala Gly Leu Pro Gly
                495                 500 ctg ctg ctg agt cta ctc agg cac agt cag gag agc aac         1662
Leu Leu Leu Ser Leu Leu Arg His Ser Gln Glu Ser Asn
505                 510                 515 agc ctc cag cag caa tct tgg tat ggg acc ttc tta cag         1701
Ser Leu Gln Gln Gln Ser Trp Tyr Gly Thr Phe Leu Gln
            520                 525 gac ctg atg gct gtg att cag gcc tac ttt gcc tgt acc         1740
Asp Leu Met Ala Val Ile Gln Ala Tyr Phe Ala Cys Thr
530                 535                 540 ttc aat ctg gag agg agc cag aca agt gac agc ctg cag         1779
Phe Asn Leu Glu Arg Ser Gln Thr Ser Asp Ser Leu Gln
            545                 550                 555 gtg ttt cag gag gct gcc aac ctt ttt ctg gac ctg ttg         1818
Val Phe Gln Glu Ala Ala Asn Leu Phe Leu Asp Leu Leu
                560                 565 ggg aaa ctg ctg gcc caa cca gat gac tct gag cag act         1857
Gly Lys Leu Leu Ala Gln Pro Asp Asp Ser Glu Gln Thr
570                 575                 580 ttg cgg agg gac agc ctt atg tgc ttt act gtc ctg tgc         1896
Leu Arg Arg Asp Ser Leu Met Cys Phe Thr Val Leu Cys
            585                 590 gaa gcc atg gat ggg aac agc cgg gcc atc tcc aaa gcc         1935
Glu Ala Met Asp Gly Asn Ser Arg Ala Ile Ser Lys Ala
595                 600                 605 ttt tac tcc agc ttg ctg acg aca cag cag gtt gtc ttg         1974
Phe Tyr Ser Ser Leu Leu Thr Thr Gln Gln Val Val Leu
            610                 615                 620 gat ggg ctc ctt cat ggc ttg aca gtt cca cag ctc cct         2013
Asp Gly Leu Leu His Gly Leu Thr Val Pro Gln Leu Pro
                625                 630 gtc cac act ccc caa ggt tcc cta ctc ctg ctg cca tgt         2052
Val His Thr Pro Gln Gly Ser Leu Leu Leu Leu Pro Cys
    635                 640                 645 cgg tga g t actggtgcta ttgtctaggg caagagcctc              2090
Arg aggcctttgg agt tac tct ttg ctt ttc tcc aca gga gcc         2130
            Ser Tyr Ser Leu Leu Phe Ser Thr Gly Ala
              1               5                  10 ccg caa gtg agc cag cca ctg cga gag cag agt gag gat         2169
Pro Gln Val Ser Gln Pro Leu Arg Glu Gln Ser Glu Asp
                15                  20 ata cct gga gcc att tcc tct gcc ctg gca gcc ata tgc         2208
Ile Pro Gly Ala Ile Ser Ser Ala Leu Ala Ala Ile Cys
    25                  30                  35
```

| | |
|---|---|
| act gct cct gtg gga ctg ccc gac tgc tgg gat gcc aag<br>Thr Ala Pro Val Gly Leu Pro Asp Cys Trp Asp Ala Lys<br>            40                  45 | 2247 |
| gag cag gtc tgt tgg cat ttg gca aat cag cta act gaa<br>Glu Gln Val Cys Trp His Leu Ala Asn Gln Leu Thr Glu<br>50                  55                  60 | 2286 |
| gac agc agc cag ctc agg cca tcc ctc atc tct ggc ctg<br>Asp Ser Ser Gln Leu Arg Pro Ser Leu Ile Ser Gly Leu<br>        65                  70                  75 | 2325 |
| cag cat ccc atc ctg tgc ctg cac ctt ctc aag gtt cta<br>Gln His Pro Ile Leu Cys Leu His Leu Leu Lys Val Leu<br>                80                  85 | 2364 |
| tac tcc tgc tgc ctt gtc agt gag ggc ctg tgc cgt ctt<br>Tyr Ser Cys Cys Leu Val Ser Glu Gly Leu Cys Arg Leu<br>        90                  95              100 | 2403 |
| ctg ggg cag gag ccc ctg gcc ttg gaa tcc ctg ttt atg<br>Leu Gly Gln Glu Pro Leu Ala Leu Glu Ser Leu Phe Met<br>                105                 110 | 2442 |
| ttg att cag ggc aag gta aaa gta gta gat tgg gaa gag<br>Leu Ile Gln Gly Lys Val Lys Val Val Asp Trp Glu Glu<br>115                  120                 125 | 2481 |
| tct act gaa gtg aca ctc tac ttc ctc tcc ctt ctt gtc<br>Ser Thr Glu Val Thr Leu Tyr Phe Leu Ser Leu Leu Val<br>                130                 135               140 | 2520 |
| ttt cgg ctc caa aac ctg cct tgt gga atg gag aag cta<br>Phe Arg Leu Gln Asn Leu Pro Cys Gly Met Glu Lys Leu<br>                    145                 150 | 2559 |
| ggc agt gac gtt gct act ctc ttt acc cat tcg cat gtc<br>Gly Ser Asp Val Ala Thr Leu Phe Thr His Ser His Val<br>155                  160                 165 | 2598 |
| gtc tct ctt gtg agt gca gca gcc tgt cta ttg gga cag<br>Val Ser Leu Val Ser Ala Ala Ala Cys Leu Leu Gly Gln<br>                170                 175 | 2637 |
| ctt ggt cag caa ggg gtg acc ttt gac ctc cag ccc atg<br>Leu Gly Gln Gln Gly Val Thr Phe Asp Leu Gln Pro Met<br>180                  185                 190 | 2676 |
| gaa tgg atg gct gca gcc aca cat gcc ttg tct gcc cct<br>Glu Trp Met Ala Ala Ala Thr His Ala Leu Ser Ala Pro<br>                195                 200               205 | 2715 |
| gca gag ctc ctc act gag gta cag atg gat ctt ggg atg<br>Ala Glu Leu Leu Thr Glu Val Gln Met Asp Leu Gly Met<br>                    210                 215 | 2754 |
| gat ggg aag taaagag agaggaactg gcattttgg ggagcctctg<br>Asp Gly Lys<br>        220 221 | 2800 |
| gaccagagga atgaagaagc aacccacagc cttccctctc aagctactgt | 2850 |
| gcctgtgata gccttggaac ttccccgcct gccctcagta ctgacccttt | 2900 |
| gaaggaaacc attcgctgcg tcccctggga tccagtggga gataaaatga | 2950 |
| attccctggg tttcagcaga catacacatg agttgtgagg tcagagggtt | 3000 |
| aaggtttgat aagaaaatga aataagacga cagggaaata ctaggtggga | 3050 |
| aagcggaagg aattatttct gggacttcct ttacttgtaa gtcagggaca | 3100 |
| ggaatgaata aaagcatttg gattcctgac ttctgtcttt ccccccgccc | 3150 |
| tctttcactt ttatctctag cagggggaagg ctagcctaat cagggatatg | 3200 |
| tccagttcag aaatgtggac cgttttgtgg caccgcttct ccatggtcct | 3250 |
| gaggctcccc gaggaggcat ctgcacagga aggggagctt tcgctatcca | 3300 |

```
gtccaccaag ccctgagcca gactggacac tgatttctcc ccagggcatg    3350
gcagccctgc tgagcctggc catggccacc tttacccagg agccccagtt    3400
atgcctgagc tgcctgtccc agcatggaag tatcctcatg tccatcctga    3450
agcatctgct tgccccagc ttcctgaatc aactgcgcca ggcgcctcat     3500
gggtctgagt ttctccctgt cgtggtgctc tctgtctgcc agctcctttg    3550
cttccccttt gcgctggaca tggatgctga cctccttata ggtgtcttgg    3600
ccgacctcag ggactcagaa gttgcagccc atctgctgca ggtctgctgc    3650
taccatcttc cgttgatgca agtggagctg cccatcagcc ttctcacacg    3700
cctggccctc atggatccca cctctctcaa ccagtttgtg aacacagtgt    3750
ctgcctcccc tagaaccatc gtctcgtttc tctcagttgc cctcctgagt    3800
gaccagccac tgttgacctc cgaccttctc tctctgctgg cccatactgc    3850
cagggtcctg tctcccagcc acttgtcctt tatccaagag cttctggctg    3900
gctctgatga atcctatcgg cccctgcgca gcctcctggg ccacccagag    3950
aattctgtgc gggcacacac ttataggctc ctgggacact tgctccaaca    4000
cagcatggcc ctgcgtgggg cactgcagag ccagtctgga ctgctcagcc    4050
ttctgctgct tgggcttgga acaaggatc ctgttgtgcg gtgcagtgcc     4100
agctttgctg tgggcaatgc agcctaccag gctggtcctc tgggacctgc    4150
cctggcagct gcagtgccca gtatgaccca gctgcttgga gatcctcagg    4200
ctggtatccg gcgcaatgtt gcatcagctc tgggcaactt gggacctgaa    4250
ggtttgggag aggagctgtt acagtgcgaa gtaccccagc ggctcctaga    4300
aatggcatgt ggagaccccc agccaaatgt gaaggaggct gccctcattg    4350
ccctccggag cctgcaacag gagcctggca tccatcaggt actggtgtcc    4400
ctgggtgcca gtgagaaact atccttgctc tctctgggga atcagtcact    4450
gccacacagc agtcctaggc ctgcctctgc caaacactgc aggaaactca    4500
ttcacctcct gaggccagcc catagcatgt gattccagat tcctgcggtc    4550
cagcctccaa cttttggttgc cagctctttc ttattctact acacaagccg    4600
ccaactcaac tgagagctaa agagactaga aaagagataa gctgccaact    4650
caactgagaa caagaaacta gaagagattt atatataaag cttcttcctt    4700
ctcccagatg caggatgttt tcaaccagta aattttattg ctgttggtgc    4750
cagagaagag tcctttcttc tctacatcca ggggccttt ctccaataat     4800
gtgcctttaa ctctagggac ctgcctcacg gaccttaggg aaaaacctca    4850
acctgaaaga tctcttcctt tctggagctc ctttaatctt cccagcaggt    4900
ttttgcctta gacgtgctgg ccccaggaca gtgatgaaga cagagcctgt    4950
ctcagctcta ggctgtgggg atcaatgcca tcagtccctg ttattgaggg    5000
attatccctt agccaacatt cctatctgtg ggtgggcgtg gagagtgtat    5050
ctttttttgg ggtgtgtgtg tatatgtgtg tgtgtatgtg tgtgtgtgtt    5100
taatagttct gtttgtaaac tcttttaata aagttgtgc ctcaccatac     5150
ttgaagctcc caggacaagg gttgagaggc tcaaccccct tttcagcttc    5200
tatgtggtgt tggaggtgct ggtatcgtgt tcacacaaaa aaaaaaaaaa    5250
aa                                                        5252
```

```
<210> SEQ ID NO 7
<211> LENGTH: 647
<212> TYPE: PRT
<213> ORGANISM: Homo sapiens

<400> SEQUENCE: 7

Met Glu Lys Tyr His Val Leu Glu Met Ile Gly Glu Gly Ser Phe
 1               5                  10                  15

Gly Arg Val Tyr Lys Gly Arg Arg Lys Tyr Ser Ala Gln Val Val
                20                  25                  30

Ala Leu Lys Phe Ile Pro Lys Leu Gly Arg Ser Glu Lys Glu Leu
                35                  40                  45

Arg Asn Leu Gln Arg Glu Ile Glu Ile Met Arg Gly Leu Arg His
                50                  55                  60

Pro Asn Ile Val His Met Leu Asp Ser Phe Glu Thr Asp Lys Glu
                65                  70                  75

Val Val Val Val Thr Asp Tyr Ala Glu Gly Glu Leu Phe Gln Ile
                80                  85                  90

Leu Glu Asp Asp Gly Lys Leu Pro Glu Asp Gln Val Gln Ala Ile
                95                 100                 105

Ala Ala Gln Leu Val Ser Ala Leu Tyr Tyr Leu His Ser His Arg
               110                 115                 120

Ile Leu His Arg Asp Met Lys Pro Gln Asn Ile Leu Leu Ala Lys
               125                 130                 135

Gly Gly Gly Ile Lys Leu Cys Asp Phe Gly Phe Ala Arg Ala Met
               140                 145                 150

Ser Thr Asn Thr Met Val Leu Thr Ser Ile Lys Gly Thr Pro Leu
               155                 160                 165

Tyr Met Ser Pro Glu Leu Val Glu Glu Arg Pro Tyr Asp His Thr
               170                 175                 180

Ala Asp Leu Trp Ser Val Gly Cys Ile Leu Tyr Glu Leu Ala Val
               185                 190                 195

Gly Thr Pro Pro Phe Tyr Ala Thr Ser Ile Phe Gln Leu Val Ser
               200                 205                 210

Leu Ile Leu Lys Asp Pro Val Arg Trp Pro Ser Thr Ile Ser Pro
               215                 220                 225

Cys Phe Lys Asn Phe Leu Gln Gly Leu Leu Thr Lys Asp Pro Arg
               230                 235                 240

Gln Arg Leu Ser Trp Pro Asp Leu Leu Tyr His Pro Phe Ile Ala
               245                 250                 255

Gly His Val Thr Ile Ile Thr Glu Pro Ala Gly Pro Asp Leu Gly
               260                 265                 270

Thr Pro Phe Thr Ser Arg Leu Pro Pro Glu Leu Gln Val Leu Lys
               275                 280                 285

Asp Glu Gln Ala His Arg Leu Ala Pro Lys Gly Asn Gln Ser Arg
               290                 295                 300

Ile Leu Thr Gln Ala Tyr Lys Arg Met Ala Glu Glu Ala Met Gln
               305                 310                 315

Lys Lys His Gln Asn Thr Gly Pro Ala Leu Glu Gln Glu Asp Lys
               320                 325                 330

Thr Ser Lys Val Ala Pro Gly Thr Ala Pro Leu Pro Arg Leu Gly
               335                 340                 345

Ala Thr Pro Gln Glu Ser Ser Leu Leu Ala Gly Ile Leu Ala Ser
               350                 355                 360
```

Glu Leu Lys Ser Ser Trp Ala Lys Ser Gly Thr Gly Glu Val Pro
            365                 370                 375

Ser Ala Pro Arg Glu Asn Arg Thr Thr Pro Asp Cys Glu Arg Ala
        380                 385                 390

Phe Pro Glu Glu Arg Pro Glu Val Leu Gly Gln Arg Ser Thr Asp
            395                 400                 405

Val Val Asp Leu Glu Asn Glu Pro Asp Ser Asp Asn Glu Trp
        410                 415                 420

Gln His Leu Leu Glu Thr Thr Glu Pro Val Pro Ile Gln Leu Lys
            425                 430                 435

Ala Pro Leu Thr Leu Leu Cys Asn Pro Asp Phe Cys Gln Arg Ile
        440                 445                 450

Gln Ser Gln Leu His Glu Ala Gly Gly Gln Ile Leu Lys Gly Ile
            455                 460                 465

Leu Glu Gly Ala Ser His Ile Leu Pro Ala Phe Arg Val Leu Ser
        470                 475                 480

Ser Leu Leu Ser Ser Cys Ser Asp Ser Val Ala Leu Tyr Ser Phe
            485                 490                 495

Cys Arg Glu Ala Gly Leu Pro Gly Leu Leu Ser Leu Leu Arg
        500                 505                 510

His Ser Gln Glu Ser Asn Ser Leu Gln Gln Gln Ser Trp Tyr Gly
            515                 520                 525

Thr Phe Leu Gln Asp Leu Met Ala Val Ile Gln Ala Tyr Phe Ala
        530                 535                 540

Cys Thr Phe Asn Leu Glu Arg Ser Gln Thr Ser Asp Ser Leu Gln
            545                 550                 555

Val Phe Gln Glu Ala Ala Asn Leu Phe Leu Asp Leu Leu Gly Lys
        560                 565                 570

Leu Leu Ala Gln Pro Asp Asp Ser Glu Gln Thr Leu Arg Arg Asp
            575                 580                 585

Ser Leu Met Cys Phe Thr Val Leu Cys Glu Ala Met Asp Gly Asn
        590                 595                 600

Ser Arg Ala Ile Ser Lys Ala Phe Tyr Ser Ser Leu Leu Thr Thr
            605                 610                 615

Gln Gln Val Val Leu Asp Gly Leu Leu His Gly Leu Thr Val Pro
        620                 625                 630

Gln Leu Pro Val His Thr Pro Gln Gly Ser Leu Leu Leu Leu Pro
            635                 640                 645

Cys Arg
    647

<210> SEQ ID NO 8
<211> LENGTH: 32
<212> TYPE: DNA
<213> ORGANISM: artificial sequence
<220> FEATURE:
<223> OTHER INFORMATION: artificial sequence

<400> SEQUENCE: 8
caatacaatg gtgctgacat ccatcaaagg ca                                 32

<210> SEQ ID NO 9
<211> LENGTH: 23
<212> TYPE: DNA
<213> ORGANISM: artificial sequence
<220> FEATURE:
<223> OTHER INFORMATION: artificial sequence

```
<400> SEQUENCE: 9
gaagggaggg gtgcctactg cca                                       23

<210> SEQ ID NO 10
<211> LENGTH: 38
<212> TYPE: DNA
<213> ORGANISM: artificial sequence
<220> FEATURE:
<223> OTHER INFORMATION: artificial sequence

<400> SEQUENCE: 10
ctccagctct ggagacatat agagtggtgt gcctttga                       38

<210> SEQ ID NO 11
<211> LENGTH: 60
<212> TYPE: DNA
<213> ORGANISM: artificial sequence
<220> FEATURE:
<223> OTHER INFORMATION: artificial sequence

<400> SEQUENCE: 11
ccatcgatgt acccatacga cgtcccagac tacgctgaaa agtaccacgt          50
gttggagatg                                                      60

<210> SEQ ID NO 12
<211> LENGTH: 32
<212> TYPE: DNA
<213> ORGANISM: artificial sequence
<220> FEATURE:
<223> OTHER INFORMATION: artificial sequence

<400> SEQUENCE: 12
gctctagact aaggggcagg tcctgtgttc tg                             32

<210> SEQ ID NO 13
<211> LENGTH: 21
<212> TYPE: DNA
<213> ORGANISM: artificial sequence
<220> FEATURE:
<223> OTHER INFORMATION: artificial sequence

<400> SEQUENCE: 13
ctgacgacac agcaggttgt c                                         21

<210> SEQ ID NO 14
<211> LENGTH: 21
<212> TYPE: DNA
<213> ORGANISM: artificial sequence
<220> FEATURE:
<223> OTHER INFORMATION: artificial sequence

<400> SEQUENCE: 14
cagatgcttc aggatggaca t                                         21

<210> SEQ ID NO 15
<211> LENGTH: 19
<212> TYPE: DNA
<213> ORGANISM: artificial sequence
<220> FEATURE:
<223> OTHER INFORMATION: artificial sequence

<400> SEQUENCE: 15
agagtagcaa cgtcactgc                                            19

<210> SEQ ID NO 16
```

```
<211> LENGTH: 21
<212> TYPE: DNA
<213> ORGANISM: artificial sequence
<220> FEATURE:
<223> OTHER INFORMATION: artificial sequence

<400> SEQUENCE: 16
cctcactgac aaggcagcag g                                        21

<210> SEQ ID NO 17
<211> LENGTH: 21
<212> TYPE: DNA
<213> ORGANISM: artificial sequence
<220> FEATURE:
<223> OTHER INFORMATION: artificial sequence

<400> SEQUENCE: 17
cccgaggagg catctgcaca g                                        21

<210> SEQ ID NO 18
<211> LENGTH: 21
<212> TYPE: DNA
<213> ORGANISM: artificial sequence
<220> FEATURE:
<223> OTHER INFORMATION: artificial sequence

<400> SEQUENCE: 18
cagaacttca ggtcctaaag g                                        21

<210> SEQ ID NO 19
<211> LENGTH: 32
<212> TYPE: DNA
<213> ORGANISM: artificial sequence
<220> FEATURE:
<223> OTHER INFORMATION: artificial sequence

<400> SEQUENCE: 19
tcgacaagca gggaacaccc aagtagaagc tc                            32

<210> SEQ ID NO 20
<211> LENGTH: 32
<212> TYPE: DNA
<213> ORGANISM: artificial sequence
<220> FEATURE:
<223> OTHER INFORMATION: artificial sequence

<400> SEQUENCE: 20
tcgacaagca gggaagtggg aagtagaagc tc                            32

<210> SEQ ID NO 21
<211> LENGTH: 685
<212> TYPE: PRT
<213> ORGANISM: Homo sapiens

<400> SEQUENCE: 21

Ser Tyr Ser Leu Leu Phe Ser Thr Gly Ala Pro Gln Val Ser Gln
 1               5                  10                  15

Pro Leu Arg Glu Gln Ser Glu Asp Ile Pro Gly Ala Ile Ser Ser
                20                  25                  30

Ala Leu Ala Ala Ile Cys Thr Ala Pro Val Gly Leu Pro Asp Cys
                35                  40                  45

Trp Asp Ala Lys Glu Gln Val Cys Trp His Leu Ala Asn Gln Leu
                50                  55                  60

Thr Glu Asp Ser Ser Gln Leu Arg Pro Ser Leu Ile Ser Gly Leu
                65                  70                  75
```

```
Gln His Pro Ile Leu Cys Leu His Leu Leu Lys Val Leu Tyr Ser
                80                  85                  90

Cys Cys Leu Val Ser Glu Gly Leu Cys Arg Leu Leu Gly Gln Glu
                95                 100                 105

Pro Leu Ala Leu Glu Ser Leu Phe Met Leu Ile Gln Gly Lys Val
               110                 115                 120

Lys Val Val Asp Trp Glu Glu Ser Thr Glu Val Thr Leu Tyr Phe
               125                 130                 135

Leu Ser Leu Leu Val Phe Arg Leu Gln Asn Leu Pro Cys Gly Met
               140                 145                 150

Glu Lys Leu Gly Ser Asp Val Ala Thr Leu Phe Thr His Ser His
               155                 160                 165

Val Val Ser Leu Val Ser Ala Ala Ala Cys Leu Leu Gly Gln Leu
               170                 175                 180

Gly Gln Gln Gly Val Thr Phe Asp Leu Gln Pro Met Glu Trp Met
               185                 190                 195

Ala Ala Ala Thr His Ala Leu Ser Ala Pro Ala Glu Val Arg Leu
               200                 205                 210

Thr Pro Pro Gly Ser Cys Gly Phe Tyr Asp Gly Leu Leu Ile Leu
               215                 220                 225

Leu Leu Gln Leu Leu Thr Glu Gln Gly Lys Ala Ser Leu Ile Arg
               230                 235                 240

Asp Met Ser Ser Ser Glu Met Trp Thr Val Leu Trp His Arg Phe
               245                 250                 255

Ser Met Val Leu Arg Leu Pro Glu Glu Ala Ser Ala Gln Glu Gly
               260                 265                 270

Glu Leu Ser Leu Ser Ser Pro Ser Pro Glu Pro Asp Trp Thr
               275                 280                 285

Leu Ile Ser Pro Gln Gly Met Ala Ala Leu Leu Ser Leu Ala Met
               290                 295                 300

Ala Thr Phe Thr Gln Glu Pro Gln Leu Cys Leu Ser Cys Leu Ser
               305                 310                 315

Gln His Gly Ser Ile Leu Met Ser Ile Leu Lys His Leu Leu Cys
               320                 325                 330

Pro Ser Phe Leu Asn Gln Leu Arg Gln Ala Pro His Gly Ser Glu
               335                 340                 345

Phe Leu Pro Val Val Leu Ser Val Cys Gln Leu Leu Cys Phe
               350                 355                 360

Pro Phe Ala Leu Asp Met Asp Ala Asp Leu Leu Ile Val Val Leu
               365                 370                 375

Ala Asp Leu Arg Asp Ser Glu Val Ala Ala His Leu Leu Gln Val
               380                 385                 390

Cys Cys Tyr His Leu Pro Leu Met Gln Val Glu Leu Pro Ile Ser
               395                 400                 405

Leu Leu Thr Arg Leu Ala Leu Met Asp Pro Thr Ser Leu Asn Gln
               410                 415                 420

Phe Val Asn Thr Val Ser Ala Ser Pro Arg Thr Ile Val Ser Phe
               425                 430                 435

Leu Ser Val Ala Leu Leu Ser Asp Gln Pro Leu Leu Thr Ser Asp
               440                 445                 450

Leu Leu Ser Leu Leu Ala His Thr Ala Arg Val Leu Ser Pro Ser
               455                 460                 465

His Leu Ser Phe Ile Gln Glu Leu Leu Ala Gly Ser Asp Glu Ser
```

```
                     470                 475                 480
Tyr Arg Pro Leu Arg Ser Leu Leu Gly His Pro Glu Asn Ser Val
                485                 490                 495

Arg Ala His Thr Tyr Arg Leu Leu Gly His Leu Leu Gln His Ser
                500                 505                 510

Met Ala Leu Arg Gly Ala Leu Gln Ser Gln Ser Gly Leu Leu Ser
                515                 520                 525

Leu Leu Leu Leu Gly Leu Gly Asp Lys Asp Pro Val Val Arg Cys
                530                 535                 540

Ser Ala Ser Phe Ala Val Gly Asn Ala Ala Tyr Gln Ala Gly Pro
                545                 550                 555

Leu Gly Pro Ala Leu Ala Ala Val Pro Ser Met Thr Gln Leu
                560                 565                 570

Leu Gly Asp Pro Gln Ala Gly Ile Arg Arg Asn Val Ala Ser Ala
                575                 580                 585

Leu Gly Asn Leu Gly Pro Glu Gly Leu Gly Glu Glu Leu Leu Gln
                590                 595                 600

Cys Glu Val Pro Gln Arg Leu Leu Glu Met Ala Cys Gly Asp Pro
                605                 610                 615

Gln Pro Asn Val Lys Glu Ala Ala Leu Ile Ala Leu Arg Ser Leu
                620                 625                 630

Gln Gln Glu Pro Gly Ile His Gln Val Leu Val Ser Leu Gly Ala
                635                 640                 645

Ser Glu Lys Leu Ser Leu Leu Ser Leu Gly Asn Gln Ser Leu Pro
                650                 655                 660

His Ser Ser Pro Arg Pro Ala Ser Ala Lys His Cys Arg Lys Leu
                665                 670                 675

Ile His Leu Leu Arg Pro Ala His Ser Met
                680                 685

<210> SEQ ID NO 22
<211> LENGTH: 221
<212> TYPE: PRT
<213> ORGANISM: Homo sapiens

<400> SEQUENCE: 22

Ser Tyr Ser Leu Leu Phe Ser Thr Gly Ala Pro Gln Val Ser Gln
  1               5                  10                  15

Pro Leu Arg Glu Gln Ser Glu Asp Ile Pro Gly Ala Ile Ser Ser
                 20                  25                  30

Ala Leu Ala Ala Ile Cys Thr Ala Pro Val Gly Leu Pro Asp Cys
                 35                  40                  45

Trp Asp Ala Lys Glu Gln Val Cys Trp His Leu Ala Asn Gln Leu
                 50                  55                  60

Thr Glu Asp Ser Ser Gln Leu Arg Pro Ser Leu Ile Ser Gly Leu
                 65                  70                  75

Gln His Pro Ile Leu Cys Leu His Leu Leu Lys Val Leu Tyr Ser
                 80                  85                  90

Cys Cys Leu Val Ser Glu Gly Leu Cys Arg Leu Leu Gly Gln Glu
                 95                 100                 105

Pro Leu Ala Leu Glu Ser Leu Phe Met Leu Ile Gln Gly Lys Val
                110                 115                 120

Lys Val Val Asp Trp Glu Glu Ser Thr Glu Val Thr Leu Tyr Phe
                125                 130                 135

Leu Ser Leu Leu Val Phe Arg Leu Gln Asn Leu Pro Cys Gly Met
```

```
                    140                 145                 150
Glu Lys Leu Gly Ser Asp Val Ala Thr Leu Phe Thr His Ser His
                155                 160                 165
Val Val Ser Leu Val Ser Ala Ala Ala Cys Leu Leu Gly Gln Leu
                170                 175                 180
Gly Gln Gln Gly Val Thr Phe Asp Leu Gln Pro Met Glu Trp Met
                185                 190                 195
Ala Ala Ala Thr His Ala Leu Ser Ala Pro Ala Glu Leu Leu Thr
                200                 205                 210
Glu Val Gln Met Asp Leu Gly Met Asp Gly Lys
                215                 220 221

<210> SEQ ID NO 23
<211> LENGTH: 795
<212> TYPE: PRT
<213> ORGANISM: Drosophila virilis

<400> SEQUENCE: 23

Met Asp Arg Tyr Ala Val Ser Ser Leu Val Gly Gln Gly Ser Phe
  1               5                  10                  15
Gly Cys Val Tyr Lys Ala Gln Arg Arg Asp Asp Asp Lys Val Val
                 20                  25                  30
Ala Ile Lys Val Ile Ser Lys Arg Gly Arg Ser Asn Arg Glu Leu
                 35                  40                  45
Lys Asn Leu Arg Arg Glu Cys Asp Ile Gln Ala Arg Leu Lys His
                 50                  55                  60
Pro His Val Ile Glu Met Val Glu Ser Phe Glu Ser Lys Phe Asp
                 65                  70                  75
Leu Phe Val Val Thr Glu Phe Ala Leu Met Asp Leu His Arg Tyr
                 80                  85                  90
Leu Ser Phe Asn Gly Ala Met Pro Glu Glu His Ala Gln Arg Val
                 95                 100                 105
Val Cys His Leu Val Ser Ala Leu Tyr Tyr Leu His Ser Asn Arg
                110                 115                 120
Ile Leu His Arg Asp Leu Lys Pro Gln Asn Val Leu Leu Asp Lys
                125                 130                 135
Asn Met His Ala Lys Leu Cys Asp Phe Gly Leu Ala Arg Asn Met
                140                 145                 150
Thr Met Gly Thr His Val Leu Thr Ser Ile Lys Gly Thr Pro Leu
                155                 160                 165
Tyr Met Ala Pro Glu Leu Leu Ala Glu Gln Pro Tyr Asp His Gln
                170                 175                 180
Ala Asp Met Trp Ser Leu Gly Cys Ile Ala Tyr Glu Ser Met Ala
                185                 190                 195
Gly Gln Pro Pro Phe Cys Ala Thr Ser Ile Leu His Leu Val Lys
                200                 205                 210
Leu Ile Lys His Glu Asp Val Lys Trp Pro Ser Thr Leu Ser Ser
                215                 220                 225
Glu Cys Arg Ser Phe Leu Gln Gly Leu Leu Glu Lys Asp Pro Ser
                230                 235                 240
Met Arg Ile Ser Trp Thr Gln Leu Leu Cys His Pro Phe Val Glu
                245                 250                 255
Gly Lys Leu Tyr Ile Ala Glu Val Gln Ala Gln Thr Ser Pro
                260                 265                 270
Phe Ile Asn Pro Gln Leu Ala Lys Asp Thr Lys Lys Ser Gln Gln
```

-continued

```
                275                 280                 285
Leu Arg His Val Gly Ala Asp Leu Gly Asp Val Leu Ala Ala Leu
                290                 295                 300
Lys Leu Ser Asp Val Ala Asn Glu Asn Leu Ser Thr Ser Arg Asp
                305                 310                 315
Ser Ile Asn Ala Ile Ala Pro Ser Asp Ile Glu Gln Leu Glu Thr
                320                 325                 330
Asp Val Glu Asp Asn Val His Arg Leu Ile Val Pro Phe Ala Asp
                335                 340                 345
Ile Ser Tyr Arg Glu Leu Pro Cys Gly Thr Ala Ala Ala Ala Arg
                350                 355                 360
Arg Ala Gly Ala Met Pro Leu Ile Asn Ser Gln Thr Cys Phe Val
                365                 370                 375
Ser Gly Asn Ser Asn Met Ile Leu Asn His Leu Asn Asp Asn Phe
                380                 385                 390
Ala Ile Glu Ala Pro Ala Ser Ser Ala Thr Lys Ser Met Lys Ser
                395                 400                 405
Lys Leu Lys Leu Ala Leu Asn Ile Lys Gln Ser Arg Ser Lys Asp
                410                 415                 420
Leu Glu Lys Arg Lys Leu Ser Gln Asn Leu Asp Asn Phe Ser Leu
                425                 430                 435
Arg Leu Gly Gln Ser Ile Asp Ile Glu Val Gln Arg Lys Thr Thr
                440                 445                 450
Glu Met Leu Thr Gln Gln Ser Gln Ala Gln Gln Leu Gln Asp Arg
                455                 460                 465
Lys Thr Gln Gln Leu Lys Gln Ser Met His Ser Thr Asn Asp Glu
                470                 475                 480
Lys Leu Ser Ser Asp Asn Ser Pro Pro Cys Leu Leu Pro Gly Trp
                485                 490                 495
Asp Ser Cys Asp Glu Ser Gln Ser Pro Pro Ile Glu Asn Asp Glu
                500                 505                 510
Trp Leu Ala Phe Leu His Arg Ser Ile Gln Glu Leu Leu Asp Gly
                515                 520                 525
Glu Phe Asp Ser Leu Lys Gln His Asn Leu Val Ser Ile Ile Val
                530                 535                 540
Ala Pro Leu Arg Asn Ser Lys Ala Ile Pro Lys Val Leu Gln Ser
                545                 550                 555
Val Ala Gln Leu Leu Ser Leu Pro Phe Val Leu Ala Glu Gln His
                560                 565                 570
Leu Val Ala Glu Ala Ile Lys Gly Val Tyr Ile Asp Val Lys Leu
                575                 580                 585
Val Pro Asn Leu Met Tyr Ala Cys Lys Leu Leu Leu Ser Gln Arg
                590                 595                 600
His Leu Thr Asp Ser Ala Ala Ser Leu Pro Ala Gly Thr Gly Val
                605                 610                 615
Ser Leu Ser Arg Thr Val Arg Ser Cys Ser Asp Leu Ser Ala Glu
                620                 625                 630
Glu Met Ser Thr Ala Cys Ser Leu Tyr Glu Leu Val Cys His Leu
                635                 640                 645
Val His Gln Gln Gln Gln Phe Leu Thr Gln Phe Cys Asp Ala Val
                650                 655                 660
Ala Ile Leu Ala Val Asn Asp Met Phe Ile Asn Phe Leu Thr His
                665                 670                 675
```

```
Asp Phe Lys Asp Ser Arg Pro Val Arg Leu Ala Ser Cys Met Leu
            680                 685                 690

Ala Leu Phe Cys Cys Val Leu Arg Glu Leu Pro Glu Asn Ala Glu
            695                 700                 705

Leu Val Glu Lys Ile Val Phe Asp Ser Arg Leu Gln Leu Ala Val
            710                 715                 720

Leu Leu Gln Ser Arg His His Leu Leu Arg Gln Arg Ala Cys Gln
            725                 730                 735

Met Leu Leu Leu Leu Ala Arg Phe Ser Leu Arg Gly Val Gln Cys
            740                 745                 750

Ile Trp Ser Gly Glu Leu Lys Ser Ala Leu Gln Ala Trp Pro Met
            755                 760                 765

Gln Gln Thr Cys Gln Ser Leu Arg Leu Glu Ala Ala Gln Thr Leu
            770                 775                 780

Asp Glu Leu Ser Gln Phe Ser Phe Phe Val Ala Gln Ala Thr Ala
            785                 790                 795

<210> SEQ ID NO 24
<211> LENGTH: 260
<212> TYPE: PRT
<213> ORGANISM: Homo sapiens

<400> SEQUENCE: 24

Met Glu Lys Tyr His Val Leu Glu Met Ile Gly Glu Gly Ser Phe
  1               5                  10                  15

Gly Arg Val Tyr Lys Gly Arg Arg Lys Tyr Ser Ala Gln Val Val
             20                  25                  30

Ala Leu Lys Phe Ile Pro Lys Leu Gly Arg Ser Glu Lys Glu Leu
             35                  40                  45

Arg Asn Leu Gln Arg Glu Ile Glu Ile Met Arg Gly Leu Arg His
             50                  55                  60

Pro Asn Ile Val His Met Leu Asp Ser Phe Glu Thr Asp Lys Glu
             65                  70                  75

Val Val Val Val Thr Asp Tyr Ala Glu Gly Glu Leu Phe Gln Ile
             80                  85                  90

Leu Glu Asp Asp Gly Lys Leu Pro Glu Asp Gln Val Gln Ala Ile
             95                 100                 105

Ala Ala Gln Leu Val Ser Ala Leu Tyr Tyr Leu His Ser His Arg
            110                 115                 120

Ile Leu His Arg Asp Met Lys Pro Gln Asn Ile Leu Leu Ala Lys
            125                 130                 135

Gly Gly Gly Ile Lys Leu Cys Asp Phe Gly Phe Ala Arg Ala Met
            140                 145                 150

Ser Thr Asn Thr Met Val Leu Thr Ser Ile Lys Gly Thr Pro Leu
            155                 160                 165

Tyr Met Ser Pro Glu Leu Val Glu Glu Arg Pro Tyr Asp His Thr
            170                 175                 180

Ala Asp Leu Trp Ser Val Gly Cys Ile Leu Tyr Glu Leu Ala Val
            185                 190                 195

Gly Thr Pro Pro Phe Tyr Ala Thr Ser Ile Phe Gln Leu Val Ser
            200                 205                 210

Leu Ile Leu Lys Asp Pro Val Arg Trp Pro Ser Thr Ile Ser Pro
            215                 220                 225

Cys Phe Lys Asn Phe Leu Gln Gly Leu Leu Thr Lys Asp Pro Arg
            230                 235                 240
```

-continued

Gln Arg Leu Ser Trp Pro Asp Leu Leu Tyr His Pro Phe Ile Ala
            245                 250                 255

Gly His Val Thr Ile
            260

<210> SEQ ID NO 25
<211> LENGTH: 1315
<212> TYPE: PRT
<213> ORGANISM: artificial sequence
<220> FEATURE:
<223> OTHER INFORMATION: artificial sequence

<400> SEQUENCE: 25

Met Glu Lys Tyr His Val Leu Glu Met Ile Gly Glu Gly Ser Phe
 1               5                  10                  15

Gly Arg Val Tyr Lys Gly Arg Lys Tyr Ser Ala Gln Val Val
                20                  25                  30

Ala Leu Arg Phe Ile Pro Lys Leu Gly Arg Ser Glu Lys Glu Leu
                35                  40                  45

Arg Asn Leu Gln Arg Glu Ile Glu Ile Met Arg Gly Leu Arg His
                50                  55                  60

Pro Asn Ile Val His Met Leu Asp Ser Phe Glu Thr Asp Lys Glu
                65                  70                  75

Val Val Val Val Thr Asp Tyr Ala Glu Gly Glu Leu Phe Gln Ile
                80                  85                  90

Leu Glu Asp Asp Gly Lys Leu Pro Glu Asp Gln Val Gln Ala Ile
                95                  100                 105

Ala Ala Gln Leu Val Ser Ala Leu Tyr Tyr Leu His Ser His Arg
                110                 115                 120

Ile Leu His Arg Asp Met Lys Pro Gln Asn Ile Leu Leu Ala Lys
                125                 130                 135

Gly Gly Gly Ile Lys Leu Cys Asp Phe Gly Phe Ala Arg Ala Met
                140                 145                 150

Ser Thr Asn Thr Met Val Leu Thr Ser Ile Lys Gly Thr Pro Leu
                155                 160                 165

Tyr Met Ser Pro Glu Leu Val Glu Glu Arg Pro Tyr Asp His Thr
                170                 175                 180

Ala Asp Leu Trp Ser Val Gly Cys Ile Leu Tyr Glu Leu Ala Val
                185                 190                 195

Gly Thr Pro Pro Phe Tyr Ala Thr Ser Ile Phe Gln Leu Val Ser
                200                 205                 210

Leu Ile Leu Lys Asp Pro Val Arg Trp Pro Ser Thr Ile Ser Pro
                215                 220                 225

Cys Phe Lys Asn Phe Leu Gln Gly Leu Leu Thr Lys Asp Pro Arg
                230                 235                 240

Gln Arg Leu Ser Trp Pro Asp Leu Leu Tyr His Pro Phe Ile Ala
                245                 250                 255

Gly His Val Thr Ile Ile Thr Glu Pro Ala Gly Pro Asp Leu Gly
                260                 265                 270

Thr Pro Phe Thr Ser Arg Leu Pro Pro Glu Leu Gln Val Leu Lys
                275                 280                 285

Asp Glu Gln Ala His Arg Leu Ala Pro Lys Gly Asn Gln Ser Arg
                290                 295                 300

Ile Leu Thr Gln Ala Tyr Lys Arg Met Ala Glu Glu Ala Met Gln
                305                 310                 315

Lys Lys His Gln Asn Thr Gly Pro Ala Leu Glu Gln Glu Asp Lys

|     |     |     | 320 |     |     |     | 325 |     |     |     | 330 |
| --- | --- | --- | --- | --- | --- | --- | --- | --- | --- | --- | --- |
| Thr | Ser | Lys | Val | Ala | Pro | Gly | Thr | Ala | Pro | Leu | Pro | Arg | Leu | Gly |
|     |     |     | 335 |     |     |     | 340 |     |     |     | 345 |
| Ala | Thr | Pro | Gln | Glu | Ser | Ser | Leu | Leu | Ala | Gly | Ile | Leu | Ala | Ser |
|     |     |     | 350 |     |     |     | 355 |     |     |     | 360 |
| Glu | Leu | Lys | Ser | Ser | Trp | Ala | Lys | Ser | Gly | Thr | Gly | Glu | Val | Pro |
|     |     |     | 365 |     |     |     | 370 |     |     |     | 375 |
| Ser | Ala | Pro | Arg | Glu | Asn | Arg | Thr | Thr | Pro | Asp | Cys | Glu | Arg | Ala |
|     |     |     | 380 |     |     |     | 385 |     |     |     | 390 |
| Phe | Pro | Glu | Glu | Arg | Pro | Glu | Val | Leu | Gly | Gln | Arg | Ser | Thr | Asp |
|     |     |     | 395 |     |     |     | 400 |     |     |     | 405 |
| Val | Val | Asp | Leu | Glu | Asn | Glu | Glu | Pro | Asp | Ser | Asp | Asn | Glu | Trp |
|     |     |     | 410 |     |     |     | 415 |     |     |     | 420 |
| Gln | His | Leu | Leu | Glu | Thr | Thr | Glu | Pro | Val | Pro | Ile | Gln | Leu | Lys |
|     |     |     | 425 |     |     |     | 430 |     |     |     | 435 |
| Ala | Pro | Leu | Thr | Leu | Cys | Asn | Pro | Asp | Phe | Cys | Gln | Arg | Ile |
|     |     |     | 440 |     |     |     | 445 |     |     |     | 450 |
| Gln | Ser | Gln | Leu | His | Glu | Ala | Gly | Gly | Gln | Ile | Leu | Lys | Gly | Ile |
|     |     |     | 455 |     |     |     | 460 |     |     |     | 465 |
| Leu | Glu | Gly | Ala | Ser | His | Ile | Leu | Pro | Ala | Phe | Arg | Val | Leu | Ser |
|     |     |     | 470 |     |     |     | 475 |     |     |     | 480 |
| Ser | Leu | Leu | Ser | Ser | Cys | Ser | Asp | Ser | Val | Ala | Leu | Tyr | Ser | Phe |
|     |     |     | 485 |     |     |     | 490 |     |     |     | 495 |
| Cys | Arg | Glu | Ala | Gly | Leu | Pro | Gly | Leu | Leu | Ser | Leu | Leu | Arg |
|     |     |     | 500 |     |     |     | 505 |     |     |     | 510 |
| His | Ser | Gln | Glu | Ser | Asn | Ser | Leu | Gln | Gln | Gln | Ser | Trp | Tyr | Gly |
|     |     |     | 515 |     |     |     | 520 |     |     |     | 525 |
| Thr | Phe | Leu | Gln | Asp | Leu | Met | Ala | Val | Ile | Gln | Ala | Tyr | Phe | Ala |
|     |     |     | 530 |     |     |     | 535 |     |     |     | 540 |
| Cys | Thr | Phe | Asn | Leu | Glu | Arg | Ser | Gln | Thr | Ser | Asp | Ser | Leu | Gln |
|     |     |     | 545 |     |     |     | 550 |     |     |     | 555 |
| Val | Phe | Gln | Glu | Ala | Ala | Asn | Leu | Phe | Leu | Asp | Leu | Leu | Gly | Lys |
|     |     |     | 560 |     |     |     | 565 |     |     |     | 570 |
| Leu | Leu | Ala | Gln | Pro | Asp | Asp | Ser | Glu | Gln | Thr | Leu | Arg | Arg | Asp |
|     |     |     | 575 |     |     |     | 580 |     |     |     | 585 |
| Ser | Leu | Met | Cys | Phe | Thr | Val | Leu | Cys | Glu | Ala | Met | Asp | Gly | Asn |
|     |     |     | 590 |     |     |     | 595 |     |     |     | 600 |
| Ser | Arg | Ala | Ile | Ser | Lys | Ala | Phe | Tyr | Ser | Ser | Leu | Leu | Thr | Thr |
|     |     |     | 605 |     |     |     | 610 |     |     |     | 615 |
| Gln | Gln | Val | Val | Leu | Asp | Gly | Leu | Leu | His | Gly | Leu | Thr | Val | Pro |
|     |     |     | 620 |     |     |     | 625 |     |     |     | 630 |
| Gln | Leu | Pro | Val | His | Thr | Pro | Gln | Gly | Ala | Pro | Gln | Val | Ser | Gln |
|     |     |     | 635 |     |     |     | 640 |     |     |     | 645 |
| Pro | Leu | Arg | Glu | Gln | Ser | Glu | Asp | Ile | Pro | Gly | Ala | Ile | Ser | Ser |
|     |     |     | 650 |     |     |     | 655 |     |     |     | 660 |
| Ala | Leu | Ala | Ala | Ile | Cys | Thr | Ala | Pro | Val | Gly | Leu | Pro | Asp | Cys |
|     |     |     | 665 |     |     |     | 670 |     |     |     | 675 |
| Trp | Asp | Ala | Lys | Glu | Gln | Val | Cys | Trp | His | Leu | Ala | Asn | Gln | Leu |
|     |     |     | 680 |     |     |     | 685 |     |     |     | 690 |
| Thr | Glu | Asp | Ser | Ser | Gln | Leu | Arg | Pro | Ser | Leu | Ile | Ser | Gly | Leu |
|     |     |     | 695 |     |     |     | 700 |     |     |     | 705 |
| Gln | His | Pro | Ile | Leu | Cys | Leu | His | Leu | Leu | Lys | Val | Leu | Tyr | Ser |
|     |     |     | 710 |     |     |     | 715 |     |     |     | 720 |

-continued

Cys Cys Leu Val Ser Glu Gly Leu Cys Arg Leu Leu Gly Gln Glu
            725                 730                 735

Pro Leu Ala Leu Glu Ser Leu Phe Met Leu Ile Gln Gly Lys Val
            740                 745                 750

Lys Val Val Asp Trp Glu Glu Ser Thr Glu Val Thr Leu Tyr Phe
            755                 760                 765

Leu Ser Leu Leu Val Phe Arg Leu Gln Asn Leu Pro Cys Gly Met
            770                 775                 780

Glu Lys Leu Gly Ser Asp Val Ala Thr Leu Phe Thr His Ser His
            785                 790                 795

Val Val Ser Leu Val Ser Ala Ala Ala Cys Leu Leu Gly Gln Leu
            800                 805                 810

Gly Gln Gln Gly Val Thr Phe Asp Leu Gln Pro Met Glu Trp Met
            815                 820                 825

Ala Ala Ala Thr His Ala Leu Ser Ala Pro Ala Glu Val Arg Leu
            830                 835                 840

Thr Pro Pro Gly Ser Cys Gly Phe Tyr Asp Gly Leu Leu Ile Leu
            845                 850                 855

Leu Leu Gln Leu Leu Thr Glu Gln Gly Lys Ala Ser Leu Ile Arg
            860                 865                 870

Asp Met Ser Ser Glu Met Trp Thr Val Leu Trp His Arg Phe
            875                 880                 885

Ser Met Val Leu Arg Leu Pro Glu Glu Ala Ser Ala Gln Glu Gly
            890                 895                 900

Glu Leu Ser Leu Ser Ser Pro Ser Pro Gly Pro Asp Trp Thr
            905                 910                 915

Leu Ile Ser Pro Gln Gly Met Ala Ala Leu Leu Ser Leu Ala Met
            920                 925                 930

Ala Thr Phe Thr Gln Glu Pro Gln Leu Cys Leu Ser Cys Leu Ser
            935                 940                 945

Gln His Gly Ser Ile Leu Met Ser Ile Leu Lys His Leu Leu Cys
            950                 955                 960

Pro Ser Phe Leu Asn Gln Leu Arg Gln Ala Pro His Gly Ser Glu
            965                 970                 975

Phe Leu Pro Val Val Leu Ser Val Cys Gln Leu Leu Cys Phe
            980                 985                 990

Pro Phe Ala Leu Asp Met Asp Ala Asp Leu Leu Ile Val Val Leu
            995                1000                1005

Ala Asp Leu Arg Asp Ser Glu Val Ala Ala His Leu Leu Gln Val
            1010                1015                1020

Cys Cys Tyr His Leu Pro Leu Met Gln Val Glu Leu Pro Ile Ser
            1025                1030                1035

Leu Leu Thr Arg Leu Ala Leu Met Asp Pro Thr Ser Leu Asn Gln
            1040                1045                1050

Phe Val Asn Thr Val Ser Ala Ser Pro Arg Thr Ile Val Ser Phe
            1055                1060                1065

Leu Ser Val Ala Leu Leu Ser Asp Gln Pro Leu Leu Thr Ser Asp
            1070                1075                1080

Leu Leu Ser Leu Leu Ala His Thr Ala Arg Val Leu Ser Pro Ser
            1085                1090                1095

His Leu Ser Phe Ile Gln Glu Leu Leu Ala Gly Ser Asp Glu Ser
            1100                1105                1110

Tyr Arg Pro Leu Arg Ser Leu Leu Gly His Pro Glu Asn Ser Val
            1115                1120                1125

```
Arg Ala His Thr Tyr Arg Leu Leu Gly His Leu Leu Gln His Ser
            1130                1135                1140

Met Ala Leu Arg Gly Ala Leu Gln Ser Gln Ser Gly Leu Leu Ser
        1145                1150                1155

Leu Leu Leu Leu Gly Leu Gly Asp Lys Asp Pro Val Val Arg Cys
    1160                1165                1170

Ser Ala Ser Phe Ala Val Gly Asn Ala Ala Tyr Gln Ala Gly Pro
        1175                1180                1185

Leu Gly Pro Ala Leu Ala Ala Ala Val Pro Ser Met Thr Gln Leu
        1190                1195                1200

Leu Gly Asp Pro Gln Ala Gly Ile Arg Arg Asn Val Ala Ser Ala
        1205                1210                1215

Leu Gly Asn Leu Gly Pro Glu Gly Leu Gly Glu Glu Leu Leu Gln
        1220                1225                1230

Cys Glu Val Pro Gln Arg Leu Leu Glu Met Ala Cys Gly Asp Pro
        1235                1240                1245

Gln Pro Asn Val Lys Glu Ala Ala Leu Ile Ala Leu Arg Ser Leu
        1250                1255                1260

Gln Gln Glu Pro Gly Ile His Gln Val Leu Val Ser Leu Gly Ala
        1265                1270                1275

Ser Glu Lys Leu Ser Leu Leu Ser Leu Gly Asn Gln Ser Leu Pro
        1280                1285                1290

His Ser Ser Pro Arg Pro Ala Ser Ala Lys His Cys Arg Lys Leu
        1295                1300                1305

Ile His Leu Leu Arg Pro Ala His Ser Met
        1310                1315

<210> SEQ ID NO 26
<211> LENGTH: 4586
<212> TYPE: DNA
<213> ORGANISM: Drosophila virilis

<400> SEQUENCE: 26
tgcagagtct gggccatcgg ctagctctgt agatgtgtaa tagaggcatc         50
ttcgcgcgca gcatcgattc gcgctccagt tggttgagat gccgaatgtt        100
ggtgcgcgtc tcaaagatga cgccgacatg gtgcatatac agaaaaaaga        150
aacccgagcc taatggccgc gtattatcgc tgaggcggcc ggcgattttc        200
aacaaatgct acttaccaat tagcgcgtgc gataaaatta cgtacaaatt        250
ggcgtcgcgc atatttctgg cgtttgtgtt gcgtgtatct agttagtggg        300
ctcgtctatt cattatttac ttttggggcg tctgtttgat caaattagca        350
gtgtctccta tgatatgcct gcagctttta cccgtaaaca aaattatttg        400
ccacagctga tttattcgtt gccatgtaga ttaatcagct gtttcgcaat        450
ttttaaaacc aggtgacttt ttaaaattgt accagctgtg tgtatcgatg        500
tgcaagcata ctcattacgc catatgctgg tatatttata tcgaatataa        550
acggttttgg tattttaata atcttaaaga agaaatagtt atgtgctgtg        600
tatatgttca tcaagaactg ttcaaaatgt gcgccatact gatgttaatt        650
ttgttttgct ggttttttt  gggaaaataa attgacgtgt tgatgtctcc        700
gaatatatcg atacaatagc tatcattcgg acaagatatc gatatgtgga        750
gtgtgttcgg tattttgcct ttagtttttt gttttaaat tgcagtcaca         800
```

```
ctgcggctta ttgaatttaa ggcacttcaa agcgcatttt actgtagaaa        850
gttgagttct atttgcggtg acaatggacc gctacgcggt tagctctctg        900
gtaggacaag gctcatttgg ctgtgtgtac aaggcccagc ggcgcgatga        950
tgacaaagtg gtggccatca aagtcatatc aaaggtgagc tcaattgcat       1000
cccggcttag ctgaataaaa gagtattcta cgaattggcg tgttctttgt       1050
ttgcagcgtg gtcgttccaa tcgcgagctt aagaacctgc gtcgcgaatg       1100
tgacattcag gcgcgtctca agcatccgca tgttatagaa atggtggagt       1150
cgttcgaatc caaattcgat tgttcgtgg tcaccgagtt cgctctaatg        1200
gacttgcatc gatatttgtc ctttaatggc gccatgcccg aggagcacgc       1250
acagcgtgtt gtctgtcatt tggtgtcggc gctctattat ctgcactcga       1300
atcgcatact gcatcgggat ctaaagccgc aaaatgtgct gttggacaaa       1350
aacatgcacg ccaagctctg cgactttggg ctggcacgca acatgacgat       1400
gggcacacat gtgttgactt ccataaaggg cacgccgctt tatatggcgc       1450
cggagctgct ggctgagcag ccgtacgatc accaggcaga tatgtggtcg       1500
ctgggatgca ttgcctatga gagtatggcg ggccagccgc cgttctgcgc       1550
aacctctata ctgcatctgg tgaagctgat caagcacgag gacgtcaaat       1600
ggccgagcac gctgagcagc gagtgccgtt ccttttttgca gggcttgctc      1650
gagaaggatc ctagcatgcg catctcatgg acgcagctgc tttgccatcc       1700
ttttgtcgag ggcaagctat acatagccga ggtacaggca gcacaaactt       1750
cgcccttat aaatccccag ctggccaagg acaccaaaaa atcacagcaa        1800
ttgaggtgcg tttataacgt gtactgtagc cagctccact tatcgttcaa       1850
tttttatgta ggcatgtagg cgcagatttg ggcgatgtct tggcagcgtt       1900
aaagttgagc gatgtggcca atgaaaactt gagcacatcg cgagatagta       1950
tcaatgccat tgcgccgagt gacattgagc agctggaaac cgatgttgag       2000
gataatgtgc atcggcttat agtgccattt gcagatattt cctacagaga       2050
gttgccatgc ggcactgcag cagctgctcg tcgagctggt gccatgccac       2100
tgattaattc gcaaacctgc tttgtaagtg caactccaa tatgatactc        2150
aatcatctga acgacaattt tgcaatcgaa gcgcctgctt cgagcgcaac       2200
caagtccatg aagtcgaagc tgaagctggc tctcaatata aaacagtcgc       2250
gtagcaagga tttggaaaag cgtaagctga gtcaaaattt ggataacttt       2300
tcgctgcgcc tgggacagag cattgacata gaagtgcagc gcaaaacaac       2350
tgagatgctc acgcagcaat cgcaggcaca acagctgcag gataggaaga       2400
cacagcagct gaagcaatcg atgcattcca ccaacgacga gaaattgagc       2450
agcgagtgag taaatgcatc catatttaaa agtgaagctc tctaaagcta       2500
tttggtttat aatagcaatt cgccgccttg tctgttgccc ggttgggaca       2550
gctgcgatga atctcagagc ccgcccattg agaatgacga gtggctggcg       2600
ttcttgcatc gctccataca ggagctgctg acggcgaat ttgattcgct        2650
gaagcagcac aatctagtca gcataattgt ggcgccattg cgaaactcca       2700
aggccatacc caaggtgctg cagagcgtgg cgcagctgct gtcgctgccc       2750
tttgtgctgg ccgaacagca tttggtagcg gaggccataa aaggagttta       2800
```

| | |
|---|---|
| tattgatgtc aagctggtgc ccaacttaat gtacgcctgc aagctgcttc | 2850 |
| tctcgcagcg ccaccttacc gattcggctg cttcactgcc agccggcacg | 2900 |
| ggcgtctccc tgagtcgaac cgtacgcagc tgctccgacc tgagtgccga | 2950 |
| ggagatgagc accgcctgca gcctgtacga gctggtctgc catctggtcc | 3000 |
| atcagcagca gcagttcctc acccagttct gtgacgctgt ggcaatactc | 3050 |
| gccgtcaacg acatgttcat aaatttctt acacatggtg agcagctggc | 3100 |
| tggacacagt gtgagacgca agcttaacca ttccttgctt tgcagatttt | 3150 |
| aaggatagca ggccggtgcg actcgctagc tgcatgctgg cattgttctg | 3200 |
| ttgcgttttg cgtgaactac ccgagaacgc cgagctggtg gagaaaattg | 3250 |
| tatttgactc gcgcctacag ctggccgtcc tgctgcagag ccgtcatcat | 3300 |
| ttgttgcgtc agcgcgcctg tcaaatgctg ttgctattgg cacgctttag | 3350 |
| cctgcgcggc gtacagtgca tctggagtgg ggagctgaag agtgcgctcc | 3400 |
| aggcgtggcc gatgcagcaa acgtgtcaat cattgcgact ggaagccgcc | 3450 |
| caaacgctgg atgagcttag ccagttcagc ttctttgttg ctcaggcaac | 3500 |
| tgcttagtct ttattaataa ttgtacttgt atttgtttaa taaatcttaa | 3550 |
| tccttgtcta gccgaacaga ccttccaaat tgccttgaaa gtagtcgagc | 3600 |
| agctcgtcca gatagctgct aaagccatca agcccaaaa ggtagctacc | 3650 |
| attacagtcc tgctcgtaca tctcgtttag tttcgaaata tccttatccg | 3700 |
| acagccgcgc gctggcccag tgaggcatac ggatcctaat gataatagca | 3750 |
| tgcattatta ttatttttca caatgtgtta ttcgtttaat acttataaaa | 3800 |
| ccttaaattg tatgcatgta tgtatctatc ttatacctaa ttaatgaatg | 3850 |
| aaatttatta acttgtctat ggatgtatgt gcatgtatgt atgtatgtat | 3900 |
| gtatgcataa aaatgtatgt tcatttataa caaacgcaga caaagataac | 3950 |
| gatctgctgc tctacttccc gaatctcata aattcaagta cgccccgcag | 4000 |
| atttcacgag tacatcacaa gtgttttttt ttaacaagta atgttggtat | 4050 |
| gtatttatgt atatatgtat ttaagtatgt atgtatttat gtatgtatgt | 4100 |
| atgtatttat gtatgtatgt atttatgtat gtatgtattt atgtatgtat | 4150 |
| gtatttatgt atgtatttat ttatgtatat atgtatttaa gtatgtatgt | 4200 |
| atgtatttat gcatttatgt atttatgtat gtatgtataa gagtatgtgt | 4250 |
| gtgtgtagat acatgtatgt atgtatgtat gtatgcgtgt atatttattt | 4300 |
| atagtaaaca taccaacttt acttcccgct gccttgcgaa tttaaaataa | 4350 |
| cgtatttta aatgatgccc tactcctcga ttctcaaaca tttaagtaag | 4400 |
| ctctacaggt ttttccgatt tgattgtttt gtaaagttgt gttttttttt | 4450 |
| ctgctcgatc tcttgtgtat tctctactct ttgtgtgcct ctctttagtt | 4500 |
| ttctctcctt ctctcttgct ctccctgtt ctctctctat ctctctccct | 4550 |
| ccctctttcc acctatctca ttctctttct aagctt | 4586 |

<210> SEQ ID NO 27
<211> LENGTH: 1055
<212> TYPE: PRT
<213> ORGANISM: Homo sapiens

<400> SEQUENCE: 27

```
Ile Thr Glu Pro Ala Gly Pro Asp Leu Gly Thr Pro Phe Thr Ser
  1               5                  10                  15

Arg Leu Pro Pro Glu Leu Gln Val Leu Lys Asp Glu Gln Ala His
                 20                  25                  30

Arg Leu Ala Pro Lys Gly Asn Gln Ser Arg Ile Leu Thr Gln Ala
                 35                  40                  45

Tyr Lys Arg Met Ala Glu Glu Ala Met Gln Lys Lys His Gln Asn
                 50                  55                  60

Thr Gly Pro Ala Leu Glu Gln Glu Asp Lys Thr Ser Lys Val Ala
                 65                  70                  75

Pro Gly Thr Ala Pro Leu Pro Arg Leu Gly Ala Thr Pro Gln Glu
                 80                  85                  90

Ser Ser Leu Leu Ala Gly Ile Leu Ala Ser Glu Leu Lys Ser Ser
                 95                 100                 105

Trp Ala Lys Ser Gly Thr Gly Glu Val Pro Ser Ala Pro Arg Glu
                110                 115                 120

Asn Arg Thr Thr Pro Asp Cys Glu Arg Ala Phe Pro Glu Glu Arg
                125                 130                 135

Pro Glu Val Leu Gly Gln Arg Ser Thr Asp Val Val Asp Leu Glu
                140                 145                 150

Asn Glu Glu Pro Asp Ser Asp Asn Glu Trp Gln His Leu Leu Glu
                155                 160                 165

Thr Thr Glu Pro Val Pro Ile Gln Leu Lys Ala Pro Leu Thr Leu
                170                 175                 180

Leu Cys Asn Pro Asp Phe Cys Gln Arg Ile Gln Ser Gln Leu His
                185                 190                 195

Glu Ala Gly Gly Gln Ile Leu Lys Gly Ile Leu Glu Gly Ala Ser
                200                 205                 210

His Ile Leu Pro Ala Phe Arg Val Leu Ser Ser Leu Leu Ser Ser
                215                 220                 225

Cys Ser Asp Ser Val Ala Leu Tyr Ser Phe Cys Arg Glu Ala Gly
                230                 235                 240

Leu Pro Gly Leu Leu Leu Ser Leu Leu Arg His Ser Gln Glu Ser
                245                 250                 255

Asn Ser Leu Gln Gln Gln Ser Trp Tyr Gly Thr Phe Leu Gln Asp
                260                 265                 270

Leu Met Ala Val Ile Gln Ala Tyr Phe Ala Cys Thr Phe Asn Leu
                275                 280                 285

Glu Arg Ser Gln Thr Ser Asp Ser Leu Gln Val Phe Gln Glu Ala
                290                 295                 300

Ala Asn Leu Phe Leu Asp Leu Leu Gly Lys Leu Leu Ala Gln Pro
                305                 310                 315

Asp Asp Ser Glu Gln Thr Leu Arg Arg Asp Ser Leu Met Cys Phe
                320                 325                 330

Thr Val Leu Cys Glu Ala Met Asp Gly Asn Ser Arg Ala Ile Ser
                335                 340                 345

Lys Ala Phe Tyr Ser Ser Leu Leu Thr Thr Gln Gln Val Val Leu
                350                 355                 360

Asp Gly Leu Leu His Gly Leu Thr Val Pro Gln Leu Pro Val His
                365                 370                 375

Thr Pro Gln Gly Ala Pro Gln Val Ser Gln Pro Leu Arg Glu Gln
                380                 385                 390

Ser Glu Asp Ile Pro Gly Ala Ile Ser Ser Ala Leu Ala Ala Ile
                395                 400                 405
```

-continued

```
Cys Thr Ala Pro Val Gly Leu Pro Asp Cys Trp Asp Ala Lys Glu
            410                 415                 420
Gln Val Cys Trp His Leu Ala Asn Gln Leu Thr Glu Asp Ser Ser
            425                 430                 435
Gln Leu Arg Pro Ser Leu Ile Ser Gly Leu Gln His Pro Ile Leu
            440                 445                 450
Cys Leu His Leu Leu Lys Val Leu Tyr Ser Cys Cys Leu Val Ser
            455                 460                 465
Glu Gly Leu Cys Arg Leu Leu Gly Gln Glu Pro Leu Ala Leu Glu
            470                 475                 480
Ser Leu Phe Met Leu Ile Gln Gly Lys Val Lys Val Val Asp Trp
            485                 490                 495
Glu Glu Ser Thr Glu Val Thr Leu Tyr Phe Leu Ser Leu Leu Val
            500                 505                 510
Phe Arg Leu Gln Asn Leu Pro Cys Gly Met Glu Lys Leu Gly Ser
            515                 520                 525
Asp Val Ala Thr Leu Phe Thr His Ser His Val Val Ser Leu Val
            530                 535                 540
Ser Ala Ala Ala Cys Leu Leu Gly Gln Leu Gly Gln Gln Gly Val
            545                 550                 555
Thr Phe Asp Leu Gln Pro Met Glu Trp Met Ala Ala Ala Thr His
            560                 565                 570
Ala Leu Ser Ala Pro Ala Glu Val Arg Leu Thr Pro Pro Gly Ser
            575                 580                 585
Cys Gly Phe Tyr Asp Gly Leu Leu Ile Leu Leu Leu Gln Leu Leu
            590                 595                 600
Thr Glu Gln Gly Lys Ala Ser Leu Ile Arg Asp Met Ser Ser Ser
            605                 610                 615
Glu Met Trp Thr Val Leu Trp His Arg Phe Ser Met Val Leu Arg
            620                 625                 630
Leu Pro Glu Glu Ala Ser Ala Gln Glu Gly Glu Leu Ser Leu Ser
            635                 640                 645
Ser Pro Pro Ser Pro Glu Pro Asp Trp Thr Leu Ile Ser Pro Gln
            650                 655                 660
Gly Met Ala Ala Leu Leu Ser Leu Ala Met Ala Thr Phe Thr Gln
            665                 670                 675
Glu Pro Gln Leu Cys Leu Ser Cys Leu Ser Gln His Gly Ser Ile
            680                 685                 690
Leu Met Ser Ile Leu Lys His Leu Leu Cys Pro Ser Phe Leu Asn
            695                 700                 705
Gln Leu Arg Gln Ala Pro His Gly Ser Glu Phe Leu Pro Val Val
            710                 715                 720
Val Leu Ser Val Cys Gln Leu Leu Cys Phe Pro Phe Ala Leu Asp
            725                 730                 735
Met Asp Ala Asp Leu Leu Ile Val Val Leu Ala Asp Leu Arg Asp
            740                 745                 750
Ser Glu Val Ala Ala His Leu Leu Gln Val Cys Cys Tyr His Leu
            755                 760                 765
Pro Leu Met Gln Val Glu Leu Pro Ile Ser Leu Leu Thr Arg Leu
            770                 775                 780
Ala Leu Met Asp Pro Thr Ser Leu Asn Gln Phe Val Asn Thr Val
            785                 790                 795
Ser Ala Ser Pro Arg Thr Ile Val Ser Phe Leu Ser Val Ala Leu
```

```
                    800                 805                 810

Leu Ser Asp Gln Pro Leu Leu Thr Ser Asp Leu Leu Ser Leu Leu
                815                 820                 825

Ala His Thr Ala Arg Val Leu Ser Pro Ser His Leu Ser Phe Ile
                830                 835                 840

Gln Glu Leu Leu Ala Gly Ser Asp Glu Ser Tyr Arg Pro Leu Arg
                845                 850                 855

Ser Leu Leu Gly His Pro Glu Asn Ser Val Arg Ala His Thr Tyr
                860                 865                 870

Arg Leu Leu Gly His Leu Leu Gln His Ser Met Ala Leu Arg Gly
                875                 880                 885

Ala Leu Gln Ser Gln Ser Gly Leu Leu Ser Leu Leu Leu Leu Gly
                890                 895                 900

Leu Gly Asp Lys Asp Pro Val Val Arg Cys Ser Ala Ser Phe Ala
                905                 910                 915

Val Gly Asn Ala Ala Tyr Gln Ala Gly Pro Leu Gly Pro Ala Leu
                920                 925                 930

Ala Ala Ala Val Pro Ser Met Thr Gln Leu Leu Gly Asp Pro Gln
                935                 940                 945

Ala Gly Ile Arg Arg Asn Val Ala Ser Ala Leu Gly Asn Leu Gly
                950                 955                 960

Pro Glu Gly Leu Gly Glu Glu Leu Leu Gln Cys Glu Val Pro Gln
                965                 970                 975

Arg Leu Leu Glu Met Ala Cys Gly Asp Pro Gln Pro Asn Val Lys
                980                 985                 990

Glu Ala Ala Leu Ile Ala Leu Arg Ser Leu Gln Gln Glu Pro Gly
                995                 1000                1005

Ile His Gln Val Leu Val Ser Leu Gly Ala Ser Glu Lys Leu Ser
                1010                1015                1020

Leu Leu Ser Leu Gly Asn Gln Ser Leu Pro His Ser Ser Pro Arg
                1025                1030                1035

Pro Ala Ser Ala Lys His Cys Arg Lys Leu Ile His Leu Leu Arg
                1040                1045                1050

Pro Ala His Ser Met
                1055

<210> SEQ ID NO 28
<211> LENGTH: 24
<212> TYPE: PRT
<213> ORGANISM: Artificial Sequence
<220> FEATURE:
<223> OTHER INFORMATION: Artificial Sequence 1-24

<400> SEQUENCE: 28

Cys Ala Leu Lys Phe Ile Pro Lys Leu Gly Arg Ser Glu Lys Glu
  1               5                   10                  15

Leu Arg Asn Leu Gln Arg Glu Ile Glu
                20                  24
```

NUCLEIC ACID ENCODING FUSED

RELATED APPLICATIONS

This application is a continuation of U.S. Ser. No. 10/174,653 filed Jun. 17, 2002, now U.S. Pat. No. 7,259,245, which is a Divisional of U.S. Ser. No. 09/392,277, filed Sep. 3, 1999, now U.S. Pat. No. 6,451,977, which is a Continuation-in-Part of U.S. Ser. No. 09/258,000, filed Feb. 25, 1999, now U.S. Pat. No. 6,531,579, which claims the benefit under 35 U.S.C. §119 of U.S. Ser. No. 60/076,072, filed Feb. 26, 1998, now expired; the contents all of which are incorporated herein by reference.

FIELD OF THE INVENTION

The present invention relates generally to signaling molecules, specifically to signaling and mediator molecules in the hedgehog (Hh) cascade which are involved in cell proliferation and differentiation.

BACKGROUND OF THE INVENTION

Development of multicellular organisms depends, at least in part, on mechanisms which specify, direct or maintain positional information to pattern cells, tissues, or organs. Various secreted signaling molecules, such as members of the transforming growth factor-beta (TGF-β), Wnt, fibroblast growth factors and hedgehog families have been associated with patterning activity of different cells and structures in Drosophila as well as in vertebrates. Perrimon, Cell: 80: 517-520 (1995).

Hedgehog (Hh) was first identified as a segment-polarity gene by a genetic screen in Drosophila melanogaster, Nusslein-Volhard et al., Roux. Arch. Dev. Biol. 193: 267-282 (1984), that plays a wide variety of developmental functions. Perrimon, supra.; Hammerschmidt et al., Trends Genet. 13: 14-21 (1997). Although only one Drosophila Hh gene has been identified, three mammalian Hh homologues have been isolated: Sonic Hh (Shh), Desert Hh (DHh) and Indian Hh (IHh). Reviewed by Hammerschmidt et al., Trends Genet. 13: 14-21 (1997). Shh is expressed at high level in the notochord and floor plate of developing vertebrate embryos where it plays a key role in neural tube patterning. Echelard et al., Cell 75: 1417-30 (1993), Ericson et al., Cell 81: 747-56 (1995), Hynes et al., Neuron 19: 15-26 (1997), Krauss et al., Cell 75, 1431-44 (1993), Marti et al., Nature 375: 322-25 (1995), Roelink et al, Cell 81: 445-55 (1995). Shh also plays a role in the development of limbs (Laufer et al., Cell 79, 993-1003 (1994)), somites (Fan and Tessier-Lavigne, Cell 79, 1175-86 (1994); Johnson et al., Cell 79: 1165-73 (1994)), gut (Roberts et al., Development 121: 3163-74 (1995), lungs (Bellusci et al., Develop. 124: 53-63 (1997) and skin (Oro et al., Science 276: 817-21 (1997), as well as the regulation of left-right asymmetry (reviewed by Ramsdell and Yost, Trends in Genetics 14: 459-65 (1998)). Likewise, IHh and DHh are involved in bone and germinal cell development, Vortkamp et al., Science 273: 613-22 (1996), Bitgood et al., Curr. Biol. 6: 298-304. Shh knockout mice further strengthened the notion that Shh is critical to many aspect of vertebrate development, Chiang et al., Nature 383: 407-13 (1996). These mice show defects in midline structures such as the notochord and the floor plate, absence of ventral cell types in neural tube, absence of distal limb structures, cyclopia, and absence of the spinal column and most of the ribs.

At the cell surface, the Hh signals is thought to be relayed by the 12 transmembrane domain protein Patched (Ptch) [Hooper and Scott, Cell 59: 751-65 (1989); Nakano et al., Nature 341: 508-13 (1989)] and the G-protein coupled like receptor Smoothened (Smo) [Alcedo et al., Cell 86: 221-232 (1996); van den Heuvel and Ingham, Nature 382: 547-551 (1996)]. Both genetic and biochemical evidence support a receptor model where Ptch and Smo are part of a multicomponent receptor complex, Chen and Struhl, Cell 87: 553-63 (1996); Marigo et al., Nature 384: 176-9 (1996); Stone et al., Nature 384: 129-34 (1996). Upon binding of Hh to Ptch, the normal inhibitory effect of Ptch on Smo is relieved, allowing Smo to transduce the Hh signal across the plasma membrane. Loss of function mutations in the Ptch gene have been identified in patients with the basal cell nevus syndrome (BCNS), a hereditary disease characterized by multiple basal cell carcinomas (BCCs). Disfunctional Ptch gene mutations have also been associated with a large percentage of sporadic basal cell carcinoma tumors, Chidambaram et al., Cancer Research 56: 4599-601 (1996); Gailani et al., Nature Genet. 14: 78-81 (1996); Hahn et al., Cell 85: 841-51 (1996); Johnson et al., Science 272: 1668-71 (1996); Unden et al., Cancer Res. 56: 4562-5 (1996); Wicking et al., Am. J. Hum. Genet. 60: 21-6 (1997). Loss of Ptch function is thought to cause an uncontrolled Smo signaling in basal cell carcinoma. Similarly, activating Smo mutations have been identified in sporatic BCC tumors (Xie et al., Nature 391: 90-2 (1998)), emphasizing the role of Smo as the signaling subunit in the receptor complex for Shh.

However, the exact mechanism by which Ptch controls Smo activity still has yet to be clarified and the signaling mechanisms by which the Hh signal is transmitted from the receptor to downstream targets is unclear. Genetic epistatic analysis in Drosophila has identified several segment-polarity genes which appear to function as components of the Hh signal transduction pathway, Ingham, Curr. Opin. Genent. Dev. 5: 492-98 (1995); Perrimon, supra.

Signaling by hedgehog has been shown to be transduced in vertebrates through the Gli family of zinc finger transcription factors, Hynes et al., Neuron 19: 15-26 (1997); Lee et al., Development 124: 2537-52 (1997); Sasaki et al., Development 124: 1313-22 (1997); Ruiz, i Altaba, Development 125: 2203-12 (1998), and in Drosophila by the Gli homologue Cubitus interruptus (Ci) (Orenic et al., Genes Dev. 4: 1053-67 (1990); Alexandre et al., Genes Dev. 10: 2003-13 (1996); Dominquez et al., Science 272: 1621-25 (1996). Consistent with a pivotal role for Ci in transducing the Hh signal, several genes have been identified genetically in Drosophila and shown to modulate Ci activity (reviewed by Goodrich and Scott, Neuron 21: 1243-57 (1998); Ingham, Embo. J. 17: 3505-11 (1998). These include the putative serine threonine kinase fused (Fu), Preat et al., Genetics 135: 1047-62 (1993), a novel protein designated Suppressor of fused (Su(fu)) [Pham et al., Genetics 140: 587-98 (1995); Preat, Genetics 132: 725-36 (1992)] protein kinase A (PKA), Li et al., Cell 80: 553-562 (1995); Pan and Rubin, Cell 80: 543-52 (1995)], the kinesin-like molecule, Costal-2 (Cos-2) [Robbins et al., Cell 90: 225-34 (1997); Sisson et al., Cell 90: 235-45 (1997)], and the F-box/WD40 repeat protein slimb [Jiang and Struhl, Nature 391: 493-496 (1998)]. Additional elements implicated in Hh signaling include the transcription factor CBP [Akimaru et al., Nature 386: 735-738 (1997)], and the Shh response element COUP-TFII [Krishnan et al., Science 278: 1947-1950 (1997)].

Mutations in Cos-2 are embryonicly lethal and display a phenotype similar to Hh over expression, including duplications of the central component of each segment and expansion domain of Hh responsive genes. In contrast, mutant embryos for Ci of fused show a phenotype similar to Hh loss of function, while mutations in negative regulators of the Hh pathway, such as ptch or PKA, induce ectopic expression of Hh-target genes (reviewed by Ingham, *Embo. J.* 17: 3505-11 (1998)). For example, fused and Ci mutants exhibited deletion of the posterior part of each segment and replacement of a mirror-like image duplication of the anterior part or each segment and replacement of a mirror-like duplication of the anterior part, Busson et al., *Roux. Arch. Dev. Biol.* 197: 221-230 (1988). Molecular characterizations of Ci suggested that it is a transcription factor which directly activates Hh responsive genes such as Wingless and Dpp, Alexandre et al., (1996) supra, Dominguez et al., (1996) supra. Likewise, molecular analysis of fused reveals that it is structurally related to serine threonine kinases and that both intact N-terminal kinase domain and a C-terminal regulatory region are required for its proper function, Preat et al., *Nature* 347: 87-9 (1990); Robbins et al., (1997), supra; Therond et al., *Proc. Natl. Acad. Sci. USA* 93: 4224-8 (1996). However, whereas fused null mutations and N-terminal kinase domain mutations can be fully suppressed by Suppressor of fused mutations, C-terminus mutations of fused display a strong Cos-2 phenotype in a Suppressor of fused background. This suggests that the fused kinase domain can act as a constitutive activator of Shh signaling when Suppressor of Fused is not present.

Su(fu) was originally isolated as a gene, which when activated, was able to suppress the embryonic and adult phenotypes of fused mutants, and when duplicated, enhanced the fused mutant phenotype, suggesting that fused and Su(fu) have antagonistic roles. [Preat, *Genetics* 132: 725-36 (1992); Preat et al., *Genetics* 135: 1047-62 (1993)]. Su(fu) mutant flies have a wing phenotype similar to but not as strong as patched or PKA mutants (Ohlmeyer and Kalderon, *Nature* 396: 749-53 (1998). The combination of patched or PKA mutations in a Su(fu) mutant background enhances the mutant phenotype of patched and PKA, suggesting a cooperative effect of these genes in modulating hedgehog signaling. Ohlmeyer and Kalderon, supra. Fused, Su(fu), Cos-2 and Ci have been shown to form a microtubule-associated multi-protein complex and hedgehog signaling leads to dissociation of this complex from microtubules. Robbins et al., *Cell* 90: 225-34 (1997); Sisson et al., *Cell* 90: 235-45 (1997); Monnier et al., *Curr. Biol.* 8: 583-86 (1998).

Both fused and Cos-2 become phosphorylated in response to Hh treatment, Robbins et al., supra; Therond et al., *Genetics* 142: 1181-98 (1996), but the kinase(s) responsible for this activity(ies) remain(s) to be characterized. To date, the only known vertebrate homologues for these components are members of the Gli protein family (e.g., Gli-1, Gli-2 and Gli-3). These are zinc finger putative transcription factors that are structurally related to Ci. Among these, Gli-1 was shown to be a candidate mediator of the Shh signal [Hynes et al., *Neuron* 15: 35-44 (1995), Lee et al., *Development* 124: 2537-52 (1997); Alexandre et al., *Genes Dev.* 10: 2003-13 (1996)] suggesting that the mechanism of gene activation in response to Hh may be conserved between *Drosophila* and vertebrates.

In the absence of hedgehog, full length Ci (Ci-155) is proteolytically processed into an N-terminal repressor fragment (Ci-75). Aza-Blanc et al., *Cell* 89: 1043-53 (1997). Recent studies demonstrate that complex formation is necessary to target Ci for proteolysis. Methot and Basler, *Cell* 96: 819-31 (1999). The cleavage of Ci potentially requires PKA phosphorylation of Ci and ubiquitination by Slimb, which targets Ci to the proteosome. Chen et al., *Proc. Natl. Acad. Sci. USA* 95: 2349-54 (1998); Jiang and Struhl, *Nature* 391: 493-96 (1998). In response to Hh, Ci cleavage is blocked and Ci-155 is activated into a labile but still uncharacterized form. Ohlmeyer and Kalderon, supra; Methot and Basler, *Cell* 96: 819-31 (1999).

To determine whether other signaling components in the Hh cascade are evolutionarily conserved and to examine the function of fused in the Hh signaling cascade on the biochemical level, Applicants have isolated and characterized human used cDNA, a kinase homologous the *Drosophila* Fu (dFu). Tissue distribution on the mouse indicates that fused is expressed in Shh and other hedgehog responsive tissues, and also displays the same subcellular localization as human Gli1 (hGli1) and hSu(fu), the human homologue of *Drosophila* Su(fu) (dSu(fu)).

Biochemical studies demonstrate that fused is a functional kinase and that it forms a complex with hSu(fu) and hGli1. Functional studies provide evidence that fused is an activator of Gli and that a dominant negative form of fused is capable of blocking Shh signaling in *Xenopus* embryos. Applicant also herein show that Shh signaling leads to the reversible dissociation of human Su(fu) from human Gli-1 (hGli-1) in mammalian cells. Applicants also demonstrate herein that the catalytic subunit of protein kinase A (PKAc) is present in a complex in association with hSu(fu). PKAc phosphorylates both hSu(fu) and Gli, and thereby promotes the binding of hSu(fu) to Gli, while ectopic hFu or Shh stimulation trigger the dissociation of hSu(fu) from Gli. These biochemical observations correlate with data obtained in a functional readout where fused abrogates hSu(fu)-mediated repression of Gli in a Gli reporter assay. Together this data demonstrated generally that fused is directly involved in Hh signaling and specifically that fused antagonizes PKAc activity, thereby triggering the dissociation of hSu(fu) from hGli-1. Regulation of the hSu(fu)-hGli-1 interaction is central to the control of hGli-1 activity and is promoted by PKAc and inhibited by Shh and hFu.

Applicants have identified a cDNA encoding a human fused (hfused) polypeptide and thus have provided for the first time a vertebrate fused molecule.

SUMMARY OF THE INVENTION

In one embodiment, the invention provides an isolated nucleic acid molecule comprising a nucleotide sequence that encodes an isolated vertebrate fused polypeptide.

In one embodiment, the invention provides an isolated nucleic acid molecule having at least about 80% sequence identity to (a) a DNA molecule encoding a fused polypeptide comprising the sequence of amino acids 1 to 260 of FIG. 1 (SEQ ID NO:24), or (b) the complement of the DNA molecule of (a); and encoding a polypeptide having fused biological activity. The sequence identity preferably is about 85%, more preferably about 90%, most preferably about 95%. In one aspect, the isolated nucleic acid has at least about 80%, preferably at least about 85%, more preferably at least about 90%, and most preferably at least about 95% sequence identity with a polypeptide having amino acid residues 1 to about 1315 of FIG. 1 (SEQ ID NO:2). Preferably, the highest degree of sequence identity occurs within the kinase domain (amino acids 1 to about 260 of FIG. 1 (SEQ ID NO:2)). Especially preferred are those nucleic acid molecule containing a coding sequence for a lysine at amino acid position 33. In a further aspect, the isolated nucleic acid molecule comprises DNA encoding a human fused polypeptide having amino acid residues 1 to about 260 of FIG. 1 (SEQ ID NO:2) as shown in FIG. 1. In yet a further aspect, the nucleic acid encodes a human fused polypeptide having amino acid residues 261 to 1315 of FIG. 1 (SEQ ID NO:27).

In another embodiment, the isolated nucleic acid molecule comprises a nucleotide sequence having at least about 80% nucleic acid sequence identity, preferably at least about 81% nucleic acid sequence identity, more preferably at least about 82% nucleic acid sequence identity, yet more preferably at least about 83% nucleic acid sequence identity, yet more preferably at least about 84% nucleic acid sequence identity, yet more preferably at least about 85% nucleic acid sequence identity, yet more preferably at least about 86% nucleic acid sequence identity, yet more preferably at least about 87% nucleic acid sequence identity, yet more preferably at least about 88% nucleic acid sequence identity, yet more preferably at least about 89% nucleic acid sequence identity, yet more preferably at least about 90% nucleic acid sequence identity, yet more preferably at least about 91% nucleic acid sequence identity, yet more preferably at least about 92% nucleic acid sequence identity, yet more preferably at least about 93% nucleic acid sequence identity, yet more preferably at least about 94% nucleic acid sequence identity, yet more preferably at least about 95% nucleic acid sequence identity, yet more preferably at least about 96% nucleic acid sequence identity, yet more preferably at least about 97% nucleic acid sequence identity, yet more preferably at least about 98% nucleic acid sequence identity and yet more preferably at least about 99% nucleic acid sequence identity to (a) a DNA molecule encoding a fused polypeptide having the sequence of amino acid residues from about 1 to about 1315, inclusive, of FIG. 1 (SEQ ID NO:2), or (b) the complement of the DNA molecule of (a).

In another aspect, the isolated nucleic acid molecule comprises (a) a nucleotide sequence encoding a fused polypeptide having the sequence of amino acid residues from about 1 to about 1315, inclusive, of FIG. 1 (SEQ ID NO:2), or (b) the complement of the nucleotide sequence of (a).

In other aspects, the isolated nucleic acid molecule comprises a nucleotide sequence having at least about 80% sequence identity, preferably at least about 81% sequence identity, more preferably at least about 82% sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity and yet more preferably at least about 99% sequence identity to (a) a DNA molecule having the sequence of nucleotides from about 161 to about 4105, inclusive, of FIG. 1 (SEQ ID NO: 1), or (b) the complement of the DNA molecule of (a).

In another aspect, the isolated nucleic acid molecule comprises (a) the nucleotide sequence from about 161 to about 4105, inclusive, of FIG. 1 (SEQ ID NO:1), or (b) the complement of the nucleotide sequence of (a).

In yet another aspect, the invention provides for an isolated nucleic acid comprising DNA having at least a 95% sequence identity to a DNA molecule encoding the same mature polypeptide encoded by the cDNA in ATCC Deposit No. 209637 (designation: pRK5tkneo.hFused-1272), alternatively the coding sequence of clone pRK5tkneo.hFused-1272, deposited under accession number ATCC 209637. In a still further aspect, the invention provides for a nucleic acid comprising human fused encoding sequence of the cDNA in ATCC deposit No. 209637 (designation: pRK5tkneo.hFused-1272) or a sequence which hybridizes thereto under stringent conditions.

In a further aspect, the invention concerns an isolated nucleic acid molecule comprising a nucleotide sequence having at least about 80% nucleic acid sequence identity, preferably at least about 81% nucleic acid sequence identity, more preferably at least about 82% nucleic acid sequence identity, yet more preferably at least about 83% nucleic acid sequence identity, yet more preferably at least about 84% nucleic acid sequence identity, yet more preferably at least about 85% nucleic acid sequence identity, yet more preferably at least about 86% nucleic acid sequence identity, yet more preferably at least about 87% nucleic acid sequence identity, yet more preferably at least about 88% nucleic acid sequence identity, yet more preferably at least about 89% nucleic acid sequence identity, yet more preferably at least about 90% nucleic acid sequence identity, yet more preferably at least about 91% nucleic acid sequence identity, yet more preferably at least about 92% nucleic acid sequence identity, yet more preferably at least about 93% nucleic acid sequence identity, yet more preferably at least about 94% nucleic acid sequence identity, yet more preferably at least about 95% nucleic acid sequence identity, yet more preferably at least about 96% nucleic acid sequence identity, yet more preferably at least about 97% nucleic acid sequence identity, yet more preferably at least about 98% nucleic acid sequence identity and yet more preferably at least about 99% nucleic acid sequence identity to (a) a DNA molecule that encodes the same mature polypeptide encoded by the human protein cDNA deposited with the ATCC on Feb. 19, 1998 under ATCC Deposit No. 209637 (designation: pRK5tkneo.hFused-1272) or (b) the complement of the DNA molecule of (a). In a preferred embodiment, the isolated nucleic acid molecule comprises (a) a nucleotide sequence encoding the same mature polypeptide encoded by the human protein cDNA deposited with the ATCC on Feb. 19, 1998 under ATCC Deposit No. 209637 (designation: pRK5tkneo.hFused-1272) or (b) the complement of the nucleotide sequence of (a).

In another aspect, the invention concerns an isolated nucleic acid molecule comprising a nucleotide sequence having at least about 80% nucleic acid sequence identity, preferably at least about 81% nucleic acid sequence identity, more preferably at least about 82% nucleic acid sequence identity, yet more preferably at least about 83% nucleic acid sequence identity, yet more preferably at least about 84% nucleic acid sequence identity, yet more preferably at least about 85% nucleic acid sequence identity, yet more preferably at least about 86% nucleic acid sequence identity, yet more preferably at least about nucleic acid 87% sequence identity, yet more preferably at least about 88% nucleic acid sequence identity, yet more preferably at least about 89% nucleic acid sequence identity, yet more preferably at least about 90% nucleic acid sequence identity, yet more preferably at least about 91% nucleic acid sequence identity, yet more preferably at least about 92% nucleic acid sequence identity, yet more preferably at least about 93% nucleic acid sequence identity, yet more preferably at least about 94% nucleic acid sequence identity, yet more preferably at least about 95% nucleic acid sequence identity, yet more preferably at least about 96% nucleic acid sequence identity, yet more preferably at least about 97% nucleic acid sequence identity, yet more preferably at least about 98% nucleic acid sequence identity and yet more preferably at least about 99% nucleic acid sequence identity to (a) the portion of cDNA which encodes the full-length human polypeptide of the cDNA deposited with the ATCC on Feb. 19, 1998 under ATCC Deposit No. 209637 (designation: pRK5tkneo.hFused-1272) or (b) the complement of the nucleotide sequence of (a). In a preferred embodiment, the isolated nucleic acid molecule comprises (a) the portion of cDNA which encodes the full-length human polypeptide of the DNA deposited with the ATCC on Feb. 19, 1998 under ATCC Deposit No. 209637 (designation: pRK5tkneo.hFused-1272) or (b) the complement of the nucleotide sequence of (a).

In another aspect, the invention concerns an isolated nucleic acid molecule which encodes an active vertebrate fused polypeptide comprising a nucleotide sequence that hybridizes to the complement of a nucleic acid sequence that encodes amino acids 1 to about 1315, inclusive of FIG. 1 (SEQ ID NO:2). Preferably, hybridization occurs under stringent hybridization and wash conditions.

In yet another aspect, the invention concerns an isolated nucleic acid molecule which encodes an active vertebrate fused polypeptide comprising a nucleotide sequence that hybridizes to the complement of the nucleic acid sequence between about nucleotides 161 and about 4105, inclusive, of FIG. 1 (SEQ ID NO:2). Preferably, hybridization occurs under stringent hybridization and wash conditions.

In a further aspect, the invention concerns an isolated nucleic acid molecule having at least about 201 nucleotides and which is produced by hybridizing a test DNA molecule under stringent conditions with (a) a DNA molecule encoding a vertebrate fused polypeptide having the sequence of amino acid residues from about 1 to about 1315, inclusive, of FIG. 1 (SEQ ID NO:2), or (b) the complement of the DNA molecule of (a), and, if the test DNA molecule has at least about an 80% nucleic acid sequence identity, preferably at least about an 81% nucleic acid sequence identity, more preferably at least about an 82% nucleic acid sequence identity, yet more preferably at least about an 83% nucleic acid sequence identity, yet more preferably at least about an 84% nucleic acid sequence identity, yet more preferably at least about an 85% nucleic acid sequence identity, yet more preferably at least about an 86% nucleic acid sequence identity, yet more preferably at least about an 87% nucleic acid sequence identity, yet more preferably at least about an 88% nucleic acid sequence identity, yet more preferably at least about an 89% nucleic acid sequence identity, yet more preferably at least about a 90% nucleic acid sequence identity, yet more preferably at least about a 91% nucleic acid sequence identity, yet more preferably at least about a 92% nucleic acid sequence identity, yet more preferably at least about a 93% nucleic acid sequence identity, yet more preferably at least about a 94% nucleic acid sequence identity, yet more preferably at least about a 95% nucleic acid sequence identity, yet more preferably at least about a 96% nucleic acid sequence identity, yet more preferably at least about a 97% nucleic acid sequence identity, yet more preferably at least about a 98% nucleic acid sequence identity and yet more preferably at least about a 99% nucleic acid sequence identity to (a) or (b), and isolating the test DNA molecule.

In another aspect, the invention concerns an isolated nucleic acid molecule comprising (a) a nucleotide sequence encoding a polypeptide scoring at least about 80% positives, preferably at least about 81% positives, more preferably at least about 82% positives, yet more preferably at least about 83% positives, yet more preferably at least about 84% positives, yet more preferably at least about 85% positives, yet more preferably at least about 86% positives, yet more preferably at least about 87% positives, yet more preferably at least about 88% positives, yet more preferably at least about 89% positives, yet more preferably at least about 90% positives, yet more preferably at least about 91% positives, yet more preferably at least about 92% positives, yet more preferably at least about 93% positives, yet more preferably at least about 94% positives, yet more preferably at least about 95% positives, yet more preferably at least about 96% positives, yet more preferably at least about 97% positives, yet more preferably at least about 98% positives and yet more preferably at least about 99% positives when compared with the amino acid sequence of residues about 1 or about 1315, inclusive, of FIG. 1 (SEQ ID NO:2), or (b) the complement of the nucleotide sequence of (a).

Another embodiment is directed to fragments of a vertebrate fused polypeptide coding sequence that may find use as, for example, hybridization probes or for encoding fragments of a vertebrate fused polypeptide that may optionally encode a polypeptide comprising a binding site for an anti-fused antibody. Such nucleic acid fragments are usually at least about 20 nucleotides in length, preferably at least about 30 nucleotides in length, more preferably at least about 40 nucleotides in length, yet more preferably at least about 50 nucleotides in length, yet more preferably at least about 60 nucleotides in length, yet more preferably at least about 70 nucleotides in length, yet more preferably at least about 80 nucleotides in length, yet more preferably at least about 90 nucleotides in length, yet more preferably at least about 100 nucleotides in length, yet more preferably at least about 110 nucleotides in length, yet more preferably at least about 120 nucleotides in length, yet more preferably at least about 130 nucleotides in length, yet more preferably at least about 140 nucleotides in length, yet more preferably at least about 150 nucleotides in length, yet more preferably at least about 160 nucleotides in length, yet more preferably at least about 170 nucleotides in length, yet more preferably at least about 180 nucleotides in length, yet more preferably at least about 190 nucleotides in length, yet more preferably at least about 200 nucleotides in length, yet more preferably at least about 250 nucleotides in length, yet more preferably at least about 300 nucleotides in length, yet more preferably at least about 350 nucleotides in length, yet more preferably at least about 400 nucleotides in length, yet more preferably at least about 450 nucleotides in length, yet more preferably at least about 500 nucleotides in length, yet more preferably at least about 600 nucleotides in length, yet more preferably at least about 700 nucleotides in length, yet more preferably at least about 800 nucleotides in length, yet more preferably at least about 900 nucleotides in length and yet more preferably at least about 1000 nucleotides in length, wherein in this context the term "about" means the referenced nucleotide sequence length plus or minus 10% of that referenced length. In a preferred embodiment, the nucleotide sequence fragment is derived from any coding region of the nucleotide sequence shown in FIG. 1 (SEQ ID NO:1). It is noted that novel fragments of a vertebrate fused polypeptide-encoding nucleotide sequence may be determined in a routine manner by aligning the vertebrate fused polypeptide-encoding nucleotide sequence with other known nucleotide sequences using any of a number of well known sequence alignment programs and determining which fused polypeptide-encoding nucleotide sequence fragment(s) are novel. All of such vertebrate fused polypeptide-encoding nucleotide sequences are contemplated herein and can be determined without undue experimentation. Also contemplated are the vertebrate fused polypeptide fragments encoded by these nucleotide molecule fragments, preferably those vertebrate fused polypeptide fragments that comprise a binding site for an anti-fused antibody.

In another embodiment, the invention provides a vector comprising DNA encoding a vertebrate fused polypeptide or its variants. The vector may comprise any of the isolated nucleic acid molecules hereinabove identified.

A host cell comprising such a vector is also provided. By way of example, the host cells may be mammalian cells, (e.g., CHO cells), prokaryotic cells (e.g., *E. coli*) or yeast cells (e.g., *Saccharomyces cerevisiae*). A process for producing vertebrate fused polypeptides is further provided and comprises culturing host cells under conditions suitable for expression of vertebrate fused and recovering the same from the cell culture.

In another embodiment, the invention provides isolated vertebrate fused polypeptide encoded by any of the isolated nucleic acid sequences hereinabove identified.

In a specific aspect, the invention provides isolated native sequence vertebrate fused polypeptide, which in certain embodiments, includes an amino acid sequence comprising residues from about 1 to about 1315 of FIG. 1 (SEQ ID NO:2).

In yet another embodiment, the invention provides an isolated vertebrate fused polypeptide. In particular, the invention provides isolated native sequence vertebrate fused polypeptide, which in one embodiment is a human fused including an amino acid sequence comprising residues 1 to about 1315 of (SEQ ID NO:2) as shown in FIG. 1. Human and other native vertebrate fused polypeptides with or without the initiating methionine are specifically included. Alternatively, the invention provides a vertebrate fused polypeptide encoded by the cDNA insert of the nucleic acid deposited under deposit number ATCC 209637.

In another aspect, the invention concerns an isolated vertebrate fused polypeptide, comprising an amino acid sequence having at least about 80% amino acid sequence identity, preferably at least about 81% amino acid sequence identity, more preferably at least about 82% amino acid sequence identity, yet more preferably at least about 83% amino acid sequence identity, yet more preferably at least about 84% amino acid sequence identity, yet more preferably at least about 85% amino acid sequence identity, yet more preferably at least about 86% amino acid sequence identity, yet more preferably at least about 87% amino acid sequence identity, yet more preferably at least about 88% amino acid sequence identity, yet more preferably at least about 89% amino acid sequence identity, yet more preferably at least about 90% amino acid sequence identity, yet more preferably at least about 91% amino acid sequence identity, yet more preferably at least about 92% amino acid sequence identity, yet more preferably at least about 93% amino acid sequence identity, yet more preferably at least about 94% amino acid sequence identity, yet more preferably at least about 95% amino acid sequence identity, yet more preferably at least about 96% amino acid sequence identity, yet more preferably at least about 97% amino acid sequence identity, yet more preferably at least about 98% amino acid sequence identity and yet more preferably at least about 99% amino acid sequence identity to the sequence of amino acid residues from about 1 to about 1315, inclusive, of FIG. 1 (SEQ ID NO:2).

In a further aspect, the invention concerns an isolated vertebrate fused polypeptide comprising an amino acid sequence having at least about 80% amino acid sequence identity, preferably at least about 81% amino acid sequence identity, more preferably at least about 82% amino acid sequence identity, yet more preferably at least about 83% amino acid sequence identity, yet more preferably at least about 84% amino acid sequence identity, yet more preferably at least about 85% amino acid sequence identity, yet more preferably at least about 86% amino acid sequence identity, yet more preferably at least about 87% amino acid sequence identity, yet more preferably at least about 88% amino acid sequence identity, yet more preferably at least about 89% amino acid sequence identity, yet more preferably at least about 90% amino acid sequence identity, yet more preferably at least about 91% amino acid sequence identity, yet more preferably at least about 92% amino acid sequence identity, yet more preferably at least about 93% amino acid sequence identity, yet more preferably at least about 94% amino acid sequence identity, yet more preferably at least about 95% amino acid sequence identity, yet more preferably at least about 96% amino acid sequence identity, yet more preferably at least about 97% amino acid sequence identity, yet more preferably at least about 98% amino acid sequence identity and yet more preferably at least about 99% amino acid sequence identity to an amino acid sequence encoded by the human protein cDNA deposited with the ATCC on Feb. 19, 1998 under ATCC Deposit No. 209637 (designation: pRK5tkneo.hFused-1272). In a preferred embodiment, the isolated vertebrate fused polypeptide comprises an amino acid sequence encoded by the human protein cDNA deposited with the ATCC on Feb. 19, 1998 under ATCC Deposit No. 209637 (designation: pRK5tkneo.hFused-1272).

In a further aspect, the invention concerns an isolated vertebrate fused polypeptide comprising an amino acid sequence scoring at least about 80% positives, preferably at least about 81% positives, more preferably at least about 82% positives, yet more preferably at least about 83% positives, yet more preferably at least about 84% positives, yet more preferably at least about 85% positives, yet more preferably at least about 86% positives, yet more preferably at least about 87% positives, yet more preferably at least about 88% positives, yet more preferably at least about 89% positives, yet more preferably at least about 90% positives, yet more preferably at least about 91% positives, yet more preferably at least about 92% positives, yet more preferably at least about 93% positives, yet more preferably at least about 94% positives, yet more preferably at least about 95% positives, yet more preferably at least about 96% positives, yet more preferably at least about 97% positives, yet more preferably at least about 98% positives and yet more preferably at least about 99% positives when compared with the amino acid sequence of residues from about 1 to about 1315, inclusive, of FIG. 1 (SEQ ID NO:2).

In yet another aspect, the invention concerns an isolated vertebrate fused polypeptide, comprising the sequence of amino acid residues from about 1 to about 1315, inclusive, of FIG. 1 (SEQ ID NO:2), or a fragment thereof which is biologically active or sufficient to provide a binding site for an anti-fused antibody, wherein the identification of fused polypeptide fragments that possess biological activity or provide a binding site for an anti-fused antibody may be accomplished in a routine manner using techniques which are well known in the art. Preferably, the vertebrate used fragment retains a qualitative biological activity of a native vertebrate fused polypeptide.

In a still further aspect, the invention provides a polypeptide produced by (i) hybridizing a test DNA molecule under stringent conditions with (a) a DNA molecule encoding a vertebrate fused polypeptide having the sequence of amino acid residues from about 1 to about 1315, inclusive, of FIG. 1 (SEQ ID NO:2), or (b) the complement of the DNA molecule of (a), and if the test DNA molecule has at least about an 80% nucleic acid sequence identity, preferably at least about an 81% nucleic acid sequence identity, more preferably at least about an 82% nucleic acid sequence identity, yet more preferably at least about an 83% nucleic acid sequence identity, yet more preferably at least about an 84% nucleic acid sequence identity, yet more preferably at least about an 85% nucleic acid sequence identity, yet more preferably at least about an 86% nucleic acid sequence identity, yet more preferably at least about an 87% nucleic acid sequence identity, yet more preferably at least about an 88% nucleic acid sequence identity, yet more preferably at least about an 89% nucleic acid sequence identity, yet more preferably at least about a 90% nucleic acid sequence identity, yet more preferably at least about a 91% nucleic acid sequence identity, yet more preferably at least about a 92% nucleic acid sequence identity, yet more preferably at least about a 93% nucleic acid sequence identity, yet more preferably at least about a 94% nucleic acid sequence identity, yet more preferably at least about a 95% nucleic acid sequence identity, yet more preferably at least about a 96% nucleic acid sequence identity, yet more preferably at least about a 97% nucleic acid sequence identity, yet more preferably at least about a 98% nucleic acid sequence identity and yet more preferably at least about a 99% nucleic acid sequence identity to (a) or (b), (ii) culturing a host cell comprising the test DNA molecule under conditions suitable for expression of the polypeptide, and (iii) recovering the polypeptide from the cell culture.

In yet another embodiment, the invention provides chimeric molecules comprising a vertebrate fused polypeptide fused to a heterologous polypeptide or amino acid sequence, wherein the vertebrate fused polypeptide may comprise any fused polypeptide, variant or fragment thereof as hereinbefore described. An example of such a chimeric molecule comprises a vertebrate fused polypeptide fused to an epitope tag sequence or a constant region of an immunoglobulin.

In another embodiment, the invention provides an antibody as defined below which specifically binds to a vertebrate fused polypeptide as hereinbefore described. Optionally, the antibody is a monoclonal antibody, an antibody fragment or a single chain antibody.

In yet another embodiment, the invention provides an expressed sequence tag (EST) comprising the nucleotide sequences identified in FIG. 2 as 2515662 (SEQ ID NO:3).

In yet another embodiment, the invention provides for compounds and methods for developing antagonists against and agonist promoting fused modulation of Hedgehog signaling. In particular, an antagonist of vertebrate fused which blocks, prevents, inhibits and/or neutralized the normal functioning of fused in the Shh signaling pathway, including anti-fused antibodies, small bioorganic molecules and antisense nucleotides.

In yet another embodiment, the invention provides for alternatively spliced variants of human fused. In still yet a further embodiment, the invention provides a method of screening or assaying for identifying molecules that modulate the fused activation of hedgehog signaling. Preferably, the molecules either prevent interaction of fused with its associative complexing proteins or prevent or inhibit dissociation of complexes. The assay comprises the incubation of a mixture comprising fused and a substrate (e.g., Gli, COUP-TFII, slimb, CBP, MBP) with a candidate molecule and detection of the ability of the candidate molecule to modulate fused phosphorylation of its substrate. The screened molecules preferably are small molecule drug candidates. In particular, the method relates to a technique for screening for antagonists or agonists of fused biological activity comprising:
(a) exposing the fused expressing target cells in culture to a candidate compound; and (b) analyzing cell lysates to asses the level and/or identity of phosphorylation; or
(c) scoring phenotypic or functional changes in treated cells;
and comparing the results to control cells which were not exposed to the candidate compound.

In yet another embodiment, the method relates to a technique of diagnosing to determine whether a particular disorder is modulated by hedgehog signaling, comprising:
(a) culturing test cells or tissues;
(b) administering a compound which can inhibit fused modulated hedgehog signaling; and
(c) measuring the degree of kinase attenuation on the fused substrate in cell lysates or hedgehog mediated phenotypic effects in the test cells.

In a still further embodiment, the invention concerns a composition of matter comprising a vertebrate fused polypeptide, or an agonist or antagonist of a vertebrate fused polypeptide as herein described, or an anti-fused antibody, in combination with a carrier. Optionally, the carrier is a pharmaceutically-acceptable carrier.

Another embodiment of the present invention is directed to the use of a vertebrate fused polypeptide, or an agonist or antagonist thereof as herein described, or an anti-fused antibody, for the preparation of a medicament useful in the treatment of a condition which is responsive to the fused polypeptide and/or hedgehog signaling, an agonist or antagonist thereof or an anti-fused antibody.

BRIEF DESCRIPTION OF THE DRAWINGS

FIGS. 1A-1F show the nucleotide (SEQ ID NO:1) and derived amino acid (SEQ ID NO:2) sequence of a native sequence of human fused polypeptide. Included are the kinase domain (residues 1 to about 260 (SEQ ID NO:24)), the C-terminal portion (residues about 261 to about 1315 (SEQ ID NO:27)) and the ATP binding site at about amino acid position 33.

FIG. 2 shows the EST 2515662 (SEQ ID NO:3) that was used in the cloning of the human full-length fused sequence.

FIGS. 3A-3E show a comparison between human and Drosophila fused (SEQ ID NOS: 2 and 23, respectively). Gaps introduced for optimal alignment are indicated by dashes. Identical amino acids are boxed. The lysine residue mutated in fused-DN (dominant negative, lysine at amino acid position 33) is highlighted. Putative glycosylation sites are marked with asterisks. The end of the hFu ΔC construct is marked with a black arrow.

FIGS. 4A-4F show the sequence of DNA28495 (SEQ ID NOS:4, 5 and 21) that was an incorrectly spliced variant of human fused isolated from a fetal lung library. This clone contains a potential initiation methionine at position 116 followed by an open reading frame of 1944 bp. A second open reading frame is present from about position 2295 to 4349. There is one nucleotide difference between clone DNA28495 (SEQ ID NO:4) and clone DNA28494 (SEQ ID NO:6) located in the first ORF at position 1863 of clone DNA28495 (SEQ ID NO:4) (A vs. G) which changes the coding sequence from an Gln to a Arg at position 583. The first open reading frame of DNA28494 (SEQ ID NO:6) starts at residue 115 and is followed by a 630 amino acid long open reading frame.

FIGS. 5A-5F show the sequence of DNA28494 (SEQ ID NOS:6, 7 and 22) that was another incorrectly spliced variant of human fused isolated from a fetal lung library.

FIG. 6 is a western blot of the PCR product of an epitope tag of DNA 28495 (SEQ ID NO:4) and DNA28494 (SEQ ID NO:6). A specific band of 150 kDa was detected in the cell pellet of cells transfected with the construct corresponding to clone DNA28494 (SEQ ID NO:6) and a specific band of approximately 100 kDa could be detected for clone DNA28495 (SEQ ID NO:4) (FIG. 6). These bands were not present in the mock transfected control. The presence of the 100 kDa band suggests the two open reading frames of DNA28494 (SEQ ID NO:6) can be spliced together to direct the synthesis of a large protein of 150 kDa. The absence of this band for DNA28495 (SEQ ID NO:4) suggested that this clone apparently cannot be correctly spliced.

FIG. 7 is a northern blot analysis of human fused (SEQ ID NO:1). Multiple human fetal and adult tissue northern blots were probed with a ClaI-AccI cDNA fragment encoding the first 510 amino acids of human fused (SEQ ID NO:1).

FIGS. 8A-8F are photographs showing in situ hybridization of embryonic and adult tissues with fused (SEQ ID NO:1). Sagittal sections of E11.5 (FIG. 8A) and E13.5 (FIG. 8B) mouse embryos. Coronal section through the spinal chord of E11.5 (FIG. 8C) and E13.5 (FIG. 8D) mouse embryo. Sagittal section through P1 (FIG. 8E) and adult (FIG. 8F) mouse. Cp, choroid plexus; hb, hindbrain; hip, hippocampal formation; ht, heart; hy, hypothalamus; kd, kidney; 1 g, lung; mb, midbrain; md, midgut; mnd, mandibular component of first bronchial arch; sc, spinal cord; st, stomach; tec, midbrain tectum; vh, ventral horn of spinal cord; vm, ventral midbrain. Scale bars: FIG. 8A, 1.0 mm; FIG. 8B, 1.62 mm; FIG. 8C, 0.14 mm; FIG. 8D, 0.17 mm; FIG. 8E, 2.0 mm; FIG. 8F, 3.1 mm.

FIGS. 9A-9C are photographs showing in situ hybridization showing the presence of fused mRNA in high levels in the adult mouse testes. (FIG. 9A) High magnification reveals differences in levels of expression within somniferous tubules (FIG. 9C). Hybridization of the testis with a sense strand control probe to fused gave no hybridization (FIG. 9B).

FIGS. 10A-10B are bar graphs representing the activation of Gli by fused. (FIG. 10A) C3H10T1/2 cells were cotransfected with a p9XGliLus, ptkRenilla luciferase and fused or various fused mutants. Cells were harvested 48 h after transfection and the luciferase activity was assayed as described in Example 7. (FIG. 10B) Fused transactivation of a Gli reporter construct. C3H10T1/2 cells were cotransfected with a p9XGliLuc reporter construct, ptkRenilla luciferase and a CMV driven expression vector for fused or various fused mutants. Cells were harvested 48 hours after transfection and the luciferase activity was assayed as described in the Examples. The data represents the mean of duplicative determinations.

FIGS. 11A-11E are photographs showing that fused-DN (SEQ ID NO:25) inhibits Shh signaling in early *Xenopus* development. Depicted are: (FIG. 11A) Dorsal view of tadpole stage embryos. Top embryo is fused-DN (SEQ ID NO. 25) injection and bottom embryo is the control; (FIG. 11B) Side view of tadpole stage embryo. Top embryo is fused-DN injection and bottom embryo is the control; (FIGS. 11C & 11D) Pax-6 staining of stage 16 neurula embryos injected with control DNA and fused-DN (SEQ ID NO:25), respectively; (FIG. 11E) Shh expression in the floor plate of neurula stage control embryo (left) or fused-DN injected embryo (right).

FIG. 12 is a photograph which confirms the kinase activity of fused (SEQ ID NO:2) and its activation of Gli. Depicted are 293 cells transfected with HA tagged fused constructs as indicated in Example 10 and immunoprecipitated with anti-HA antibodies and protein A sepharose. Protein A beads were subjected to in vitro kinase assay as described in Example 10 in the presence of MBP.

FIG. 13 are gel images which indicate the modulation of the hSu(fu)-hGli-1 complex by Shh and PKA. In FIG. 13(A), Shh is shown to trigger dissociation of hSu(fu) from hGli-1. C3H10T1/2 (ATCC 226-CCL) cells were transfected with expression plasmids for N-Myc hGli-1 and hSu(fu) C-flag, phospholabeled, and stimulated with N-Shh conditioned media for different times. Cell lysates were first immunoprecipitated with the anti-flag M2 gel to deplete the pool of hSu(fu), and then the supernatants were immunoprecipitated again with the anti-Myc antibody followed by immunoblotting. FIG. 13(B) depicts co-precipitation of a hSu(fu)-associated kinase activity using GST-hSu(fu). Lysates from 293 cells in 15 cm plates were incubated with 1 µg/ml GST-hSu (fu) or GST, followed by glutathione sepharose beads precipitation and kinase assay. The blot was incubated with the anti-Fu 01 antibody (data not shown), striped and reprobed with an anti-PKAc polyclonal antibody (Upstate biotechnology). FIG. 13(C) shows in vitro phosphorylation of GST-hSu (fu) by PKAc. The kinase assay was performed as described in Example 10 in the presence of absence of 200 µM PKI. FIG. 13(D) shows that PKA phosphorylation increases the binding of hSu(fu) to hGli-1. 293 cells were transfected with N-Myc hGli-1, hSu(fu) and hPKAc C-V5 (Clone H-M34181M, Invitrogen) in different combinations. Cell lysates were immunoprecipitated with anti-Myc and PKA activity was measured as described in Example 10. hSu(fu), and hGli-1 were detected by immunoblotting after exposure. Confirmation of protein expression was performed by immunoblotting aliquots of total cell lysates for the indicated protein (total lysate, bottom panels).

FIG. 14 describes the biochemical interaction of hFu, hSu(fu) and hGli-1. FIG. 14(A) depicts the interaction of hFu with hSu(fu) in mammalian cells. 293 cells were transfected with hfused and hSu(fu) C-Flag or hfused C-Flag and hSu(fu) C-Myc either alone or in combination. Cell lysates were subjected to anti-Flag immunoprecipitation, and co-precipitating proteins were detected by immunoblotting. FIG. 14(B) depicts the interaction of hfused with hGli-1 in mammalian cells. 293 cells were transfected with hfused C-Flag or N-Myc hGli-1 both alone or in combination, and immunoprecipitated with anti-Myc or anti-Flag antibodies. Proteins were detected by immunoblotting. FIG. 14(C) shows the hfused modulation of the binding of Su(fu) to hGli-1. 293 cells were transfected with N-Myc hGli-1, hSu(fu) C-Flag and increasing amounts of hfused. The amount of hfused and hSu(fu) bound to hGli-1 was determined by anti-Myc immunoprecipitation and immunoblotting. Protein expression was analyzed by immunoblotting aliquots of total cell lysates (bottom panel).

FIG. 15 describes the hfused modulation of hSu(fu) binding to hGli-1 antagonizing PKAc. FIG. 15(A) shows hfused antagonism of hSu(fu)-kinase activity. 293 cells were transfected with hSu(fu) C-Flag with or without hfused. Cell lysates immunoprecipitated with anti-Flag M2 gel were submitted to a kinase assay as described in Example 10, the membrane was subsequently probed with the anti-Fus 01 and anti-Su(fu) antibodies. Addition of PKI inhibited the hSu(fu)-associated kinase activity to a similar extent as ectopic hfused. FIG. 15(B) shows hfused and hfused K33R mutant can inhibit PKA phosphorylation of hSu(fu). 293 cells were transfected with hSu(fu) C-Myc, hfused, hfused K33R, hfused ΔC, and hPKAc C-V5 (GeneStomm™ clone H-M34181M; Invitrogen) as indicated. Cell lysates were immunoprecipitated with the anti-Myc antibody, followed by a PKA kinase assay. Levels of hSu(fu), hPKAc and hfused were determined by immunoblotting after exposure. FIG. 15(C) shows the regulation of the hSu(fu)-hGli-1 complex by hfused. 293 cells were transfected with expression plasmids encoding N-Myc hGli-1, hSu(fu) C-Flag, hFu K33R, hFu ΔC, hPKAc C-V5, followed by immunoprecipitation with the anti-Myc antibody, then the PKA kinase assay. Levels of hGli-1, hSu(fu), hfused and hPKAc were determined by immunoblotting after expresure. Protein expression was confirmed by immunoblotting aliquots of total cell lysates for the indicated protein (total lysate, bottom panels).

FIG. 16 are bar graphs of Gli luciferase activity. FIG. 16(A) is a titration of hfused versus hfused K33R (hFu K33R). C3H10T1/2 cells (ATCC 226-CCL) were co-transfected with the Gli-BS reporter, pRL-TK, hFu and hFu K33R plasmids as indicated, and the total amount of effector plasmid was normalized with GFP. FIG. 16(B) shows the hFu-mediated antagonism of hSu(fu)-mediated repression of hGli. C3H10T1/2 cells were co-transfected with the Gli-BS luciferase reporter construct, pRL-TK, and an expression vector for hGli-1, GFP (control), hSu(fu), hFu, hFu K33R, hFu ΔC in various combinations. Numbers indicate μgs of effector plasmid. Luciferase activity was assayed as described in Example 7. Data represents the mean±SD of duplicate determinations of duplicate transfections. P<0.01 between hGli-1+hSu(fu) and hGli-1+hSu(fu)+hFu using an analysis of variance (ANOVA).

FIG. 17 shows a model for Gli regulation by Su(fu), Fu and PKAc.

FIGS. 18A-D show hypothetical exemplifications for using the below described method to determine % amino acid sequence identity (FIGS. 18A-B) and % nucleic acid sequence identity (FIGS. 18C-D) using the ALIGN-2 sequence comparison computer program, wherein "PRO" represents the amino acid sequence of a hypothetical vertebrate fused polypeptide of interest, "Comparison Protein" represents the amino acid sequence of a polypeptide against which the "PRO" polypeptide of interest is being compared, "PRO-DNA" represents a hypothetical fused-encoding nucleic acid sequence of interest, "Comparison DNA" represents the nucleotide sequence of a nucleic acid molecule against which the "PRO-DNA" nucleic acid molecule of interest is being compared, "X, "Y" and "Z" each represent different hypothetical amino acid residues and "N", "L" and "V" each represent different hypothetical nucleotides.

FIGS. 19A-E, 19F1-F2, 19G-H, 19I1-I2, 19J-O, 19P1-P2 and 19Q provide the complete source code for the ALIGN-2 sequence comparison computer program. This source code may be routinely compiled for use on a UNIX operating system to provide the ALIGN-2 sequence comparison computer program.

FIG. 20 is an immunoprecipitation describing the role of the C-terminus region of hFu to displace hPKA from hSu(fu). 293 cells were transfected with hPKA alone, or with hPKA in combination with hSu(fu) C-Myc, with various hFu constructs or GFP. The hFu constructs used were hFu, hFu K33R, hFu ΔC or hFu C-term (SEQ ID NO:27). Cell lysates were immunoprecipitated with the anti-Myc antibody, followed by a PKA kinase assay. Levels of hSu(fu), hFu and hPKA were determined by immunoblotting after exposure (data not shown).

DETAILED DESCRIPTION OF THE PREFERRED EMBODIMENTS

I. Definitions

The terms "vertebrate fused" and "vertebrate fused polypeptide" (abbreviated Fu) when used herein encompass native sequence vertebrate fused and vertebrate fused variants (which are further defined herein) having fused biological activity. Fused may be isolated from a variety of sources, such as from human tissue types or from another source, or prepared by recombinant or synthetic methods.

A "native sequence vertebrate fused" comprises a polypeptide having the same amino acid sequence as a vertebrate fused derived from nature. Such native sequence vertebrate fused can be isolated from nature or can be produced by recombinant and/or synthetic means. The term "native sequence vertebrate fused" specifically encompasses naturally occurring truncated forms of vertebrate fused, naturally occurring variant forms (e.g., alternatively spliced forms) and naturally-occurring allelic variants of vertebrate fused. Native vertebrate fused includes e.g., fused in mammals such as human, murine, bovine, porcine, equine, feline, canine, etc., and preferably refers to human. Thus, one embodiment of the invention, the native sequence human vertebrate fused is a mature or full-length native human vertebrate fused comprising amino acids 1 to 1315 of (hFu; SEQ ID NO:2) as shown in FIG. 1 with or without the initiating methionine at position 1. Also, while the vertebrate fused polypeptide disclosed in FIG. 1 (SEQ ID NO:2) is shown to begin with the methionine residue designated herein as amino acid position 1, it is conceivable and possible that another methionine residue located either upstream or downstream from amino acid position 1 in FIG. 1 (SEQ ID NO:2) may be employed as the starting amino acid residue for the vertebrate fused polypeptide.

"fused variant polypeptide" means an active fused polypeptide as defined below having at least about 80% amino acid sequence identity with the amino acid sequence of: (a) residues 1 to about 1315 of the vertebrate fused polypeptide shown in FIG. 1 (SEQ ID NO:2); (b) residues 1 to about 260 (SEQ ID NO:24) or residues about 261 to 1315 (SEQ ID NO:27) or (c) another specifically derived fragment of the amino acid sequence shown in FIG. 1 (SEQ ID NO:2). Such vertebrate fused variant polypeptides include, for instance, fused polypeptides wherein one or more amino acid residues are added, or deleted, at the N- and/or C-terminus, as well as within one or more internal domains, of the sequence of FIG. 1 (SEQ ID NO:2). Ordinarily, a vertebrate fused variant polypeptide will have at least about 80% amino acid sequence identity, more preferably at least about 81% amino acid sequence identity, more preferably at least about 82% amino acid sequence identity, more preferably at least about 83% amino acid sequence identity, more preferably at least about 84% amino acid sequence identity, more preferably at least about 85% amino acid sequence identity, more preferably at least about 86% amino acid sequence identity, more preferably at least about 87% amino acid sequence identity, more preferably at least about 88% amino acid sequence identity, more preferably at least about 89% amino acid sequence identity, more preferably at least about 90% amino acid sequence identity, more preferably at least about 91% amino acid sequence identity, more preferably at least about 92% amino acid sequence identity, more preferably at least about 93% amino acid sequence identity, more preferably at least about 94% amino acid sequence identity, more preferably at least about 95% amino acid sequence identity, more preferably at least about 96% amino acid sequence identity, more preferably at least about 97% amino acid sequence identity, more preferably at least about 98% amino acid sequence identity and yet more preferably at least about 99% amino acid sequence identity with (a) residues 1 to 1315 of the vertebrate fused polypeptide shown in FIG. 2 (SEQ ID NO:2), (b) residues 1 to about 260 (SEQ ID NO:24) or residues about 261 to 1315 (SEQ ID NO:27) or (c) another specifically derived fragment of the amino acid sequence shown in FIG. 1 (SEQ ID NO:2). Vertebrate fused variant polypeptides do not encompass the native vertebrate fused polypeptide sequence. Ordinarily, vertebrate fused variant polypeptides are at least about 10 amino acids in length, often at least about 20 amino acids in length, more often at least about 30 amino acids in length, more often at least about 40 amino acids in length, more often at least about 50 amino acids in length, more often at least about 60 amino acids in length, more often at least about 70 amino acids in length, more often at least about 80 amino acids in length, more often at least about 90 amino acids in length, more often at least about 100 amino acids in length, more often at least about 150 amino acids in length, more often at least about 200 amino acids in length, more often at least about 250 amino acids in length, more often at least about 300 amino acids in length, or more.

"Percent (%) amino acid sequence identity" with respect to the vertebrate fused sequences identified herein is defined as the percentage of amino acid residues in a candidate sequence that are identical with the amino acid residues in the vertebrate fused sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are obtained as described below by using the sequence comparison computer program ALIGN-2, wherein the complete source code for the ALIGN-2 program is provided in FIGS. 19A-Q. The ALIGN-2 sequence comparison computer program was authored by Genentech, Inc. and the source code shown in FIGS. 19A-Q has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in FIGS. 19A-Q. The ALIGN-2 program should be compiled for use on a UNIX operating system, preferably digital UNIX V4.0D. All sequence comparison parameters are set by the ALIGN-2 program and do not vary.

For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. As examples of % amino acid sequence identity calculations, FIGS. 18A-B demonstrate how to calculate the % amino acid sequence identity of the amino acid sequence designated "Comparison Protein" to the amino acid sequence designated "PRO".

Unless specifically stated otherwise, all % amino acid sequence identity values used herein are obtained as described above using the ALIGN-2 sequence comparison computer program. However, % amino acid sequence identity may also be determined using the sequence comparison program NCBI-BLAST2 (Altschul et al., *Nucleic Acids Res.* 25:3389-3402 (1997)). The NCBI-BLAST2 sequence comparison program may be obtained from the National Institute of Health, Bethesda, Md. 20892. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program NCBI-BLAST2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

Vertebrate "fused variant polynucleotide" or vertebrate "fused variant nucleic acid sequence" means a nucleic acid molecule which encodes an active vertebrate fused polypeptide as defined below and which has at least about 80% nucleic acid sequence identity with either (a) a nucleic acid sequence which encodes residues 1 to 1315 of the vertebrate fused polypeptide shown in FIG. 1 (SEQ ID NO:2), (b) residues 1 to about 260 (SEQ ID NO:24) or residues about 261 to 1315 (SEQ ID NO:27) or (d) a nucleic acid sequence which encodes another specifically derived fragment of the amino acid sequence shown in FIG. 1 (SEQ ID NO:2). Ordinarily, a vertebrate fused variant polynucleotide will have at least about 80% nucleic acid sequence identity, more preferably at least about 81% nucleic acid sequence identity, more preferably at least about 82% nucleic acid sequence identity, more preferably at least about 83% nucleic acid sequence identity, more preferably at least about 84% nucleic acid sequence identity, more preferably at least about 85% nucleic acid sequence identity, more preferably at least about 86% nucleic acid sequence identity, more preferably at least about 87% nucleic acid sequence identity, more preferably at least about 88% nucleic acid sequence identity, more preferably at least about 89% nucleic acid sequence identity, more preferably at least about 90% nucleic acid sequence identity, more preferably at least about 91% nucleic acid sequence identity, more preferably at least about 92% nucleic acid sequence identity, more preferably at least about 93% nucleic acid sequence identity, more preferably at least about 94% nucleic acid sequence identity, more preferably at least about 95% nucleic acid sequence identity, more preferably at least about 96% nucleic acid sequence identity, more preferably at least about 97% nucleic acid sequence identity, more preferably at least about 98% nucleic acid sequence identity and yet more preferably at least about 99% nucleic acid sequence identity with either (a) a nucleic acid sequence which encodes residues 1 to 1315 of the vertebrate fused polypeptide shown in FIG. 1 (SEQ ID NO:2), (b) residues 1 to about 260 (SEQ ID NO:24) or residues about 261 to 1315 (SEQ ID NO:27) or (d) a nucleic acid sequence which encodes another specifically derived fragment of the amino acid sequence shown in FIG. 1 (SEQ ID NO:2). Vertebrate fused polynucleotide variants do not encompass the native vertebrate fused nucleotide sequence.

Ordinarily, vertebrate fused variant polynucleotides are at least about 30 nucleotides in length, often at least about 60 nucleotides in length, more often at least about 90 nucleotides in length, more often at least about 120 nucleotides in length, more often at least about 150 nucleotides in length, more often at least about 180 nucleotides in length, more often at least about 210 nucleotides in length, more often at least about 240 nucleotides in length, more often at least about 270 nucleotides in length, more often at least about 300 nucleotides in length, more often at least about 450 nucleotides in length, more often at least about 600 nucleotides in length, more often at least about 900 nucleotides in length, or more.

"Percent (%) nucleic acid sequence identity" with respect to the vertebrate fused sequences identified herein is defined as the percentage of nucleotides in a candidate sequence that are identical with the nucleotides in the vertebrate fused sequence, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % nucleic acid sequence identity values are obtained as described below by using the sequence comparison computer program ALIGN-2, wherein the complete source code for the ALIGN-2 program is provided in FIGS. 19A-Q. The ALIGN-2 sequence comparison computer program was authored by Genentech, Inc. and the source code shown in FIGS. 19A-Q has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in FIGS. 19A-Q. The ALIGN-2 program should be compiled for use on a UNIX operating system, preferably digital UNIX V4.0D. All sequence comparison parameters are set by the ALIGN-2 program and do not vary.

For purposes herein, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program ALIGN-2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C. As examples of % nucleic acid sequence identity calculations, FIGS. 18C-D demonstrate how to calculate the % nucleic acid sequence identity of the nucleic acid sequence designated "Comparison DNA" to the nucleic acid sequence designated "PRO-DNA".

Unless specifically stated otherwise, all % nucleic acid sequence identity values used herein are obtained as described above using the ALIGN-2 sequence comparison computer program. However, % nucleic acid sequence identity may also be determined using the sequence comparison program NCBI-BLAST2 (Altschul et al., *Nucleic Acids Res.* 25:3389-3402 (1997)). The NCBI-BLAST2 sequence comparison program may be obtained from the National Institute of Heath, Bethesda, Md., 20892. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program NCBI-BLAST2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C.

In other embodiments, vertebrate fused variant polynucleotides are nucleic acid molecules that encode an active vertebrate fused polypeptide and which are capable of hybridizing, preferably under stringent hybridization and wash conditions, to nucleotide sequences encoding the full-length vertebrate fused polypeptide shown in FIG. 1 (SEQ ID NO:2). Vertebrate fused variant polypeptides may be those that are encoded by a vertebrate fused variant polynucleotide.

The term "positives", in the context of the amino acid sequence identity comparisons performed as described above, includes amino acid residues in the sequences compared that are not only identical, but also those that have similar properties. Amino acid residues that score a positive value to an amino acid residue of interest are those that are either identical to the amino acid residue of interest or are a preferred substitution (as defined in Table 1 below) of the amino acid residue of interest.

For purposes herein, the % value of positives of a given amino acid sequence A to, with, or against a given amino acid sequence B (which can alternatively be phrased as a given amino acid sequence A that has or comprises a certain % positives to, with, or against a given amino acid sequence B) is calculated as follows:

100 times the fraction X/Y where X is the number of amino acid residues scoring a positive value as defined above by the sequence alignment program ALIGN-2 in that program's alignment of A and B, and where Y is the total number of amino acid residues in B.

It will be appreciated that where the length of amino acid sequence A is not equal to the length of amino acid sequence B, the % positives of A to B will not equal the % positives of B to A.

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the vertebrate fused natural environment will not be present. Ordinarily, however, isolated polypeptide will be prepared by at least one purification step.

An "isolated" vertebrate fused nucleic acid molecule is a nucleic acid molecule that is identified and separated from at least one contaminant nucleic acid molecule with which it is ordinarily associated in the natural source of the vertebrate fused nucleic acid. Preferably, the isolated nucleic acid is free of association with all components with which it is naturally associated. An isolated vertebrate fused nucleic acid molecule is other than in the form or setting in which it is found in nature. Isolated nucleic acid molecules therefore are distinguished from the vertebrate fused-encoding nucleic acid molecule as it exists in natural cells. However, an isolated nucleic acid molecule encoding a vertebrate fused polypeptide includes fused-encoding nucleic acid molecules contained in cells that ordinarily express vertebrate fused where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends upon the ability of denatured DNA to reanneal when complementary strands are present in an environment near but below their $T^m$ (melting temperature). The higher the degree of desired homology between the probe and hybridizable sequence, the higher the relative temperature which can be used. As a result, it follows that higher relative temperatures would tend to make the reaction conditions more stringent, while lower temperatures less so. Moreover, stringency is also inversely proportional to salt concentrations. For additional details and explanation of stringency of hybridization reactions, see Ausubel et al., *Current Protocols in Molecular Biology* (1995).

"Stringent conditions," as defined herein may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al, *Molecular Cloning: A Laboratory Manual* (New York: Cold Spring Harbor Laboratory Press, 1989), and include the use of a washing solution and hybridization conditions (e.g., temperature, ionic strength and % SDS) less stringent than described above. An example of moderately stringent conditions is a condition such as overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "epitope tagged" when used herein refers to a chimeric polypeptide comprising vertebrate fused polypeptide, or a portion thereof, fused to a "tag polypeptide". The tag polypeptide has enough residues to provide an epitope against which an antibody can be made, yet is short enough such that it does not interfere with activity of the vertebrate fused polypeptide. The tag polypeptide preferably also is fairly unique so that the antibody does not substantially cross-react with other epitopes. Suitable tag polypeptides generally have at least six amino acid residues and usually between about 8 to about 50 amino acid residues (preferably, between about 10 to about 20 residues).

As used herein, the term "immunoadhesin" designates antibody-like molecules which combine the binding specificity of a heterologous protein (an "adhesin") with the effector functions of immunoglobulin constant domains. Structurally, the immunoadhesin comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesins may be obtained from any immunoglobulin, such as IgG-1, IgG-2, IgG-3 or IgG-4 subtypes, IgA (including IgA-1 and IgA-2, IgE, IgD or IgM.

"Active" or "activity" for the purposes herein refers to form(s) of vertebrate fused which retain a biological and/or an immunological activity of native or naturally-occurring vertebrate fused, wherein "biological" activity refers to a biological function (either inhibitory or stimulatory) caused by a native or naturally-occurring vertebrate fused other than the ability to induce the production of an antibody against an antigenic epitope possessed by a native or naturally-occurring vertebrate fused and an "immunological" activity refers to the ability to induce the production of an antibody against an antigenic epitope possessed by a native or naturally-occurring vertebrate fused. A preferred activity is the ability to bind to and affect, e.g., block or otherwise modulate, hedgehog signaling. The activity preferably involves the regulation of the pathogenesis of Basal cell carcinoma. Another preferred biological activity is the ability to phosphorylate or modulate the phosphorylation of Gli.

The term "antibody" is used in the broadest sense and specifically covers, for example, single anti-fused monoclonal antibodies (including agonist, antagonist antibodies and neutralizing antibodies), anti-fused antibody compositions with polyepitopic specificity, single chain anti-fused antibodies, as well as antibody fragments (see below), so long as they exhibit the desired biological activity.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler & Milstein, Nature 256:495 (1975), or may be made by recombinant DNA methods [see, e.g., U.S. Pat. No. 4,816,567 (Cabilly et al.)].

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity [U.S. Pat. No. 4,816,567; Cabilly et al; Morrison et al, Proc. Natl. Acad. Sci. USA 81, 6851-6855 (1984)].

"Humanized" forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, corresponding non-human residues replace Fv framework residues of the human immunoglobulin. Furthermore, humanized antibody may comprise residues that are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. For further details see: Jones et al, Nature 321, 522-525 (1986); Reichmann et al., Nature 332, 323-329 (1988); Presta, Curr. Op. Struct. Biol. 2 593-596 (1992) and U.S. Pat. No. 5,225, 539 (Winter) issued Jul. 6, 1993.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (Zapata et al., Protein Eng. 8(10): 1057-1062 [1995]); single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2.

"Single-chain Fv" or "sFv" antibody fragments comprise the VH and VL domains of antibody, wherein these domains are present in a single polypeptide chain. Preferably, the Fv polypeptide further comprises a polypeptide linker between the VH and VL domains which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90: 6444-6448 (1993).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The word "label" when used herein in conjunction with describing an antibody per se, refers to a detectable compound or composition which is conjugated directly or indirectly to the antibody so as to generate a "labeled" antibody. The label may be detectable by itself (e.g., radioisotope labels or fluorescent labels) or, in the case of an enzymatic label, may catalyze chemical alteration of a substrate compound or composition which is detectable.

The term "antagonist" is used herein in the broadest sense to include any molecule that partially or fully blocks, prevents, inhibits or neutralizes the normal functioning of vertebrate fused in the Hh signaling pathway. One particular form of antagonist includes a molecule that interferes with the interaction between vertebrate fused and its binding or complexing proteins. In a similar manner, the term "agonist" is used herein to include any molecule which promotes, enhances or stimulates the normal functioning of vertebrate fused in the Hh signaling pathway.

Suitable agonist or antagonist molecules that affect the protein-protein interaction of vertebrate fused and its binding proteins include agonist or antagonist antibodies or antibody fragments, fragments or amino acid sequence variants of native sequence vertebrate fused polypeptides, peptides, small bioorganic molecules, e.g., peptidomimetics, which will prevent or enhance, as the case may be, the interaction of proper complex formation. Non-limiting examples include proteins, peptides, glycoproteins, glycopeptides, glycolipids, polysaccharides, oligosaccharides, nucleic acids, bioorganic molecules, peptidomimetics, pharmacological agents and their metabolites, transcriptional and translation control sequences, and the like. Another preferred form of antagonist includes antisense nucleotides that inhibit proper transcription of wild type fused. Preferred forms of antagonists are small molecules, which specifically bind to or block binding of the ATP binding site of fused.

Methods for identifying agonists or antagonists of a vertebrate fused polypeptide may comprise contacting a vertebrate fused polypeptide with a candidate agonist or antagonist molecule and measuring a detectable change in one or more biological activities normally associated with the vertebrate fused polypeptide.

The term "modulation" or "modulating" means upregulation or downregulation of a signaling pathway. Cellular processes under the control of signal transduction may include, but are not limited to, transcription of specific genes; normal cellular functions, such as metabolism, proliferation, differentiation, adhesion, apoptosis and survival, as well as abnormal processes, such as transformation, blocking of differentiation and metastasis.

"Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

"Mammal" for purposes of treatment refers to any animal classified as a mammal, including humans, domestic and farm animals, and zoo, sports, or pet animals, such as dogs, cats, cattle, horses, sheep, pigs, goats, rabbits, etc. Preferably, the mammal is human.

Administration "in combination with" one or more further therapeutic agents includes simultaneous (concurrent) and consecutive administration in any order.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

By "solid phase" is meant a non-aqueous matrix to which the antibody of the present invention can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as a vertebrate fused polypeptide or antibody thereto) to a mammal. The components of the liposome are commonly arranged in a bilayer formation, similar to the lipid arrangement of biological membranes.

A "small molecule" is defined herein to have a molecular weight below about 500 Daltons.

The techniques of "polymerase chain reaction," or "PCR", as used herein generally refers to a procedure wherein minute amounts of a specific piece of nucleic acid, RNA and/or DNA are amplified as described in U.S. Pat. No. 4,683,195 issued 28 Jul. 1987. Generally, sequence information from the ends of the region of interest or beyond needs to be available, such that oligonucleotide primers can be designed; these primer will be identical or similar in sequence to opposite strands of the template to be amplified. The 5' terminal nucleotides of the two primers may coincide with the ends of the amplified material. PCR sequences form total genomic DNA, and cDNA transcribed from total cellular RNA, bacteriophage, or plasmid sequences, etc. See generally Mullis et al., *Cold Spring Harbor Symp. Quant. Biol.* 51: 263 (1987); Erlich, Ed., PCR Technology, (Stockton Press, NY, 1989). As used herein, PCR is considered to be one, but not the only, example of a nucleic acid test sample comprising the use of a known nucleic acid as a primer and a nucleic acid polymerase to amplify or generate a specific piece of nucleic acid.

II. Compositions and Methods of the Invention

A. Full-Length Vertebrate Fused

The present invention provides newly identified and isolated nucleotide sequences encoding polypeptides referred to in the present application as human and vertebrate fused. In particular, Applicants have identified and isolated cDNA encoding a vertebrate fused polypeptide, as disclosed in further detail in the Examples below. Using BLAST, BLAST-2 and FastA sequence alignment computer programs, Applicants found that a full-length native sequence human fused (shown in FIG. 3 (SEQ ID NO:2)) has 28% amino acid sequence identity with *Drosophila* fused (SEQ ID NO:23). Accordingly, it is presently believed that the human fused disclosed in the present application is a newly identified member of the hedgehog signaling cascade.

The full-length native sequence of human vertebrate fused gene, or portions thereof, may be used as hybridization probes for a cDNA library to isolate the full-length gene or to isolate still other vertebrate homolog genes (for instance, those encoding naturally-occurring variants of vertebrate fused or vertebrate fused from other species) which have a desired sequence identity to the vertebrate fused sequence disclosed in FIG. 1 (SEQ ID NO:1). Optionally, the length of the probes will be about 20 to about 50 bases. The hybridization probes may be derived from the nucleotide sequence of FIG. 1 (SEQ ID NO:1) or from genomic sequences including promoters, enhancer elements and introns of native sequence vertebrate fused. By way of example, a screening method will comprise isolating the coding region of the vertebrate fused gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the vertebrate fused gene of the present invention can be used to screen libraries of human cDNA, genomic DNA or mRNA to determine which members of such libraries the probe hybridizes to.

B. Vertebrate Fused Variants

In addition to the full-length native sequence vertebrate fused described herein, it is contemplated that vertebrate fused variants can be prepared. Vertebrate fused variants can be prepared by introducing appropriate nucleotide changes into a known vertebrate fused DNA, or by synthesis of the desired vertebrate fused polypeptides. Those skilled in the art will appreciate that amino acid changes may alter post-translational processes of the vertebrate fused.

Variations in the native full-length sequence vertebrate fused or in various domains of the vertebrate fused described herein, can be made, for example, using any of the techniques and guidelines for conservative and non-conservative mutations set forth, for instance, in U.S. Pat. No. 5,364,934. Variations may be a substitution, deletion or insertion of one or more codons encoding the vertebrate fused that results in a change in the amino acid sequence of the vertebrate fused as compared with the native sequence vertebrate fused. Optionally the variation is by substitution of at least one amino acid with any other amino acid in one or more of the domains of the vertebrate fused. Guidance in determining which amino acid residue may be inserted, substituted or deleted without adversely affecting the desired activity may be found by comparing the sequence of the vertebrate fused with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of 1 to 5 amino acids. The variation allowed may be determined by systematically making insertions, deletions or substitutions of amino acids in the sequence and testing the resulting variants for activity exhibited by the full-length or mature native sequence such as the in vitro assay described in the Examples below.

Vertebrate fused polypeptide fragments are also provided herein. Such fragments may be truncated at the N-terminus or C-terminus, or may lack internal residues, for example, when compared with a full length native protein. Certain fragments lack amino acid residues that are not essential for a desired biological activity of the vertebrate fused polypeptide.

Vertebrate fused fragments may be prepared by any of a number of conventional techniques. Desired peptide fragments may be chemically synthesized. An alternative approach involves generating vertebrate fused fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired polypeptide fragment, by polymerase chain reaction (PCR). Oligonucleotides that define the desired termini of the DNA fragment are employed at the 5' and 3' primers in the PCR. Preferably, vertebrate fused polypeptide fragments share at least one biological and/or immunological activity with the native vertebrate fused polypeptide shown in FIG. 1 (SEQ ID NO:2), e.g., block or modulate hedgehog signaling, regulation of pathogenesis of basal cell carcinoma, modulation of phosphorylation of Gli.

In particular embodiments, conservative substitutions of interest are shown in Table 1 under the heading of preferred substitutions. If such substitutions result in a change in biological activity, then more substantial changes, denominated exemplary substitutions in Table 1, or as further described below in reference to amino acid classes, are introduced and the products screened.

TABLE 1

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine, ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in function or immunological identity of the vertebrate fused polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis [Carter et al, *Nucl Acids Res.*, 13:4331 (1986); Zoller et al, *Nucl Acids Res.*, 10:6487 (1987)], cassette mutagenesis [Wells et al., *Gene*, 34:315 (1985)], restriction selection mutagenesis [Wells et al, *Philos. Trans. R. Soc. London SerA*, 317: 415 (1986)] or other known techniques can be performed on the cloned DNA to produce the vertebrate fused variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions [Creighton, *The Proteins*, (W.H. Freeman & Co., N.Y.); Chothia, *J. Mol. Biol.*, 150: 1 (1976)]. If alanine substitution does not yield adequate amounts of variant, an isoteric amino acid can be used.

C. Modifications of Vertebrate Fused

Covalent modifications of vertebrate fused are included within the scope of this invention. One type of covalent modification includes reacting targeted amino acid residues of the vertebrate fused with an organic derivatizing agent that is capable of reacting with selected side chains or the N- or C-terminal residues of the vertebrate fused. Derivatization with bifunctional agents is useful, for instance, for crosslinking vertebrate fused to a water-insoluble support matrix or surface for use in the method for purifying anti-vertebrate fused antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis-(succinimidyl-propionate), bifunctional maleimides such as bis-N-maleimido-1,8-octane and agents such as methyl-3-[(p-azidophenyl)-dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, *Proteins: Structure and Molecular Properties*, W.H. Freeman & Co., San Francisco, pp. 79-86 (1983)], acetylation of the N-terminal amine, and amidation of any C-terminal carboxyl group.

Another type of covalent modification of vertebrate fused comprises linking the vertebrate fused polypeptide to one of a variety of nonproteinaceous polymers, e.g., polyethylene glycol, polypropylene glycol, or polyoxyalkylenes, in the manner set forth in U.S. Pat. No. 4,640,835; 4,496,689; 4,301,144; 4,670,417; 4,791,192 or 4,179,337. Such modifications would be expected to increase the half-life of the molecules in circulation in a mammalian system; Extended half-life of fused molecules might be useful under certain circumstances, such as where the fused variant is administered as a therapeutic agent.

The vertebrate fused of the present invention may also be modified in a way to form a chimeric molecule comprising vertebrate fused bonded to another, heterologous polypeptide or amino acid sequence. In one embodiment, such a chimeric molecule comprises a fusion of the vertebrate fused with a tag polypeptide, which provides an epitope to which an anti-tag antibody can selectively bind. The epitope tag is generally placed at the amino- or carboxyl-terminus of the vertebrate fused. The presence of such epitope-tagged forms of the vertebrate fused can be detected using an antibody against the tag polypeptide. Also, provision of the epitope tag enables the vertebrate fused to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.*, 8:2159-2165 (1988)]; the c-myc tag and the 8F9, 3C7, 6E10, G4, B7 and 9E10 antibodies thereto [Evan et al., *Molecular and Cellular Biology*, 5:3610-3616 (1985)]; and the Herpes Simplex virus glycoprotein D (gD) tag and its antibody [Paborsky et al., *Protein Engineering*, 3(6):547-553 (1990)]. Other tag polypeptides include the Flag-peptide [Hopp et al., *BioTechnology*, 6:1204-1210 (1988)]; the KT3 epitope peptide [Martin et al., *Science*, 255:192-194 (1992)]; an α-tubulin epitope peptide [Skinner et al., *J. Biol. Chem.*, 266: 15163-15166 (1991)]; and the T7 gene 10 protein peptide tag [Lutz-Freyermuth et al., *Proc. Natl. Acad. Sci. USA*, 87: 6393-6397 (1990)].

In an alternative embodiment, the chimeric molecule may comprise a fusion of the vertebrate fused with an immunoglobulin or a particular region of an immunoglobulin. For a bivalent form of the chimeric molecule, such a fusion could be to the Fc region of an IgG molecule. Ordinarily, the C-terminus of a contiguous amino acid sequence of a vertebrate fused sequence is fused to the N-terminus of a contiguous amino acid sequence of an immunoglobulin constant region, in place of the variable region(s), however N-terminal fusions are also possible.

Typically, such fusions retain at least functionally active hinge, CH2 and CH3 domains of the constant region of an immunoglobulin heavy chain. Fusions are also made to the C-terminus of the Fc portion of a constant domain, or immediately N-terminal to the CH1 of the heavy chain or the corresponding region of the light chain. This ordinarily is accomplished by constructing the appropriate DNA sequence and expressing it in recombinant cell culture. Alternatively, immunoadhesins may be synthesized according to known methods.

The precise site at which the fusion is made is not critical; particular sites are well known and may be selected in order to optimize the biological activity, secretion or binding characteristics of the immunoadhesins.

D. Preparation of Vertebrate Fused

The description below relates primarily to production of a particular vertebrate fused by culturing cells transformed or transfected with a vector containing vertebrate fused nucleic acid. It is, of course, contemplated that alternative methods, which are well known in the art, may be employed to prepare vertebrate fused. For instance, the vertebrate fused sequence, or portions thereof, may be produced by direct peptide synthesis using solid-phase techniques [see, e.g., Stewart et al., *Solid-Phase Peptide Synthesis*, W.H. Freeman Co., San Francisco, Calif. (1969); Merrifield, *J. Am. Chem. Soc.*, 85:2149-2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the vertebrate fused may be chemically synthesized separately and combined using chemical or enzymatic methods to produce the full-length vertebrate fused.

1. Isolation of DNA Encoding Vertebrate Fused

DNA encoding vertebrate fused may be obtained from a cDNA library prepared from tissue believed to possess the vertebrate fused mRNA and to express it at a detectable level. Accordingly, human vertebrate fused DNA can be conveniently obtained from a cDNA library prepared from human tissue, such as described in the Examples. The vertebrate fused-encoding gene may also be obtained from a genomic library or by oligonucleotide synthesis (e.g., automated nucleic acid synthesis).

Libraries can be screened with probes (such as antibodies to the vertebrate fused or oligonucleotides of at least about 20-80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding vertebrate fused is to use PCR methodology [Sambrook et al., supra; Dieffenbach et al., *PCR Primer: A Laboratory Manual* (Cold Spring Harbor Laboratory Press, 1995)].

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined using methods known in the art and as described herein.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for vertebrate fused production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: A Practical Approach*, M. Butler, ed. (IRL Press, 1991) and Sambrook et al., supra.

Methods of transfection are known to the ordinarily skilled artisan, for example, CaPO$_4$ and electroporation. Depending on the host cell used, transformation is performed using standard techniques appropriate to such cells. The calcium treatment employing calcium chloride, as described in Sambrook et al., supra, or electroporation is generally used for prokaryotes or other cells that contain substantial cell-wall barriers. Infection with *Agrobacterium tumefaciens* is used for transformation of certain plant cells, as described by Shaw et al., *Gene*, 23:315 (1983) and WO 89/05859 published 29 Jun. 1989. For mammalian cells without such cell walls, the calcium phosphate precipitation method of Graham and van der Eb, *Virology* 52:456-457 (1978) can be employed. General aspects of mammalian cell host system transformations have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci.* (USA), 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology*, 185:527-537 (1990) and Mansour et al., *Nature*, 336: 348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3 phoA E15 (argF-lac)169 degP ompT kan$^r$; *E. coli* W3110 strain 37D6, which has the complete genotype tonA ptr3 phoA E15 (argF-lac)169 degP ompT rbs7 ilvG kan$^r$; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued 7 Aug. 1990. Alternatively, in vitro methods of cloning, e.g., PCR or other nucleic acid polymerase reactions, are suitable.

In addition to prokaryotes, eukaryotic microbes such as filamentous fungi or yeast are suitable cloning or expression hosts for vertebrate fused-encoding vectors. *Saccharomyces cerevisiae* is a commonly used lower eukaryotic host microorganism. Others include *Schizosaccharomyces pombe* (Beach and Nurse, *Nature*, 290: 140 [1981]; EP 139,383 published 2 May 1985); *Kluyveromyces* hosts (U.S. Pat. No. 4,943,529; Fleer et al., *Bio/Technology*, 9:968-975 (1991)) such as, e.g., *K. lactis* (MW98-8C, CBS683, CBS4574; de Louvencourt et al., *J. Bacteriol.* 154 (2):737-42 (1983), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., *Bio/Technology*, 8:135 (1990)), *K. thermotolerans*, and *K. marxianus; yarrowia* (EP 402,226); *Pichia pastoris* (EP 183,070; Sreekrishna et al., *J. Basic Microbiol.*, 28:265-278 [1988]); *Candida; Trichoderma reesia* (EP 244,234); *Neurospora crassa* (Case et al., *Proc. Natl. Acad. Sci. USA*, 76:5259-5263 [1979]); *Schwanniomyces* such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., *Biochem. Biophys. Res. Commun.*, 112:284-289 [1983]; Tilburn et al., *Gene*, 26:205-221 [1983]; Yelton et al., *Proc. Natl. Acad. Sci. USA*, 81: 1470-1474 [1984]) and *A. niger* (Kelly and Hynes, *EMBO J.*, 4:475-479 [1985]). Methylotropic yeasts are suitable herein and include, but are not limited to, yeast capable of growth on methanol selected from the genera consisting of *Hansenula, Candida, Kloeckera, Pichia, Saccharomyces, Torulopsis*, and *Rhodotorula*. A list of specific species that are exemplary of this class of yeasts may be found in C. Anthony, *The Biochemistry of Methylotrophs*, 269 (1982).

Additional host cells for the expression of vertebrate fused are derived from multicellular organisms. Examples of invertebrate cells include insect cells such as *Drosophila* S2 and *Spodoptera* Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977)); Chinese hamster ovary cells/-DHFR(CHO, Urlaub and Chasin, *Proc. Natl. Acad. Sci. USA*, 77:4216 (1980)); mouse sertoli cells (TM4, Mather, *Biol. Reprod.* 23:243-251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

3. Selection and Use of a Replicable Vector

The nucleic acid (e.g., cDNA or genomic DNA) encoding vertebrate fused may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques, which are known to the skilled artisan.

The vertebrate fused may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the fused-encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including *Saccharomyces* and *Kluyveromyces* α-factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2 μl plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up the vertebrate fused nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA,* 77:4216 (1980). A suitable selection gene for use in yeast is the trp1 gene present in the yeast plasmid YRp7 [Stinchcomb et al, *Nature,* 282:39 (1979); Kingsman et al., *Gene,* 7:141 (1979); Tschemper et al., *Gene,* 10:157 (1980)]. The trp1 gene provides a selection marker for a mutant strain of yeast lacking the ability to grow in tryptophan, for example, ATCC No. 44076 or PEP4-1 [Jones, *Genetics,* 85:12 (1977)].

Expression and cloning vectors usually contain a promoter operably linked to the vertebrate fused nucleic acid sequence to direct mRNA synthesis. Promoters recognized by a variety of potential host cells are well known. Promoters suitable for use with prokaryotic hosts include the β-lactamase and lactose promoter systems [Chang et al., *Nature,* 275:615 (1978); Goeddel et al., *Nature,* 281:544 (1979)], alkaline phosphatase, a tryptophan (trp) promoter system [Goeddel, *Nucleic Acids Res.,* 8:4057 (1980); EP 36,776], and hybrid promoters such as the tac promoter [deBoer et al, *Proc. Natl. Acad. Sci. USA,* 80:21-25 (1983)]. Promoters for use in bacterial systems also will contain a Shine-Dalgarno (S.D.) sequence operably linked to the DNA encoding vertebrate fused.

Examples of suitable promoting sequences for use with yeast hosts include the promoters for 3-phosphoglycerate kinase [Hitzeman et al, *J. Biol. Chem.,* 255:2073 (1980)] or other glycolytic enzymes [Hess et al., *J. Adv. Enzyme Reg.,* 7:149 (1968); Holland, *Biochemistry,* 17:4900 (1978)], such as enolase, glyceraldehyde-3-phosphate dehydrogenase, hexokinase, pyruvate decarboxylase, phospho-fructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

Vertebrate fused transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the vertebrate fused by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the vertebrate fused coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding vertebrate fused.

Still other methods, vectors, and host cells suitable for adaptation to the synthesis of vertebrate fused in recombinant vertebrate cell culture are described in Gething et al., *Nature,* 293:620-625 (1981); Mantei et al., *Nature,* 281:40-46 (1979); EP 117,060; and EP 117,058.

4. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA,* 77:5201-5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence vertebrate fused polypeptide or against a synthetic peptide based on the DNA sequences provided herein or against exogenous sequence fused to vertebrate fused DNA and encoding a specific antibody epitope.

5. Purification of Polypeptide

Forms of vertebrate fused may be recovered from host cell lysates. If membrane-bound, it can be released from the membrane using a suitable detergent solution (e.g., Triton-X 100) or by enzymatic cleavage. Cells employed in expression of vertebrate fused can be disrupted by various physical or chemical means, such as freeze-thaw cycling, sonication, mechanical disruption, or cell lysing agents.

It may be desired to purify vertebrate fused from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the vertebrate fused. Various methods of protein purification may be employed and such methods are known in the art and described for example in Deutscher, *Methods in Enzymology*, 182 (1990); Scopes, *Protein Purification: Principles and Practice*, Springer-Verlag, New York (1982). The purification step(s) selected will depend, for example, on the nature of the production process used and the particular vertebrate fused produced.

E. Uses for Vertebrate Fused (1) Fused is Universal Mediator of Hh Signaling

Hedgehog (Hh) is a secreted protein involved in patterning the *Drosphila* fly embryo and its three mammalian homologues, Sonic, Indian and Desert all of which play key roles in vertebrate development. The action of Hh ultimately leads to the activation of the zinc finger transcription factor Ci/Gli, which is sufficient in many cases to mediate Hh functions. [Alexandre et al., *Genes Dev.* 10, 2003-12 (1996); Dominguez et al., *Science* 272: 1621-25 (1996); Hynes et al., *Neuron* 19: 15-26 (1997); Lee et al., *Development* 124: 2537-52 (1997)]. However, the intracellular mechanisms controlling Gli activity have not been completely understood. Several molecules identified as segment polarity genes in *Drosophila* are thought to participate in Gli activity. (reviewed by Goodrich and Scott, *Neuron* 21: 1243-57 (1998); Ingham, *Embo. J.* 17: 3505-11 (1998). One molecule required to modulate Ci activity in *Drosophila* is the putative serine-threonine kinase dfused. Alves et al., *Mech. Dev.* 78: 17-31 (1998); Ohlmeyer and Kalderon, *Nature* 396: 749-53 (1998). hSu(fu) is a negative regulator of the hedgehog pathway that forms a complex with hGli-1 and inhibits its activity. Applicants have demonstrated herein that Shh regulates hGli-1 in part by inducing dissociation of human Supressor of Fused [hSu(fu)] from hGli-1. Stimulation of cells with N-Shh triggers dissociation of hSu(fu) from hGli-1 withing 15-30 minutes, and is followed 45 minutes after stimulation by reassociation of these two proteins. This reassociation may result from a negative feedback loop aimed at limited Shh signaling.

The human fused full length molecule (hfused) of human (FIG. 1 (SEQ ID NO:1)) encodes a protein with a predicted molecular weight (gel reading of 150 kDa, protein translation: 100 kDa), which is significantly larger that *Drosophila* fused (gel reading: 100 kDa, protein translation 92 kDa, dfused (SEQ ID NO:23)). Human fused (hfused) shows notable homology (55%) to the *Drosophila* homologue in the kinase domain, but little homology with dfused or any other known protein over the remaining ≈1000 (i.e., 1052) amino acids. The kinase domain extends from residue 1 to about residue 260, as is represented in FIG. 1 (SEQ ID NOS:24 and 2). An ATP binding site is at about amino acid position 33 and is required for kinase activity. However, the C-terminal portion (residues 261-1315) (e.g., SEQ ID NO:27) appears to be required to displace PKA from Su(fu) (FIG. 20).

While the divergence at the C-terminus of the molecules may appear to be unexpected given that the C-terminus of the *Drosophila* molecule is required for its activity, Preat et al., *Nature* 347: 87-9 (1990), it is not altogether unsimilar to other members of the hedgehog signal transduction pathway. For example, there is little homology between the intracellular domain regions of vertebrate and *Drosophila* Smoothened (dSmo)(Stone et al., *Nature* 384: 129-34 (1996) or between Gli and Ci outside the zinc finger region (Orenic et al., *Genes Dev.* 4: 1053-67 (1990). Thus it is highly probable that the functional homology of these protein has been preserved despite the divergence in their primary structure.

Prior studies in *Drosophila* indicate that dfused is necessary for Hh signal to occur but have not addressed the issue whether fused is sufficient to activate this signaling system. As depicted in the Examples, applicants have herein used a Gli DNA binding element present in the HNF3β promoter, in front of a luciferase mediator of the Hh cascade, which clearly demonstrates that fused alone is capable of activating Gli mediated transcription in this system. It is further apparent that both an intact kinase domain and an intact C-terminal non-catalytic domain are required for this activation, which supports the notion that fused functions as a kinase and that the C-terminus may play a role in the substrate recognition or in regulating the kinase activity.

Applicants have shown in the present application that hfused is a kinase which is capable of phosphorylating artificial substrates such as MBP. However, the identity of the physiological substrate for hfused remains to be determined.

To determine if human fused is essential for Hh signaling in vertebrates, a mutant was constructed by altering a conserved lysine in the ATP binding site (about amino acid residue 33). Typically, such mutants act as inhibitor of the corresponding wild type kinase by blocking access to substrate and/or regulatory factors, He et al, *Nature* 374, 617-22 (1995). When overexpressed in 2-cell stage *Xenopus* embryos, the most remarkable phenotype was the presence of fused eyes in about 30% of the injected embryos. Several lines of evidence indicate that this phenotype is likely to result from the inhibition of Hh signaling. First, Shh knockouts display a cyclopia phenotype attributed recently to mutations in the Shh gene, Chiang et al, *Nature* 383: 407-13 (1996). Second, zebrafish embryos (cyclops) with reduced expression of Shh or injected with constitutively active form of PKA, a negative regulator of the Hh pathway are cyclops. Third, Shh, emanating from prechordal plate, has been shown to inhibit expression of Pax-6, a key transcription factor required for eye development, in the center of a continuous eyefield, Ekker et al., *Curr. Biol.* 5: 944-55 (1995); Li et al., *Development.* 124: 603-15 (1997); Macdonald et al., *Development* 121: 3267-78 (1995). Finally, staining for Pax-6 embryos injected with fused-DN revealed a single field of expression suggesting a failure of Shh emanating from the prechordal plate to downregulate the expression of Pax-6 at the center of the eyefield.

hFused-DN also appears to affect normal development of tissues such as the frog gut which is regulated by Indian Hh. This, combined with the fact that fused is expressed in the gut and testis, sites of Ihh and Dhh action respectively, suggest that fused may be a universal mediator of signaling for all members of the Hh protein family.

Very high levels of fused mRNA was found on germ cell, the development of which appears to be regulated by Dhh. Homozygous mutant mice for Dhh fail to develop germ cells and are viable but sterile (Bitgood et al., *Curr. Biol.* 6: 298-304 (1996). However, Patched, a Hedgehog receptor is expressed on interstitial Leydig cells and not on germ cells where fused is expressed, Bitgood et al, supra. This discrepancy suggests that there may be additional hedgehog receptors.

Applicants have shown in the Examples that wild type hfused is capable of activating Gli in a reporter assay. Furthermore, expression of Shh in the floor plate of frog embryos injected with hfused-DN could be rescued by coinjection of Gli-1. Taken together these observations are consistent with the assertion that fused acts downstream of Smo and upstream of Gli in this signaling pathway, which is consistent with the genetic evidence in *Drosophila* to date.

It has been demonstrated herein that hfused and the catalytic domain of PKA (PKAc) were associated with the hSu(fu)-hGli-1 complex. PKAc can phosphorylate both hSu(fu) and hGli-1 but not hfused and phosphorylation of hSu(fu) by PKAc promotes the association of hSu(fu) with hGli-1. We propose here that PKAc plays an inhibitory role on the hedgehog pathway in part by promoting the physical association of Su(fu) with Gli. However, the exact mechanism by which the interaction of hSu(fu) with hGli-1 prevent its activation remains unclear. Su(fu) may be involved in targeting Gli for degradation through the proteasome pathway. hSu(fu) may prevent the transformation of Gli into an activated form, for example by interfering with the association of a cofactor. It may also be involved in tethering Gli into the cytoplasm, as suggested by subcellular localization studies showing that Ci is part of the multiprotein complex associated to microtubules (Robbins et al., *Cell* 90: 225-34 (1997); Sisson et al, *Cell* 90: 235-45 (1997). Finally, in *Drosophila*, phosphorylation of Ci by PKA appears to be required for the cleavage and conversion of Ci into a transcription repressor (Chen et al., *Proc. Natl. Acad. Sci. USA* 95: 2349-54 (1998). Although it is not yet clear what the equivalent to that repressor form is in vertebrates, hSu(fu) may be involved in recruiting PKAc to Gli. hGli-1 was indeed found to be a phosphoprotein whose phosphorylation level increases in the presence of ectopic hSu(fu) (FIGS. 13D and 15C), suggesting that phosphorylation of hGli-1 is potentially mediated by endogenous hSu(fu)-associated PKA activity.

Several lines of evidence indicate the PKAc regulates the hedgehog pathway and the Su(fu)-Gli interaction in a cAMP independent manner: i) in *Drosophila* embryos, cAMP-dependent regulation of PKA activity is not required for hedgehog signaling (Ohlmeyer and Kalderon, *Genes Dev.* 11: 2250-58 (1997); (ii) stimulation of cells with N-Shh or various Smo constructs does not produce any changes in cAMP (Murone et al., *Curr. Biol.* 9: 76-84 (1999); (iii) during in vivo phospholabeling experiments, addition of a cAMP antagonist does not modify the level of hSu(fu) phosphorylation (data not shown). cAMP independent PKAc activity has been described in other systems such as p65 NFκB activation. Zhong et al., *Cell* 89: 413-24 (1997).

In contrast to PKAc, which promotes the association of hSu(fu) with hGli-1, Applicants have discovered that hfused promotes the dissociation of hSu(fu) from hGli-1. hfused appears to modulate this interaction by preventing the association of PKAc with hSu(fu). The kinase activity of hfused does not appear to be involved in the regulation of the PKAc activity/binding to hSu(fu). However, when expressed at limiting amounts in a functional readout for Gli activation, the kinase activity of hFu is required for maximum activation of a Gli-BS reporter. These data suggest a dual role for hfused in the Hh signaling cascase where the putative kinase dead molecule is sufficient for inducing dissociation of Su(fu) from Gli but is not as effective as wild type at activating the Gli-BS reporter when expressed at limiting amounts. In support of this dual role of hfused, different *Drosophila* fused mutant alleles display similar loss of Hh function phenotype. However, when combined with mutant alleles of Su(fu), fused mutations in the kinase domain (type (I) lead to a wild type phenotype, while fused alleles carrying mutations in the C-terminus (type II) display a gain of Hh function (Therond et al, *Genetics* 142: 1181-98 (1996). Nevertheless, it is not obvious to determine the corresponding functional domains in the C-terminus of dfused and hfused because of the lack of homology.

Taken together, these data support a model where, in the absence of Shh, hGli-1 is present in a complex with hSu(f), PKAc and an inactive form of hfused. PKAc-phosphorylated hSu(fu) binds hGli-1 and prevents its activation through a still unidentified mechanism (FIG. 17). In response to Shh, activation of hfused independently of its kinase activity but through a mechanism involving its C-terminus, lead to the displacement/removal of PKAc and the detachment of hSu(fu) from hGli-1. Although this step may be required for the activation of Gli, it may not be sufficient. A second step leading to an activated and labile form of Gli (Ohlmeyer and Kalderon, supra, 1998) might be necessary for its full activation. This later step may for example involve the kinase activity of hfused (FIG. 17). Activation of the Hh signaling pathway has recently been implicated in the formation of a number of human cancers, including basal cell carcinomas (Hahn et al., *Cell* 85: 841-51 (1996); Johnson et al., *Science* 272: 1668-71 (1996); Xie et al, *Nature* 391: 90-92 (1998). The identification of hfused as a component required for vertebrate Hh signaling could therefore lead to rational therapeutic approaches for cancer treatment.

(2) Tissue Distribution of Vertebrate Fused

The tissue distribution of fused shows that it is expressed in all Shh responsive cells, in particular, the nervous system where it is expressed in the ventral neural tube. Its expression pattern overlaps well with the Shh receptor components, Smo and Ptch. Stone et al., *Nature* 384: 129-34 (1996). Murine fused is also expressed in Ihh and Dhh target tissues, suggesting that it might participate in transducing the signal for all the mammalian hedgehogs.

The gene encoding hfused was mapped to human chromosome 2q35, close to the PAX3 gene which is implicated in the Klein-Waardenburg syndrome. This condition is characterized by a combination of upper limb abnormalities including fusion of the carpal bones and syndactyly, as well as facial and ocular abnormalities. Interestingly, PAX3 is also a target of Shh and it has been suggested that additional loci in the 2q35 region may regulate the PAX3 locus and the development of the Klein-Waardenburg phenotype (Pasteris et al, *Hum. Hol. Genet.* 2: 953-59 (1993).

These data suggest that fused is involved in mediating a wide variety of effect Shh has on different tissues. Functionally, this was observed again in frog embryos where, fused-DN inhibited eye development as well as Shh expression in the floor plate.

To confirm the position of fused in the Hh signaling pathway, expression of Shh in the floor plate of *Xenopus* embryos injected with hfused-DN could be rescued by coinjection of Gli-1. This suggests that fused acts in association with Gli in the Shh signaling pathway.

(3) Shh Signaling Leads to the Dissociation of hGli-1 from hSu(fu)

The characterization of the human homologue of *Drosophila* Su(fu) (dSu(fu)) indicates that it forms a complex with Gli family members and represses Gli activity in a reporter assay, consistent with a role of negative regulator of the pathway. To evaluate whether Shh could modulate the hGli-1/hSu(fu) interaction, we transfected the Shh responsive cell line C3H10T1/2 with expression plasmids encoding N-Myc hGli1 and hSu(fu) C-Flag, and immunoprecipitated the complex after $^{32}$P in vivo phospholabeling and stimulation with N-terminus Shh (N-Shh) FIG. 13A). Both bSu(fu) and Gli-1 were found to be highly phosphorylated proteins but no change in phosphorylation levels was detected upon Shh stimulation. Fifteen to thirty minutes after stimulation, the amount of hSu(fu) associated with hGli-1 was reduced, suggesting that N-Shh was able to trigger dissociation of the complex (FIG. 13A, FIG. 14C). Forty-five minutes after stimulation, hSu(fu) reassociated with hGli-1, suggesting that the effect of Shh is transient, and that a putative negative feedback loop aimed at limiting the response to Shh might exist.

(4) PKA Promotes the Association of hSu(fu) with hGli-1

In an effort to determine factors involved in regulating the hSu(fu)-hGli-1 interaction, we coprecipitated with hSu(fu) transfected in 293 cells an endogenous kinase activity able to phosphorylate hSu(fu) (FIG. 15A). To determine the identity of this kinase, we incubated 293 cell extracts with purified GST-hSu(fu) followed by glutathione sepharose beads and were able to pull-down the hSu(fu)-associated kinase activity (FIG. 13B). In *Drosophila*, two kinases have been shown to participate in hedgehog signaling; fused and PKA. Therefore, a GST-hSu(fu) blot was probed with a polyclonal antibody directed against PKAc and another against human fused While the presence of endogenous human fused was not detected, the presence of PKAc was readily detected (FIG. 13B). Both *Drosophila* Su(fu) and hSu(fu) contain several potential PKA phosphorylation sites, and when tested in vitro, GST-hSu(fu) was highly phosphorylated by purified PKAc. This reaction was blocked by addition of PKI, a PKA specific inhibitory peptide (FIG. 13C).

Also examined was whether PKAc-mediated phosphorylation of hSu(fu) influences the hSu(fu)-hGli-1 interaction. 293 cells were transfected with plasmids encoding N-Myc-hGli-1, hSu(fu) and PKAc in various combinations, the lysates were immunoprecipitated with an anti-Myc antibody, and a PKA kinase assay was performed (FIGS. 13D and 15C). Both hSu(fu) and hGli-1 displayed a basal level of phosphorylation which was increased in the presence of ectopic PKAc. Probing of the blot with anti-Myc and anti-Su(fu) antibodies indicated that the increase in hSu(fu) phosphorylation in the presence of PKAc is accompanied by an increase in the amount of hSu(fu) protein co-precipitated with hGli-1 (FIGS. 13D and 15C). PKA is a negative regulator of the hedgehog pathway in both *Drosophila* and vertebrates (reviewed by Goodrich and Scott, *Neuron* 21: 1243-57 (1998); Ingham, *Embo. J.* 17: 3505-11 (1998), our data suggests it may exert its inhibitory role by promoting the physical association of hSu(fu) with hGli-1.

(5) Human Fused Interacts with hSu(fu) and hGli-1

In order to identify additional regulators of this complex in vertebrates, Applicants have isolated cDNAs encoding the human homologue of *Drosophila* protein fused (dfused). Human fused shows significant homology with dfused in the kinase domain (55%), but only limited homology over the remaining 1052 amino acids, a regulatory region not homologous to any other known protein (FIG. 3). Similarly, there is little homology between Gli and Ci outside of the zinc finger region (Orenic et al., *Genes Dev.* 4: 1053-67 (1990) or between the intracellular domains of vertebrate and *Drosophila* Smoothened (Smo) (Stone et al., *Nature* 384: 129-34 (1996), suggesting that the functional homology of proteins in this pathway may have been retained despite their divergence in primary structure. The gene encoding hfused was mapped to human chromosome 2q35, close to the PAX3 gene, which is implicated in the Klein-Waardenburg syndrome. This condition is characterized by a combination of upper limb abnormalities including fusion of the carpal bones and syndactyly, as well as facial and ocular abnormalities. Interestingly, PAX3 is a target of Shh, and it has been suggested that additional loci in the 2q35 region may regulate the PAX3 locus and the development of the Klein-Waardenburg phenotype (Pasteris et al., *Hum. Mol. Genet.* 2: 953-59 (1993).

Northern blot analysis indicates that a 5 kb hfused transcript was expressed at low levels in most fetal tissues and adult ovaries, and at high levels in adult testis (FIG. 7A), where it is localized in germ cells with other components of the hedgehog pathway, such as patched-2, Su(fu), Gli-1 and Gli-3 (Carpenter et al., *Proc Natl Acad Sci USA* 95 (23): 13630-4 (1998). Examination of mouse tissues by in situ hybridization revealed that the murine fused mRNA is widely distributed in Shh responsive tissues, including the neural tube, somites, developing limb buds and skin (FIGS. 7B and C). In the mouse nervous system, high levels of murine fused transcripts were detected throughout the forebrain, midbrain, hindbrain and spinal cord. This expression pattern was retained at embryonic day 13.5, where murine fused mRNA was detected mainly in the ventral aspect of the neural tube, in regions that are exposed to the ventral midline-derived Shh (FIGS. 7D and 7E).

The formation of a complex between human fused and hSu(fu) or hGli-1 was investigated biochemically by co-transfection in 293 cells and immunoprecipitation. Human fused could be co-immunoprecipitated with hSu(fu) (FIG. 14A) and with hGli-1 (FIG. 4B). Human fused, hSu(fu) and hGli-1 were also found in the same complex (FIG. 14C). Consistent with these data, we observed colocalization of the human fused and hSu(fu), or hGli-1 by immunofluorescence when co-transfected in C3H10T1/2 cells (data not shown).

To determine whether hFu regulates the hSu(fu)-hGli-1 complex in a manner similar to Shh, we transfected C3H10T1/2 cells with expression plasmids encoding N-Myc hGli-1 and hSu(fu) C-Flag in the presence or absence of hfused and immunoprecipitated the complex. As observed previously, 15 to 30 minutes after stimulation with N-Shh, the amount of hSu(fu) associated with hGli-1 was reduced (FIG. 14C). Interestingly, the association between hSu(fu) and hGli-1 was decreased in cells co-transfected with human fused before stimulation of these cells with N-Shh. The amount of complex was further reduced upon stimulation of these cells with N-Shh. In both cases, reassociation of hSu(fu) with hGli-1 was observed about 45 minutes after stimulation. These data suggest that ectopic human fused mimics the effects of Shh and promotes the dissociation of hSu(fu) from hGli.

(6) PKAc and Human Fused Have Opposing Effects on hSu(Fu) Binding to hGli-1

We next attempted to test whether human fused was able to phosphorylate human Su(fu) or hGli-1. Surprisingly, we found that human fused inhibited the endogenous PKA activity co-precipitated with hSu(fu). (FIG. 15A). This inhibition was specific to hfused, and was not observed with an unrelated serine threonine kinase, Akt (data not shown). hFused was also able to antagonize phosphorylation of hSu(fu) mediated by ectopic human PKAc (hPKAc) after co-transfection in 293 cells, and appears to act by preventing the association of hPKAc with hSu(fu) (FIG. 15B). To evaluate the role of the kinase domain of human fused, we constructed a putative catalytically dead mutant of hfused by mutating a conserved lysine residue in the ATP binding site at position 33 (hfused K33R) (FIG. 3). This residue is necessary for the catalytic activity of all kinases (Hanks and Quinn, *Methods Enzymol.* 200:38-62 (1991) and the corresponding point mutation in dfused produced as fused mutant phenotype (Therond et al., *Genetics* 142: 1181-98 (1996). Interestingly, this kinase mutant behaved exactly as the wild type in this assay and was able to prevent human Su(fu) phosphorylation by hPKAc. However, a hfused construct lacking 492 amino acids at the C-terminus (hFuΔC) (FIG. 3) was not able to inhibit hSu(fu) phosphorylation by hPKAc, nor was it able to prevent the association of hPKAc with hSu(fu), but was still binding to hSu(fu). Together these data indicate that the C-terminus of hfused, but not its kinase activity, is required to prevent hPKAc from binding and phosphorylating hSu(fu). This domain is different from the domain required for binding to hSu(fu) which is adjacent to the kinase domain (data not shown)(Monnier et al., Curr. Biol. 9: 76-84 (1998).

Next, the consequences of the inhibitory effect of hfused and PKA on the interaction between hSu(fu) and hGli-1 was examined. 293 cells transfected with hFu, hfused K33R or hfused ΔC in addition to N-Myc hGli-1, hSu(fu) and hPKAc were analyzed for hSu(fu) and hGli-1 phosphorylation and for the presence of hSu(fu)-hGli complexes (FIG. 15C). When hfused was co-transfected, hPKAc-induced phosphorylation of hSu(fu) and hGli-1 was greatly reduced as was the binding of hSu(fu) to hGli-1. Again, this effect does not require hfused kinase activity since co-transfection of hfused K33R produced the same effects as hfused, but it does require the C-terminus, as hfused ΔC failed to inhibit the effect of ectopic hPKAc. Therefore, while PKAc promotes the association of hSu(fu) with hGli-1, hfused prevents phosphorylation of hSu(fu) by PKAc and promotes the dissociation of these two proteins.

(7) General Uses for Vertebrate Fused

Nucleotide sequences (or their complement) encoding vertebrate fused have various applications in the art of molecular biology, including uses as hybridization probes, in chromosome and gene mapping and in the generation of anti-sense RNA and DNA. Vertebrate fused nucleic acid will also be useful for the preparation of vertebrate fused polypeptides by the recombinant techniques described herein.

The full-length native sequence vertebrate fused gene, or portions thereof, may be used as hybridization probes for a cDNA library to isolate the full-length gene or to isolate still other genes (for instance, those encoding naturally-occurring variants of vertebrate fused or vertebrate fused from other species) which have a desired sequence identity to the vertebrate fused sequence disclosed in FIG. 1 (SEQ ID NO:1). Optionally, the length of the probes will be about 20 to about 50 bases. The hybridization probes may be derived from the nucleotide sequence of FIG. 1 or from genomic sequences including promoters, enhancer elements and introns of native sequence vertebrate fused. By way of example, a screening method will comprise isolating the coding region of the vertebrate fused gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the vertebrate fused gene of the present invention can be used to screen libraries of human cDNA, genomic DNA or mRNA to determine to which members of such libraries the probe hybridizes. Hybridization techniques are described in further detail in the Examples below.

The probes may also be employed in PCR techniques to generate a pool of sequences for identification of closely related vertebrate fused sequences. Any EST or other nucleotide fragment disclosed in the present application may similarly by employed as probes, using the methods disclosed herein.

Nucleotide sequences encoding a vertebrate fused can also be used to construct hybridization probes for mapping the gene, which encodes vertebrate fused and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

Vertebrate fused polypeptides can be used in assays to identify the other proteins or molecules involved in complexing with fused which ultimately results in the modulation of hedgehog signaling. Alternatively, these molecules can modulate the fused kinase phosphorylation of its substrate. By such methods, inhibitors of the binding interaction can be identified. Proteins involved in such binding interactions can also be used to screen for peptide or small molecule inhibitors or agonists of the binding interaction. Also, the substrate of vertebrate fused can be used to isolate correlative complexing proteins. Screening assays can be designed to find lead compounds that mimic the biological activity of a native vertebrate fused or to find those that act as a substrate for vertebrate fused. Such screening assays will include assays amenable to high-throughput screening of chemical libraries, making them particularly suitable for identifying small molecule drug candidates. Such small molecule inhibitors could block the enzymatic action of fused, and thereby inhibit hedgehog signaling. Small molecules contemplated include synthetic organic or inorganic compounds. The assays can be performed in a variety of formats, including protein-protein binding assays, biochemical screening assays, immunoassays and cell based assays, which are well characterized in the art.

Nucleic acids which encode vertebrate fused or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA that is integrated into the genome of a cell from which a transgenic animal develops. In one embodiment, cDNA encoding vertebrate fused can be used to clone genomic DNA encoding vertebrate fused in accordance with established techniques and the genomic sequences used to generate transgenic animals that contain cells which express DNA encoding vertebrate fused. Methods for generating transgenic animals, particularly animals such as mice or rats, have become conventional in the art and are described, for example, in U.S. Pat. Nos. 4,736,866 and 4,870,009. Typically, particular cells would be targeted for vertebrate fused transgene incorporation with tissue-specific enhancers. Transgenic animals that include a copy of a transgene encoding vertebrate fused introduced into the germ line of the animal at an embryonic stage can be used to examine the effect of increased expression of DNA encoding vertebrate fused. Such animals can be used as tester animals for reagents thought to confer protection from, for example, pathological conditions associated with its overexpression. For example, for basal cell carcinoma, fused can be overexpressed in the basal cell layer of the skin using a Keratin 5 or 14 promoter. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of vertebrate fused can be used to construct a vertebrate fused "knock out" animal which has a defective or altered gene encoding vertebrate fused as a result of homologous recombination between the endogenous gene encoding vertebrate fused and altered genomic DNA encoding vertebrate used introduced into an embryonic cell of the animal. For example, cDNA encoding vertebrate fused can be used to clone genomic DNA encoding vertebrate fused in accordance with established techniques. A portion of the genomic DNA encoding vertebrate fused can be deleted or replaced with another gene, such as a gene encoding a selectable marker that can be used to monitor integration. Typically, several kilobases of unaltered flanking DNA (both at the 5' and 3' ends) are included in the vector [see e.g., Thomas and Capecchi, Cell, 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., Cell, 69:915 (1992)]. The selected cells are then injected into a blastocyst of an animal (e.g., a mouse or rat) to form aggregation chimeras [see e.g., Bradley, in Teratocarcinomas and Embryonic Stem Cells: A Practical Approach, E. J. Robertson, ed. (IRL, Oxford, 1987), pp. 113-152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the vertebrate fused polypeptide.

Nucleic acid encoding the vertebrate fused polypeptides may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., Proc. Natl. Acad. Sci. USA 83: 4143-4146 [1986]). The oligonucleotides can be modified to enhance their uptake, e.g., by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., Trends in Biotechnology 11, 205-210 [1993]). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g., capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., J. Biol. Chem. 262: 4429-4432 (1987); and Wagner et al., Proc. Natl. Acad. Sci. USA 87: 3410-3414 (1990). For review of gene marking and gene therapy protocols see Anderson et al., Science 256: 808-813 (1992).

The vertebrate fused polypeptides described herein may also be employed as molecular weight markers for protein electrophoresis purposes.

The nucleic acid molecules encoding the vertebrate used polypeptides or fragments thereof described herein are useful for chromosome identification. In this regard, there exists an ongoing need to identify new chromosome markers, since relatively few chromosome marking reagents, based upon actual sequence data are presently available. Each vertebrate fused nucleic acid molecule of the present invention can be used as a chromosome marker.

The vertebrate fused polypeptides and nucleic acid molecules of the present invention may also be used for tissue typing, wherein the vertebrate fused polypeptides of the present invention may be differentially expressed in one tissue as compared to another. Vertebrate fused nucleic acid molecules will find use for generating probes for PCR, Northern analysis, Southern analysis and Western analysis.

As fused has been implicated as a universal mediator for all member of the Hh family (Shh, Ihh, Dhh), disease states or disorders which are associated with general Hh signaling, would also be treatable with fused and antagonists and agonists thereof. For example, Shh activation (e.g., fused agonists) has recently been promoted as a treatment for various degenerative disorders of the nervous system, e.g., Parkinson's disease, memory deficits, Alzheimer's disease, Lou Gehrig's disease, Huntington's disease, schizophrenia, stroke and drug addiction. Recent studies suggest that Dhh mutant males are infertile due to the failure of spermatocytes to complete their differentiation into mature sperm, Bitgood et al., Curr. Biol. 6: 298-304 (1996); Bitgood et al., Dev. Biol 172: 126-138 (1995). Additionally, fused agonists could be used to great gut diseases, bone diseases, skin diseases, diseases of the testis, ulcers, lung diseases, diseases of the pancreas, diabetes, osteoporosis.

The presence of the protein kinase domain suggests that fused may act similarly as members of the protein kinase family in the modulation of Hh signaling. Protein kinases are essential elements of regulatory circuits in differentiated as well as growing cells; Preat et al, Nature 347: 87-89 (1990). Many of these enzyme are involved in transduction of extracellular signals and operate through a cascade of phosphorylation events that amplify and disseminate the effects of a primary signal. As described earlier, Drosophila fused bears significant homology to other intracellular serine/threonine kinases. Many serine/threonine kinases are implicated in cell-cycle control in yeasts and in mammals, Hunter, Cell 50: 823-829 (1987); Dunphy & Newport, Cell 55: 925-928 (1988); Lee & Nurse, Trend. Genet. 4: 287-290 (1988).

Suppression or inhibition of Hh signaling is also an objective of therapeutic strategies. Since inactive fused has been shown to inhibit Hh signaling, it follows that a fused antagonist would also be expected to be antagonistic to Hh signaling. Limiting Hh signaling would be useful in disease states or disorders characterized by Hh signaling. For example, Shh is known to be active in Basal Cell Carcinoma; DHh is known to be active in spermatogenesis. Inhibitor or antagonist of Hh signaling would be effective therapeutics in the treatment of Basal Cell Carcinoma or male contraception, respectively.

The stimulation of Hh signaling is also an objective of therapeutic strategies. Activating Hh signaling would be useful in disease states or disorders characterized by inactive or insufficient Hh signaling. For example, degenerative disorders of the nervous system, e.g., Parkinson's disease, memory deficits, Alzheimer's disease, Lou Gehrig's disease, Huntington's disease, schizophrenia, stroke and drug addiction. Additionally, fused agonists could be used to great gut diseases, bone diseases, skin diseases, diseases of the testis (including infertility), ulcers, lung diseases, diseases of the pancreas, diabetes, osteoporosis.

F. Anti-Vertebrate Fused Antibodies

The present invention further provides anti-vertebrate fused antibodies. Exemplary antibodies include polyclonal, monoclonal, humanized, bispecific, and heteroconjugate antibodies.

1. Polyclonal Antibodies

The anti-vertebrate fused antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the vertebrate fused polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants that may be employed include Freund's complete adjuvant and MPL-TDM adjuvant (monophosphoryl Lipid A, synthetic trehalose dicorynomycolate). The immunization protocol may be selected by one skilled in the art without undue experimentation.

2. Monoclonal Antibodies

The anti-vertebrate fused antibodies may, alternatively, be monoclonal antibodies. Monoclonal antibodies may be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the vertebrate fused polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59-103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies [Kozbor, *J. Immunol.*, 133:3001 (1984); Brodeur et al., *Monoclonal Antibody Production Techniques and Applications*, Marcel Dekker, Inc., New York, (1987) pp. 51-63].

The culture medium in which the hybridoma cells are cultured can then be assayed for the presence of monoclonal antibodies directed against vertebrate fused. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107: 220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

3. Humanized Antibodies

The anti-vertebrate fused antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues that are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*, 321:522-525 (1986); Riechmann et al., *Nature*, 332:323-329 (1988); and Presta, *Curr. Op. Struct. Biol.*, 2:593-596 (1992)].

Methods for humanizing non-human antibodies are well known in the art. Generally, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers [Jones et al., *Nature*, 321: 522-525 (1986); Riechmann et al., *Nature*, 332: 323-327 (1988); Verhoeyen et al., *Science*, 239: 1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, *J. Mol. Biol.*, 227: 381 (1991); Marks et al., *J. Mol. Biol.*, 222: 581 (1991)]. The techniques of Cole et al. and Boerner et al. are also available for the preparation of human monoclonal antibodies (Cole et al., *Monoclonal Antibodies and Cancer Therapy*, Alan R. Liss, p. 77 (1985) and Boerner et al., *J. Immunol.*, 147(1):86-95 (1991)]. Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545, 807; 5,545,806; 5,569,825; 5,625,126; 5,633,425; 5,661,016, and in the following scientific publications: Marks et al., *Bio/Technology* 10: 779-783 (1992); Lonberg et al., *Nature* 268: 856-859 (1994); Morrison, *Nature* 368: 812-13 (1994); Fishwild et al., *Nature Biotechnology* 14: 845-51 (1996); Neuberger, *Nature Biotechnology* 14: 826 (1996); Lonberg and Huszar, *Intern. Rev. Immunol.* 13: 65-93 (1995).

4. Bispecific Antibodies

Bispecific antibodies are monoclonal, preferably human or humanized, antibodies that have binding specificities for at least two different antigens. In the present case, one of the binding specificities is for the vertebrate fused, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, *Nature*, 305:537-539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., *EMBO J.*, 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology*, 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies can be prepared as full length antibodies or antibody fragments (e.g., F(ab')$_2$ bispecific antibodies). Techniques for generating bispecific antibodies from antibody fragments have been described in the literature. For example, bispecific antibodies can be prepared using chemical linkage. Brennan et al., *Science* 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Fab' fragments may be directly recovered from *E. coli* and chemically coupled to form bispecific antibodies. Shalaby et al., *J. Exp. Med.* 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various technique for making and isolating bispecific antibody fragments directly from recombinant cell culture have also been described. For example, bispecific antibodies have been produced using leucine zippers. Kostelny et al., *J. Immunol.* 148(5): 1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al, *Proc. Natl. Acad. Sci. USA* 90: 6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., *J. Immunol.* 152: 5368 (1994).

Antibodies with more than two valencies are contemplated. For example, trispecific antibodies can be prepared. Tutt et al, *J. Immunol.* 147: 60 (1991).

Exemplary bispecific antibodies may bind to two different epitopes on a given vertebrate fused polypeptide herein. Alternatively, an anti-fused polypeptide arm may be combined with an arm which binds to a triggering molecule on a leukocyte such as a T-cell receptor molecule (e.g., CD2, CD3, CD28, or B7), or Fc receptors for IgG (FcεR), such as FcεRI (CD64), FcεRII (CD32) and FcεRIII (CD16) so as to focus cellular defense mechanisms to the cell expressing the particular vertebrate fused polypeptide. Bispecific antibodies may also be used to localize cytotoxic agents to cells which express a particular vertebrate fused polypeptide. These antibodies possess a fused-binding arm and an arm which binds a cytotoxic agent or a radionuclide chelator, such as EOTUBE, DPTA, DOTA, or TETA. Another bispecific antibody of interest binds the vertebrate fused polypeptide and further binds tissue factor (TF).

5. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

6. Effector Function Engineering

It may be desirable to modify the antibody of the invention with respect to effector function, so as to enhance, e.g., the effectiveness of the antibody in treating cancer. For example, cysteine residue(s) may be introduced into the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.*, 176: 1191-1195 (1992) and Shopes, *J. Immunol.*, 148: 2918-2922 (1992). Homodimeric antibodies with enhanced anti-tumor activity may also be prepared using heterobifunctional cross-linkers as described in Wolff et al *Cancer Research*, 53: 2560-2565 (1993). Alternatively, an antibody can be engineered that has dual Fc regions and may thereby have enhanced complement lysis and ADCC capabilities. See Stevenson et al, *Anti-Cancer Drug Design*, 3: 219-230 (1989).

7. Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis(p-azidobenzoyl) hexanediamine), his-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science*, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody may be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g., avidin) that is conjugated to a cytotoxic agent (e.g., a radionucleotide).

8. Immunoliposomes

The antibodies disclosed herein may also be formulated as immunoliposomes. Liposomes containing the antibody are prepared by methods known in the art, such as described in Epstein et al., *Proc. Natl. Acad. Sci. USA*, 82: 3688 (1985); Hwang et al., *Proc. Natl. Acad. Sci. USA*, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.*, 257: 286-288 (1982) via a disulfide-interchange reaction. A chemotherapeutic agent (such as Doxorubicin) is optionally contained within the liposome. See Gabizon et al., *J. National Cancer Inst.*, 81 (19): 1484 (1989).

9. Pharmaceutical Compositions of Antibodies

Antibodies specifically binding a vertebrate fused polypeptide identified herein, as well as other molecules identified by the screening assays disclosed hereinbefore, can be administered for the treatment of various disorders in the form of pharmaceutical compositions.

Because vertebrate fused polypeptide is intracellular, internalizing antibodies are preferred. However, lipofections or liposomes can also be used to deliver the antibody, or an antibody fragment, into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., *Proc. Natl. Acad. Sci. USA*, 90: 7889-7893 (1993). The formulation herein may also contain more than one active compound as necessary for the particular indication being treated, preferably those with complementary activities that do not adversely affect each other. Alternatively, or in addition, the composition may comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles, and nanocapsules) or in macroemulsions. Such techniques are disclosed in *Remington's Pharmaceutical Sciences*, supra.

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and α-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

G. Uses for Anti-Vertebrate Fused Antibodies

The anti-vertebrate fused antibodies of the invention have various utilities. For example, anti-vertebrate fused antibodies may be used in diagnostic assays for vertebrate used, e.g., detecting its expression in specific cells, tissues, or serum. Various diagnostic assay techniques known in the art may be used, such as competitive binding assays, direct or indirect sandwich assays and immunoprecipitation assays conducted in either heterogeneous or homogeneous phases [Zola, *Monoclonal Antibodies: A Manual of Techniques*, CRC Press, Inc. (1987) pp. 147-158]. The antibodies used in the diagnostic assays can be labeled with a detectable moiety. The detectable moiety should be capable of producing, either directly or indirectly, a detectable signal. For example, the detectable moiety may be a radioisotope, such as $^3$H, $^{14}$C, $^{32}$P, $^{35}$S, or $^{125}$I, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature*, 144: 945 (1962); David et al., *Biochemistry*, 13:1014 (1974); Pain et al., *J. Immunol. Meth.*, 40: 219 (1981); and Nygren, *J. Histochem. and Cytochem.*, 30:407 (1982).

Anti-vertebrate fused antibodies also are useful for the affinity purification of vertebrate fused from recombinant cell culture or natural sources. In this process, the antibodies against vertebrate fused are immobilized on a suitable support, such a Sephadex resin or filter paper, using methods well known in the art. The immobilized antibody then is contacted with a sample containing the vertebrate fused to be purified, and thereafter the support is washed with a suitable solvent that will remove substantially all the material in the sample except the vertebrate fused, which is bound to the immobilized antibody. Finally, the support is washed with another suitable solvent that will release the vertebrate fused from the antibody.

H. Vertebrate Fused Antagonists and/or Agonists

The invention encompasses methods of screening compounds to identify those that mimic the vertebrate fused polypeptide (agonists) or prevent the effect of the vertebrate fused polypeptide (antagonists). Screening assays for antagonist drug candidates are designed to identify compounds that bind or complex with the vertebrate fused polypeptides encoded by the genes identified herein, or otherwise interfere with the interaction of the encoded polypeptides with other cellular proteins. Such screening assays will include assays amenable to high-throughput screening of chemical libraries, making them particularly suitable for identifying small molecule drug candidates.

Several approaches may be suitably employed to create the vertebrate fused antagonist and agonist compounds of the present invention. Any approach where the antagonist molecule can be targeted to the interior of the cell, which interferes or prevents wild type vertebrate fused from normal operation is suitable. For example, competitive inhibitors, including mutant fused such as dominant negative mutant identified in the Examples, which prevent vertebrate fused from properly binding with other proteins necessary for Hh signaling. Additional properties of such antagonist or agonist molecules are readily determinable by one of ordinary skill, such as size, charge and hydrophobicity suitable for transmembrane transport.

The assays can be performed in a variety of formats, including protein-protein binding assays, biochemical screening assays, immunoassays, and cell-based assays, which are well characterized in the art. All assays for antagonists are common in that they call for contacting the drug candidate with a vertebrate fused polypeptide encoded by a nucleic acid identified herein under conditions and for time sufficient to allow these two components to interact.

Where mimics or other mammalian homologues of fused are to be identified or evaluated, the cells are exposed to the test compound and compared to positive controls which are exposed only to vertebrate fused, and to negative controls which were not exposed to either the compound or the natural ligand. Where antagonists or agonists of vertebrate fused signal modulation are to be identified or evaluated, the cells are exposed to the compound of the invention in the presence of the natural ligand and compared to controls which are not exposed to the test compound.

Detection assays may by employed as a primary screen to evaluate the phosphatase inhibition/enhancing activity of the antagonist/agonist compounds of the invention. The assays may also be used to assess the relative potency of a compound by testing a range of concentrations, in a range from 100 mM to 1 pM, for example, and computing the concentration at which the amount of phosphorylation or signal transduction is reduced or increased by 50% ($IC_{50}$) compared to controls.

Assays can be performed to identify compounds that affect phosphorylation of fused substrates. Specifically, assays can be performed to identify compounds that increase the phosphorylation activity of fused or assays can be performed to identify compounds that decrease the phosphorylation of fused substrates. These assays can be performed either on whole cells themselves or on cell extracts. The assays can be performed in a variety of formats, including protein-protein binding assays, biochemical screening assays, immunoassays, cell based assays, etc. Such assay formats are well known in the art.

The screening assays of the present invention are amenable to high-throughput screening of chemical libraries, and are particularly suitable for identifying small molecule drug candidates.

(1) Antagonist and Agonist Molecules

To screen for antagonists and/or agonists of fused signaling, the assay mixture is incubated under conditions whereby, but for the presence of the candidate pharmacological agent, fused induces hedgehog signaling with a reference activity. The mixture components can be added in any order that provides for the requisite hedgehog activity. Incubation may be performed at any temperature that facilitates optimal binding, typically between about 4° and 40° C., more commonly between about 15° and 40° C. Incubation periods are likewise selected for optimal binding but also minimized to facilitate rapid, high-throughput screening, and are typically between about 0.1 and 10 hours, preferably less than 5 hours, more preferably less than 2 hours. After incubation, the effect of the candidate pharmacological agent on the fused signaling is determined in any convenient way. For cell-free binding-type assays, a separation step is often used to separate bound and unbound components. Separation may, for example, be effected by precipitation (e.g., TCA precipitation, immunoprecipitation, etc.), immobilization (e.g., on a solid substrate), followed by washing. The bound protein is conveniently detected by taking advantage of a detectable label attached to it, e.g., by measuring radioactive emission, optical or electron density, or by indirect detection using, e.g., antibody conjugates.

For example, a method of screening for suitable fused antagonists and/or agonists could involve the application of agents present in the fused activating Gli reporter assay described in the Examples. Such a screening assay could compare in situ hybridization in the presence and absence of the candidate antagonist and/or agonist in a fused expressing tissue as well as confirmation or absence of fused modulated cellular development. Typically these methods involve exposing an immobilized fused to a molecule suspected of binding thereto and determining binding or phosphorylation of the molecule to the immobilized fused and/or evaluating whether or not the molecule activates (or blocks activation of) fused. In order to identify such fused binding ligands, fused can be expressed on the surface of a cell and used to screen libraries of synthetic candidate compounds or naturally-occurring compounds (e.g., from endogenous sources such as serum or cells).

Suitable molecules that affect the protein-protein interaction of fused and its binding proteins include fragments of the latter or small molecules, e.g., peptidomimetics, which will prevent interaction and proper complex formation. Such small molecules, which are usually less than 10 K molecular weight, are preferable as therapeutics since they are more likely to be permeable to cells, are less susceptible to degradation by various cellular mechanisms, and are not as apt to elicit an immune response as proteins. Small molecules include but are not limited to synthetic organic or inorganic compounds. Many pharmaceutical companies have extensive libraries of such molecules, which can be conveniently screened by using the assays of the present invention. Non-limiting examples include proteins, peptides, glycoproteins, glycopeptides, glycolipids, polysaccharides, oligosaccharides, nucleic acids, bioorganic molecules, peptidomimetics, pharmacological agents and their metabolites, transcriptional and translation control sequences, and the like.

A preferred technique for identifying molecules which bind to fused utilizes a chimeric substrate (e.g., epitope-tagged fused or fused immunoadhesin) attached to a solid phase, such as the well of an assay plate. The binding of the candidate molecules, which are optionally labeled (e.g., radiolabeled), to the immobilized receptor can be measured. Alternatively, competition for activation of Gli can be measured. In screening for antagonists and/or agonists, fused can be exposed to a fused substrate followed by the putative antagonist and/or agonist, or the fused binding protein and antagonist and/or agonist can be added simultaneously, and the ability of the antagonist and/or agonist to block fused activation can be evaluated.

(2) Detection Assays

The vertebrate fused polypeptides are useful in assays for identifying lead compounds for therapeutically active agents that modulate vertebrate fused hedgehog signaling. Specifically, lead compounds that either prevent the formation of vertebrate fused signaling complexes or prevent or attenuate vertebrate fused modulated hedgehog signaling (e.g, binding to fused itself or to a substrate) can be conveniently identified.

Various procedures known in the art may be used for identifying, evaluating or assaying the inhibition of activity of the vertebrate fused proteins of the invention. As vertebrate fused is believed to operate in a similar manner as other kinases, techniques known for use with identifying kinase/phosphatase modulators may also be employed with the present invention. In general, such assays involve exposing target cells in culture to the compounds and a) biochemically analyzing cell lysates to assess the level and/or identity of phosphorylation; or (b) scoring phenotypic or functional changes in treated cells as compared to control cells that were not exposed to the test substance. Such screening assays are described in U.S. Pat. No. 5,602,171, U.S. Pat. No. 5,710,173, WO 96/35124 and WO 96/40276.

In binding assays, the interaction is binding and the complex formed can be isolated or detected in the reaction mixture. In a particular embodiment, the vertebrate fused polypeptide encoded by the gene identified herein or the drug candidate is immobilized on a solid phase, e.g., on a microtiter plate, by covalent or non-covalent attachments. Non-covalent attachment generally is accomplished by coating the solid surface with a solution of the vertebrate fused polypeptide and drying. Alternatively, an immobilized antibody, e.g., a monoclonal antibody, specific for the vertebrate fused polypeptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to a particular vertebrate fused polypeptide encoded by a gene identified herein, its interaction with that polypeptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, *Nature* (London), 340:245-246 (1989); Chien et al., *Proc. Natl. Acad. Sci. USA*, 88: 9578-9582 (1991)) as disclosed by Chevray and Nathans, *Proc. Natl. Acad. Sci. USA*, 89: 5789-5793 (1991). Many transcriptional activators, such as yeast GAL4, consist of two physically discrete modular domains, one acting as the DNA-binding domain, the other one functioning as the transcription-activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

Compounds that interfere with the interaction of a gene encoding a vertebrate fused polypeptide identified herein and other intra- or extracellular components can be tested as follows: usually a reaction mixture is prepared containing the product of the gene and the intra- or extracellular component under conditions and for a time allowing for the interaction and binding of the two products. To test the ability of a candidate compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described hereinabove. The formation of a complex in the control reaction(s) but not in the reaction mixture containing the test compound indicates that the test compound interferes with the interaction of the test compound and its reaction partner.

To assay for antagonists, the vertebrate fused polypeptide may be added to a cell along with the compound to be screened for a particular activity and the ability of the compound to inhibit the activity of interest in the presence of the vertebrate fused polypeptide indicates that the compound is an antagonist to the vertebrate fused polypeptide. Alternatively, antagonists may be detected by combining the vertebrate fused polypeptide and a potential antagonist with membrane-bound vertebrate fused polypeptide receptors or recombinant receptors under appropriate conditions for a competitive inhibition assay. The vertebrate fused polypeptide can be labeled, such as by radioactivity, such that the number of vertebrate fused polypeptide molecules bound to the receptor can be used to determine the effectiveness of the potential antagonist. The gene encoding the receptor can be identified by numerous methods known to those of skill in the art, for example, ligand panning and FACS sorting. Coligan et al, *Current Protocols in Immun.*, 1(2): Chapter 5 (1991). Preferably, expression cloning is employed wherein polyadenylated RNA is prepared from a cell responsive to the vertebrate fused polypeptide and a cDNA library created from this RNA is divided into pools and used to transfect COS cells or other cells that are not responsive to the vertebrate fused polypeptide. Transfected cells that are grown on glass slides are exposed to labeled vertebrate fused polypeptide. The vertebrate fused polypeptide can be labeled by a variety of means including iodination or inclusion of a recognition site for a site-specific protein kinase. Following fixation and incubation, the slides are subjected to autoradiographic analysis. Positive pools are identified and sub-pools are prepared and re-transfected using an interactive sub-pooling and re-screening process, eventually yielding a single clone that encodes the putative receptor.

As an alternative approach for receptor identification, labeled vertebrate fused polypeptide can be photoaffinity-linked with cell membrane or extract preparations that express the receptor molecule. Cross-linked material is resolved by PAGE and exposed to X-ray film. The labeled complex containing the receptor can be excised, resolved into peptide fragments, and subjected to protein micro-sequencing. The amino acid sequence obtained from micro-sequencing would be used to design a set of degenerate oligonucleotide probes to screen a cDNA library to identify the gene encoding the putative receptor.

In another assay for antagonists, mammalian cells or a membrane preparation expressing the receptor would be incubated with labeled vertebrate fused polypeptide in the presence of the candidate compound. The ability of the compound to enhance or block this interaction could then be measured.

More specific examples of potential antagonists include an oligonucleotide that binds to the fusions of immunoglobulin with vertebrate fused polypeptide, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. Alternatively, a potential antagonist may be a closely related protein, for example, a mutated form of the vertebrate fused polypeptide that recognizes the receptor but imparts no effect, thereby competitively inhibiting the action of the vertebrate fused polypeptide.

(a) Biochemical Detection Techniques

Biochemical analysis techniques can be evaluated by a variety of techniques. One typical assay mixture which can be used with the present invention contains vertebrate fused and a protein with which vertebrate fused is normally associated (e.g., Gli), usually in an isolated, partially pure or pure form. One or both of these components may be vertebrate fused to another peptide or polypeptide, which may, for example, provide or enhance protein-protein binding, improve stability under assay conditions, etc. In addition, one of the components usually comprises or is coupled to a detectable label. The label may provide for direct detection by measuring radioactivity, luminescence, optical or electron density, etc., or indirect detection such as an epitope tag, an enzyme, etc. The assay mixture can additionally comprise a candidate pharmacological agent, and optionally a variety of other components, such as salts, buffers, carrier proteins, e.g., albumin, detergents, protease inhibitors, nuclease inhibitors, antimicrobial agents, etc., which facilitate binding, increase stability, reduce non-specific or background interactions, or otherwise improve the efficiency or sensitivity of the assay.

The following detection methods may also be used in a cell-free system wherein cell lysate containing the signal transducing substrate molecule and fused is mixed with a compound of the invention. The substrate is phosphorylated by initiating the kinase reaction by the addition of adenosine triphosphate (ATP). To assess the activity of the compound, the reaction mixture may be analyzed by the SDS-PAGE technique or it may be added to substrate-specific anchoring antibody bound to a solid support, and a detection procedure as described above is performed on the separated or captured substrate to assess the presence or absence of pSer/Thr. The results are compared to those obtained with reaction mixtures to which the compound is not added. The cell-free system does not require the natural ligand or knowledge of its identity. The cell-free system does not require mixtures to which the compound is not added. The cell-free system does not require the natural ligand or knowledge of its identity. For example, U.S. Pat. No. 5,155,031 describes the use of insulin receptor as a substrate and rat adipocytes as target cells to demonstrate the ability of pervanadate to inhibit PTP activity. Another example, Burke et al., *Biochem. Biophys. Res. Comm.* 204: 129-134 (1994) describes the use of autophosphorylated insulin receptor and recombinant PTP1B in assessing the inhibitory activity of a phosphotyrosyl mimetic.

(i) Whole Cell Detection

A common technique involves incubating cells with vertebrate fused and radiolabeled phosphate, lysing the cells, separating cellular protein components of the lysate using an SDS-polyacrylamide gel (SDS-PAGE) technique, in either one or two dimensions, and detecting the presence of phosphorylated proteins by exposing X-ray film. Detection can also be effected without using radioactive labeling. In such a technique, the protein components (e.g., separated by SDS-PAGE) are transferred to a nitrocellulose membrane where the presence of phosphorylated serine/threonines is detected using an antiphosphoserine/threonine antibody (anti-pS/T).

Alternatively, the anti-pS/T can be conjugated with an enzyme, such as horseradish peroxidase, and detected by subsequent addition of a colorimetric substrate for the enzyme. A further alternative involves detecting the anti-PS/T by reacting with a second antibody that recognizes the anti-PS/T, this second antibody being labeled with either a radioactive moiety or an enzyme as previously described. Examples of these and similar techniques are described in Hansen et al., *Electrophoresis* 14: 112-126 (1993); Campbell et al., *J. Biol. Chem.* 268: 7427-7434 (1993); Donato et al., *Cell Growth Diff.* 3: 258-268 (1992); Katagiri et al., *J. Immunol.* 150: 585-593 (1993). Additionally, the anti-pS/T can be detected by labeling it with a radioactive substance, followed by scanning the labeled nitrocellulose to detect radioactivity or exposure of X-ray film.

(ii) Kinase Assays

When the screening methods of the present invention for fused antagonists/agonists are carried out as an ex vivo assay, the target kinase (e.g., used) can be a substantially purified polypeptide. The kinase substrate (e.g., MBP, Gli) is a substantially purified substrate, which in the assay is phosphorylated in a reaction with a substantially purified phosphate source that is catalyzed by the kinase. The extent of phosphorylation is determined by measuring the amount of substrate phosphorylated in the reaction. A variety of possible substrates may be used, including the kinase itself in which instance the phosphorylation reaction measured in the assay is autophosphorylation. Exogenous substrates may also be used, including standard protein substrates such as myelin basic protein (MBP); yeast protein substrates; synthetic peptide substrates, and polymer substrates. Of these, MBP and other standard protein substrates may be regarded as preferred (see Example 10). Other substrates may be identified, however, which are superior by way of affinity for the kinase, minimal perturbation of reaction kinetics, possession of single or homogenous reaction sites, ease of handling and post-reaction recover, potential for strong signal generation, and resistance or inertness to test compounds.

Measurement of the amount of substrate phosphorylated in the ex vivo assay of the invention may be carried out by means of immunoassay, radioassay or other well-known methods. In an immunoassay measurement, an antibody (such as a goat or mouse anti-phosphoserine/threonine antibody) may be used which is specific for phosphorylated moieties formed during the reaction. Using well-known ELISA techniques, the phosphoserine/threonine antibody complex would itself be detected by a further antibody linked to a label capable of developing a measurable signal (as for example a fluorescent or radioactive label). Additionally, ELISA-type assays in microtitre plates may be used to test purified substrates. Peraldi et al., *J. Biochem.* 285: 71-78 (1992); Schraag et al., *Anal. Biochem.* 211: 233-239 (1993); Cleavland, *Anal. Biochem.* 190: 249-253 (1990); Farley, *Anal. Biochem.* 203: 151-157 (1992) and Lozaro, *Anal. Biochem.* 192: 257-261 (1991).

For example, detection schemes can measure substrate depletion during the kinase reaction. Initially, the phosphate source may be radiolabeled with an isotope such as $^{32}P$ or $^{33}P$, and the amount of substrate phosphorylation may be measured by determining the amount of radiolabel incorporated into the substrate during the reaction. Detection may be accomplished by: (a) commercially available scintillant-containing plates and beads using a beta-counter, after adsorption to a filter or a microtitre well surface, or (b) photometric means after binding to a scintillation proximity assay bead or scintillant plate. Weernink and Kijken, *J. Biochem. Biophs. Methods* 31: 49, 1996; Braunwalder et al., *Anal. Biochem.* 234: 23 (1996); Kentrup et al., *J. Biol. Chem.* 271: 3488 (1996) and Rusken et al., *Meth. Enzymol.* 200: 98 (1991).

Preferably, the substrate is attached to a solid support surface by means of non-specific or, preferably, specific binding. Such attachment permits separation of the phosphorylated substrate from unincorporated, labeled phosphate source (such as adenosine triphosphate prior to signal detection. In one embodiment, the substrate may be physically immobilized prior to reaction, as through the use of Nunc™ high protein binding plate (Hanke et al., *J. Biol. Chem.* 271: 695 (1996)) or Wallac ScintiStrip™ plates (Braunwalder et al., *Anal. Biochem.* 234: 23 (1996). Substrate may also be immobilized after reaction by capture on, for example, P81 phosphocellulose (for basic peptides), PEI/acidic molybdate resin or DEAE, or TCA precipitation onto Whatman™ 3MM paper, Tiganis et al., *Arch. Biochem. Biophys.* 325: 289 (1996); Morawetz et al., *Mol. Gen. Genet.* 250; 17 (1996); Budde et al, *Int J. Pharmacognosy* 33: 27 (1995) and Casnellie, *Meth. Enz.* 200: 115 (1991). Yet another possibility is the attachment of the substrate to the support surface, as by conjugation with binding partners such as glutathione and streptavidin (in the case of GST and biotin), respectively) which have been attached to the support, or via antibodies specific for the tags which are likewise attached to the support.

Further detection methods may be developed which are preferred to those described above. Especially for use in connection with high-throughput screening, it is expected that such methods would exhibit good sensitivity and specificity, extended linear range, low background signal, minimal fluctuation, compatibility with other reagents, and compatibility with automated handling systems.

The in vivo efficacy of the treatment of the present invention can be studied against chemically induced tumors in various rodent models. Tumor cell lines propagated in in vitro cell cultures can be introduced in experimental rodents, e.g., mice by injection, for example by the subcutaneous route. Techniques for chemical inducement of tumors in experimental animals are well known in the art.

(b) Biological Detection Techniques:

The ability of the antagonist/agonist compounds of the invention to modulate the activity vertebrate fused, which itself modulates hedgehog signaling, may also be measured by scoring for morphological or functional changes associated with ligand binding. Any qualitative or quantitative technique known in the art may be applied for observing and measuring cellular processes which comes under the control of vertebrate fused. The activity of the compounds of the invention can also be assessed in animals using experimental models of disorders caused by or related to dysfunctional hedgehog signaling. For example, ineffective Dhh hedgehog signaling in mice leads to viable but sterile mice. The effects of mutant fused (hfused-DN) also affects gut development, which is regulated by Ihh expression. Additionally, proper Shh signaling is critical to murine embryonic development at the notochord and floor plate, neural tube, distal limb structures, spinal column and ribs. Improper Shh signaling, is also correlative with cyclopia. Any of these phenotypic properties could be evaluated and quantified in a screening assay for fused antagonists and/or agonist. Disease states associated with overexpression of hedgehog is associated with basal cell carcinoma while inactive sonic hedgehog signaling leads to improper neural development.

The data obtained from these cell culture assays and animal studies can be used in formulating a range of dosages for use in humans. The dosage of the compounds of the invention should lie within a range of circulating concentrations with little or no toxicity. The dosage may vary within this range depending on the dosage form employed and the route of administration.

(2) Antisense or Sense Nucleotides

Another preferred class of antagonists involves the use of gene therapy techniques, include the administration of antisense and/or sense nucleotides. Antisense or sense nucleotides may comprise a single-stranded nucleic acid sequence (either RNA or DNA) capable of binding to target vertebrate fused mRNA (sense) or vertebrate fused DNA (antisense) sequences. Antisense or sense oligonucleotides, according to the present invention, comprise a fragment of the coding region of vertebrate fused DNA. Such a fragment generally comprises at least about 14 nucleotides, preferably from about 14 to 30 nucleotides. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature vertebrate fused polypeptides herein, is used to design an antisense RNA oligonucleotide form about 10 to 40 base pairs in length. A DNA oligonucleotide is designed to be complementary to a region of the gene involved in transcription (triple helix—see Lee et al., *Nucl. Acids Res.* 6: 3073 (1979); Cooney et al., *Science* 241: 456 (1988); Dervan et al., *Science* 251: 1360 (1991)), thereby preventing transcription and the production of the vertebrate fused polypeptide. The ability to derive an antisense or a sense oligonucleotide, based upon a cDNA sequence encoding a given protein is described in, for example, Stein and Cohen, *Cancer Res.* 48: 2659, 1988 and van der Krol et al., *BioTechniques* 6: 958, 1988). The antisense RNA oligonucleotide hybridizes to the mRNA in vivo and blocks translation of the mRNA molecule into the vertebrate fused polypeptide (antisense—Okan, *Neurochem.* 56: 560 (1991); *Oligodeoxynucleotides as Antisense Inhibitors of Gene Expression*, CRC Press: Boca Raton, Fla. 1988). The oligonucleotides described above can also be delivered to cells such that the antisense RNA or DNA may be expressed in vivo to inhibit production of the vertebrate fused polypeptide. When antisense DNA is used, oligodeoxyribonucleotides derived from the translation-initiation site, e.g., between about −10 and +10 positions of the target gene nucleotide sequence, are preferred.

Binding of antisense or sense oligonucleotides to target nucleic acid sequences results in the formation of duplexes that block transcription or translation of the target sequence by one of several means, including enhanced degradation of the duplexes, premature termination of transcription or translation, or by other means. The antisense oligonucleotides further comprise oligonucleotides having modified sugar-phosphodiester backbones (or other sugar linkages, such as those described in WO91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Other examples of sense or antisense oligonucleotides include those oligonucleotides which are covalently linked to organic moieties, such as those described in WO 90/10048, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, $CaPO_4$-mediated DNA transfection, electroporation, or by using gene transfer vectors such as Epstein-Barr virus. In a preferred procedure, an antisense or sense oligonucleotide is inserted into a suitable retroviral vector. A cell containing the target nucleic acid sequence is contacted with the recombinant retroviral vector, either in vivo or ex vivo. Suitable retroviral vectors include, but are not limited to, those derived from the murine retrovirus M-MuLV, N2 (a retrovirus derived from M-MuLV), or the double copy vectors designated DCT5A, DCT5B and DCT5C (see WO 90/13641).

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Applicable gene therapy techniques include single or multiple administrations of therapeutically effective DNA or mRNA. Antisense RNAs and DNAs can be used as therapeutic agents for blocking the expression of certain genes in vivo. Short antisense oligonucleotides can be imported into cells where they act as inhibitors, despite their low intracellular concentrations caused by restricted uptake by the cell membrane, Zamecnik et al., Proc. Natl. Acad. Sci. USA 83: 4143-4146 (1986). The oligonucleotides can be modified to enhance their uptake, e.g., by substituting their negatively charged phosphodiester groups by uncharged groups.

There are a variety of techniques known for introducing nucleic acids into viable cells. The techniques vary depending upon whether the nucleic acid is transferred into cultured cells in vitro, ex vivo, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection, Dzau et al., Trends Biotech. 11: 205-210 (1993). In some situations it is desirable to provide the nucleic acid source with an agent that targets the target cells. For example, for targeting and/or facilitating uptake, an antibody specific for a cell surface membrane protein associated with endocytosis may be used. Additional examples include, e.g., capsid proteins or fragments thereof specific for a particular cell type, antibodies for proteins which undergo internalization in cycling, and proteins that target intracellular localization and enhance intracellular half-life. The technique of receptor-mediated endocytosis is described, for example, by Wu et al., J. Biol. Chem. 262: 4429-4432 (1987); Wagner et al., Proc. Natl. Acad. Sci. USA 87: 3410-3414 (1990). For a review of known gene marking and gene therapy protocols, see Anderson et al., Science 256: 808-813 (1992).

In one embodiment, fused antagonist and/or agonist molecules may be used to bind endogenous ligand in the cell, thereby causing the cell to be unresponsive to fused wild type, especially when the levels of fused in the cell exceed normal physiological levels. Also, it may be beneficial to bind endogenous fused substrates or complexing agents that are activating undesired cellular responses (such as proliferation of tumor cells).

In a further embodiment of the invention, fused expression may be reduced by providing fused-expressing cells with an amount of fused antisense RNA or DNA effective to reduce expression of the fused protein.

I. Diagnostic Uses

Another use of the compounds of the invention (e.g., human and vertebrate fused, vertebrate fused variant and anti-vertebrate fused antibodies) described herein is to help diagnose whether a disorder is driven, to some extent, fused or hedgehog signaling. For example, basal cell carcinoma cells are associated with active hedgehog signaling.

A diagnostic assay to determine whether a particular disorder is driven by hedgehog signaling, can be carried out using the following steps: (1) culturing test cells or tissues; (2) administering a compound which can inhibit fused modulated hedgehog signaling; and (3) measuring the degree of kinase attenuation on the fused substrate in cell lysates or hedgehog mediated phenotypic effects in the test cells. The steps can be carried out using standard techniques in light of the present disclosure. For example, standard techniques can be used to isolate cells or tissues and culturing or in vivo.

Compounds of varying degree of selectivity are useful for diagnosing the role of fused. For example, compounds which inhibit fused in addition to another form of kinase can be used as an initial test compound to determine if one of several serine/threonine kinases drive the disorder. The selective compounds can then be used to further eliminate the possible role of the other serine/threonine kinases in driving the disorder. Test compounds should be more potent in inhibiting serine/threonine kinase activity than in exerting a cytotoxic effect (e.g., an $IC_{50}/LD_{50}$ of greater than one). The $IC_{50}$ and $LD_{50}$ can be measured by standard techniques, such as an MTT assay, or by measuring the amount of LDH released. The degree of $IC_{50}/LD_{50}$ of a compound should be taken into account in evaluating the diagnostic assay. Generally, the larger the ratio the more relative the information. Appropriate controls take into account the possible cytotoxic effect of a compound of a compound, such as treating cells not associated with a cell proliferative disorder (e.g., control cells) with a test compound, can also be used as part of the diagnostic assay. The diagnostic methods of the invention involve the screening for agents that modulate the effects of fused upon hedgehog signaling. Exemplary detection techniques include radioactive labeling and immunoprecipitating (U.S. Pat. No. 5,385,915).

J. Therapeutic Uses and Compositions

The vertebrate fused polypeptides described herein may also be employed as therapeutic agents. The vertebrate fused polypeptides of the present invention can be formulated according to known methods to prepare pharmaceutically useful compositions, whereby the vertebrate fused product hereof is combined in admixture with a pharmaceutically acceptable carrier vehicle. Therapeutic formulations are prepared for storage by mixing the active ingredient having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™ or PEG.

The formulations to be used for in vivo administration must be sterile. This is readily accomplished by filtration through sterile filtration membranes, prior to or following lyophilization and reconstitution.

Therapeutic compositions herein generally are placed into a container having a sterile access port, for example, an intravenous solution bag or vial having a stopper pierceable by a hypodermic injection needle.

The route of administration is in accord with known methods, e.g., injection or infusion by intravenous, intraperitoneal, intracerebral, intramuscular, intraocular, intraarterial or intralesional routes, topical administration, or by sustained release systems.

Dosages and desired drug concentrations of pharmaceutical compositions of the present invention may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" In Toxicokinetics and New Drug Development, Yacobi et al., Eds., Pergamon Press, New York 1989, pp. 42-96.

When in vivo administration of a vertebrate fused polypeptide or agonist or antagonist thereof is employed, normal dosage amounts may vary from about 10 ng/kg to up to 100 mg/kg of mammal body weight or more per day, preferably about 1 µg/kg/day to 10 mg/kg/day, depending upon the route of administration. Guidance as to particular dosages and methods of delivery is provided in the literature; see, for example, U.S. Pat. No. 4,657,760; 5,206,344; or 5,225,212. It is anticipated that different formulations will be effective for different treatment compounds and different disorders, that administration targeting one organ or tissue, for example, may necessitate delivery in a manner different from that to another organ or tissue.

Where sustained-release administration of a vertebrate fused polypeptide is desired in a formulation with release characteristics suitable for the treatment of any disease or disorder requiring administration of the vertebrate fused polypeptide, microencapsulation of the vertebrate fused polypeptide is contemplated. Microencapsulation of recombinant proteins for sustained release has been successfully performed with human growth hormone (rhGH), interferon- (rhIFN-), interleukin-2, and MN rgp120. Johnson et al., Nat. Med. 2:795-799 (1996); Yasuda, Biomed. Ther., 27:1221-1223 (1993); Hora et al., Bio/Technology 8:755-758 (1990); Cleland, "Design and Production of Single Immunization Vaccines Using Polylactide Polyglycolide Microsphere Systems," in Vaccine Design: The Subunit and Adjuvant Approach, Powell and Newman, eds, (Plenum Press: New York, 1995), pp. 439-462; WO 97/03692, WO 96/40072, WO 96/07399; and U.S. Pat. No. 5,654,010.

The sustained-release formulations of these proteins were developed using poly-lactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition. Lewis, "Controlled release of bioactive agents from lactide/glycolide polymer," in: M. Chasin and R. Langer (Eds.), Biodegradable Polymers as Drug Delivery Systems (Marcel Dekker: New York, 1990), pp. 1-41.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, 10801 University Boulevard, Manassas, Va. 20110-2209.

Example 1

Isolation of Human Fused cDNA Clones

An expressed sequence tag (EST) DNA database (LIFESEQ®, Incyte Pharmaceuticals, Palo Alto, Calif.) was searched for a human homologue of the Drosophila segment polarity gene fused (SEQ ID NO:26) (Preat et al., Nature 347: 87-9 (1990)). The EST Incyte #2515662 (FIG. 2 (SEQ ID NO:3)) was identified as a potential candidate. In order to identify human cDNA libraries containing human fused clones, human cDNA libraries in pRK5 were first screened by PCR using the following primers:

```
h-FUSED.f
5'-CAATACAATGGTGCTGACATCCATCAAAGGCA-    (SEQ ID NO:
3'                                       8)

h-FUSED.r
5'-'GAAGGGAGGGGTGCCTACTGCCA-3'          (SEQ ID NO:
                                         9)
```

A fetal lung library was selected and enriched for fused cDNA clones by extension of single stranded DNA from plasmid libraries grown in dug⁻/bung⁻ host using the h-FUSED.f primer in a reaction containing 10 μl of 10×PCR Buffer (Perkin Elmer), 1 μl dNTP (20 mM), 1 μl library DNA (200 ng), 0.5 ml primer, 86.5 μl H₂O and 1 μl of Amplitaq® (Perkin Elmer) after a hot start. The reaction was denatured for 1 min. at 95° C., annealed for 1 min. at 60° C. then extended for 20 min. at 72° C. DNA was extracted with phenol/CHCl₃, ethanol precipitated, then transformed by electroporation into DH10B host bacteria. Colonies from each transformation were plated and lifted on nylon membranes and screened with an oligo probe derived from the EST sequence of the following sequence:

```
h-FUSED.p
5'-CTCCAGCTCTGGAGACATATAGAGTGGTGTGCC    (SEQ ID NO: 10)
TTTGA-3'
```

The oligo probe was labeled with [γ-$^{32}$P]-ATP and T4 polynucleotide kinase. Filters were hybridized overnight at 42° C. in 50% formamide, 5×SSC, 10×Denhardt's, 0.05M sodium phosphate (pH 6.5), 0.1% sodium pyrophosphate, 50 μg/ml of sonicated salmon sperm DNA. The filters were then rinsed in 2×SSC and washed in 0.1×SSC, 0.1% SDS then exposed to Kodak® X Ray films. Two positive clones (DNA28494 and DNA28495—FIGS. 4 & 5 (SEQ ID NOS:6 and 4), respectively) containing an insert of approximately 5 kb were isolated and sequenced. The sequence of clone DNA28495 (SEQ ID NO:4) contains a potential initiation methionine at position 116 followed by an open reading frame of 1944 bp (FIG. 4). However, this open reading frame (ORF) encodes a protein that is only 648 amino acids long, somewhat shorter than the 795 amino acid sequence of the *Drosophila* fused. Interestingly, a second open reading frame is present in the 3' region of the cDNA, from nucleotide 2295 to 4349 (FIG. 4), which suggests that the cDNA may have been improperly spliced and that an intron remains between the 2 ORFs, or correspond to an alternatively spliced variant of fused. The sequence of clone DNA28494 (SEQ ID NO:6) is very similar. There is one nucleotide difference between clone DNA28495 (SEQ ID NO:4) and clone DNA28494 (SEQ ID NO:6) located in the first ORF at position 1863 of clone 28495 (A vs. G) which changes the coding sequence from an Gln to a Arg at position 583. (FIG. 4). This change is likely due to an allelic variation. The first open reading frame of DNA28494 (SEQ ID NO:6) starts at residue 115 and is followed by a 647 amino acid long open reading frame. The sequences are identical except for the one change described above at position 583 and for the last 9 residues in the first open reading frame.

The vertebrate fused polypeptide shown in FIG. 1 (SEQ ID NO:2) contains potential N-glycosylation sites at residues 297, 381 and 1286, glycosaminoglycan attachment site at 369-372, cAMP and cGMP dependent protein kinase phosphorylation sites at residues 23-27 and 583-586, casein kinase II phosphorylation sites at residues 41-43, 72-75, 244-247, 347-350, 383-387, 416-419, 485-488, 783-876 and 896-899, N-myristoylation sites at residues 138-143, 270-275, 356-361, 400-405, 464-469, 503-508, 599-604, 622-627, 656-661, 671-676, 784-789, 1106-1111, 1145-1150 and 1207-1212, an amidation site at residues 20-23, prokaryotic membrane lipoprotein lipid attachment site at residues 795-805, leucine zippers at residues 769-790 and 987-1008 and a serine/threonine protein kinase active-site signature at residues 121-133.

Example 2

Expression of Vertebrate Fused Clones

In order to determine the size of the protein expressed from the cDNA corresponding to DNA28495 and DNA28494 (SEQ ID NOS:4 and 6), respectively, an HA epitope tag was inserted at the N-terminus of the protein by PCR using the following primers:

```
Hfus.Cla-HA.F:
5'-CCATCGATGTACCCATACGACGTCCCAGACTAC   (SEQ ID NO: 11)
GCTGAAAAGTACCACGTGTTGGAGATG-3'
and hFus.Xba.R:
5'-GCTCTAGACTAAGGGGCAGGTCCTGTGTTCT     (SEQ ID NO: 12)
G-3'.
```

The PCR product was purified, digested with ClaI-SmaI and subcloned into the pRK5 plasmids containing DNA28494 and DNA28495 (SEQ ID NO:6 and 4), respectively. DNA from each of the constructs was transfected overnight into 293 cells using the CaPO₄ method (Sambrook et al, supra; Ausubel et al., supra). After about 24 h. to 48 h. after transfection, the cells were harvested and the cell pellet was lysed in 1 ml of lysine buffer (50 mM Tris pH 8.0, 150 mM NaCl, 1 mM EDTA, 1% NP40, Aprotinin, Leupeptin, -PMSF, 1 mM NaF and 1 mM Sodium Vanadate) for 20 min at 4° C. The extract was spun for 10 min at 10K then the supernatant was transferred to a new tube and precleared with 20 μl Protein A sepharose for 1 h. The protein A sepharose was spun down and 1 μl of anti-HA antibody (5 μg, Boehringer) was added to each tube. After overnight incubation at 4° C., 30 μl of Protein G sepharose was added and the tubes incubated at 4° C. for 1 hour. The protein G beads were then sun down for 1 min., washed 3 times with lysis buffer, resuspended in 20 μl of laemli buffer in the presence of β-mercapto ethanol. Samples were denatured for 5 min. at 100° C. then loaded on a 6% polyacrylamide gel. Proteins were then transferred to nitrocellulose and analyzed by Western blot using the same anti-HA antibody overnight at 1 μg/ml in blocking buffer (PBS, 0.5% Tween®, 5% non fat dry milk, 3% goat serum followed by an anti-mouse HRP. ECL was used for the detection and the membrane was exposed for 90 seconds to X-Ray films. A specific band of 150 kDa was detected in the cell pellet of cells transfected with the construct with construct corresponding to clone DNA28494 (SEQ ID NO:6) and a specific band of approximately 100 kDa could be detected for clone DNA28495 (SEQ ID NO:4) (FIG. 6). These bands were not present in the mock transfected control. The presence of the 150 kDa band suggests the two open reading frames of DNA28494 (SEQ ID NO:6) can be spliced together to direct the synthesis of a large protein of 150 kDa. The absence of this band for DNA28495 (SEQ ID NO:4) suggested that this clone apparently cannot be correctly spliced. Alternative splicing of the fused gene seems to lead to the production of several different products and may be a mechanism or regulation of fused activity. Specific regions at the C-terminus of the *Drosophila* fused protein is known to be required for the activity of the molecule, Therond et al., *Genetics* 142: 1181-1198 (1996); Robbins et al., *Cell* 90: 225-234 (1997). Shorter fused molecules truncated at the C-terminus may therefore correspond to inactive or to dominant negative forms of the molecule.

Example 3

Northern Blots

In order to determine the best tissue source to isolate more fused cDNAs and to identify a transcript encoding a full length 150 kDa fused molecule, human multiple tissue northern blots I, II and fetal blot from Clontech were probed with a 1.6 kb, ClaI-AccI fragment derived from clone DNA28494 (SEQ ID NO:6) labeled by random priming. The blots were hybridized in 50% formamide, 5×SSC, 10×Denhardt's, 0.05M Sodium phosphate (pH 6.5), 0.1% Sodium pyrophosphate, 50 mg/ml sonicated salmon sperm DNA, all in the presence of $1\times10^6$ cpm/ml $^{32}$P-labeled probe at 42° C. overnight. The blots were washed in 2×SSC at RT for 10 minutes and washed in 0.2×SSC/0.1% SDS at 42° C. for 30 minutes then exposed to x-ray film overnight. FIG. 7 shows that the fused message is expressed at high levels in testis and at low levels in most other tissues, including fetal tissues. (FIG. 7).

Example 4

PCR on Different Tissues to Identify the Correct Splice Form

In order to isolate a cDNA where the 2 potential ORFs were spliced together correctly, we designed the following primers flanking the potential intron and amplified various tissues including human fetal brain, brain, keratinocyte, testis, ovary, fetal liver, and lung templates.

```
F1   5'-CTGACGACACAGCAGGTTGTC-3'    (SEQ ID NO: 13)

R4   5'-CAGATGCTTCAGGATGGACAT-3'    (SEQ ID NO: 14)
```

Two microliters of each cDNA library was used as the template and PCR was done with Klentaq® polymerase. PCR was performed for 45 cycles of amplification with 94° C. denaturation for 1 min., 55° C. annealing for 1 min., and 68° C. extensions for 2 min. One fifth of the reaction was loaded on 1% agarose gel and was Southern blotted. The blot was hybridized overnight with full-length fused probe labeled by random priming as described for the Northern blot.

A 1 kb PCR fragment was identified in fetal brain, testis and ovary. This fragment was gel-purified and subjected to direct PCR sequencing using both the F1 and R4 primer identified above as well a the following primers:

```
hf16  5'-AGAGTAGCAACGTCACTGC-3'    (SEQ ID NO: 15)

hf8   5'-CCTCACTGACAAGGCAGCAGG-3'  (SEQ ID NO: 16)

hf19  5'-CCCGAGGAGGCATCTGCACAG-3'  (SEQ ID NO: 17)
```

The sequence of this 1 kb fragment revealed that intron sequences were absent and that the 2 ORFs were connected together in the same reading frame. The sequence of the correctly spliced sequence is shown in FIG. 1 (SEQ ID NO:1). The initiator ATG is present at position 161 and is followed by an ORF of 3945 nucleotides which encodes a 1315 amino acid long protein with a predicted molecular weight of 144 kDa.

The overall similarity with *Drosophila* fused (SEQ ID NO:23) is 28% (FIG. 2). The N-terminal 263 amino acid domain of the protein containing the kinase domain is 55% homologous to the *Drosophila* fused kinase domain. The remaining 1052 amino acids portion of the protein is not appreciably homologous to other known proteins and, interestingly, is not homologous to the corresponding region in *Drosophila* fused. Interestingly, this region of non-homology includes the very C-terminus of the fly protein which appears to be required for activity, Robbins et al., *Cell* 90: 225-34 (1997); Therond et al., *Genetics* 142: 1181-98 (1996). The improperly spliced cDNAs described above may reflect alternative splicing of the fused gene which leads to the production of a molecule with a truncated C-terminus and may be a mechanism to regulate fused activity.

Example 5

Reconstitution of the Correctly Spliced Full Length Human Fused

The fused clone DNA28495 was subcloned from the pRK5B plasmid into pRK5.tkneo using ClaI-HindIII. PCR was performed using human testis cDNA as a template and the primers hf3 (SEQ ID NO:18) (CAGAACTTCAGGTC-CTAAAGG) and R4 (sequence see above, Example 4). PCR conditions were 45 cycles of (94° C., 1 min, 46° C. to 68° C. temperature gradient annealing for 1 min, and 68° C., 4 min). The PCR fragment was digested with AccI and ligated in the pRK5.tkneo.fused plasmid cut with AccI in order to replace the region containing the intron with the correct spliced form. Two subclones were sequenced between the two AccI site and had the same correct sequence.

Example 6

In Situ Hybridization

E11.3 and E13.5 mouse embryos were immersion-fixed overnight at 4° C. in 4% paraformaldehyde, cryoprotected overnight in 15% sucrose, embedded in O.T.C. and frozen on liquid nitrogen. Adult mouse brains were fresh frozen with powdered dry ice. P1 mouse brains, adult mouse testis and adult rat spinal cords were embedded in O.T.C. and frozen on liquid nitrogen. Sections were cut at 16 mm, and processed for in situ hybridization for fused by the method of Phillips et al., *Science* 250: 290-294 (1990). RNA probes were labeled with $^{33}$P-UTP as described by Melton et al., *Nucleic Acids Res.* 12: 7035-7052 (1984). Sense and antisense probes were synthesized from a mouse fused DNA fragment using T3 and T7, respectively, corresponding to the region encoding amino acid residues 317-486 of the human sequence.

FIG. 8 reveals that the mouse fused mRNA is widely distributed in Shh responsive tissues, including the neural tube, pre-somitic mesoderm, somites, developing limb buds and skin. Transcripts for fused were also found in the embryonic gut, testis, cartilage and muscle—tissues that are exposed to the other members of the Hh protein family; Desert and Indian. In the E11-5 mouse nervous system, high levels of fused transcripts were detected throughout the forebrain, midbrain, hindbrain and spinal cord. These high levels of expression were retained in embryonic day 13.5. In both embryonic days 11.5 and 13.5, fused mRNA was detected mainly in the ventral aspect of the neural tube, in regions that are likely to be exposed to the ventral midline-derived Shh. By post natal day −1, widespread expression of fused is still maintained throughout the brain with high levels of transcripts detected in the cortex, hypocampus, ependima and choroid plexus. In the adult, low levels of fused expression are detected all through the brain with higher levels confined to the ependima.

The tissue distribution of fused and the Hh receptor components, Smo and Ptch show considerable overlap. All of them are initially expressed through the neural tube as well as in other Hh responsive tissues. However, whereas Smo mRNA was evenly distributed along the dorso-ventral axis, Ptch and fused mRNAs are found at higher levels ventrally, suggesting that they may be upregulated by Hh. In addition while by day E12, expression of both Smo and Ptch is found mainly in cells which are in close proximity to the ventricular zone, fused mRNA is still widely expressed and its levels decline only later. In the adult expression of both Smo and fused is confined to the ependima where neurogenesis continues.

Detailed analysis of fused expression in adult testis was also performed by in situ hybridization (FIG. 9). Fused was found to be expressed at very high levels on stages I and II germ cells in the somniferous tubules. Levels of fused vary in different somniferous tubules, suggesting that its expression is regulated according to the germinal cell state of differentiation.

Example 7

Gli Luciferase Assay

Given the low homology between dfused and hfused, it was prudent to determine whether in fact the isolated hfused is indeed a mediator of Hh signaling. The following assay was developed to measure the activation of the transcription factor Gli, the mammalian homologue of the *Drosophila cubitus interruptus* (Ci). It has been shown that Gli is a transcription factor activated upon Shh stimulation of cells.

Nine (9) copies of a GLI binding site present in the HNF3β enhancer, (Sasaki et al., *Development* 124: 1313-1322 (1997)), were introduced in front of a thymidine kinase minimal promoter driving the luciferase reporter gene in the pGL3 plasmid (Promega). The sequence of the Gli binding sequence was: TCGACAAGCAGG GAACACCCAAGTAGAAGCTC (p9XGliLuc) (SEQ ID NO:19), while the negative control sequence was: TCGA-CAAGCAGGGAAGTGGGAAGTAGAAGCTC (p9XmGliLuc) (SEQ ID NO:20). These constructs were cotransfected with the full length fused construct or with a plasmid encoding sonic hedgehog in C3H10T1/2 cells grown in F12, DMEM (50:50), 10% FCS heat inactivated. The Gli-BS luciferase reporter plasmid is described in Murone et al., *Curr. Biol.* 9: 76-84 (1999). The day before transfection 1×10$^5$ cells per well was inoculated in 6 well plates, in 2 ml of media. The following day, 1 µg of each construct was cotransfected in duplicate with an appropriate combination of reporter, expression plasmid and reference 0.025 µg ptkRenilla luciferase plasmid (pRL-TK, Promega) using lipofectamine (Gibco-BRL) in 100 µl OptiMem (with GlutaMAX) as per manufacturer's instructions for 3 hours at 37° C. Serum (20%, 1 ml) was then added to each well and the cells were incubated for 3 more hours at 37° C. Cells were then washed twice with PBS, then incubated for 48 hours at 37° C. in 2 ml of media. Each well was then washed with PBS, and the cells lysed in 0.5 ml Passive Lysis Buffer (Promega) for 15 min. at room temperature on a shaker. The lysate was transferred in eppendorf tubes on ice, spun in a refrigerated centrifuge for 30 seconds and the supernatant saved on ice. For each measure, 20 µl of cell lysate was added to 100 µl of LARII (luciferase assay reagent, Promega) in a polypropylene tube and the luciferase light activity measured. The reaction was stopped by the addition of Stop and Glow buffer (Promega), mixed by pipetting up and down 3 to 5 times and *Renilla* luciferase lights activity was measured on the luminometer.

As shown in FIG. 6, fused can induce Gli activity (9.5 fold) in a similar manner as Shh (5.5 fold). This result suggests that the fused gene isolated is a mediator of Shh signaling. An irrelevant serine-threonine kinase, Akt, was not active in this assay (data not shown). Maximal fused activity is dependent on an intact kinase domain as molecules with deletion of this region (fused C-term (SEQ ID NO:27)) or mutation of a conserved lysine residue at about amino acid position 33 in the ATP binding site (fused-DN (SEQ ID NO:25)) were not able to activate GLI when transfected at limiting concentration. Similarly, the C-terminal tail of the protein is necessary for this activity since the kinase domain alone was not active in this assay (fused KD (SEQ ID NO:24)). Expression of each protein was verified by Western blot using an HA tag inserted at the N-terminus of the molecule (data not shown). These results substantiate the conclusion that the homologue of the dfused isolated by Applicants is indeed hfused. Furthermore, these results indicate that fused is capable of and sufficient for the activation of Gli, the major target of Shh signaling and is thus likely to be a direct mediator of the Shh signal in vertebrates.

Example 8

Induced Cyclopia in Frog Embryos

Introduction:

In order to demonstrate that the human fused gene is not only capable of but also required to transduce the Shh signal in vertebrates, a mutant version of fused known as fused-DN (dominant negative) having a mutation of the lysine at position 33 in the ATP binding site was created (SEQ ID NO:25). This residue is conserved among all kinases and is necessary for kinase activity (Hanks et al., *Methods Enzymol.* 200: 38-62 (1991) and its conversion to any other residue in most cases results in the creation of dominant negative mutants.
Methods:
Plasmid Construction:

Wild type fused cDNA with an HA tag inserted at the carboxy terminus was subcloned into pRK5 and a dominant negative form was generated by conversion of lysine at positive 33 to an arginine. Supercoiled plasmid DNA was prepared by Qiagen and used for injection into *Xenopus laevis* embryo.
Manipulation of *Xenopus* Embryos:

Adult female frogs were boosted with 200 I.U. pregnant mare serum 3 days before use and with 800 I.U. of human chorionic gonadotropin the night before injection. Fresh oocytes were squeezed out from female frogs the next morning and in vitro fertilization of oocytes was performed by mixing oocytes with minced testis from sacrificed male frogs. Developing embryos were maintained and staged according to Nieuwkoop and Faber, Normal Table of *Xenopus laevis*, N.-H. P. Co., ed. (Amsterdam, 1967).

Fertilized eggs were dejellied with 2% cysteine (pH 7.8) for 10 minutes, washed once with distilled water and transferred to 0.1×MBS with 5% Ficoll. Fertilized eggs were lined on injection trays in 0.1×MBS with 5% Ficoll. Two-cell stage developing *Xenopus* embryos were injected with 200 pg of either pRK5 containing wild type fused (WT) (SEQ ID NO:1) or dominant negative fused (DN) (SEQ ID NO:25). Injected embryos were kept on trays for another 6 hours, after which they were transferred to 0.1×MBS with 50 mg/ml gentamycin for 3 days until reaching Nieuwkoop stage 35 when eye development is complete.

Results:

To test whether human fused gene acts as a signal transducer of Hedgehog signaling, we injected wild type (SEQ ID NO:2) or dominant negative form (SEQ ID NO:25) of human fused in developing frog embryos. Embryos injected with 120 pg of DNA divided normally in blastula stage and gastrulate normally. While eye development was normal in wild type, fused (SEQ ID NO:2) injected and mock injected embryos, about 30% (Table 1) of the embryos that were injected with fused-DN showed fused eye structure or two eyes connected by some pigmented retina tissue (FIG. 11A). In Table 2, 200 pg of plasmid DNA was delivered to the animal pole of 2-cell stage embryos. Each sample represents the results of at least 3 independent experiments. Embryos were scored visually for cyclopia defects.

TABLE 2

Fused-DN Induced Cyclopia in *Xenopus* Embryos

| Injected DNA | Normal | Cyclop | n |
|---|---|---|---|
| Hu-fused (SEQ ID NO: 2) | 45 | 0 | 45 |
| Kinase domain (SEQ ID NO: 24) | 43 | 0 | 43 |
| C-terminus (SEQ ID NO: 27) | 53 | 1 | 54 |
| fused DN (SEQ ID NO: 25) | 32 | 15 | 47 |
| Uninjected | 61 | 0 | 61 |

The observed cyclopia phenotype is strikingly similar to the one of mouse embryos deficient in Shh (Chiang et al., Nature 383: 407-13 (1996) and of zebrafish embryos where Shh signaling has been blocked by overexpression of a constitutive active PKA, Hammerschmidt et al., Genes Dev. 10: 647-58 (1996); Ungar and Moon, Dev. Biol. 178: 186-91 (1996). In addition, both brain (forebrain) and gut development appeared normal at later stages of tadpole development in the fused-DN (SEQ ID NO:25) injected embryos (FIG. 11B). In contrast, embryos overexpressing either wild type fused (SEQ ID NO:2) or N or C-terminal terminal truncation mutants (SEQ ID NOS:27 and 24), respectively, did not present any abnormalities.

During normal development of the *Xenopus* eye, the eye primordium starts as a single field expressing transcription factor Pax-6, which is a vertebrate homologue of *Drosophila* eyeless, Li et al., Development. 124: 603-15 (1997). At the neurula stage, this eye field is separated into two eye primordia due to an inhibiting signal from prechordal mesoderm. It has been further demonstrated that Shh is the prechordal mesoderm derived signal that is responsible for the inhibition of Pax-6 expression in the midline of the eyefield.

To further understand how overexpression of fused-DN (SEQ ID NO:25) induced a fused eye in *Xenopus* embryos, whole mount in situ hybridization was performed in order to determine the expression pattern of Pax-6 in injected embryos. As shown in FIG. 11C, Pax-6 expression in embryos injected with fused-DN (SEQ ID NO:25) remains as a single field (FIG. 11D). Thus fused-DN (SEQ ID NO:25) induces a cyclopia phenotype by most likely preventing Shh from inhibiting Pax-6 expression in the midline of the eyefield.

Example 9

Rescue of Fused-DN Injected *Xenopus* Embryos by Gli

Shh expression in early floor plate cells is induced by Shh produced by the notochord. To test whether Shh expression in the floor plate will also be inhibited when Shh signaling is blocked, early neurula stage embryos injected with fused-DN or wild-type constructs were stained for Shh expression (See Example 8 for procedure). Shh expression in floor plate cells or early neurula stage embryos was completely suppressed in 26 out of 28 embryos injected when the mutated fused is overexpressed (Table 3, FIG. 11C, left embryo), while the expression of Shh was unaffected in control embryos (FIG. 6E, right embryo). Table 3 represents scored data from three independent experiments. 100 pg of fused-DN, 100 pg of fused-wt or 50 pg of Gli-1 plasmid were injected in 2-cell stage embryos. Embryos were harvested at early neurula stage for Shh staining.

TABLE 3

Wild type fused and Gli rescue Shh expression in floor plate when coexpressed with fused-DN

| | Shh staining | Percentage |
|---|---|---|
| fused-DN (SEQ ID NO: 25) | 2/28 | 7% |
| fused-DN + fused WT | 20/24 | 83% |
| fused-DN + Gli | 36/36 | 100% |

To confirm that this phenotype was due to specific inhibition of the Shh signaling pathway in the floor plate, we attempted to rescue the phenotype by coinjection of wt fused RNA with fused-DN RNA in a 1:1 ratio. Table 2 shows that more than 80% of the embryos coinjected with wt fused and fused-DN RNAs show normal Shh staining in the floor plate. This demonstrates that Shh expression in fused-DN injected embryos is specifically blocked by inhibition of endogenous fused activity.

To further demonstrate that the observed phenotype of fused-DN are due to disruption of the Shh signal cascade and to confirm that hfused works upstream of Gli in this pathway, we asked whether the overexpression of Gli can also rescue the phenotype of *Xenopus* embryos injected with fused-DN. As shown in Table 3, the rescue of Shh expression in the floor plate of fused-DN injected embryos is complete when Gli is overexpressed. Taken together, these findings are consistent with Applicants hypothesis that vertebrate fused functions in the Shh pathway and that is a necessary mediator in the Shh signal transduction pathway, which acts upstream of Gli.

Example 10

Immunoprecipitations and In Vitro Kinase Assay

To directly determine whether hfused has kinase activity, fused, fused-DN and fused-kd cDNAs were tagged with the influenza HA epitope tag and transiently transfected into 293 cells. Immunoprecipitates were tested for kinase activity in the presence of myelin basic protein (MBP) and [$\gamma$-$^{32}$P]-ATP. The amount of $^{32}$P incorporated into MBP was determined after SDS-PAGE and found to be was about 3 times higher than in fused-KD (SEQ ID NO:25) and 2 times higher in wt fused (SEQ ID NO:2) containing extracts compared to controls, while mutation of Lys33 to Arg (fused-DN) (SEQ ID NO:25) neutralizes the activity (FIG. 12).

For immunoprecipitation experiments human embryonic kidney 293 cells or C3H10T1/2 cells (ATCC 226-CCL) were transiently transfected with the various expression plasmids in 10 cm plates with lipofectamine (Gibco MRL). For every transfection, the total amount of DNA was normalized with an expression plasmid encoding EGFP. After 24 hours, the transfected cells were collected and lysed for 20-30 min. at 4°

C. in 1 ml of lysis buffer (50 mM Tris, pH 8.0), 150 mM NaCl, 1 mM EDTA, 1 mM sodium fluoride, 1 mM sodium orthovanadate, 1 mM PMSF and protease inhibitors (Complete, Boehringer Mannheim) containing 1% NP-40, 0.5% deoxycholic acid. Cell debris was removed by passing 5 times through a 25-gauge needle and centrifuged for 10 min. at 10,000 rpm (4° C.) and the sodium chloride concentration of the cell lysates was increased to 250 mM. The supernatant was precleared for 1 hour with 20 µl Protein A Sepharose (Pharmacia). Lysates were immunoprecipitated using anti-HA (or anti-Myc, 9E10) antibodies followed by Protein A Sepharose or anti-Flag M2 gel (Sigma). The beads were washed twice with lysis buffer containing 250 mM sodium chloride, twice with lysis buffer containing 1 M sodium chloride, and then twice with kinase assay buffer (20 mM HEPES, pH 7.6), 1 mM DTT, 1 mM NaF and 1 mM sodium orthovanadate).

For the kinase assays, after the last wash, the beads were resuspended in 20 µl kinase assay buffer supplemented with 10 mCi [$\gamma$-$^{32}$P]-ATP, 20 mM β-glycerophosphate, 20 mM PNPP, 20 mM MgCl$_2$, 1 mM EGTA, 100 µM cold ATP and 0.5 mg/ml Myelin Basic Protein (Sigma), and incubated for 20 min. at 37° C. Reactions were stopped with 20 µl SDS-sample buffer, run on a denaturing 4-20% SDS polyacrylamide gel, and analyzed by phosphorimager.

For the hSu(fu) reactions, the samples were run on denaturing 4-12% SDS-PAGE or 4-12% NuPAGE (Novex), transferred to a PDVF membrane and probed with the anti-Fus 01 antibody, a polyclonal antibody directed against hSu(fu) [described in copending U.S. application Ser. No. 60/135,736] field May 25, 1999], or anti-Myc, Flag (Kodak) or V5 (Invitrogen) monoclonal antibodies. The anti-Fus 01 polyclonal antibody was produced by immunization of rabbits with a 24-mer peptide (CALKFIPKLGRSEKELRNLQREIE)(SEQ ID NO:28) corresponding to the N-terminal portion of hfused. The antibody was purified on a Protein A column. The blots were developed using the enhanced chemiluminescence detection system (Amersham).

Metabolic $^{32}$P labeling of proteins was carried out by washing transfected C3H10T1/2 cells in 10 cm plates with phosphate-free DMEM 10% heat inactivated FBSmedia (Gibco BRL) 24 hours after transfection, and then incubating cells for 3 hours in the same media supplemented with 0.5 mCi of $^{32}$P per ml.

Example 11

PKA Kinase Assay

Immunoprecipitations were prepared from transfected 293 cells as described in Example 10 using anti-Flag M2 gel or anti-Myc antibody followed by Protein A Sepharose. The beads were extensively washed 2 times with lysis buffer, 2 times with lysis buffer containing 1M NaCl, and 3 times with kinase buffer (20 mM Hepes pH 7.6, 1 mM DTT, 1 mM NaF, 1 mM sodium orthovanadate), resuspended in 20 ml of kinase reaction buffer (kinase buffer supplemented with 10 µCi of [$\gamma^{32}$P] ATP, 15 mM MgCl$_2$, 15 mM MnCl$_2$, 15 mM 4-nitrophenyl phosphate, 60 mM β-glycerophosphate, 100 mM ATP) and incubated 20 minutes at 30° C. The kinase reactions were run on SDS-PAGE or NuPAGE (Novex), and transferred to a PVDF membrane. For PKA kinase assays, immunoprecipitations and washes were carried out as described above except that the final washes were done in PKA kinase assay buffer (20 mM MOPS pH 7.2, 25 mM β-glycerophosphate, 5 mM EGTA, 1 mM sodium orthovanadate, 1 mM DTT) (Upstate biotechnology). The kinase assay was performed using the reagents of the PKA assay kit (upstate biotechnology) with the following modifications: the reaction was done at 30° C. for 10 minutes in 20 ml of kinase assay buffer supplemented with 10 µCi of [$\gamma$-$^{32}$P] ATP, 15 mM MgCl$_2$, 15 mM MgCl$_2$ and 125 µM ATP, in the presence of 0.5 mM PKC inhibitor peptide and 5 µM compound R24571. Reactions were stopped with 20 µl of SDS-sample buffer, boiled for 5 minutes, fractionated on NuPAGE and transferred to a PVDF membrane.

For in vitro kinase assays using purified PKAc (Upstate biotechnology), 50 ng GST or 10 ng GST-hSu(fu) were incubated 15 minutes at 30° C. in the presence of PKAc in 20 mM Tris pH 7.5, 10 mM MgCl$_2$, 5 mM ATP and 5 µCi of [$\gamma$-$^{32}$p] ATP.

Example 12

Use of Vertebrate Fused as Hybridization Probes

The following method describes use of a nucleotide sequence encoding vertebrate fused as a hybridization probe.

DNA comprising the coding sequence of full-length or mature vertebrate fused is employed as a probe to screen for homologous DNAs (such as those encoding naturally-occurring variants of vertebrate fused) in human tissue cDNA libraries or human tissue genomic libraries.

Hybridization and washing of filters containing either library DNAs is performed under the following high stringency conditions. Hybridization of radiolabeled vertebrate fused-derived probe to the filters is performed in a solution of 50% formamide, 5×SSC, 0.1% SDS, 0.1% sodium pyrophosphate, 50 mM sodium phosphate, pH 6.8, 2×Denhardt's solution, and 10% dextran sulfate at 42° C. for 20 hours. Washing of the filters is performed in an aqueous solution of 0.1×SSC and 0.1% SDS at 42° C.

DNAs having a desired sequence identity with the DNA encoding full-length native sequence vertebrate fused can then be identified using standard techniques known in the art.

Example 13

Expression of Fused in E. Coli

This example illustrates the preparation of an unglycosylated form of vertebrate fused by recombinant expression in E. coli.

The DNA sequence encoding human fused is initially amplified using selected PCR primers. The primers should contain restriction enzyme sites that correspond to the restriction enzyme sites on the selected expression vector. A variety of expression vectors may be employed. An example of a suitable vector is pBR322 (derived from E. coli; see Bolivar et al, Gene, 2:95 (1977)) which contains genes for ampicillin and tetracycline resistance. The vector is digested with restriction enzyme and dephosphorylated. The PCR amplified sequences are then ligated into the vector. The vector will preferably include sequences that encode for an antibiotic resistance gene, a trp promoter, a polyhis leader (including the first six STII codons, polyhis sequence, and enterokinase cleavage site), the vertebrate fused coding region, lambda transcriptional terminator, and an argU gene.

The ligation mixture is then used to transform a selected E. coli strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized vertebrate fused protein can then be purified using a metal chelating column under conditions that allow tight binding of the protein.

Vertebrate fused may be expressed in *E. coli* in a poly-His tagged form, using the following procedure. The DNA encoding vertebrate fused is initially amplified using selected PCR primers. The primers will contain restriction enzyme sites which correspond to the restriction enzyme sites on the selected expression vector, and other useful sequences providing for efficient and reliable translation initiation, rapid purification on a metal chelation column, and proteolytic removal with enterokinase. The PCR-amplified, poly-His tagged sequences are then ligated into an expression vector, which is used to transform an *E. coli* host based on strain 52 (W3110 fuhA(tonA) lon galE rpoHts(htpRts) clpP(lacIq). Transformants are first grown in LB containing 50 mg/ml carbenicillin at 30° C. with shaking until an O.D. 600 of 3-5 is reached. Cultures are then diluted 50-100 fold into CRAP media (prepared by mixing 3.57 g $(NH_4)_2SO_4$, 0.71 g sodium citrate.$2H_2O$, 1.07 g KCl, 5.36 g Difco yeast extract, 5.36 g Sheffield hycase SF in 500 mL water, as well as 110 mM MPOS, pH 7.3, 0.55% (w/v) glucose and 7 mM $MgSO_4$) and grown for approximately 20-30 hours at 30° C. with shaking. Samples are removed to verify expression by SDS-PAGE analysis, and the bulk culture is centrifuged to pellet the cells. Cell pellets are frozen until purification and refolding.

*E. coli* paste from 0.5 to 1 L fermentations (6-10 g pellets) is resuspended in 10 volumes (w/v) in 7 M guanidine, 20 mM Tris, pH 8 buffer. Solid sodium sulfite and sodium tetrathionate is added to make final concentrations of 0.1M and 0.02 M, respectively, and the solution is stirred overnight at 4° C. This step results in a denatured protein with all cysteine residues blocked by sulfitolization. The solution is centrifuged at 40,000 rpm in a Beckman Ultracentifuge for 30 min. The supernatant is diluted with 3-5 volumes of metal chelate column buffer (6 M guanidine, 20 mM Tris, pH 7.4) and filtered through 0.22 micron filters to clarify. The clarified extract is loaded onto a 5 ml Qiagen Ni-NTA metal chelate column equilibrated in the metal chelate column buffer. The column is washed with additional buffer containing 50 mM imidazole (Calbiochem, Utrol grade), pH 7.4. The protein is eluted with buffer containing 250 mM imidazole. Fractions containing the desired protein are pooled and stored at 4° C. Protein concentration is estimated by its absorbance at 280 nm using the calculated extinction coefficient based on its amino acid sequence.

The proteins are refolded by diluting the sample slowly into freshly prepared refolding buffer consisting of: 20 mM Tris, pH 8.6, 0.3 M NaCl, 2.5 M urea, 5 mM cysteine, 20 mM glycine and 1 mM EDTA. Refolding volumes are chosen so that the final protein concentration is between 50 to 100 micrograms/ml. The refolding solution is stirred gently at 4° C. for 12-36 hours. The refolding reaction is quenched by the addition of TFA to a final concentration of 0.4% (pH of approximately 3). Before further purification of the protein, the solution is filtered through a 0.22 micron filter and acetonitrile is added to 2-10% final concentration. The refolded protein is chromatographed on a Poros R1/H reversed phase column using a mobile buffer of 0.1% TFA with elution with a gradient of acetonitrile from 10 to 80%. Aliquots of fractions with A280 absorbance are analyzed on SDS polyacrylamide gels and fractions containing homogeneous refolded protein are pooled. Generally, the properly refolded species of most proteins are eluted at the lowest concentrations of acetonitrile since those species are the most compact with their hydrophobic interiors shielded from interaction with the reversed phase resin. Aggregated species are usually eluted at higher acetonitrile concentrations. In addition to resolving misfolded forms of proteins from the desired form, the reversed phase step also removes endotoxin from the samples.

Fractions containing the desired folded vertebrate fused polypeptide are pooled and the acetonitrile removed using a gentle stream of nitrogen directed at the solution. Proteins are formulated into 20 mM Hepes, pH 6.8 with 0.14 M sodium chloride and 4% mannitol by dialysis or by gel filtration using G25 Superfine (Pharmacia) resins equilibrated in the formulation buffer and sterile filtered.

Example 14

Expression of Fused in Mammalian Cells

This example illustrates the preparation of a potentially glycosylated form of vertebrate fused by recombinant expression in mammalian cells.

The vector, pRK5 (see EP 307,247, published Mar. 15, 1989), is employed as the expression vector. Optionally, the vertebrate fused DNA is ligated into pRK5 with selected restriction enzymes to allow insertion of the vertebrate fused DNA using ligation methods such as described in Sambrook et al., supra. The resulting vector is called pRK5-fused.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 μg pRK5-fused DNA is mixed with about 1 μg DNA encoding the VA RNA gene [Thimmappaya et al., *Cell*, 31:543 (1982)] and dissolved in 500 μl of 1 mM Tris-HCl, 0.1 mM EDTA, 0.227 M $CaCl_2$. To this mixture is added, dropwise, 500 μl of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 μCi/ml $^{35}$S-cysteine and 200 μCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of vertebrate fused polypeptide. The cultures containing transfected cells may undergo further incubation (in serum free medium) and the medium is tested in selected bioassays.

In an alternative technique, vertebrate fused may be introduced into 293 cells transiently using the dextran sulfate method described by Somparyrac et al., *Proc. Natl. Acad. Sci.*, 12:7575 (1981). 293 cells are grown to maximal density in a spinner flask and 700 μg pRK5-fused DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 µg/ml bovine insulin and 0.1 µg/ml bovine transferrin. After about four days, the conditioned media is centrifuged and filtered to remove cells and debris. The sample containing expressed vertebrate fused can then be concentrated and purified by any selected method, such as dialysis and/or column chromatography.

In another embodiment, vertebrate fused can be expressed in CHO cells. A suitable CHO-expression vector containing fused, e.g., pRK5-fused can be transfected into CHO cells using known reagents such as $CaPO_4$ or DEAE-dextran. As described above, the cell cultures can be incubated, and the medium replaced with culture medium (alone) or medium containing a radiolabel such as $^{35}S$-methionine. After determining the presence of vertebrate fused polypeptide, the culture medium may be replaced with serum free medium. Preferably, the cultures are incubated for about 6 days, and then the conditioned medium is harvested. The medium containing the expressed vertebrate fused can then be concentrated and purified by any selected method.

Epitope-tagged vertebrate used may also be expressed in host CHO cells. The vertebrate fused may be subcloned out of the pRK5 vector. The subclone insert can undergo PCR to fuse in frame with a selected epitope tag such as a poly-his tag into an expression vector. The poly-his tagged vertebrate fused insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged vertebrate fused can then be concentrated and purified by any selected method, such as by $Ni^{2+}$-chelate affinity chromatography.

Vertebrate fused may also be expressed in CHO and/or COS cells by a transient expression procedure or in CHO cells by another stable expression procedure.

Stable expression in CHO cells is performed using the following procedure. The proteins are expressed as an IgG construct (immunoadhesin), in which the coding sequences for the soluble forms (e.g., extracellular domains) of the respective proteins are fused to an IgG1 constant region sequence containing the hinge, CH2 and CH2 domains and/or is a poly-His tagged form.

Following PCR amplification, the respective DNAs are subcloned in a CHO expression vector using standard techniques as described in Ausubel et al., *Current Protocols of Molecular Biology*, Unit 3.16, John Wiley and Sons (1997). CHO expression vectors are constructed to have compatible restriction sites 5' and 3' of the DNA of interest to allow the convenient shuttling of cDNA's. The vector used expression in CHO cells is as described in Lucas et al., *Nucl. Acids Res.* 24:9 (1774-1779 (1996), and uses the SV40 early promoter/enhancer to drive expression of the cDNA of interest and dihydrofolate reductase (DHFR). DHFR expression permits selection for stable maintenance of the plasmid following transfection.

Twelve micrograms of the desired plasmid DNA is introduced into approximately 10 million CHO cells using commercially available transfection reagents Superfect® (Qiagen), Dosper® or Fugene® (Boehringer Mannheim). The cells are grown as described in Lucas et al., supra. Approximately $3 \times 10^{-7}$ cells are frozen in an ampule for further growth and production as described below.

The ampules containing the plasmid DNA are thawed by placement into water bath and mixed by vortexing. The contents are pipetted into a centrifuge tube containing 10 mLs of media and centrifuged at 1000 rpm for 5 minutes. The supernatant is aspirated and the cells are resuspended in 10 mL of selective media (0.2 µm filtered PS20 with 5% 0.2 µm diafiltered fetal bovine serum). The cells are then aliquoted into a 100 mL spinner containing 90 mL of selective media. After 1-2 days, the cells are transferred into a 250 mL spinner filled with 150 µL selective growth medium and incubated at 37° C. After another 2-3 days, 250 mL, 500 mL and 2000 mL spinners are seeded with $3 \times 10^5$ cells/mL. The cell media is exchanged with fresh media by centrifugation and resuspension in production medium. Although any suitable CHO media may be employed, a production medium described in U.S. Pat. No. 5,122,469, issued Jun. 16, 1992 may actually be used. A 3 L production spinner is seeded at $1.2 \times 10^6$ cells/mL. On day 0, the cell number pH is determined. On day 1, the spinner is sampled and sparging with filtered air is commenced. On day 2, the spinner is sampled, the temperature shifted to 33° C., and 30 mL of 500 g/L glucose and 0.6 mL of 10% antifoam (e.g., 35% polydimethylsiloxane emulsion, Dow Corning 365 Medical Grade Emulsion) taken. Throughout the production, the pH is adjusted as necessary to keep it at around 7.2. After 10 days, or until the viability dropped below 70%, the cell culture is harvested by centrifugation and filtering through a 0.22 µm filter. The filtrate was either stored at 4° C. or immediately loaded onto columns for purification.

For the poly-His tagged constructs, the proteins are purified using a Ni-NTA column (Qiagen). Before purification, imidazole is added to the conditioned media to a concentration of 5 mM. The conditioned media is pumped onto a 6 ml Ni-NTA column equilibrated in 20 mM Hepes, pH 7.4, buffer containing 0.3 M NaCl and 5 mM imidazole at a flow rate of 4-5 ml/min. at 4° C. After loading, the column is washed with additional equilibration buffer and the protein eluted with equilibration buffer containing 0.25 M imidazole. The highly purified protein is subsequently desalted into a storage buffer containing 10 mM Hepes, 0.14 M NaCl and 4% mannitol, pH 6.8, with a 25 ml G25 Superfine (Pharmacia) column and stored at -80° C.

Immunoadhesin (Fc-containing) constructs are purified from the conditioned media as follows. The conditioned medium is pumped onto a 5 ml Protein A column (Pharmacia) which had been equilibrated in 20 mM Na phosphate buffer, pH 6.8. After loading, the column is washed extensively with equilibration buffer before elution with 100 mM citric acid, pH 3.5. The eluted protein is immediately neutralized by collecting 1 ml fractions into tubes containing 275 µL of 1 M Tris buffer, pH 9. The highly purified protein is subsequently desalted into storage buffer as described above for the poly-His tagged proteins. The homogeneity is assessed by SDS polyacrylamide gels and by N-terminal amino acid sequencing by Edman degradation.

Example 15

Expression of Vertebrate Fused in Yeast

The following method describes recombinant expression of vertebrate fused in yeast.

First, yeast expression vectors are constructed for intracellular production or secretion of vertebrate fused from the ADH2/GAPDH promoter. DNA encoding vertebrate fused, a selected signal peptide and the promoter is inserted into suitable restriction enzyme sites in the selected plasmid to direct intracellular expression of vertebrate fused. For secretion, DNA encoding vertebrate fused can be cloned into the selected plasmid, together with DNA encoding the ADH2/GAPDH promoter, the yeast alpha-factor secretory signal/leader sequence, and linker sequences (if needed) for expression of vertebrate fused.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant vertebrate fused can subsequently be isolated and purified by removing the yeast cells from the fermentation medium by centrifugation and then concentrating the medium using selected cartridge filters. The concentrate containing vertebrate fused may further be purified using selected column chromatography resins.

Example 16

Expression of Vertebrate Fused in Baculovirus-Infected Insect Cells

The following method describes recombinant expression of vertebrate fused in Baculovirus-infected insect cells.

The vertebrate fused is fused upstream of an epitope tag contained within a baculovirus expression vector. Such epitope tags include poly-his tags and immunoglobulin tags (like Fc regions of IgG). A variety of plasmids may be employed, including plasmids derived from commercially available plasmids such as pVL1393 (Novagen). Briefly, the vertebrate fused or the desired portion of the vertebrate fused (such as the sequence encoding the extracellular domain of a transmembrane protein) is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BaculoGold™ virus DNA (Pharmingen) into *Spodoptera frugiperda* ("Sf9") cells (ATCC CRL 1711) using lipofectin (commercially available from GIBCO-BRL). After 4-5 days of incubation at 28° C., the released viruses are harvested and used for further amplifications. Viral infection and protein expression is performed as described by O'Reilley et al., *Baculovirus expression vectors: A laboratory Manual*, Oxford: Oxford University Press (1994).

Expressed poly-his tagged vertebrate fused can then be purified, for example, by $Ni^{2+}$-chelate affinity chromatography as follows. Extracts are prepared from recombinant virus-infected Sf9 cells as described by Rupert et al, *Nature*, 362:175-179 (1993). Briefly, Sf9 cells are washed, resuspended in sonication buffer (25 mL Hepes, pH 7.9; 12.5 mM $MgCl_2$; 0.1 mM EDTA; 10% Glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% Glycerol, pH 7.8) and filtered through a 0.45 μm filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% Glycerol, pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or western blot with $Ni^{2+}$-NTA-conjugated to alkaline phosphatase (Qiagen). Fractions containing the eluted $His_{10}$-tagged vertebrate fused are pooled and dialyzed against loading buffer.

Alternatively, purification of the IgG tagged (or Fe tagged) vertebrate fused can be performed using known chromatography techniques, including for instance, Protein A or protein G column chromatography Example 17

Preparation of Antibodies that Bind Vertebrate Fused

This example illustrates preparation of monoclonal antibodies, which can specifically bind vertebrate fused.

Techniques for producing the monoclonal antibodies are known in the art and are described, for instance, in Goding, supra. Immunogens that may be employed include purified vertebrate fused, fusion proteins containing vertebrate fused, and cells expressing recombinant vertebrate fused on the cell surface. Selection of the immunogen can be made by the skilled artisan without undue experimentation.

Mice, such as Balb/c, are immunized with the vertebrate fused immunogen emulsified in complete Freund's adjuvant and injected subcutaneously or intraperitoneally in an amount from 1-100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect vertebrate fused antibodies.

After a suitable antibody titer has been detected, the animals "positive" for antibodies can be injected with a final intravenous injection of vertebrate fused. Three to four days later, the mice are sacrificed and the spleen cells are harvested. The spleen cells are then fused (using 35% polyethylene glycol) to a selected murine myeloma cell line such as P3X63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against vertebrate fused. Determination of "positive" hybridoma cells secreting the desired monoclonal antibodies against vertebrate fused is within the skill in the art.

The positive hybridoma cells can be injected intraperitoneally into syngeneic Balb/c mice to produce ascites containing the anti-vertebrate fused monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Example 18

Purification of Vertebrate Fused Polypeptides Using Specific Antibodies

Native or recombinant vertebrate fused polypeptides may be purified by a variety of standard techniques in the art of protein purification. For example, pro-fused polypeptide, mature fused polypeptide, or pre-fused polypeptide is purified by immunoaffinity chromatography using antibodies specific for the vertebrate fused polypeptide of interest. In general, an immunoaffinity column is constructed by covalently coupling the anti-fused polypeptide antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated SEPHAROSE™ (Pharmacia LKB Biotechnology). The antibody is coupled to the resin, the resin is blocked, and the derivative resin is washed according to the manufacturer's instructions.

Such an immunoaffinity column is utilized in the purification of vertebrate fused polypeptide by preparing a fraction from cells containing vertebrate fused polypeptide in a soluble form. This preparation is derived by solubilization of the whole cell or of a subcellular fraction obtained via differential centrifugation by the addition of detergent or by other methods well known in the art. Alternatively, soluble vertebrate fused polypeptide containing a signal sequence may be secreted in useful quantity into the medium in which the cells are grown.

A soluble vertebrate fused polypeptide-containing preparation is passed over the immunoaffinity column, and the column is washed under conditions that allow the preferential absorbance of vertebrate fused polypeptide (e.g., high ionic strength buffers in the presence of detergent). Then, the column is eluted under conditions that disrupt antibody/vertebrate fused polypeptide binding (e.g., a low pH buffer such as approximately pH 2-3, or a high concentration of a chaotrope such as urea or thiocyanate ion), and vertebrate fused polypeptide is collected.

Example 19

Drug Screening

This invention is particularly useful for screening compounds by using vertebrate fused polypeptides or binding fragment thereof in any of a variety of drug screening techniques. The vertebrate fused polypeptide or fragment employed in such a test may either be free in solution, affixed to a solid support, borne on a cell surface; or located intracellularly. One method of drug screening utilizes eukaryotic or prokaryotic host cells which are stably transformed with recombinant nucleic acids expressing the vertebrate fused polypeptide or fragment. Drugs are screened against such transformed cells in competitive binding assays. Such cells, either in viable or fixed form, can be used for standard binding assays. One may measure, for example, the formation of complexes between vertebrate fused polypeptide or a fragment and the agent being tested. Alternatively, one can examine the diminution in complex formation between the vertebrate fused polypeptide and its target cell or target receptors caused by the agent being tested.

Thus, the present invention provides methods of screening for drugs or any other agents which can affect a vertebrate fused polypeptide-associated disease or disorder. These methods comprise contacting such an agent with an vertebrate fused polypeptide or fragment thereof and assaying (i) for the presence of a complex between the agent and the vertebrate fused polypeptide or fragment, or (ii) for the presence of a complex between the vertebrate fused polypeptide or fragment and the cell, by methods well known in the art. In such competitive binding assays, the vertebrate fused polypeptide or fragment is typically labeled. After suitable incubation, free vertebrate fused polypeptide or fragment is separated from that present in bound form, and the amount of free or uncomplexed label is a measure of the ability of the particular agent to bind to vertebrate fused polypeptide or to interfere with the vertebrate fused polypeptide/cell complex.

Another technique for drug screening provides high throughput screening for compounds having suitable binding affinity to a polypeptide and is described in detail in WO84/03564, published on Sep. 13, 1984. Briefly stated, large numbers of different small peptide test compounds are synthesized on a solid substrate, such as plastic pins or some other surface. As applied to a vertebrate fused polypeptide, the peptide test compounds are reacted with vertebrate fused polypeptide and washed. Bound vertebrate fused polypeptide is detected by methods well known in the art. Purified vertebrate fused polypeptide can also be coated directly onto plates for use in the aforementioned drug screening techniques. In addition, non-neutralizing antibodies can be used to capture the peptide and immobilize it on the solid support.

This invention also contemplates the use of competitive drug screening assays in which neutralizing antibodies capable of binding vertebrate fused polypeptide specifically compete with a test compound for binding to vertebrate fused polypeptide or fragments thereof. In this manner, the antibodies can be used to detect the presence of any peptide which shares one or more antigenic determinants with vertebrate fused polypeptide.

Deposit of Material

The following materials have been deposited with the American Type Culture Collection, 10801 University Boulevard, Manassas, Va., USA 20110-2209 (ATCC):

| Designation: | ATCC Dep. No. | Deposit Date |
| --- | --- | --- |
| pRK5tkneo.hFused-1272 | 209637 | Feb. 19, 1998 |

This deposit was made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposit will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the construct deposited, since the deposited embodiment is intended as a single illustration of certain aspects of the invention, and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

---

What is claimed is:

1. An isolated nucleic acid molecule encoding a polypeptide comprising an amino acid sequence of at least about 80% amino acid sequence identity to the sequence of amino acid residues from about 1 to about 260 of FIG. 1 (SEQ ID NO:24), wherein said polypeptide comprises fused kinase activity.

2. An isolated nucleic acid molecule encoding a polypeptide comprising an amino acid sequence of at least about 80% amino acid sequence identity to the sequence of amino acid residues from about 261 to about 1315 of FIG. 1 (SEQ ID NO:27), wherein said polypeptide comprises the activity of displacing PKA from Su(fu).

3. An isolated nucleic acid molecule encoding a fused polypeptide comprising an amino acid sequence of at least about 80% amino acid sequence identity to the sequence of amino acid residues from 1 to about 1315 of FIG. 1 (SEQ ID NO:2), wherein said polypeptide phosphorylates Gli.

4. The nucleic acid of claim 3 that encodes a polypeptide comprising the amino acid sequence of residues 1 to about 1315 of FIG. 1 (SEQ ID NO:2).

5. The nucleic acid of claim 4 that encodes a polypeptide consisting of the amino acid sequence of residues 1 to about 1315 of FIG. 1 (SEQ ID NO:2).

6. The nucleic acid of claim 1 selected from the group consisting of: (a) nucleic acid that encodes the polypeptide of SEQ ID NO:24 with at least one conservatively substituted amino acid residue; and (b) nucleic acid encoding the polypeptide of SEQ ID NO:24 with at least one addition or deletion of one to five amino acid residues.

7. The nucleic acid of claim 2 selected from the group consisting of: (a) nucleic acid encoding the polypeptide of SEQ ID NO:27 with at least one conservatively substituted amino acid residue; and (b) nucleic acid encoding the polypeptide of SEQ ID NO:27 with at least one addition or deletion of one to five amino acid residues.

8. The nucleic acid of claim 3 selected from the group consisting of: (a) nucleic acid encoding the polypeptide of SEQ ID NO:2 with at least one conservatively substituted amino acid residue; and (b) nucleic acid encoding the polypeptide of SEQ ID NO:2 with at least one addition or deletion of one to five amino acid residues.

9. An isolated nucleic acid encoding a fused polypeptide having at least about 80% amino acid sequence identity to the polypeptide encoded by the cDNA insert of the vector deposited with the ATCC under Deposit number 209637, wherein said fused polypeptide phosphorylates Gli.

10. The nucleic acid of claim 9 comprising the nucleic acid encoding the polypeptide encoded by the cDNA insert of the vector deposited with the ATCC under Deposit number 209637.

11. An isolated nucleic acid encoding a polypeptide comprising the sequence of amino acid residues from 1 to about 260 of FIG. 1 (SEQ ID NO:24), or a fragment thereof sufficient to provide a binding site for an anti fused antibody, wherein said fragment comprises at least 20 residues.

12. An isolated nucleic acid encoding a polypeptide comprising the sequence of amino acid residues from about 261 to about 1315 of FIG. 1 (SEQ ID NO:27), or a fragment thereof sufficient to provide a binding site for an anti fused antibody, wherein said fragment comprises at least 20 residues.

13. An isolated nucleic acid encoding a polypeptide comprising the sequence of amino acid residues from 1 to about 1315 of FIG. 1 (SEQ ID NO:2), or a fragment thereof sufficient to provide a binding site for an anti fused antibody, wherein said fragment comprises at least 20 residues.

14. An isolated nucleic acid (a) that hybridizes under stringent conditions with a DNA molecule encoding a fused polypeptide comprising the sequence of amino acid residues from 1 to 260 of FIG. 1 (SEQ ID NO:24), or (b) the complement of the DNA molecule of (a), wherein said isolated nucleic acid encodes a polypeptide that comprises fused kinase activity.

15. An isolated nucleic acid (a) that hybridizes under stringent conditions with a DNA molecule encoding a fused polypeptide comprising the sequence of amino acid residues from 261 to 1315 of FIG. 1 (SEQ ID NO:27), or (b) the complement of the DNA molecule of (a), wherein said polypeptide comprises the activity of displacing PKA from Su(fu).

16. An isolated nucleic acid (a) that hybridizes under stringent conditions with a DNA molecule encoding a fused polypeptide comprising the sequence of amino acid residues from 1 to 1315 of FIG. 1 (SEQ ID NO:2), or (b) the complement of the DNA molecule of (a), wherein said isolated nucleic acid encodes a polypeptide that phosphorylates Gli.

\* \* \* \* \*